US009439960B2

(12) United States Patent
Shenk et al.

(10) Patent No.: US 9,439,960 B2
(45) Date of Patent: Sep. 13, 2016

(54) CYTOMEGALOVIRUS VACCINES AND METHODS OF PRODUCTION

(75) Inventors: Thomas Shenk, Princeton, NJ (US); Dai Wang, Blue Bell, PA (US)

(73) Assignee: The Trustees of Princeton University, Princeton, NJ (US)

(*) Notice: Subject to any disclaimer, the term of this patent is extended or adjusted under 35 U.S.C. 154(b) by 373 days.

(21) Appl. No.: 12/681,504

(22) PCT Filed: Oct. 1, 2008

(86) PCT No.: PCT/US2008/079494
§ 371 (c)(1),
(2), (4) Date: Jul. 22, 2010

(87) PCT Pub. No.: WO2009/049138
PCT Pub. Date: Apr. 16, 2009

(65) Prior Publication Data
US 2010/0285059 A1    Nov. 11, 2010

(51) Int. Cl.
*A61K 39/245* (2006.01)
*A61K 39/12* (2006.01)
*A61K 39/00* (2006.01)

(52) U.S. Cl.
CPC ............ *A61K 39/245* (2013.01); *A61K 39/12* (2013.01); *A61K 2039/5254* (2013.01); *C12N 2710/16134* (2013.01)

(58) Field of Classification Search
CPC .......... C12N 2760/16151; C12N 2760/16234; C12N 7/02; C12N 2710/16134; C12N 2710/16162; C12N 7/00; C12N 2710/24143; C12N 2730/10134; C12N 2740/16034; C12N 2740/16134; C12N 15/869; C12N 2710/16111; A61K 2039/5254; A61K 39/245; C07K 14/02; C07K 14/045; C07K 16/088; C07K 14/005; C07K 16/085; G01N 2333/045; G01N 33/56994
See application file for complete search history.

(56) References Cited

U.S. PATENT DOCUMENTS

| 3,959,466 A | 5/1976 | Plotkin |
| 4,058,598 A | 11/1977 | Stern et al. |
| 6,471,965 B1 | 10/2002 | Golubev et al. |
| 7,704,510 B2 | 4/2010 | Shenk et al. |
| 8,173,362 B2 * | 5/2012 | Shenk et al. ............ 435/5 |
| 2005/0064394 A1 | 3/2005 | Liu et al. |

FOREIGN PATENT DOCUMENTS

| WO | WO 2005/012545 A2 | 2/2005 |
| WO | WO 2007/146024 A2 | 12/2007 |
| WO | WO 2009/049138 A1 | 4/2009 |

OTHER PUBLICATIONS

Sinlair J. J. Clin. Virol. 2008, 41(3):180-5.*
Zhong J. Expert. Rev. Anti. Infec. Ther. 2007, vol. 5 (3), pp. 449-459.*
Wang et al. J. Virol. 2005, vol. 79, (16). . pp. 10330-10338.*
Revello et al. J. Gene. Virol. 2001, vol. 82, pp. 1429-143).*
Gerna et al. J. Gene Virol. 2005, vol. 86, No. part 2, pp. 275-284.*
Mousavi-Jazi et al. (J. Medical Virology, 2000, vol. 62, pp. 117-126).*
Gonczol et al. Expert Opinion on Biological Therapy 2001, vol. 1 (3), pp. 401-412.*
Cicin-Sain et al. J. Virol. Published on Oct. 3, 2007, vol. 10, pp. 13825-13834.*
Ryckman et al. PNAS, 2008, vol. 105, (37), pp. 14118-14123.*
Adler., B., Scrivano., L., Ruzcics, Z., Rupp, B., Sinzger, C. & Koszinowski, U., "Role of Human Cytomegalovirus UL131A in Cell Type-Specific Virus Entry and Release," *Journal of General Virology.* 87: 2451-2460 (2006).
Bodaghi, B., Goureau, O., Zipeto, D., Laurent, L., Virelizier, J. L. & Michelson, S., "Role of IFN-γ-Induced Indoleamine 2,3 Dioxygenase of Human Cytomegalovirus in Retinal Pigment Epithelial Cells," *The Journal of Immunology*, 162: 957-964 (1999).
Borza, C. M. & Hutt-Fletcher, L. M., "Alternate Replication in B Cells and Epithelial Cells Switches Tropism of Epstein-Barr Virus," *Nature Medicine*, 8(6): 594-599 (Jun. 2002).
Compton, T., Nepomuceno, R. R. & Nowlin, D. M., "Human Cytomegalovirus Penetrates Host Cells by PH-Independent Fusion at the Cell Surface," *Virology*, 191: 387-395 (1992).
Haan, K. M. & Longnecker, R., "Coreceptor Restriction within the HLA-DQ Locus for Epstein-Barr Virus Infection," *PNAS*, 97(16): 9252-9257 (Aug. 2000).
Haan, K. M., Kwok, W. W., Longnecker, R. & Speck, P., "Epstein-Barr Virus Entry Utilizing HLA-DP or HLA-DQ as a Coreceptor," *Journal of Virology*, 74(5): 2451-2454 (Mar. 2000).
Hahn, G., Revello, M. G., Patrone, M., Percivalle, E., Campanini, G., Sarasini, A., Wagner, M., Gallina, A., Milanesi, G., Koszinowski, U., Baldanti, F. & Gerna, G., "Human Cytomegalovirus UL131-128 Genes Are Indispensable for Virus Growth in Endothelial Cells and Virus Transfer to Leukocytes," *Journal of Virology*, 78(18): 10023-10033 (Sep. 2004).
Hutt-Fletcher, L. M. & Lake, C. M., "Two Epstein-Barr Virus Glycoprotein Complexes," *Curr Top Microbiol Immunol*, 258: 51-64 (2001 ).
Li, Q., Turk, S. M. & Hutt-Fletcher, L. M., "The Epstein-Barr Virus (EBV) BZLF2 Gene Product Associates with the gH and gL Homologs of EBV and Carries an Epitope Critical to Infection of B Cells but Not of Epithelial Cells," *Journal of Virology.* 69(7): 3987-3994 (Jul. 1995).
Li, Q., Spriggs, M. K., Kovats, S., Turk, S. M., Comeau, M. R., Nepom, B. & Hutt- Fletcher, L. M., "Epstein-Barr Virus Uses HLA Class II as a Cofactor for Infection of B Lymphocytes," *Journal of Virology*, 71(6): 4657-4662 (Jun. 1997).

(Continued)

*Primary Examiner* — Bao Li
(74) *Attorney, Agent, or Firm* — Hamilton, Brook, Smith & Reynolds, P.C.

(57) ABSTRACT

Methods of increasing diversity in cytomegalovirus vaccines through the selection of cell type in which the virus is propagated, and the use of cytomegalovirus produced by those methods in the development of vaccine compositions, are disclosed. Vaccine compositions comprising CMV isolated from epithelial cells are also disclosed.

3 Claims, 6 Drawing Sheets

(56) References Cited

OTHER PUBLICATIONS

Miller, N. & Hutt-Fletcher, L. M., "Epstein-Barr Virus Enters B Cells and Epithelial Cells by Different Routes," *Journal of Virology*, 66(6): 3409-3414 (Jun. 1992).

Milne, R. S., Nicola, A. V., Whitbeck, J. C., Eisenberg, R. J. & Cohen, G. H., "Glycoprotein D Receptor-Dependent Low-pH-Independent Endocytic Entry of Herpes Simplex Virus Type 1," *Journal of Virology*, 79(11): 6655-6663 (Jun. 2005).

Nemerow, G. R. & Cooper, N. R., "Early Events in the Infection of Human B Lymphocytes by Epstein-Barr Virus: The Internalization Process," *Virology*, 132: 186-198 (1984).

Nicola, A. V., McEvoy, A. M. & Straus, S. E., "Roles for Endocytosis and Low pH in Herpes Simplex Virus Entry into HeLa and Chinese Hamster Ovary Cells," *Journal of Virology*, 77(9): 5324-5332 (May 2003).

Nicola, A. V., Hou, J., Major, E. O. & Straus, S. E., "Herpes Simplex Virus Type 1 Enters Human Epidermal Keratinocytes, but Not Neurons, via a pH-Dependent Endocytic Pathway," *Journal of Virology*, 79(12): 7609-7616 (Jun. 2005).

Plachter, B., Sinzger, C. & Jahn, G., "Cell Types Involved in Replication and Distribution of Human Cytomegalovirus," *Advances in Virus Research*, 46: 195-261 (1996).

Ryckman, B. J., Jarvis, M. A., Drummond, D. D., Nelson, J. A. & Johnson, D. C., "Human Cytomegalovirus Entry into Epithelial and Endothelial Cells Depends on Genes UL128 to UL150 and Occurs by Endocytosis and Low-pH Fusion," *Journal of Virology*, 80(2): 710-722 (Jan. 2006).

Wang, D. & Shenk, T., "Human Cytomegalovirus UL131 Open Reading Frame is Required for Epithelial Cell Tropism," *Journal of Virology*, 79(16): 10330-10338 (Aug. 2005).

Wang, D. & Shenk, T., "Human Cytomegalovirus Virion Protein Complex Required for Epithelial and Endothelial Cell Tropism," *PNAS*, 102(50): 18153-18158 (Dec. 2005).

Wang, X. & Hutt-Fletcher, L. M., "Epstein-Barr Virus Lacking Glycoprotein gp42 Can Bind to B Cells but is not Able to Infect," *Journal of Virology*, 72(1): 158-163 (Jan. 1998).

Wang, X., Kenyon, W. J., Li, Q., Mullberg, J. & Hutt-Fletcher, L. M., "Epstein-Barr Virus Uses Different Complexes of Glycoproteins gH and gL to Infect B Lymphocytes and Epithelial Cells," *Journal of Virology*, 72(7): 5552-5558 (Jul. 1998).

Wittels, M. & Spear, P. G., "Penetration of Cells by Herpes Simplex Virus does not Require a Low pH-Dependent Endocytic Pathway," *Virus Research*, 18: 271-290 (1990).

International Search Report of Int'l Application No. PCT/US2008/079494, Date Mailed: Dec. 18, 2008.

GenBank Accession No. AB051431, "*Homo sapiens* mRNA for KIAA1644 protein, partial cds," Oct. 6, 2001; Retrieved from the Internet on Aug. 10, 2010: http://www.ncbi.nlm.nih.gov/sviewer/viewer.fcgi?val . . . pp. 1-3.

GenBank Accession No. AC146851, "Human Herpesvirus 5 Towne-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-60.

GenBank Accession No. AC146904, "Human Herpesvirus 5 PH-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-60.

GenBank Accession No. AC146905, "Human Herpesvirus 5 Toledo-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-59.

GenBank Accession No. AC146906, "Human Herpesvirus 5 TR-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-61.

GenBank Accession No. AC146907, "Human Herpesvirus 5 FIX-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-59.

GenBank Accession No. AC146999, "Human Herpesvirus 5 ADF169-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-60.

GenBank Accession No. AF038194, "*Homo sapiens* clone 23821 mRNA sequence," Jan. 22, 1998; Retrieved from the Internet on Aug. 11, 2010: http://www.ncbi.nlm.nih.gov/sviewer/viewer.fcgi?val . . . pp. 1-2.

GenBank Accession No. AF085968, "*Homo sapiens* full length insert cDNA clone YT69G03," Aug. 29, 1998; Retrieved from the Internet on Aug. 10, 2010: http://www.ncbi.nlm.nih.gov/sviewer/viewer.fcgi?val . . . pp. 1-2.

GenBank Accession No. AF480884, "Chimpanzee cytomegalovirus, complete genome," Jan. 29, 2003; Retrieved from the Internet on Aug. 11, 2010: http://www.ncbi.nlm.nih.gov/sviewer/viewer.fcgi?val . . . pp. 1-96.

GenBank Accession No. AI369525, "$1^{st}$ strand cDNA was prepared from mRNA obtained from pooled 8-9 week (total) fetus material with a Not I—oligo(dT) primer," Jan. 11, 1999; Retrieved from the Internet on Aug. 10, 2010: http://www.ncbi.nlm.nih.gov/sviewer/viewer.fcgi?val . . . pp. 1-2.

GenBank Accession No. AI369525, GenBank gi: 4148278, Lib. Name: Soares_total_fetus_Nb2HF8_9w, Jan. 11, 1999; Retrieved from the Internet on Aug. 10, 2010: http://www.ncbi.nlm.nih.gov/sviewer/viewer.fcgi?val . . . pp. 1-2.

GenBank Accession No. AK021804, "*Homo sapiens* cDNA FLJ11742 fis, clone HEMBA1005508," Sep. 12, 2006; Retrieved from the Internet on Aug. 10, 2010: http://www.ncbi.nlm.nih.gov/sviewer/viewer.fcgi?val . . . pp. 1-2.

GenBank Accession No. AK023391, "*Homo sapiens* cDNA FLJ13329 fis, clone OVARC1001795," Sep. 12, 2006; Retrieved from the Internet on Aug. 10, 2010: http://www.ncbi.nlm.nih.gov/sviewer/viewer.fcgi?val . . . pp. 1-2.

GenBank Accession No. AK023856, "*Homo sapiens* cDNA FLJ13794 fis, clone THYRO1000092," Sep. 12, 2006; Retrieved from the Internet on Aug. 10, 2010: http://www.ncbi.nlm.nih.gov/sviewer/viewer.fcgi?val . . . pp. 1-3.

GenBank Accession No. AK055156, "*Homo sapiens* cDNA FLJ30594 fis, clone BRAWH2008903," Sep. 13, 2006; Retrieved from the Internet on Aug. 10, 2010: http://www.ncbi.nlm.nih.gov/viewer/viewer.fcgi?val . . . pp. 1-3.

GenBank Accession No. AK055386, "*Homo sapiens* cDNA FLJ30824 fis, clone FEBRA2001698," Sep. 13, 2006; Retrieved from the Internet on Aug. 10, 2010: http://www.ncbi.nlm.nih.gov/sviewer/viewer.fcgi?val . . . pp. 1-3.

GenBank Accession No. AK056190, "*Homo sapiens* cDNA FLJ31628 fis, clone NT2RI2003344, weakly similar to Presynaptic Protein SAP97," Sep. 13, 2006; Retrieved from the Internet on Aug. 10, 2010: http://www.ncbi.nlm.nih.gov/sviewer/viewer.fcgi?val . . . pp. 1-3.

GenBank Accession No. AK056703, "*Homo sapiens* cDNA FLJ32141 fis, clone PLACE5000067," Sep. 13, 2006; Retrieved from the Internet on Aug. 10, 2010: http://www.ncbi.nln.nih.gov/sviewer/viewer.fcgi?val . . . pp. 1-3.

GenBank Accession No. AK074031, "*Homo sapiens* mRNA for FLJ00072 protein," Feb. 13, 2004; Retrieved from the Internet on Aug. 10, 2010: http://www.ncbi.nlm.nih.gov/sviewer/viewer.fcgi?val . . . pp. 1-3.

GenBank Accession No. AK090308, "Mus musculus adult male gall bladder cDNA, Riken full-length enriched library, clone:G630044J09 product:betaine-homocysteine methyltransferase 2, full insert sequence," Oct. 4, 2006; Retrieved from the Internet on Aug. 10, 2010: http://www.ncbi.nlm.nih.gov/sviewer/viewer.fcgi?val . . . pp. 1-5.

GenBank Accession No. AK090803, "*Homo sapiens* cDNA FLJ33484 fis, clone BRAMY2003117," Sep. 14, 2006; Retrieved from the Internet on Aug. 11, 2010: http://www.ncbi.nlm.nih.gov/sviewer/viewer.fcgi?val . . . pp. 1-3.

GenBank Accession No. AK094143, "*Homo sapiens* cDNA FLJ36824 fis, clone ASTRO2007221, weakly similar to Periaxin," Sep. 14, 2006; Retrieved from the Internet on Aug. 10, 2010: http://www.ncbi.nlm.nih.gov/sviewer/viewer.fcgi?val . . . pp. 1-3.

(56) References Cited

OTHER PUBLICATIONS

GenBank Accession No. AK094860, "*Homo sapiens* cDNA FLJ37541 fis, clone BRCAN2026340," Sep. 14, 2006; Retrieved from the Internet on Aug. 10, 2010: http://www.ncbi.nlm.nih.gov/sviewer/viewer.fcgi?val . . . pp. 1-3.
GenBank Accession No. AK123066, "*Homo sapiens* cDNA FLJ41071 fis, clone 3NB692003538," Sep. 14, 2006; Retrieved from the Internet on Aug. 10, 2010: http://www.ncbi.nlm.nih.gov/sviewer/viewer.fcgi?val . . . pp. 1-2.
GenBank Accession No. AK124132, "*Homo sapiens* cDNA FLJ42138 fis, clone TESTI2036684," Sep. 14, 2006; Retrieved from the Internet on Aug. 10, 2010: http://www.ncbi.nlm.nih.gov/sviewer/viewer.fcgi?val . . . pp. 1-2.
GenBank Accession No. AK124390, "*Homo sapiens* cDNA FLJ42399 fis, clone ASTRO2003024," Sep. 14, 2006; Retrieved from the Internet on Aug. 10, 2010: http://www.ncbi.nlm.nih.gov/sviewer/viewer.fcgi?val . . . pp. 1-3.
GenBank Accession No. AK124941, "*Homo sapiens* cDNA FLJ42951 fis, clone BRSTN2007765," Sep. 14, 2006; Retrieved from the Internet on Aug. 10, 2010: http://www.ncbi.nlm.nih.gov/sviewer/viewer.fcgi?val . . . pp. 1-3.
GenBank Accession No. AK125975, "*Homo sapiens* cDNA FLJ43987 fis, clone TESTI4019299," Sep. 14, 2006; Retrieved from the Internet on Aug. 10, 2010: http://www.ncbi.nlm.nih.gov/sviewer/viewer.fcgi?val . . . pp. 1-2.
GenBank Accession No. AL133118, "*Homo sapiens* mRNA; cDNA DKFZp586N0121 (from clone DKFZp586N0121)," Feb. 18, 2000; Retrieved from the Internet on Aug. 10, 2010: http://www.ncbi.nlm.nih.gov/sviewer/viewer.fcgi?val . . . pp. 1-2.
GenBank Accession No. AL713743, "*Homo sapiens* mRNA; cDNA DKFZp761G0122 (from clone DKFZp761G0122)," Mar. 20, 2002; Retrieved from the Internet on Aug. 10, 2010: http://www.ncbi.nlm.nih.gov/sviewer/viewer.fcgi?val . . . pp. 1-2.
GenBank Accession No. AW444553, "The sequence contained on oligo-dT track that was present in the oligonucleotide that was used to rpime the synthesis of first strand cDNA and therefore this may represent a bonafide poly A tail," Feb. 15, 2000; Retrieved from the Internet on Aug. 10, 2010: http://www.ncbi.nlm.nih.gov/sviewer/viewer.fcgi?val . . . pp. 1-2.
GenBank Accession No. AW856073, "A mini-library was made by cloning products derived from ORESTES PCR (U.S. Letters Patent application No. 196,716—Ludwign Institute for Cancer Research) profiles into the pUC 18 vector. Reverse transcription of tissue mRNA and cDNA amplification were performed under low stringency conditions," May 19, 2000; Retrieved from the Internet on Aug. 11, 2010: http://www.ncbi.nlm.nih.gov/sviewer/viewer.fcgi?val . . . pp. 1-2.
GenBank Accession No. AW856073, GenBank gi: 7951766, Lib. Name: CT0286, May 19, 2000; Retrieved from the Internet on Aug. 10, 2010: http://www.ncbi.nlm.nih.gov/sviewer/viewer.fcgi?val . . . pp. 1-2.
GenBank Accession No. AY186194, "Rhesus cytomegalovirus strain 68-1, complete genome," Jun. 4, 2003; Retrieved from the Internet on Aug. 11, 2010: http://www.ncbi.nlm.nih.gov/sviewer/viewer.fcgi?val . . . pp. 1-97.
GenBank Accession No. AY446894, "Human herpesvirus 5 strain Merlin, complete genome," Aug. 13, 2007; Retrieved from the Internet on Aug. 11, 2010: http://www.ncbi.nlm.nih.gov/sviewer/viewer.fcgi?val . . . pp. 1-95.
GenBank Accession No. BC011595, "*Homo sapiens* glycoprotein (transmembrane) nmb, mRNA (cDNA clone Image:3345861), complete cds," Sep. 16, 2003; Retrieved from the Internet on Aug. 10, 2010: http://www.ncbi.nlm.nih.gov/sviewer/viewer.fcgi?val . . . pp. 1-3.
GenBank Accession No. BC015929, "*Homo sapiens* nuclear receptor subfamily 1, group D, member 2, mRNA (cDNA clone Image:3912370), partial cds," Jan. 2, 2004; Retrieved from the Internet on Aug. 10, 2010: http://www.ncbi.nlm.nih.gov/sviewer/viewer.fcgi?val . . . pp. 1-3.

GenBank Accession No. BC018597, "*Homo sapiens*, clone Image:3869276, mRNA," Dec. 3, 2001; Retrieved from the Internet on Aug. 10, 2010: http://www.ncbi.nlm.nih.gov/sviewer/viewer.fcgi?val . . . pp. 1-2.
GenBank Accession No. BC039151, "*Homo sapiens* chromosome 20 open reading frame 119, mRNA (cDNA clone Image:4745538), with apparent retained intron," Nov. 17, 2006; Retrieved from the Internet on Aug. 10, 2010: http://www.ncbi.nlm.nih.gov/sviewer/viewer.fcgi?val . . . pp. 1-2.
GenBank Accession No. BC043212, "*Homo sapiens* cDNA clone Image:5295205, with apparent retained intron," Sep. 16, 2003; Retrieved from the Internet on Aug. 10, 2010: http://www.ncbi.nlm.nih.gov/sviewer/viewer.fcgi?val . . . pp. 1-3.
GenBank Accession No. BC048263, "*Homo sapiens* hypothetical protein LOC146909, mRNA (cDNA clone Image:4418755), partial cds," Sep. 30, 2003; Retrieved from the Internet on Aug. 10, 2010: http://www.ncbi.nlm.nih.gov/sviewer/viewer.fcgi?val . . . pp. 1-3.
GenBank Accession No. BC071797, "*Homo sapiens* cDNA clone Image: 4618441, Warning: chimeric clone," Aug. 4, 2006; Retrieved from the Internet on Aug. 10, 2010: http://www.ncbi.nlm.nih.gov/sviewer/viewer.fcgi?val . . . pp. 1-2.
GenBank Accession No. BF514513, "The sequence contained an oligo-dT track that was present in the oligonucleotide that was used to prime the synthesis of first strand cDNA and therefore this may represent a bonafide poly A tail," Dec. 7, 2000; Retrieved from the Internet on Aug. 10, 2010: http://www.ncbi.nlm.nih.gov/sviewer/viewer.fcgi?val . . . pp. 1-2.
GenBank Accession No. BG001037, "A mini-library was made by cloning products derived from ORESTES PCR (U.S. Letters Patent application No. 196,716-18 vector. Reverse transcription of tissue mRNA and cDNA amplification were performed under low stringency conditions," Jan. 24, 2001; Retrieved from the Internet on Aug. 11, 2010: http://www.ncbi.nlm.nih.gov/sviewer/viewer.fcgi?val . . . pp. 1-2.
GenBank Accession No. BK000394, "TPA_inf: Human herpesvirus 5 strain AD169, complete genome," Sep. 5, 2006; Retrieved from the Internet on Aug. 11, 2010: http://www.ncbi.nlm.nih.gov/sviewer/viewer.fcgi?val . . . pp. 1-92.
GenBank Accession No. BU943730, "Double-stranded cDNA was prepared from a pool of 40 cell line polyA+RNAs," Oct. 17, 2002; Retrieved from the Internet on Aug. 10, 2010: http://www.ncbi.nlm.nih.gov/sviewer/viewer.fcgi?val . . . pp. 1-2.
GenBank Accession No. BX104999, "$1^{st}$ strand cDNA was primed with a Pac I—oligo(dT) primer," Jan. 22, 2003; Retrieved from the Internet on Aug. 10, 2010: http://www.ncbi.nlm.nih.gov/sviewer/viewer.fcgi?val . . . pp. 1-2.
GenBank Accession No. BX360933, "$1^{st}$ strand cDNA was primed with a NotI-oligo(dT) primer. Five prime end enriched, double-strand cDNA was digested with Not I and cloned into the Not I and EcoR V sites of the pCMVSPORT 6 vector. Library was normalized," May 5, 2003; Retrieved from the Internet on Aug. 10, 2010: http://www.ncbi.nlm.nih.gov/sviewer/viewer.fcgi?val . . . pp. 1-2.
GenBank Accession No. CR594200, "full-length cDNA clone CS0DF031yH08 of Fetal brain of *Homo sapiens* (human)," Jul. 21, 2004; Retrieved from the Internet on Aug. 11, 2010: http://www.ncbi.nlm.nih.gov/sviewer/viewer.fcgi?val . . . pp. 1-2.
GenBank Accession No. CR598364, "full-length cDNA clone CS0CAP007YJ17 of Thymus of *Homo sapiens* (human)," Jul. 21, 2004; Retrieved from the Internet on Aug. 10, 2010: http://www.ncbi.nlm.nih.gov/sviewer/viewer.fcgi?val . . . pp. 1-2.
GenBank Accession No. CR622110, "full-length cDNA clone CS0DC025YP03 of Neuroblastoma Cot 25-normalized of *Homo sapiens* (human)," Jul. 21, 2004; Retrieved from the Internet on Aug. 10, 2010: http://www.ncbi.nlm.nih.gov/sviewer/viewer.fcgi?val . . . pp. 1-2.
GenBank Accession No. DB318210, "NEDO human cDNA project (New Energy and Industrial Technology Developmental Organization, Japan); cDNA library construction: Helix Research Institute (HRI); 5'-end one pass sequencing: HRI, Research Association for Biotechnology (RAB) and Biotechnology Center, National Institute of Technology and Evaluation; 3'-end one pass sequencing; RAB," Dec. 10, 2005; Retrieved from the Internet on Aug. 11, 2010: http://www.ncbi.nlm.nih.gov/sviewer/viewer.fcgi?val . . . pp. 1-2.

(56) References Cited

OTHER PUBLICATIONS

GenBank Accession No. DB527271, "The full length cDNA libraries were prepared and sequenced using the Riken full length cDNA techniques in Genome Science Laboratory and Genome Exploration Research Group Genomic Sciences Center (GSC) in Riken. These sequences are contributed to the international ORFeome Collaboration. 3'-EST sequences are presented as anti-sense strand," Apr. 17, 2006; Retrieved from the Internet on Aug. 10, 2010: http://www.ncbi.nlm.nih.gov/sviewer/viewer.fcgi?val . . . pp. 1-2.

GenBank Accession No. DQ205516, "Natronorubrum aibiense strain 7-3 16S ribosomal RNA gene, partial sequence," Jul. 10, 2006; Retrieved from the Internet on Aug. 11, 2010: http://www.ncbi.nlm.nih.gov/sviewer/viewer.fcgi?val . . . pp. 1-2.

GenBank Accession No. HSU16307, "*Homo sapiens* glioma pathogenesis-related protein (GliPR) mRNA, complete cds," Oct. 23, 2002; Retrieved from the Internet on Aug. 10, 2010: http://www.ncbi.nlm.nih.gov/sviewer/viewer.fcgi?val . . . pp. 1-2.

GenBank Accession No. HUMYT69G03, "*Homo sapiens* full length insert cDNA clone YT69G03," Aug. 29, 1998; Retrieved from the Internet on Aug. 10, 2010: http://www.ncbi.nlm.nih.gov/sviewer/viewer.fcgi?val . . . pp. 1-2.

GenBank Accession No. L08436, "Human autonomously replicating sequence (ARS) mRNA," Nov. 8, 1993; Retrieved from the Internet on Aug. 10, 2010: http://www.ncbi.nlm.nih.gov/sviewer/viewer.fcgi?val . . . pp. 1-1.

GenBank Accession No. NM_000189, "*Homo sapiens* hexokinase 2 (HK2), mRNA," Sep. 3, 2007; Retrieved from the Internet on Aug. 10, 2010: http://www.ncbi.nlm.nih.gov/sviewer/viewer.fcgi?val . . . pp. 1-6.

GenBank Accession No. NM_000190, "*Homo sapiens* hydroxymethylbilane synthase (HMBS), transcript variant 1, mRNA," Sep. 25, 2007; Retrieved from the Internet on Aug. 11, 2010: http://www.ncbi.nlm.nih.gov/sviewer/viewer.fcgi?val . . . pp. 1-5.

GenBank Accession No. NM_000201, "*Homo sapiens* intercellular adhesion molecule 1 (CD54), human rhinovirus receptor (ICAM1), mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_000212, "*Homo sapiens* integrin, beta 3 (platelet glycoprotein IIIa, antigen CD61) (ITGB3), mRNA," Sep. 30, 2007; Retrieved from the Internet on Aug. 10, 2010: http://www.ncbi.nlm.nih.gov/sviewer/viewer.fcgi?val . . . pp. 1-6.

GenBank Accession No. NM_000322, "*Homo sapiens* peripherin 2 (retinal degeneration, slow) (PRPH2), mRNA," Sep. 17, 2007; Retrieved from the Internet on Aug. 10, 2010: http://www.ncbi.nlm.nih.gov/sviewer/viewer.fcgi?val . . . pp. 1-4.

GenBank Accession No. NM_000362, "*Homo sapiens* TIMP metallopeptidase inhibitor 3 (Sorsby fundus dystrophy, pseudoinflammatory) (TIMP3), mRNA," Sep. 24, 2007; Retrieved from the Internet on Aug. 10, 2010: http://www.ncbi.nlm.nih.gov/sviewer/viewer.fcgi?val . . . pp. 1-8.

GenBank Accession No. NM_000364, "*Homo sapiens* troponin T type 2 (cardiac) (TNNT2), transcript variant 1, mRNA," Oct. 7, 2007; Retrieved from the Internet on Aug. 10, 2010: http://www.ncbi.nlm.nih.gov/sviewer/viewer.fcgi?val . . . pp. 1-5.

GenBank Accession No. NM_000372, "*Homo sapiens* tyrosinase (oculocutaneous albinism IA) (TYR), mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_000499, "*Homo sapiens* cytochrome P450, family 1, subfamily A, polypeptide 1 (CYP1A1), mRNA," Oct. 7, 2007; Retrieved from the Internet on Aug. 10, 2010: http://www.ncbi.nlm.nih.gov/sviewer/viewer.fcgi?val . . . pp. 1-5.

GenBank Accession No. NM_000640, "*Homo sapiens* interleukin 13 receptor, alpha 2 (IL13RA2), mRNA," Sep. 17, 2007; Retrieved from the Internet on Aug. 10, 2010: http://www.ncbi.nlm.nih.gov/sviewer/viewer.fcgi?val . . . pp. 1-4.

GenBank Accession No. NM 000641, "*Homo sapiens* interleukin 11 (IL11), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_000693, "*Homo sapiens* aldehyde dehydrogenase 1 family, member A3 (ALDH1A3), mRNA," Jul. 24, 2007; Retrieved from the Internet on Aug. 10, 2010: http://www.ncbi.nlm.nih.gov/sviewer/viewer.fcgi?val . . . pp. 1-4.

GenBank Accession No. NM_000782, "*Homo sapiens* cytochrome P450, family 24, subfamily A, polypeptide 1 (CYP24A1), nuclear gene encoding mitochondrial protein, mRNA," Sep. 24, 2007; Retrieved from the Internet on Aug. 10, 2010: http://www.ncbi.nlm.nih.gov/sviewer/viewer.fcgi?val . . . pp. 1-6.

GenBank Accession No. NM_000800, "*Homo sapiens* fibroblast growth factor 1 (acidic) (FGF1), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_000808, "*Homo sapiens* gamma-aminobutyric acid (GABA), A receptor, alpha 3 (GABRA3), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_000916, "*Homo sapiens* oxytocin receptor (OXTR), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_000970, "*Homo sapiens* ribosomal protein L6 (RPL6), transcript variant 2, mRNA," Sep. 24, 2007; Retrieved from the Internet on Aug. 10, 2010: http://www.ncbi.nlm.nih.gov/sviewer/viewer.fcgi?val . . . pp. 1-4.

GenBank Accession No. NM_001002926, "*Homo sapiens* TWIST neighbor (TWISTNB), nRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NM_001003683, "*Homo sapiens* phosphodiesterase 1A, calmodulin-dependent (PDE1A), transcript variant 2, mRNA," Sep. 17, 2007; Retrieved from the Internet on Aug. 10, 2010: http://www.ncbi.nlm.nih.gov/sviewer/viewer.fcgi?val . . . pp. 1-5.

GenBank Accession No. NM_001003940, "*Homo sapiens* Bcl2 modifying factor (BMF), transcript variant 1, mRNA," Sep. 26, 2007; Retrieved from the Internet on Aug. 10, 2010: http://www.ncbi.nlm.nih.gov/sviewer/viewer.fcgi?val . . . pp. 1-5.

GenBank Accession No. NM_001004301, "*Homo sapiens* zinc finger protein 813 (ZNF813), mRNA," Jun. 27, 2007; Retrieved from the Internet on Aug. 10, 2010: http://www.ncbi.nlm.nih.gov/sviewer/viewer.fcgi?val . . . pp. 1-3.

GenBank Accession No. NM_001009954, "*Homo sapiens* FLJ20105 protein (FLJ20105), transcript variant 2, mRNA," Jun. 3, 2007; Retrieved from the Internet on Aug. 10, 2010: http://www.ncbi.nlm.sviewer/viewer.fcgi?val . . . pp. 1-3.

GenBank Accession No. NM_001010911, "*Homo sapiens* chromosome 10 open reading frame 114 (C10orf114), mRNA," Jun. 3, 2007; Retrieved from the Internet on Aug. 10, 2010: http://www.ncbi.nlm.nih.gov/sviewer/viewer.fcgi?val . . . pp. 1-3.

GenBank Accession No. NM_001018084, "*Homo sapiens* solute carrier family 26, member 10 (SLC26A10), transcript variant 1, mRNA," Sep. 24, 2005; Retrieved from the Internet on Aug. 10, 2010: http://www.ncbi.nlm.nih.gov/sviewer/viewer.fcgi?val . . . pp. 1-3.

GenBank Accession No. NM_001033086, "*Homo sapiens* chromosome 20 open reading frame 133 (C20orf133), transcript variant 1, mRNA," Sep. 24, 2005; Retrieved from the Internet on Aug. 10, 2010: http://www.ncbi.nlm.nih.gov/sviewer/viewer.fcgi?val . . . pp. 1-3.

GenBank Accession No. NM_001034, "*Homo sapiens* ribonucleotide reductase M2 polypeptide (RRM2), mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_001037442, "*Homo sapiens* Run and FYVE domain containing 3 (RUFY3), transcript variant 1, mRNA," Jul. 25, 2007; Retrieved from the Internet on Aug. 10, 2010: http://www.ncbi.nlm.nih.gov/sviewer/viewer.fcgi?val . . . pp. 1-4.

(56) References Cited

OTHER PUBLICATIONS

GenBank Accession No. NM_001039580, "*Homo sapiens* microtubule-associated protein 9 (MAP9), mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_001043, "*Homo sapiens* solute carrier family 6 (neurotransmitter transporter, noradrenalin), member 2 (SLC6A2), mRNA," Sep. 30, 2007; Retrieved from the Internet on Aug. 11, 2010: http://www.ncbi.nlm.nih.gov/sviewer/viewer.fcgi?val . . . pp. 1-5.

GenBank Accession No. NM_001165, "Homo sapiens baculoviral IAP repeat-containing 3 (BIRC3), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_001511, "Homo sapiens chemokine (C-X-C motif) ligand 1 (melanoma growth stimulating activity, alpha) (CXCL1), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_001548, "*Homo sapiens* interferon-induced protein with tetratricopeptide repeats 1 (IFIT1), transcript variant 2, mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_001624, "*Homo sapiens* absent in melanoma 1 (AIM1), mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_001673, "*Homo sapiens* asparagine synthetase (ASNS), transcript variant 2, mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_001901, "Homo sapiens connective tissue growth factor (CTGF), mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_001902, "*Homo sapiens* cystathionase (cystathionase gamma-lyase) (CTH), transcript variant 1, mRNA," Sep. 17, 2007; Retrieved from the Internet on Aug. 10, 2010: http://www.ncbi.nlm.nih.gov/sviewer/viewer.fcgi?val . . . pp. 1-4.

GenBank Accession No. NM_001946, "*Homo sapiens* dual specificity phosphatase 6 (DUSP6), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_002053, "*Homo sapiens* guanylate binding protein 1, interferon-inducible, 67kDa (GBP1), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_002104, "*Homo sapiens* granzyme K (granzyme 3; tryptase II) (GZMK), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_002167, "*Homo sapiens* inhibitor of DNA binding 3, dominant negative helix-loop-helix protein (ID3), mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_002201, "*Homo sapiens* interferon stimulated exonuclease gene 20kDa (ISG20), mRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NM_002214, "*Homo sapiens* integrin, beta 8 (ITGB8), mRNA," Sep. 25, 2007; Retrieved from the Internet on Aug. 10, 2010: http://www.ncbi.nlm.nih.gov/sviewer/viewer.fcgi?val . . . pp. 1-7.

GenBank Accession No. NM_002234, "*Homo sapiens* potassium voltage-gated channel, shaker-related subfamily, member 5 (KCNA5), mRNA," Sep. 17, 2007; Retrieved from the Internet on Aug. 10, 2010: http://www.ncbi.nlm.nih.gov/sviewer/viewer.fcgi?val . . . pp. 1-5.

GenBank Accession No. NM_002310, "*Homo sapiens* leukemia inhibitory factor receptor alpha (LIFR), mRNA," Sep. 3, 2007; Retrieved from the Internet on Aug. 11, 2010: http://www.ncbi.nlm.nih.gov/sviewer/viewer.fcgi?val . . . pp. 1-8.

GenBank Accession No. NM_002526, "*Homo sapiens* 5'-nucleotidase, ecto (CD73) (NT5E), mRNA," Sep. 26, 2007; Retrieved from the Internet on Aug. 11, 2010: http://www.ncbi.nlm.nih.gov/sviewer/viewer.fcgi?val . . . pp. 1-5.

GenBank Accession No. NM_002609, "*Homo sapiens* platelet-derived growth factor receptor, beta polypeptide (PDGFRB), mRNA," Sep. 30, 2007; Retrieved from the Internet on Aug. 10, 2010: http://www.ncbi.nlm.nih.gov/sviewer/viewer.fcgi?val . . . pp. 1-7.

GenBank Accession No. NM_002658, "*Homo sapiens* plasminogen activator, urokinase (PLAU), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_002670, "*Homo sapiens* plastin 1 (I isoform) (PLS1), mRNA," Nov. 17, 2006; Retrieved from the Internet on Aug. 10, 2010: http://www.ncbi.nlm.nih.gov/sviewer/viewer.fcgi?val . . . pp. 1-4.

GenBank Accession No. NM_002837, "*Homo sapiens* protein tyrosine phosphatase, receptor type, B (PTPRB), transcript variant 2, mRNA," Oct. 7, 2007; Retrieved from the Internet on Aug. 10, 2010: http://www.ncbi.nlm.nih.gov/sviewer/viewer.fcgi?val . . . pp. 1-9.

GenBank Accession No. NM_002849, "*Homo sapiens* protein tyrosine phosphatase, receptor type, R (PTPRR), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_002852, "*Homo sapiens* pentraxin-related gene, rapidly induced by IL-1 beta (PTX3), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_002930, "*Homo sapiens* Ras-like without CAAX 2 (RIT2), mRNA," Sep. 29, 2007; Retrieved from the Internet on Aug. 10, 2010: http://www.ncbi.nlm.nih.gov/sviewer/viewer.fcgi?val . . . pp. 1-3.

GenBank Accession No. NM_002982, "*Homo sapiens* chemokine (C-C motif) ligand 2 (CCL2), mRNA," Sep. 30, 2007; Retrieved from the Internet on Aug. 10, 2010: http://www.ncbi.nlm.nih.gov/sviewer/viewer.fcgi?val . . . pp. 1-4.

GenBank Accession No. NM_003414, "*Homo sapiens* zinc finger protein 267 (ZNF267), transcript variant 498723, mRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NM_003425, "*Homo sapiens* zinc finger protein 45 (ZNF45), mRNA," Jun. 3, 2007; Retrieved from the Internet on Aug. 10, 2010: http://www.ncbi.nlm.nih.gov/sviewer/viewer.fcgi?val . . . pp. 1-4.

GenBank Accession No. NM_003483, "*Homo sapiens* high mobility group AT-hook 2 (HMGA2), transcript variant 1, mRNA," Sep. 24, 2007; Retrieved from the Internet on Aug. 10, 2010: http://www.ncbi.nlm.nih.gov/sviewer/viewer.fcgi?val . . . pp. 1-5.

GenBank Accession No. NM_003558, "*Homo sapiens* phosphatidylinositol-4-phosphate 5-kinase, type I, beta (PIP5KIB), transcript variant 2, mRNA," Jun. 26, 2007; Retrieved from the Internet on Aug. 10, 2010: http://www.ncbi.nlm.nih.gov/sviewer/viewer.fcgi?val . . . pp. 1-5.

GenBank Accession No. NM_003706, "*Homo sapiens* phospholipase A2, group IVC (cytosolic, calcium-independent) (PLA2G4C), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_003786, "*Homo sapiens* ATP-binding cassette, sub-family C (CFTR/MRP), member 3 (ABCC3), mRNA," Sep. 25, 2007; Retrieved from the Internet on Aug. 10, 2010: http://www.ncbi.nlm.nih.gov/sviewer/viewer.fcgi?val . . . pp. 1-8.

(56) References Cited

OTHER PUBLICATIONS

GenBank Accession No. NM_003841, "*Homo sapiens* tumor necrosis factor receptor superfamily, member 10c, decoy without an intracellular domain (TNFRSF10C), mRNA," Sep. 3, 2007; Retrieved from the Internet on Aug. 11, 2010: http://www.ncbi.nlm.nih.gov/sviewer/viewer.fcgi?val . . . pp. 1-4.
GenBank Accession No. NM_003862, "*Homo sapiens* fibroblast growth factor 18 (FGF18), mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_003897, "*Homo sapiens* immediate early response 3 (IER3), mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_004170, "*Homo sapiens* solute carrier family 1 (neuronal/epithelial high affinity glutamate transporter, system Xag), member 1 (SLC1A1), mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_004185, "*Homo sapiens* wingless-type MMTV integration site family, member 2B (WNT2B), transcript variant VNT-2B1, mRNA," Sep. 26, 2007; Retrieved from the Internet on Aug. 10, 2010: http://www.ncbi.nlm.nih.gov/sviewer/viewer.fcgi?val . . . pp. 1-4.
GenBank Accession No. NM_004233, "*Homo sapiens* CD83 molecule (CD83), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_004294, "*Homo sapiens* mitochondrial translational release factor 1 (MTRF1), nuclear gene encoding mitochondrial protein, mRNA," Jun. 26, 2007; Retrieved from the Internet on Aug. 10, 2010: http://www.ncbi.nlm.nih.gov/sviewer/viewer.fcgi?val . . . pp. 1-4.
GenBank Accession No. NM_004318, "*Homo sapiens* aspartate beta-hydroxylase (ASPH), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-6.
GenBank Accession No. NM_004334, "*Homo sapiens* bone marrow stromal cell antigen 1 (BST1), mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_004464, "*Homo sapiens* fibroblast growth factor 5 (FGF5), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_004466, "*Homo sapiens* glypican 5 (GPC5), mRNA," Sep. 3, 2007; Retrieved from the Internet on Aug. 10, 2010: http://www.ncbi.nlm.nih.gov/sviewer/viewer.fcgi?val . . . pp. 1-4.
GenBank Accession No. NM_004556, "*Homo sapiens* nuclear factor of kappa light polypeptide gene enhancer in B-cells inhibitor, epsilon (NFKBIE), mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_004843, "*Homo sapiens* interleukin 27 receptor, alpha (IL27RA), mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_005031, "*Homo sapiens* FXYD domain containing ion transport regulator 1 (phospholemman) (FXYD1), transcript variant a, mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_005039, "*Homo sapiens* proline-rich protein BstNI subfamily 1 (PRB1), transcript variant 1, mRNA," Jul. 29, 2007; Retrieved from the Internet on Aug. 10, 2010: http://www.ncbi.nlm.nih.gov/sviewer/viewer.fcgi?val . . . pp. 1-4.

GenBank Accession No. NM_005185, "*Homo sapiens* calmodulin-like 3 (CALML3), mRNA," Sep. 17, 2007; Retrieved from the Internet on Aug. 10, 2010: http://www.ncbi.nlm.nih.gov/sviewer/viewer.fcgi?val . . . pp. 1-3.
GenBank Accession No. NM_005261, "*Homo sapiens* GTP binding protein overexpressed in skeletal muscle (GEM), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-4.
GenBank Accession No. NM_005341, "*Homo sapiens* zinc finger and BTB domain containing 48 (ZBTB48), mRNA," Jun. 26, 2007; Retrieved from the Internet on Aug. 10, 2010: http://www.ncbi.nlm.nih.gov/sviewer/viewer.fcgi?val . . . pp. 1-4.
GenBank Accession No. NM_005345, "*Homo sapiens* heat shock 70kDa protein 1A (HSPA1A), mRNA," Sep. 30, 2007; Retrieved from the Internet on Aug. 10, 2010: http://www.ncbi.nlm.nih.gov/sviewer/viewer.fcgi?val . . . pp. 1-4.
GenBank Accession No. NM_005347, "*Homo sapiens* heat shock 70kDa protein 5 (glucose-regulated protein, 78kDa) (HSPA5), mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_005444, "*Homo sapiens* RCD1 required for cell differentiationl homolog (S. pombe) (RQCD1), mRNA," Sep. 25, 2007; Retrieved from the Internet on Aug. 10, 2010: http://www.ncbi.nlm.nih.gov/sviewer/viewer.fcgi?val . . . pp. 1-3.
GenBank Accession No. NM_005515, "*Homo sapiens* motor neuron and pancreas homeobox 1 (MNX1), mRNA," Sep. 30, 2007; Retrieved from the Internet on Aug. 10, 2010: http://www.ncbi.nlm.nih.gov/sviewer/viewer.fcgi?val . . . pp. 1-4.
GenBank Accession No. NM_005527, "*Homo sapiens* heat shock 70kDa protein 1-like (HSPA1L), mRNA," Sep. 3, 2007; Retrieved from the Internet on Aug. 11, 2010: http://www.ncbi.nlm.nih.gov/sviewer/viewer.fcgi?val . . . pp. 1-4.
GenBank Accession No. NM_005923, "*Homo sapiens* mitogen-activated protein kinase kinase kinase 5 (MAP3K5), mRNA," Sep. 3, 2007; Retrieved from the Internet on Aug. 10, 2010: http://www.ncbi.nlm.nih.gov/sviewer/viewer.fcgi?val . . . pp. 1-7.
GenBank Accession No. NM_006187, "*Homo sapiens* 2'-5'-oligoadenylate synthetase 3, 100IcDa (OAS3), mRNA," Sep. 25, 2007; Retrieved from the Internet on Aug. 10, 2010: http://www.ncbi.nlm.nih.gov/sviewer/viewer.fcgi?val . . . pp. 1-6.
GenBank Accession No. NM_006393, "*Homo sapiens* nebulette (NEBL), transcript variant 1, mRNA," Sep. 17, 2007; Retrieved from the Internet on Aug. 10, 2010: http://www.ncbi.nlm.nih.gov/sviewer/viewer.fcgi?val . . . pp. 1-7.
GenBank Accession No. NM_006417, "*Homo sapiens* interferon-induced protein 44 (IFI44), mRNA," Jun. 26, 2007; Retrieved from the Internet on Aug. 10, 2010: http://www.ncbi.nlm.nih.gov/sviewer/viewer.fcgi?val . . . pp. 1-3.
GenBank Accession No. NM_006434, "*Homo sapiens* sorbin and SH3 domain containing 1 (SORBS1), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-7.
GenBank Accession No. NM_006509, "*Homo sapiens* v-rel reticuloendotheliosis viral oncogene homlog B, nuclear factor of kappa light polypeptide gene enhancer in B-cells 3 (avian) (RELB), mRNA," Sep. 30, 2007; Retrieved from the Internet on Aug. 10, 2010: http://www.ncbi.nlm.nih.gov/sviewer/viewer.fcgi?val . . . pp. 1-5.
GenBank Accession No. NM_006516, "*Homo sapiens* solute carrier family 2 (facilitated glucose transporter), member 1 (SLC2A1), mRNA," Sep. 24, 2007; Retrieved from the Internet on Aug. 10, 2010: http://www.ncbi.nlm.nih.gov/sviewer/viewer.fcgi?val . . . pp. 1-5.
GenBank Accession No. NM_006547, "*Homo sapiens* insulin-like growth factor 2 mRNA binding protein 3 (IGF2BP3), mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_006611, "*Homo sapiens* killer cell lectin-like receptor subfamily A, member 1 (KLRA1), mRNA," Jul.

(56) References Cited

OTHER PUBLICATIONS 29, 2007; Retrieved from the Internet on Aug. 10, 2010: http://www.ncbi.nlm.nih.gov/sviewer/viewer.fcgi?val . . . pp. 1-3.

GenBank Accession No. NM_006650, "*Homo sapiens* complexin 2 (CPLX2), transcript variant 1, mRNA," Sep. 26, 2007; Retrieved from the Internet on Aug. 10, 2010: http://www.ncbi.nlm.nih.gov/sviewer/viewer.fcgi?val . . . pp. 1-5.

GenBank Accession No. NM_006793, "*Homo sapiens* peroxiredoxin 3 (PRDX3), nuclear gene encoding mitochondrial protein, transcript variant 1, mRNA," Sep. 17, 2007; Retrieved from the Internet on Aug. 11, 2010: http://www.ncbi.nlm.nih.gov/sviewer/viewer.fcgi?val . . . pp. 1-5.

GenBank Accession No. NM_006851, "*Homo sapiens* GLI pathogenesis-related 1 (glioma) (GLIPR1), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_006933, "*Homo sapiens* solute carrier family 5 (inositol transporters), member 3 (SLC5A3), mRNA," Sep. 3, 2007; Retrieved from the Internet on Aug. 10, 2010: http://www.ncbi.nlm.nih.gov/sviewer/viewer.fcgi?val . . . pp. 1-6.

GenBank Accession No. NM_007107, "*Homo sapiens* signal sequence receptor, gamma (translocon-associated protein gamma) (SSR3), mRNA," Jun. 3, 2007; Retrieved from the Internet on Aug. 10, 2010: http://www.ncbi.nlm.nih.gov/sviewer/viewer.fcgi?val . . . pp. 1-4.

GenBank Accession No. NM_007211, "*Homo sapiens* Ras association (RalGDS/AF-6) domain family 8 (RASSF8), mRNA," Sep. 29, 2007; Retrieved from the Internet on Aug. 10, 2010: http://www.ncbi.nlm.nih.gov/sviewer/viewer.fcgi?val . . . pp. 1-3.

GenBank Accession No. NM_007282, "*Homo sapiens* ring finger protein 13 (RNF13), transcript variant 1, mRNA," Jun. 26, 2007; Retrieved from the Internet on Aug. 10, 2010: http://www.ncbi.nlm.nih.gov/sviewer/viewer.fcgi?val . . . pp. 1-4.

GenBank Accession No. NM_007314, "*Homo sapiens* v-abl Abelson murein leukemia viral oncogene homolog 2 (arg, Abelson-related gene) (ABL2), transcript variant b, mRNA," Sep. 3, 2007; Retrieved from the Internet on Aug. 10, 2010: http://www.ncbi.nlm.nih.gov/sviewer/viewer.fcgi?val . . . pp. 1-8.

GenBank Accession No. NM_012329, "*Homo sapiens* monocyte to macrophage differentiation-associated (MMD), mRNA," Jun. 26, 2007; Retrieved from the Internet on Aug. 10, 2010: http://www.ncbi.nlm.nih.gov/sviewer/viewer.fcgi?val . . . pp. 1-3.

GenBank Accession No. NM_012377, "*Homo sapiens* olfactory receptor, family 7, subfamily C, member 2 (OR7C2), mRNA," Jun. 3, 2007; Retrieved from the Internet on Aug. 10, 2010: http://www.ncbi.nlm.nih.gov/sviewer/viewer.fcgi?val . . . pp. 1-3.

GenBank Accession No. NM_012419, "*Homo sapiens* regulator of G-protein signaling 17 (RGS17), mRNA," Aug. 24, 2007; Retrieved from the Internet on Aug. 11, 2010: http://www.ncbi.nlm.nih.gov/sviewer/viewer.fcgi?val . . . pp. 1-3.

GenBank Accession No. NM_013261, "*Homo sapiens* peroxisome proliferator-activated receptor gamma, coactivator 1 alpha (PPARGC1A), mRNA," Oct. 7, 2007; Retrieved from the Internet on Aug. 10, 2010: http://www.ncbi.nlm.nih.gov/sviewer/viewer.fcgi?val . . . pp. 1-7.

GenBank Accession No. NM_013989, "*Homo sapiens* deiodinase, iodothyronine, type II (DIO2), transcript variant 1, mRNA," Sep. 24, 2007; Retrieved from the Internet on Aug. 10, 2010: http://www.ncbi.nlm.nih.gov/sviewer/viewer.fcgi?val . . . pp. 1-6.

GenBank Accession No. NM_014314, "*Homo sapiens* Dead (Asp-Glu-Ala-Asp) box polypeptide 58 (DDX58), mRNA," Sep. 30, 2007; Retrieved from the Internet on Aug. 10, 2010: http://www.ncbi.nlm.nih.gov/sviewer/viewer.fcgi?val . . . pp. 1-7.

GenBank Accession No. NM_014331, "*Homo sapiens* solute carrier family 7,"cationic amino acid transporter, y+ system) member 11 (SLC7A11), mRNA, Sep. 3, 2007; Retrieved from the Internet on Aug. 10, 2010: http://www.ncbi.nlm.nih.gov/sviewer/viewer.fcgi?val . . . pp. 1-6.

GenBank Accession No. NM 014351, "*Homo sapiens* sulfotransferase family 4A, member 1 (SULT4A1), mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_014632, "*Homo sapiens* microtubule associated monoxygenase, calponin and LIM domain containing 2 (MICAL2), mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_014729, "*Homo sapiens* thymocyte selection-associated high mobility group box (TOX), mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_015009, "*Homo sapiens* PDZ domain containing Ring finger 3 (PDZRN3), mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_015074, "*Homo sapiens* kinesin family member 1B (KIF1B), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-10.

GenBank Accession No. NM_015359, "*Homo sapiens* solute carrier family 39 (zinc transporter), member 14 (SLC39A14), mRNA," Sep. 29, 2007; Retrieved from the Internet on Aug. 10, 2010: http://www.ncbi.nlm.nih.gov/sviewer/viewer.fcgi?val . . . pp. 1-4.

GenBank Accession No. NM_016125, "*Homo sapiens* PTD016 protein (LOC51136), mRNA," Jun. 26, 2007; Retrieved from the Internet on Aug. 10, 2010: http://www.ncbi.nlm.nih.gov/sviewer/viewer.fcgi?val . . . pp. 1-3.

GenBank Accession No. NM_016239, "*Homo sapiens* myosin XVA (MYO15A), mRNA," Sep. 25, 2007; Retrieved from the Internet on Aug. 10, 2010: http://www.ncbi.nlm.nih.gov/sviewer/viewer.fcgi?val . . . pp. 1-12.

GenBank Accession No. NM_016354, "*Homo sapiens* solute carrier organic anion transporter family, member 4A1 (SLCO4A1), mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_016613, "*Homo sapiens* chromosome 4 open reading frame (C4orf18), transcript variant 2, mRNA," Sep. 29, 2007; Retrieved from the Internet on Aug. 10, 2010: http://www.ncbi.nlm.nih.gov/sviewer/viewer.fcgi?val . . . pp. 1-4.

GenBank Accession No. NM_016831, "*Homo sapiens* period homolog 3 (Drosphila) (PER3), mRNA," Sep. 26, 2007; Retrieved from the Internet on Aug. 10, 2010: http://www.ncbi.nlm.nih.gov/sviewer/viewer.fcgi?val . . . pp. 1-7.

GenBank Accession No. NM_017577, "*Homo sapiens* GRAM domain containing 1C (GRAMD1C), mRNA," Sep. 29, 2007; Retrieved from the Internet on Aug. 11, 2010: http://www.ncbi.nlm.nih.gov/sviewer/viewer.fcgi?val . . . pp. 1-4.

GenBank Accession No. NM_017600, "*Homo sapiens* golgi autoantigen, golgin subfamily a, 2-like 1 (GOLGA2L1), mRNA," Jun. 26, 2007; Retrieved from the Internet on Aug. 10, 2010: http://www.ncbi.nlm.nih.gov/sviewer/viewer.fcgi?val . . . pp. 1-4.

GenBank Accession No. NM_017638, "*Homo sapiens* mediator complex subunit 18 (MED18), mRNA," Aug. 4, 2007; Retrieved from the Internet on Aug. 11, 2010: http://www.ncbi.nlm.nih.gov/sviewer/viewer.fcgi?val . . . pp. 1-3.

GenBank Accession No. NM_017644, "*Homo sapiens* kelch-like 24 (Drosophila) (KLHL24), mRNA," Aug. 4, 2007; Retrieved from the Internet on Aug. 10, 2010: http://www.ncbi.nlm.nih.gov/sviewer/viewer.fcgi?val . . . pp. 1-4.

GenBank Accession No. NM_018027, "*Homo sapiens* FERM domain containing 4A (FRMD4A), mRNA," Jun. 23, 2007; Retrieved from the Internet on Aug. 10, 2010: http://www.ncbi.nlm.nih.gov/sviewer/viewer.fcgi?val . . . pp. 1-6.

GenBank Accession No. NM_018284, "*Homo sapiens* guanylate binding protein 3 (GBP3), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_018371, "*Homo sapiens* chondroitin beta1,4 N-acetylgalactosaminyltransferase (ChGn), mRNA," Sep. 3, 2007; Retrieved from the Internet on Aug. 10, 2010: http://www.ncbi.nlm.nih.gov/sviewer/viewer.fcgi?val . . . pp. 1-4.

(56) References Cited

OTHER PUBLICATIONS

GenBank Accession No. NM_018372, "*Homo sapiens* chromosome 1 open reading frame 103 (Clorf103), transcript variant 1, mRNA," Jun. 26, 2007; Retrieved from the Internet on Aug. 11, 2010: http://www.ncbi.nlm.nih.gov/sviewer/viewer.fcgi?val . . . pp. 1-4.
GenBank Accession No. NM_018664, "*Homo sapiens* Jun dimerization protein p21SNFT (SNFT), mRNA," Sep. 3, 2007; Retrieved from the Internet on Aug. 11, 2010: http://www.ncbi.nlm.nih.gov/sviewer/viewer.fcgi?val . . . pp. 1-2.
GenBank Accession No. NM_018836, "*Homo sapiens* adherens junction associated protein 1 (AJAP1), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-3.
GenBank Accession No. NM_019555, "*Homo sapiens* Rho guanine nucleotide exchange factor (GEF) 3 (ARHGEF3), mRNA," Sep. 26, 2007; Retrieved from the Internet on Aug. 10, 2010: http://www.ncbi.nih.gov/sviewer/viewer.fcgi?val . . . pp. 1-4.
GenBank Accession No. NM_019891, "*Homo sapiens* ERO1-like beta (S. cerevisiae) (ERO1LB), mRNA," Sep. 3, 2007; Retrieved from the Internet on Aug. 10, 2010: http://www.ncbi.nlm.nih.gov/sviewer/viewer.fcgi?val . . . pp. 1-4.
GenBank Accession No. NM_020359, "*Homo sapiens* phospholipid scramblase 2 (PLSCR2), mRNA," Nov. 17, 2006; Retrieved from the Internet on Aug. 10, 2010: http://www.ncbi.nlm.nih.gov/sviewer/viewer.fcgi?val . . . pp. 1-3.
GenBank Accession No. NM_020436, "*Homo sapiens* sal-like 4 (Drosophila) (SALL4), mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_020683, "*Homo sapiens* adenosine A3 receptor (ADORA3), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_020731, "*Homo sapiens* aryl-hydrocarbon receptor repressor (AHRR), mRNA," Sep. 30, 2007; Retrieved from the Internet on Aug. 10, 2010: http://www.ncbi.nlm.nih.gov/sviewer/viewer.fcgi?val . . . pp. 1-6.
GenBank Accession No. NM_020799, "*Homo sapiens* STAM binding protein-like 1 (STAMBPL1), mRNA," Sep. 25, 2007; Retrieved from the Internet on Aug. 10, 2010: http://www.ncbi.nlm.nih.ov/sviewer/viewer.fcgi?val . . . pp. 1-4.
GenBank Accession No. NM_020904, "*Homo sapiens* pleckstrin homology domain containing, family A (phosphoinositide binding specific) member 4 (PLEKHA4), mRNA," Nov. 17, 2006; Retrieved from the Internet on Aug. 10, 2010: http://www.ncbi.nlm.nih.gov/sviewer/viewer.fcgi?val . . . pp. 1-4.
GenBank Accession No. NM_020943, "*Homo sapiens* KIAA1604 protein (KIAA1604), mRNA," Jul. 25, 2007; Retrieved from the Internet on Aug. 10, 2010: http://www.ncbi.nlm.nih.gov/sviewer/viewer.fcgi?val . . . pp. 1-4.
GenBank Accession No. NM_020988, "*Homo sapiens* guanine nucleotide binding protein (G protein), alpha activating activity polypeptide O (GNAO1), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_021101, "*Homo sapiens* claudin 1 (CLDN1), mRNA" Sep. 26, 2007; Retrieved from the Internet on Aug. 10, 2010: http://www.ncbi.nlm.nih.gov/sviewer/viewer.fcgi?val . . . pp. 1-4.
GenBank Accession No. NM_021377, "Mus musculus VPS10 domain receptor protein SORCS 1 (Sores 1), mRNA," Sep. 3, 2007; Retrieved from the Internet on Aug. 10, 2010: http://www.ncbi.nlm.nih.gov/sviewer/viewer.fcgi?val . . . pp. 1-6.
GenBank Accession No. NM_021727, "*Homo sapiens* fatty acid desaturase 3 (FADS3), mRNA," Nov. 17, 2006; Retrieved from the Internet on Aug. 10, 2010: http://www.ncbi.nlm.nih.gov/sviewer/viewer.fcgi?val . . . pp. 1-4.

GenBank Accession No. NM_021813, "*Homo sapiens* BTB and CNC homology 1, basic leucine zipper transcription factor 2 (BACH2), mRNA," Sep. 3, 2007; Retrieved from the Internet on Aug. 11, 2010: http://www.ncbi.nlm.nih.gov/sviewer/viewer.fcgi?val . . . pp. 1-6.
GenBank Accession No. NM_021990, "*Homo sapiens* gamma-aminobutyric acid (GABA) A receptor, epsilon (GABRE), transcript variant 4, mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_022044, "*Homo sapiens* stromal cell-derived factor 2-like 1 (SDF2L1), mRNA," Jun. 27, 2007; Retrieved from the Internet on Aug. 10, 2010: http://www.ncbi.nlm.nih.gov/sviewer/viewer.fcgi?val . . . pp. 1-2.
GenBank Accession No. NM_022047, "*Homo sapiens* differentially expressed in FDCP 6 homolog (mouse) (DEF6), mRNA," Sep. 3, 2007; Retrieved from the Internet on Aug. 10, 2010: http://www.ncbi.nlm.nih.gov/sviewer/viewer.fcgi?val . . . pp. 1-4.
GenBank Accession No. NM_022097, "*Homo sapiens* calcineurin B homologous protein 2 (CHP2), mRNA," Sep. 30, 2007; Retrieved from the Internet on Aug. 11, 2010: http://www.ncbi.nlm.nih.gov/sviewer/viewer.fcgi?val . . . pp. 1-3.
GenBank Accession No. NM_022115, "*Homo sapiens* PR domain containing 15 (PRDM15), transcript variant 1, mRNA," Jun. 27, 2007; Retrieved from the Internet on Aug. 10, 2010: http://www.ncbi.nlm.nih.gov/sviewer/viewer.fcgi?val . . . pp. 1-6.
GenBank Accession No. NM_022160, "*Homo sapiens* DMRT-like family A1 (DMRTA1), mRNA," Jun. 3, 2007; Retrieved from the Internet on Aug. 10, 2010: http://www.ncbi.nlm.nih.gov/sviewer/viewer.fcgi?val . . . pp. 1-3.
GenBank Accession No. NM_022842, "*Homo sapiens* CUB domain containing protein 1 (CDCP1), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_023070, "*Homo sapiens* zinc finger protein 643 (ZNF643), mRNA," Jun. 3, 2007; Retrieved from the Internet on Aug. 10, 2010: http://www.ncbi.nlm.nih.gov/sviewer/viewer.fcgi?val . . . pp. 1-3.
GenBank Accession No. NM_024050, "*Homo sapiens* chromosome 19 open reading frame 58 (C19orf58), mRNA," Jul. 1, 2007; Retrieved from the Internet on Aug. 10, 2010: http://www.ncbi.nlm.nih.gov/sviewer/viewer.fcgi?val . . . pp. 1-2.
GenBank Accession No. NM_024050, "*Homo sapiens* chromosome 19 open reading frame 58 (C19orf58), mRNA," Jul. 1, 2007; Retrieved from the Internet on Aug. 11, 2010: http://www.ncbi.nlm.nih.gov/sviewer/viewer.fcgi?val . . . pp. 1-2.
GenBank Accession No. NM_024525, "*Homo sapiens* tetratricopeptide repeat domain 13 (TTC13), mRNA," Jun. 3, 2007; Retrieved from the Internet on Aug. 10, 2010: http://www.ncbi.nlm.nih.gov/sviewer/viewer.fcgi?val . . . pp. 1-4.
GenBank Accession No. NM_024861, "*Homo sapiens* chromosome 2 open reading frame 54 (C2orf54), transcript variant 2, mRNA," Jul. 1, 2007; Retrieved from the Internet on Aug. 10, 2010: http://www.ncbi.nlm.nih.gov/sviewer/viewer.fcgi?val . . . pp. 1-3.
GenBank Accession No. NM_025169, "*Homo sapiens* zinc finger protein 167 (ZNF167), transcript variant 2, mRNA," Jun. 26, 2007; Retrieved from the Internet on Aug. 10, 2010: http://www.ncbi.nlm.nih.gov/sviewer/viewer.fcgi?val . . . pp. 1-3.
GenBank Accession No. NM_031217, "*Homo sapiens* kinesin family member 18A (KIF18A), mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_031466, "*Homo sapiens* NIK and IKK(beta) binding protein (NIBP), mRNA," Sep. 29, 2007; Retrieved from the Internet on Aug. 10, 2010: http://www.ncbi.nlm.nih.gov/sviewer/viewer.fcgi?val . . . pp. 1-5.
GenBank Accession No. NM_031938, "*Homo sapiens* beta-carotene dioxygenase 2 (BCD02), transcript variant 1, mRNA," Jun. 26, 2007; Retrieved from the Internet on Aug. 10, 2010: http://www.ncbi.nlm.nih.gov/sviewer/viewer.fcgi?val . . . pp. 1-4.
GenBank Accession No. NM_032188, "*Homo sapiens* MYST histone acetyltransferase 1 (MYST1), transcript variant 1, mRNA,"

(56) References Cited

OTHER PUBLICATIONS

Sep. 30, 2007; Retrieved from the Internet on Aug. 10, 2010: http://www.ncbi.nlm.nih.gov/sviewer/viewer.fcgi?val . . . pp. 1-4.

GenBank Accession No. NM_032228, "*Homo sapiens* male sterility domain containing 2 (MLSTD2), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_032266, "*Homo sapiens* chromosome 2 open reading frame 16 (C2orf16), mRNA," Jul. 24, 2007; Retrieved from the Internet on Aug. 11, 2010: http://www.ncbi.nlm.nih.gov/sviewer/viewer.fcgi?val . . . pp. 1-4.

GenBank Accession No. NM_032434, "*Homo sapiens* zinc finger protein 512 (ZNF512), mRNA," Jun. 22, 2007; Retrieved from the Internet on Aug. 10, 2010: http://www.ncbi.nlm.nih.gov/sviewer/viewer.fcgi?val . . . pp. 1-4.

GenBank Accession No. NM_032523, "*Homo sapiens* oxysterol binding protein-like 6 (OSBPL6), transcript variant 1, mRNA," Nov. 17, 2006; Retrieved from the Internet on Aug. 10, 2010: http://www.ncbi.nlm.nih.gov/sviewer/viewer.fcgi?val . . . pp. 1-5.

GenBank Accession No. NM_032778, "*Homo sapiens* MYC induced nuclear antigen (MINA), transcript variant 3, mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_032866, "*Homo sapiens* cingulin-like 1 (CGNL1), mRNA," Jun. 27, 2007; Retrieved from the Internet on Aug. 10, 2010: http://www.ncbi.nlm.nih.gov/sviewer/viewer.fcgi?val . . . pp. 1-5.

GenBank Accession No. NM_033036, "*Homo sapiens* galactose-3-0-sulfotransferase 3 (GAL3ST3), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_033066, "*Homo sapiens* membrane protein, palmitoylated 4 (MAGUK p55 subfamily member 4) (MPP4) mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_033160, "*Homo sapiens* zinc finger protein 658 (ZNF658), mRNA," Aug. 18, 2007; Retrieved from the Internet on Aug. 11, 2010: http://www.ncbi.nlm.nih.gov/sviewer/viewer.fcgi?val . . . pp. 1-5.

GenBank Accession No. NM_033260, "*Homo sapiens* forkhead boX Q1 (FOXQ1), mRNA," Sep. 25, 2007; Retrieved from the Internet on Aug. 10, 2010: http://www.nebi.nlm.nih.gov/sviewer/viewer.fcgi?val . . . pp. 1-3.

GenBank Accession No. NM_052875, "*Homo sapiens* vacuolar protein sorting 26 homolog B (S. pombe) (VPS26B), mRNA," Jun. 26, 2007; Retrieved from the Internet on Aug. 10, 2010: http://www.ncbi.nlm.nih.gov/sviewer/viewer.fcgi?val . . . pp. 1-3.

GenBank Accession No. NM_052892, "*Homo sapiens* polycystic kidney disease 1-like 2 (PKD1L2), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-8.

GenBank Accession No. NM_053064, "*Homo sapiens* guanine nucleotide binding protein (G protein), gamma 2 (GNG2), mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_058179, "*Homo sapiens* phosphoserine aminotransferase 1 (PSAT1), transcript variant 1, mRNA," Sep. 25, 2007; Retrieved from the Internet on Aug. 10, 2010: http://www.nebi.nlm.nih.gov/sviewer/viewer.fcgi?val . . . pp. 1-3.

GenBank Accession No. NM_058188, "*Homo sapiens* chromosome 21 open reading frame 67 (C21orf67), mRNA," Dec. 13, 2006; Retrieved from the Internet on Aug. 10, 2010: http://www.ncbi.nlm.nih.gov/sviewer/viewer.fcgi?val . . . pp. 1-2.

GenBank Accession No. NM_080927, "*Homo sapiens* discoidin, CUB and LCCL domain containing 2 (DCBLD2), mRNA," Sep. 30, 2007; Retrieved from the Internet on Aug. 11, 2010: http://www.ncbi.nlm.nih.gov/sviewer/viewer.fcgi?val . . . pp. 1-5.

GenBank Accession No. NM_133492, "*Homo sapiens* N-acylsphingosine amidohydrolase (alkaline ceramidase) 3 (ASAH3), mRNA," Sep. 25, 2007; Retrieved from the Internet on Aug. 10, 2010: http://www.ncbi.nlm.nih.gov/sviewer/viewer.fcgi?val . . . pp. 1-3.

GenBank Accession No. NM_138440, "*Homo sapiens* vasorin (VASN), mRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NM_138467, "*Homo sapiens* tRNA-yW synthesizing protein 3 homolog (S. Cerevisiae) (TYW3), mRNA," Jul. 25, 2007; Retrieved from the Internet on Aug. 10, 2010: http://www.ncbi.nlm.nih.gov/sviewer/viewer.fcgi?val . . . pp. 1-3.

GenBank Accession No. NM_139173, "*Homo sapiens* Na+/H+ exchanger domain containing 1 (NHEDC1), transcript variant 1, mRNA," Sep. 3, 2007; Retrieved from the Internet on Aug. 11, 2010: http://www.ncbi.nlm.nih.gov/sviewer/viewer.fcgi?val . . . pp. 1-3.

GenBank Accession No. NM_139314, "*Homo sapiens* angiopoietin-like 4 (ANGPTL4), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_144620, "*Homo sapiens* leucine rich repeat containing 39 (LRRC39), mRNA," Jun. 26, 2007; Retrieved from the Internet on Aug. 11, 2010: http://www.ncbi.nlm.nih.gov/sviewer/viewer.fcgi?val . . . pp. 1-4.

GenBank Accession No. NM_144633, "*Homo sapiens* potassium voltage-gated channel, subfamily H (eag-related), member 8 (KCNH8), mRNA," Jan. 26, 2007; Retrieved from the Internet on Aug. 11, 2010: http://www.ncbi.nlm.nih.gov/sviewer/viewer.fcgi?val . . . pp. 1-5.

GenBank Accession No. NM_145023, "*Homo sapiens* coiled-coil domain containing 7 (CCDC7), transcript variant 1, mRNA," Jul. 25, 2007; Retrieved from the Internet on Aug. 10, 2010: http://www.ncbi.nlm.nih.gov/sviewer/viewer.fcgi?val . . . pp. 1-4.

GenBank Accession No. NM_145051, "*Homo sapiens* ring finger protein 183 (RNF183), mRNA," Jul. 24, 2007; Retrieved from the Internet on Aug. 11, 2010: http://www.ncbi.nlm.nih.gov/sviewer/viewer.fcgi?val . . . pp. 1-3.

GenBank Accession No. NM_145306, "*Homo sapiens* chromosome 10 open reading frame 35 (C10orf35), mRNA," Jun. 26, 2007; Retrieved from the Internet on Aug. 10, 2010: http://www.ncbi.nlm.nih.gov/sviewer/viewer.fcgi?val . . . pp. 1-3.

GenBank Accession No. NM_145867, "*Homo sapiens* leukotriene C4 synthase (LTC4S), mRNA," Sep. 25, 2007; Retrieved from the Internet on Aug. 11, 2010: http://www.ncbi.nlm.nih.gov/sviewer/viewer.fcgi?val . . . pp. 1-4.

GenBank Accession No. NM_152377, "*Homo sapiens* chromosome 1 open reading frame 87 (C1orf87), mRNA," Nov. 17, 2006; Retrieved from the Internet on Aug. 11, 2010: http://www.ncbi.nlm.nih.gov/sviewer/viewer.fcgi?val . . . pp. 1-3.

GenBank Accession No. NM_152408, "*Homo sapiens* chromosome 5 open reading frame 37 (C5orf37), transcript variant 2, mRNA," Jul. 5, 2007; Retrieved from the Internet on Aug. 10, 2010: http://www.ncbi.nlm.nih.gov/sviewer/viewer.fcgi?val . . . pp. 1-3.

GenBank Accession No. NM_152525, "*Homo sapiens* amyotrophic lateral sclerosis 2 (juvenile) chromosome region, candidate 11 (ALS2CR11), mRNA," Jun. 27, 2007; Retrieved from the Internet on Aug. 10, 2010: http://www.ncbi.nlm.nih.gov/sviewer/viewer.fcgi?val . . . pp. 1-4.

GenBank Accession No. NM_152649, "*Homo sapiens* mixed lineage kinase domain-like (MLKL), mRNA," Jun. 3, 2007; Retrieved from the Internet on Aug. 10, 2010: http://www.ncbi.nlm.nih.gov/sviewer/viewer.fcgi?val . . . pp. 1-3.

GenBank Accession No. NM_153689, "*Homo sapiens* hypothetical protein FLJ38973 (FLJ38973), mRNA," Jun. 26, 2007; Retrieved from the Internet on Aug. 10, 2010: http://www.ncbi.nlm.nih.gov/sviewer/viewer.fcgi?val . . . pp. 1-3.

GenBank Accession No. NM_172345, "*Homo sapiens* sperm associated antigen 9 (SPAG9), transcript variant 2, mRNA," Mar. 20, 2007; Retrieved from the Internet on Aug. 10, 2010: http://www.ncbi.nlm.nih.gov/sviewer/viewer.fcgi?val . . . pp. 1-4.

(56) References Cited

OTHER PUBLICATIONS

GenBank Accession No. NM_173039, "*Homo sapiens* aquaporin 11 (AQP11), mRNA," Nov. 17, 2006; Retrieved from the Internet on Aug. 10, 2010: http://www.ncbi.nlm.nih.gov/sviewer/viewer.fcgi?val . . . pp. 1-2.

GenBank Accession No. NM_173082, "*Homo sapiens* SNF2 histone linker PHD Ring helicase (SHPRH), transcript variant 2, mRNA," Sep. 25, 2007; Retrieved from the Internet on Aug. 10, 2010: http://www.ncbi.nlm.nih.gov/sviewer/viewer.fcgi?val . . . pp. 1-7.

GenBank Accession No. NM_173550; "*Homo sapiens* chromosome 9 open reading frame 93 (C9orf93), mRNA," Jun. 3, 2007; Retrieved from the Internet on Aug. 10, 2010: http://www.ncbi.nlm.nih.gov/sviewer/viewer.fcgi?val . . . pp. 1-6.

GenBank Accession No. NM_175868, "*Homo sapiens* melanoma antigen family A, 6 (MAGEA6), transcript variant 2, mRNA," Sep. 25, 2007; Retrieved from the Internet on Aug. 10, 2010: http://www.ncbi.nlm.nih.gov/sviewer/viewer.fcgi?val . . . pp. 1-3.

GenBank Accession No. NM_180989, "*Homo sapiens* G protein-coupled receptor 180 (GPR180), mRNA," Sep. 26, 2007; Retrieved from the Internet on Aug. 10, 2010: http://www.ncbi.nlm.nih.gov/sviewer/viewer.fcgi?val . . . pp. 1-4.

GenBank Accession No. NM_181795, "*Homo sapiens* protein kinase (cAMP-dependent, catalytic) inhibitor beta (PKIB), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_182728, "*Homo sapiens* solute carrier family 7 (cationic amino acid transporter, y+ system), member 8 (SLC7A8), transcript variant 2, mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_182751, "*Homo sapiens* minichromosome maintenance complex component 10 (MCM10), transcript variant 1, mRNA," Sep. 25, 2007; Retrieved from the Internet on Aug. 11, 2010: http://www.ncbi.nlm.nih.gov/sviewer/viewer.fcgi?val . . . pp. 1-6.

GenBank Accession No. NM_182920, "*Homo sapiens* ADAM metallopeptidase with thrombospondin type 1 motif, 9 (ADAMTS9), mRNA," Sep. 3, 2007; Retrieved from the Internet on Aug. 10, 2010: http://www.ncbi.nlm.nih.gov/sviewer/viewer.fcgi?val . . . pp. 1-8.

GenBank Accession No. NM_183040, "*Homo sapiens* dystrobrevin binding protein 1 (DTNBP1), transcript variant 2, mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_194303, "*Homo sapiens* chromosome 10 open reading frame 39 (C10orf39), mRNA," Nov. 17, 2006; Retrieved from the Internet on Aug. 10, 2010: http://www.ncbi.nlm.nih.gov/sviewer/viewer.fcgi?val . . . pp. 1-3.

GenBank Accession No. NM_198353, "*Homo sapiens* potassium channel tetramerisation domain containing 8 (KCTD8), mRNA," Jun. 3, 2007; Retrieved from the Internet on Aug. 10, 2010: http://www.ncbi.nlm.nih.gov/sviewer/viewer.fcgi?val . . . pp. 1-3.

GenBank Accession No. NM_198404, "*Homo sapiens* potassium channel tetramerisation domain containing 4 (KCTD4), mRNA," Jul. 1, 2007; Retrieved from the Internet on Aug. 10, 2010: http://www.ncbi.nlm.nih.gov/sviewer/viewer.fcgi?val . . . pp. 1-3.

GenBank Accession No. NM_198569, "*Homo sapiens* G protein-coupled receptor 136 (GPR126), transcript variant b1, mRNA," Sep. 3, 2007; Retrieved from the Internet on Aug. 10, 2010: http://www.ncbi.nlm.nih.gov/sviewer/viewer.fcgi?val . . . pp. 1-6.

GenBank Accession No. NM_198833, "*Homo sapiens* serpin peptidase inhibitor, clade B (ovalbumin), member 8 (SERPINB8), transcript variant 2, mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_198951, "*Homo sapiens* transglutaminase 2 (C polypeptide, protein-glutamine-gamma-glutamyltransferase) (TGM2), transcript variant 2, mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_203434, "*Homo sapiens* immediate early response 5-like (IER5L), mRNA," Jul. 1, 2007; Retrieved from the Internet on Aug. 10, 2010: http://www.ncbi.nlm.nih.gov/sviewer/viewer.fcgi?val . . . pp. 1-4.

GenBank Accession No. NM_205849, "*Homo sapiens* family with sequence similarity 9, member B (FAM9B), mRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NR_001279, "*Homo sapiens* cystatin pseudogene (LOC164380) on chromosome 20," Jun. 27, 2007; Retrieved from the Internet on Aug. 11, 2010: http://www.ncbi.nlm.nih.gov/sviewer/viewer.fcgi?val . . . pp. 1-2.

GenBank Accession No. NR_002186, "*Homo sapiens* hypothetical protein DKFZp58611420 (DKFZp58611420) on chromosome 7," Jun. 27, 2007; Retrieved from the Internet on Aug. 10, 2010: http://www.ncbi.nlm.nih.gov/sviewer/viewer.fcgi?val . . . pp. 1-2.

GenBank Accession No. NR_002802, "*Homo sapiens* trophoblast-derived noncoding RNA (TncRNA) on chromosome 11," Jun. 27, 2007; Retrieved from the Internet on Aug. 10, 2010: http://www.ncbi.nlm.nih.gov/sviewer/viewer.fcgi?val . . . pp. 1-5.

GenBank Accession No. NR_002819, "*Homo sapiens* metastasis associated lung adenocarcinomatranscript 1 (non-coding RNA) (MALAT1) on chromosome 11," Sep. 3, 2007; Retrieved from the Internet on Aug. 10, 2010: http://www.ncbi.nlm.nih.gov/sviewer/viewer.fcgi?val . . . pp. 1-4.

GenBank Accession No. XM_210365, "Predicted: *Homo sapiens* similiar to ribosomal protein L24-like (LOC284288), mRNA," Aug. 29, 2006; Retrieved from the Internet on Aug. 10, 2010: http://www.ncbi.nlm.nih.gov/sviewer/viewer.fcgi?val . . . pp. 1-2.

Adler, S.P., et al., "A Cararypox Vector Expressing Cytomegalovirus (CMV) Glycoprotein B Primes for Antibody Responses to a Live Attenuated CMV Vaccine (Towne)," *The Journal of Diseases*, 180: 843-846 (1999).

Plotkin, S.A., et al., "Candidate Cytomegalovirus Strain for Human Vaccination," *Infection and Immunity*, 12: 521-527 (1975).

Wang, D., et al., "Human Cytomegalovirus Uses Two Distinct Pathways to Enter Retinal Pigmented Epithelial Cells", *PNAS*, 104(50): 20037-20042 (2007).

International Preliminary Report on Patentability, PCT/US2008/079494 Cytomegalovirus Vaccines and Methods of Production, mailed Apr. 22, 2010.

New Zealand Application No. 584459, Examination Report, dated Jan. 26, 2011.

Australia Application. No. 2008310713, Examiner's first report, dated Apr. 19, 2011.

Singapore Application No. 201002080-8, Written Opinion, mailed Jul. 8, 2011.

Singapore Application No. 2010020808, Reply to Written Opinion filed Dec. 23, 2011.

Israel Patent Application No. 204850, Office Action, Free Translation from the Hebrew, State of Israel, Ministry of Justice re: Notification of Defects in Patent Application No. 204850, mailed Jan. 22, 2012.

Singapore Application No. 2010020808, Final Substantive Examination Report, mailed Feb. 10, 2012.

Australia Application No. 2008310713, Reply filed Apr. 19, 2012.

China Application No. 200880111084.9, First Office Action, mailed Apr. 19, 2012.

New Zealand Application No. 584459, Reply filed May 7, 2012.

Israel Patent Application No. 204850, Reply filed May 29, 2012.

European Application No. 08836810.5, Extended Search Report, mailed Jun. 13, 2012.

China Application No. 200880111084.9, Reply to First Office Action filed Jun. 29, 2012.

China Application No. 200880111084.9, Second Office Action, mailed Oct. 26, 2012.

European Application No. 08836810.5, Response to Search Report and Opinion filed on Jan. 4, 2013.

(56) References Cited

OTHER PUBLICATIONS

Israel Patent Application No. 204850, "Cytomegalovirus Vaccines and Methods of Production", Notification of Defects of Patent Application Translation from the Hebrew, State of Israel, Ministry of Justice mailed Mar. 21, 2013.
Japanese Patent Application No. 2010-529076, "Cytomegalovirus Vaccines and Methods of Production", Notice of Grounds for Rejection, Translation from Japanese, mailed Mar. 25, 2013.
Mexican Patent Application No. MX/A/210/003713, "Cytomegalovirus Vaccines and Methods of Production", Official Action, Translation of the Requirements, mailed May 22, 2013.
Wang, D., et al., "Human cytomegalovirus uses two distinct pathways to enter retinal pigmented epithelial cells," PNAS, 104:50 20037-20042 (2007).
Ando, Y., et al., "Enhanced cytopathic effect of human cytomegalovirus on a retinal pigment epithelium cell line, K-1034, by serum-free medium," *Arch. Virol.*, 142(8):1645-1658 (1997).
Esclatine, A., et al., "Human Cytomegalovirus Infects Caco-2 Intestinal Epithelial Cells Basolatterally Regardless of the Differentiation State," *Journal of Virology*, 74(1):513-517 (Jan. 2000).
Guetta, E., et al., "Effect of cytomegalovirus immediate early gene products on endothelial cell gene activity," *Cardiovascular Research*, 50:538-546 (2001).
Scholz, M., et al., "Supernatants from human cytomegalovirus (HCMV)-infected retinal glial cells increase transepithelial electrical resistance in a cell culture model: evidence of HCMV immune escape in the eye?" *Med. Microbiol. Innnunol.*, 193:205-208 (2004).
Sinclair, J., "Human cytomegalovirus: Latency and reactivation in the myeloid lineage," *Journal of Clinical Virology*, 41:180-185 (2008).
Smith, J.D., "Human Cytomegalovirus: Demonstration of Permissive Epithelial Cells and Nonpermissive Fibroblastic Cells in a Survey of Human Cell Lines," *Journal of Virology*, 60(2):583-588 (Nov. 1986).

Bodagi, et al., "Entry of Human Cytomegalovirus into Retinal Pigment Epithelial and Endothelial Cells by Endocytosis," Investigative Ophthalmology & Visual Science, 40(11):2598-2607 (1999).
Dargan, et al., "Sequential Mutations Associated with Adaptation of Human Cytomegalovirus to Growth in Cell Culture," Journal of General Virology, 91(6):1535-1546 (2010).
Detrick, et al., "Cytomegalovirus Replication in Human Retinal Pigment Epithelial Cells," Investigative Ophthalmology & Visual Science, 37(5):814-825 (1996).
Gerna, et al., "Human Cytomegalovirus and Human Umbilical Vein Endothelial Cells: Restriction of Primary Isolation to Blood Samples and Susceptibilities of Clinical Isolates from Other Sources to Adaptation," Journal of Clinical Microbiology, 40(1):233-238.
Gerna, et al., "Human Cytomegalovirus Replicates Abortively in Polymorphonuclear Leukocytes After Transfer from Infected Endothelial Cells Via Transient Microfusion Events," Journal of Virology, 74(12):5629-5638 (2000).
Gerna, et al., "Rescue of Human Cytomegalovirus Strain (Ad169) Tropism for Both Leukocytes and Human Endothelial Cells," Journal of General Virology, 84(6):pp. 1431-1436 (2003).
Momma, et al., "Differential Expression of Chemokines by Human Retinal Pigment Epithelial Cells Infected with Cytomegalovirus," Investigative Ophthalmology & Visual Science, 44(5):2026-2033 (2003).
Revello, et al., "In Vitro Generation of Human Cytomegalovirus pp65 Antigenemia, Viremia, and Leukodnaemia," Journal of Clinical Investigation, 101(12):2686-2692 (1998).
Search Report, Written Opinion and Invitation to Respond to Written Opinion for Singapore Patent Application No. 2012075594, "Cytomegalovirus Vaccines and Methods of Production", mailed Jan. 28, 2015.

\* cited by examiner

SEQUENCE LISTING

```
<160> NUMBER OF SEQ ID NOS: 50

<210> SEQ ID NO 1
<211> LENGTH: 1808
<212> TYPE: DNA
<213> ORGANISM: Homo Sapiens
<220> FEATURE:
<223> OTHER INFORMATION: AK094860

<400> SEQUENCE: 1
ttgcttcccc atgtctcaat tgttaaatc ttattgttct atgtaatttg aattgctaca      60
tcctttctgt tgactagctc cttgctcaga ataacttttc cacacctgga actttggcgt    120
aggagttctt ttcactttta tgcatttccc gcgacattac agggtgagta cgtagcagat    180
gagtgcttgt gagcctttcc tctgggattc acacagatgg ctcactccta actttggtga    240
gtcattcagt ggccagatgt ttgcctcttt cctcctcccc actctacccc cacaattcag    300
tgtactgttc tttgaatgac atcccctctt gtttttgcct ctctttctcc tgatgcaatg    360
gccaaaatgc tggaaatggc tgccttaaat gtagggacca ttaggatctc gctcaacaca    420
gaacccaggc cacctgtaat aacacagctg gctcccagtc ctgaaaccct gcctttctgc    480
cctgaatggg gtgcagagaa ccagtccaga cacctgaaac tgccacccct cttcatctgt    540
aggtgcaggg gccctctgta tcaggaagag agcctctctg aaatccactg tcattctggg    600
cttttcctgg accagctctc cttacctacc cccttctcta gcctgtcagt ttcactcatt    660
cattggacat ttataagcac taagtatgta ccaggcatca tgctggcctt tggtggtacc    720
aacaaataaa gagactgcta aatgcagaaa ataggcaca gagtaaagac ttgtaagtct    780
gtaaaggagt gctcagtgag aagtcacaca agctaagttt ccaaggacca tttgcagatc    840
actgctgaac attctccatc ctgcctactt tgtattagag gacttcttgc agggagaaat    900
ataatcagca ggatcctcgc tcagagacct ggcagacacc accttaaccc agtgatcaaa    960
gttaacctcc ccagtacatg tccaactact gctgccctga aaggatgcac tgagaacatt   1020
tctgtgtcat ttctaccaca gatgcgctac ttgaatctaa ttatgaagag acaagagaca   1080
aacccagatt gaggggcatt cagcaaaata attgccctga actctttaaa aaacggcaat   1140
gttgagaaag acaaagaaag actgaggagc tattccagtt aaagtaggct agagacactg   1200
ggaaccaaat gtgatgcatg atccaggata ttctttatt acagtgagca tcattgggac   1260
agttggtaaa atgtgaatat tgtctgaaga gtataatatt gtatcaaagt taatttcctg   1320
gtcttgagga ttgtactgtg gttatgtaag agaatgtcct tgttttttagg aaatagatgt   1380 tgaaatatct tgagataaag agcattatgt cggcgactta ttatcaaata gtacaggaaa   1440
```

| | |
|---|---:|
| atgagtgtgt gtgtgtgtgt gtgtgtgtgt gtgtgtggag agagagagag aagggaggga | 1500 |
| cagagggaca gagagatata aaaccaatgc acctgggtgc ggtggctcac gcctgtaatc | 1560 |
| ccagcacttt gggaggccag ggtgggcaga tcatgaggtc agaagttcga gaccagccta | 1620 |
| accaacatgg tgaaacccg tctctacaaa aatacaaaaa tcagccaggc gtggtggcac | 1680 |
| gcgcctgtaa tcccagctac tcaggaggct gaggcaggag aattgcttga acccaggagg | 1740 |
| cggaggttgc agtgagccaa gatcacgcca ctgcactcca gcctggtgac agagcaagac | 1800 |
| tctgtctc | 1808 |

<210> SEQ ID NO 2
<211> LENGTH: 2173
<212> TYPE: DNA
<213> ORGANISM: Homo Sapiens

<400> SEQUENCE: 2

| | |
|---|---:|
| ggcgtcgggc gcctgggacg tggcttcaac ggccccatcc ggcgccggcg gcgggtgccc | 60 |
| ggcggtcttt gctgccgccc gggggcgcag aggccgggcc ttttctttca gcacaaacgt | 120 |
| cagtttgtaa aagggaggtg ctggagtctg aggagttttc aggcttccgt ctcgaaggaa | 180 |
| gtctggcagg ctcggaattg tcatcttcct caggcaaata gttttcacc ttagagccag | 240 |
| caaggccaaa ccgcccagtc acccgacttc ccacagtctc agcaggtaca cagggcgggg | 300 |
| agcctcggga gcggctccct tagcaggacc tgagggtttc gggagagtcc tggctttgca | 360 |
| cttagttttc ccgctgcctg gctgcctccg tggcggttgt gctgcttttt atgcaggatg | 420 |
| taggatcgaa ggcaaatcat cctttcccta cgtcccctgc caacccctgc cgctctcctc | 480 |
| tattttgtac actttatcat taaaggattt gaatgaatg gaggaataag ttttttttcat | 540 |
| ctgtaatttg gaagccaagt cagtaacaaa atgaaaccag taaagcatct gttgaccacc | 600 |
| agtaacaaat cggcaaatgt tccagcatta actactaaaa aaggactaca taatttacca | 660 |
| ttatcacctg agctaaagga aaacataat gcaaaattaa ttcatgataa aattgaacca | 720 |
| atggtcctaa gatctccacc aacaggagaa tccattttac ggtatgcttt gcccattcca | 780 |
| tcgagtaaga caaagaactt actaccagaa gatgaaatga tcggaaaaat tatcaaacat | 840 |
| ctgaagatgg ttgttttccac tttggaagaa acctatggac attgcgatca gaatggagaa | 900 |
| gaaccatttg taaagcatga acatgaagaa ttatctttat ctgttgggga tgatatgaat | 960 |
| tcattcttga catattgttc gcaatttgca gctcagctag aagaagcact taagaagaa | 1020 |
| caaaatatt tggaatctct tttaagtgg tttcagtggc aggtcaatca gatgaagaa | 1080 |
| ataagtaaag atcaaactct tttacaagca gagcctccaa aacctgacaa aacagtcatt | 1140 |
| ttaaatattg cagaaatagt aaggcttgta caaagattg aagaactgaa gaatcgcctt | 1200 |
| aaacagaggt ctaaatcctc cgtgaaagtc atgttgtcta aaactatgga taagaaaat | 1260 |
| cgaccagaag cagtgaaaag ttgtgaagct ctggcacaga aaattgaaga attcttagaa | 1320 |
| gcccactcaa ctgatgaatt taaagatgtt tctgcaacag aaccacaaac tgctcattca | 1380 |
| atgactaatc gattaatgc catgttgaaa gtatttgaaa accaggcaaa tatgttggag | 1440 |
| agagctgtaa atgatcaagt tttgttagat gctgaataca aacagatgca gtgtgatttt | 1500 |
| cagttgttat cagaagagaa gttggtgctg gaaaatgaac tacaaaagtt gaaggacaaa | 1560 |
| gagaaaacta agcctacaaa taatcgaaca aagaaagctg tgaaaacagt gaagaaaaaa | 1620 |
| gacaaaggaa aatctgagga ttcagaaaag aagatgtctc cagaaaaaga gtttaaaata | 1680 |
| aagaagatt tggatcaagt acagaaagta gcacgtctgg aaattgagaa caaagtcctt | 1740 |

| | |
|---|---|
| caggagcaat tgaaacaggc tttacaggaa gctgaaaaag ctaagcatca acttaactat | 1800 |
| ttcctaaatc aagagaagtt acttaaaagt gaggggaaaa ctgagacaac aatgcaagtg | 1860 |
| ggtaatagtc aaacaaaagt taaaggtgaa gattcaaaaa atataccatt ggagaaagaa | 1920 |
| acaagaaaat cactggtttc agattcaggt ggacaaagga caagtgataa aatccaagaa | 1980 |
| tatccacaga tcactgccca aagcggaaga ctgattgaaa agagatgcta atagagtttc | 2040 |
| tgaaatactt tggaaaagtc tcccaaacct tcagagagtg gatgggagcg aagtaaggag | 2100 |
| acccccacctg agcagataca tggtattgct tacaataaag tacatttttg ctctttacaa | 2160 |
| aaaaaaaaaa aaa | 2173 |

<210> SEQ ID NO 3
<211> LENGTH: 795
<212> TYPE: DNA
<213> ORGANISM: Homo Sapiens
<400> SEQUENCE: 3

| | |
|---|---|
| atgcctagca tcttcgccta tcagagctcc gaggtggact ggtgtgagag caacttccag | 60 |
| tactcggagc tggtggccga gttctacaac acgttctcca atatccccctt cttcatcttc | 120 |
| gggccactga tgatgctcct gatgcacccg tatgcccaga gcgctcccg ctacatttac | 180 |
| gttgtctggg tcctcttcat gatcataggc ctgttctcca tgtatttcca catgacgctc | 240 |
| agcttcctgg ccagctgct ggacgagatc gccatcctgt ggctcctggg cagtggctat | 300 |
| agcatatgga tgccccgctg ctatttcccc tccttccttg gggggaacag gtcccagttc | 360 |
| atccgcctgg tcttcatcac cactgtggtc agcacccttc tgtccttcct gcggcccacg | 420 |
| gtcaacgcct acgccctcaa cagcattgcc ctgcacattc tctacatcgt gtgccaggag | 480 |
| tacaggaaga ccagcaataa ggagcttcgg cacctgattg aggtctccgt ggttttatgg | 540 |
| gctgttgctc tgaccagctg gatcagtgac cgtctgcttt gcagcttctg gcagaggatt | 600 |
| catttcttct atctgcacag catctggcat gtgctcatca gcatcaccctt cccttatggc | 660 |
| atggtcacca tggccttggt ggatgccaac tatgagatgc caggtgaaac cctcaaagtc | 720 |
| cgctactggc ctcgggacag ttggcccgtg gggctgccct acgtggaaat ccggggtgat | 780 |
| gacaaggact gctga | 795 |

<210> SEQ ID NO 4
<211> LENGTH: 7333
<212> TYPE: DNA
<213> ORGANISM: Homo Sapiens
<400> SEQUENCE: 4

| | |
|---|---|
| acttccttcg tctgggtggt tgccccagcg acacgttggg ccgaagagcg gtgttgggta | 60 |
| cccgagagac ccggcggtgg ggaagtcact tcctcccgaa gacgctgttt cctagcaacc | 120 |
| gccctccgcc tctgttatta gcccctcctc ctcgctcggt ccaggaccgg ctctgcgggc | 180 |
| gccgccaggc ccagaccaag ctactatcag aagttgaatt ctaataatta gctattttat | 240 |
| aaaggtaacg agaaaaaata cactatgtct gatgaagttt ttagcaccac tttggcatat | 300 |
| acaaagagtc caaagttac caaaagaact actttccagg atgagctaat aagagcaatt | 360 |
| acagctcgct cagccagaca aaggagttct gaatactcag atgactttga cagtgatgag | 420 |
| attgtttctt taggtgattt ttctgacact tcagcagatg aaaattcagt taataaaaaa | 480 |
| atgaatgact ttcatatatc agatgatgaa gaaaagaatc cttcaaaact attgttttg | 540 |

```
aaaaccaata aatcaaacgg taacataacc aaagatgagc cagtgtgtgc catcaaaaat    600
gaagaggaaa tggcacctga tgggtgtgaa gacattgttg taaaatcttt ctctgaatct    660
caaaataagg atgaggaatt tgaaaaagac aaaataaaaa tgaaacctaa acccagaatt    720
ctttcaatta aaagcacatc ttcagcagaa acaacagcc ttgacacaga tgatcacttt     780
aaaccatcac ctcggccaag gagtatgttg aaaagaaaa gtcacatgga ggagaaggat    840
ggactagaag ataagaaac tgccctcagt gaagaattgg agttacattc tgcaccttct     900
tcccttccaa cgccgaatgg catacaatta gaagctgaga aaaagcatt ctctgaaaac     960 cttgatcctg aggattcatg cttaacaagt ctagcatcat catcacttaa acaaattctt   1020
ggagattctt tttcaccagg atctgaggga aacgcatctg gaaaagatcc aaatgaagaa   1080
atcactgaaa accataattc cttgaaatca gatgaaaata agagaattc attttcagca    1140 gaccatgtga ctactgcagt tgagaaatcc aaggaaagtc aagtgactgc tgatgacctt   1200
gaagaagaaa aggcaaaagc ggaactgatt atggatgatg acagaacagt tgatccacta   1260
ctatctaaat ctcagagtat cttaatatct accagtgcaa cagcatcttc aaagaaaaca   1320
attgaagata gaaatataaa gaataaaaag tcaacaaata atagagcatc cagtgcatct   1380
gccagattaa tgacctctga gttttttgaag aaatctagtt ctaaaaggag aactccatcg   1440
acaactacct cttctcacta tttagggact ttaaaagtct tggaccaaaa accttcacag   1500
aaacagagca tagaacctga tagagcagat aacataaggg cagctgttta tcaggagtgg   1560
ttagaaaaga aaatgtgta tttacatgaa atgcacagaa taaaaagaat tgaaagtgaa    1620
aacttaagga tccaaaatga acagaaaaaa gctgctaaaa gagaagaagc attagcatca   1680
tttgaggcct ggaaggctat gaaagaaaag gaagcaaaga aaatagctgc caaaaagagg   1740
cttgaagaaa aaacaagaa gaaaactgaa gaagaaaatg ctgcaagaaa aggagaagca   1800
ctacaagctt ttgaaaaatg gaaagagaaa aagatggaat atcttaaaga gaaaatagaa   1860
aaggagagag aatatgaaag agcaaagaaa cagaaagagg aggaaactgt tgccgagaaa   1920
aagaaagata atttaactgc tgttgagaaa tggaatgaaa aaaaggaagc ttttttcaag   1980
caaaaggaaa aagaaaaaat aaatgagaaa agaaggaag aactgaaaag agctgagaaa   2040
aaagataaag ataaacaagc tattaatgaa tatgaaaaat ggctggaaaa taaggaaaaa   2100
caagaaagaa ttgaacgaaa acagaagaaa cgtcattcct ttcttgaaag tgaggcactt   2160
cctccgtgga gccctccaag cagaactgtg ttcgcaaaag tgttttgata attctagttc   2220
ttacattatt tggttattta tcggtttgcc aatattagcc atagatttaa aaccattcaa   2280
ttatttatag ttagaggaat atattttaat taaatgccag acactcctgc tgacaatgaa   2340
agaaatactt tggaatgtaa tcagtgaaag catttttttg aactgtagat aaactgcctc   2400
aaacaaagac ctaataatca gattgttttt accattaaga tacataagat tttatcatgt   2460
cctgataatt cttatggtgg agtgattcat gatcttttc attaagctct gtatgttatt    2520
taagtatatt taattccagt aataaaaagg aaatcatcta ggtaccataa tgatagaaat   2580
tattcctttt gtggatgatt gtgaatctag attcaggttt ttaaatgaag ggtcgctggg   2640
aagtgcgcat atattattcc ttctgaaact gatgtttagc tcaaagcagt tgcattttgta  2700 ctgtgctagt tagaatttc atcagttgag gcagtagctc agtagaactc taatcatcaa    2760 ggcttttttat ttaagaattt tgccttatgt tttaatatga gtgtacttta tctgttccag  2820
gcttatgtga taatcatagg tactttataa tgagtccacc tctgaaattt ttctttctga   2880
attctatctc actttattat ttcagtgata ccaaaagaca tcaatgtcac agtagtgata   2940
```

```
tacttatgta ttagttatgg aaattccaca ggagttcaag gtcattatca ctataattat    3000
tttcctgact aaagccataa aggtgattta ggcaattatt gtcatcttag ctagtcctgt    3060
tttatagctt atattcagca gacagctgta tgggaaggta aatatgttga caatgtccac    3120 aaagcccttta tttatttatt tatttgatct ctgcatgtcc tcgtagtaac tggtctcata    3180
cttgacctgg tcatctggtt taagacagac caagtgtatg ctcacggagc tgaaatgcat    3240
tagtcagttg tgcaatgagg agatgatgga tgagaatata tagttcctat ttattgagca    3300
tctaatatat aatctctact ggacctttac aaatgtattt aacatcttta caacaacttt    3360
tcagggtagg tgttaccggc ttcatcttac atataaaaat actggcgctc agataaacca    3420
agtaacttac cgtccatctg gagtgtgcct gagttgagat caaacgggat tcagtacgtc    3480
tgactgaatc tgcctccttc tgaaatctct atgctctttt tcacacttct ctgtagcctc    3540
agagactgcc aagttctgtc aagacctctg cataatatca acgttacaaa cacgttttaa    3600
cttttagagc ctaaaatcat gtattgttat ccaaagatga tctttctcta cagaaatagc    3660
tgcttgttct tagagatggt ggaggtcatt aaatctataa agtgagataa aaatccataa    3720
gatttcatga gttactcagg catcttataa ctactatcag aatatcagaa aactcagcaa    3780
gttatgtgac aaaggctttg agatgatcac tccagacgtt ccacatactg agcatcagcc    3840
ttcttgctgc agtgcatgtg caagataaga tgtcataggc agctttgtaa gattgtatca    3900
gtgctataga caattaagag aaatttcata gataaaacta gaacccttc tatatggcca    3960 gaactgtaat actttatgaa attgatctga ttatcagcaa tatgtagtat cagcatggaa    4020
tttaggacct ctcttactca ttcctgtgtc ccccatagta ccaaaaacag tgcctgccaa    4080
aatagattaa aagtgtttat tgtattagct gtttagagct gaaagatat ttacaaattc    4140 cagggaagta aaaggaaaaa aactgaaaaa ggtacagcta cttttgggga tgtgagatca    4200
tggatgtgta tcttatagat ttcacattat ttatttactt tccattattt tcttctacat    4260
tatcatattt agtggctaac cattattact tcttaggttg ttgtgagaac cgagttaatt    4320
aatgtaaact atttgacaca taataaggac ttaaatgttc attgttgtca ttattgattt    4380
attaccatga gccctacatt tccccattca tgagtgtgcg aacattaaca tagataggggt    4440 tgataatggt tatttgacat tacacatttt taggaagaag aaatttctgt cttgctggcc    4500
agtccaggct gtaacactca aaaaacaaa acaaaacaaa acaaaacaaa aaacagaaa    4560 gatgccttgt attagggcct tcctaaaaag aaagctaagt aagtattaat ttcttaggat    4620
tgcttctgag gtaggatgag gtgtttgcat agacccaaca agtcattcac ttcaaatttt    4680
ttttgtctta ctatgataaa taacatatta tttcctgttt acagcaacct gcactgaaat    4740
taactagtta aataaaatca cctcttctag cacaaataaa gctgagttcg gggaggtggg    4800
tgaaaataca gtactgttgt ttacttccta agatccaagg gagagaatca agcttggtaa    4860
tattctcttg aatatacatt tacctattta aaaggtatga ttttcccata tttccttagg    4920
aagtatgtca tgtcaatata gatatttact cattaggttt acattaattt gtattataag    4980
ggaatgttta attcaaatta aggacattaa aagtatatag actttcatat aaaagttccg    5040
gttttataaa ttgcgttgat cacttaaaga atgcagagat ctcaaagtaa agaaaacaaa    5100
ttttatgaat attttaaaac attacttaaa acaagtttcc ttagaaagca catttgtgga    5160
taaatttaaa tattaatact aaataataaa gtagtataca gaatttaaat ttcataataa    5220
tgaagaaagt ggtaatgcta tttaacttaa aagatgcaat atggcatttt agatcaagag    5280
```

| | |
|---|---|
| gttaaagttt tcttaatgaa agaaagtaac gatttatggg ataaaaatat tccagtggtt | 5340 |
| tgtatttgct tcatacttca aaagtgttag tccatttatt gtttaaagtt atattgaaac | 5400 |
| tgatattttc actgctgcca aagcagtacc tgacagtaga taggtatcca cagtcttatg | 5460 |
| ttccttagag ttatagaact atgcctctga aaggggtttt aatactttaa taaacctggc | 5520 |
| ctaaactgtt ttatttctaa gttgaagaaa ctgattgtca agtactttga cttgtccaat | 5580 |
| ctcatacaac taactatggt acatctagag ttagatctca gtcaggggg tcccagttgt | 5640 |
| attctgctca ccattccaca atttcgatat tgataaaact ttcacactaa cttttgaact | 5700 |
| gtggttatta ttaatttagt tgattcatgt cctcttattt atctccttac tcctccactg | 5760 |
| ctgccttcat aactgtccac cagatcaaag ctatttgggt acctacactt taaagtgagg | 5820 |
| ggaaataatg aagtttctta aatcctgtgt catggactaa gatacaataa agaaaaggaa | 5880 |
| tttcacaaag taggggaaat tacgtgttag ttataatcat tcccaagaat aaactagtaa | 5940 |
| aagaaactta gatttcccta atttaatctt gactccgatt ttgatagtgc tatataaaaa | 6000 |
| ggtatttaaa cccatatgct tccttttaca taaaagaaag atatcaactt tcctagtttg | 6060 |
| catttacact ggctaatagg ataataaaat gctgtgtaaa tgttaaactg gaagtttctc | 6120 |
| tgagttattt ttactttaaa atttcatgtg attatgccat tttgaatatg tatattacat | 6180 |
| gtaattgtat aatgttaact cgggtaggca aaattcttgg tattaaattt aggatgtttt | 6240 |
| aaaaattatt aagaagatat taatgtctgc tttttgatag catatatttt catgtaatgt | 6300 |
| ttagtgtatt aaaatcaacc attcaagatt tattttattg ggtgacacta ttgactgtgt | 6360 |
| tccaaaatgc ccatagtgtt aggaaatgtg gtgtgagttt tatttgtggg ctaaggataa | 6420 |
| aataatcata tgctaatata ccttttatta taaatgacta aaaatttgga tataaaactg | 6480 |
| atgttttact acacaaatta cagagagaga taatataatt atataattat taaataatta | 6540 |
| gaaaatgcaa ataagcaaaa gtcacccatg ttcccagttc tcatctcctg aagatagtta | 6600 |
| taactaacat attattttgt actcttcctg ttaattagtt tctagtgtac tttctcctgt | 6660 |
| agctgaaatt aagctgagaa aaaggaaga gatagttcct ccctcctctt tctctctccc | 6720 |
| actctgtctc tctcctgtgc tatctgtgtg tatatacaaa tatgtatgca tatatatata | 6780 |
| atgatgtaca taatatatat aaaatacaaa tactaatgtg catattttca aacatacaca | 6840 |
| tattttttat tatttgaaat aagaatgagt cagactacat atttggtagc cagatttttt | 6900 |
| tcactcagtg atatatcatg aacatatttc catgctaata taattttcta ataattttag | 6960 |
| atgctgtaac tacaaatttca ttgttaatgg gcaatttgtt gctttacaaa tggtaaatta | 7020 |
| tatgataaat aatatgatca ttattcttgt agccaatatc attattagaa atgatggacc | 7080 |
| gcattaaagc tataaaatta aataagaatt tataaatgta aggagttatt cagacatctt | 7140 |
| gtatctagta ttacaatatc agaaaactca gcaggttata tgacatatac actttgagat | 7200 |
| agtcactcag aggttttcac atacaggatt aaccttgctg cagtgcgtgt gcaagattaa | 7260 |
| aaaagatgtc acgggtcact ttgtaatgtc atatcgttgc tgttgataaa taaggaaat | 7320 |
| gttataaata aaa | 7333 |

<210> SEQ ID NO 5
<211> LENGTH: 4188
<212> TYPE: DNA
<213> ORGANISM: Homo Sapiens

<400> SEQUENCE: 5

| | |
|---|---|
| agattcgcga aaacccggaa gcggatcgcg tggagtgacg gtcccacggc agcgcgattg | 60 |

```
acttctaaag actcttggta tgtgaggaag aaacctggaa gaggaagagg aaagcaaagg    120
agtcagggat ggctcttcct cagggtctat tgacattcag ggatgtggcc atagaattct    180
ctcaggagga gtggaaatgc ctggaccctg ctcagaggac tctatacagg gacgtgatgc    240
tggagaatta taggaacctg gtctccctgg atatctcttc caaatgcatg atgaaggagt    300
tctcatcaac agcacaaggc aatagagaag tgatccacac agggacattg caaagacatg    360
aaagtcatca cactggagac tttcgctttc aggaaattga taaagatatt cataacttag    420
agtttcagtg gcaagaagat gaaagaaata gccatgaagc acccatgaca gaaatcaaaa    480
agttgactgg tagtgcagac cgatatgatc aaaggcatgc tggaaacaag cctattaaag    540
atcagcttgg atcaagcttt cattcgcatc tgcctgaact ccacatgttt cagacccaag    600
ggaaaattgg taatcaagtg gagaagtcta tcaacgatgc ttcctcaatt tcaacatccc    660
aaagaatttc ttgtaggccc aaaacccata tttctaataa ctatgggaat aatttccgga    720
attcttcgtt actcacacaa aaacaggagg tacacatgag agaaaagtct ttccaatgta    780
atgagagtgg caaagccttt aattatagct cactcttaag gaaacatcaa ataatccatt    840
taggagagaa acaatataaa tgtgatgtat gtggcaaggt cttttaatcgg aagcgaaacc    900
tagtgtgcca tcgtagatgt cacactgggg agaaacctta caggtgtaat gagtgtggca    960
agactttcag tcagacgtat tcccttacat gccatcgtag acttcatact ggagagaaac   1020
cttacaaatg tgaagaatgt gacaaagctt tcagtttcaa atcaaacctt aaaagacata   1080
ggagaattca tgctggagaa aaaccataca agtgtaatga atgtggcaag acctttagtc   1140
agacgtcatc ccttacatgc catcgtagac ttcatactgg agagaaacct ttcaagtgta   1200
atgagtgtgg caagaccttt agtcggaagt catcccttac atgccatcat agacttcata   1260
cgggagagaa accttataag tgtaatgaat gtggcaagac cttcagtcag gagttaaccc   1320
ttaaatgcca tcgtagactt cataccggag agaagcctta caagtgtaat gaatgtggca   1380
aggtttttaa taaaaaggca aaccttgcac gtcatcatag acttcatagt ggagagaaac   1440
cctacaagtg tactgagtgt gtcaagacgt tcagtcgaaa ttcagcccct gtaattcata   1500
aggctattca tattggagag aaacgttaca agtgtaatga gtgtggcaag acgttcagtc   1560
gaatttcagc cctcgtaatt catacggcaa ttcatactgg agagaaacct tacaagtgta   1620
atgaatgtgg caagggtttt aatcggaaaa cacaccttgc atgtcatcat agacttcata   1680
ctggagagaa accttacaag tgtaatgaat gtggcaaggt ttttaatcga aaaacacacc   1740
ttgcacatca tcatagactt catactggag ataaacctta caagtgtaat gaatgtggca   1800
aggtttttaa tcaaaaagca caccttgcac gtcaccatag acttcatact ggagagaaac   1860
cttacaagtg taatgaatgt ggcaaggttt taatcaaaa agcaaacctt gcacgtcatc   1920
atagacttca tactggagag aaaccttaca gtttaatga gtgtggcaaa gcttttaatt   1980
gaaaagcaaa gcttgcacat catcatacaa ttcatactgg aaagaaacaa gtgcaatgag   2040
tgtggcaaga ccttctgtca caattcagtc cttgtaattc ataagaattc atactggaga   2100
gaaacaagtg taatgaacgt tgcaaaattt ttaatcaaca agcacacctt ccacgtcatc   2160
atagacttca tagtggagag aaaccttaga aatgtgaagc atgtgacaaa gtttacagtg   2220
gcaaatcgag cctcaaaaga caggagaatt catactggag agaaagctta caaggtgaa   2280
gaatatcaca gagttttcag tcacaagtca aaccttgaaa gacataaaat aaatcatact   2340
gcagagaaac cataaaattg taagagttcg tgacaaggct ttcgggcatg actcacacct   2400
```

| | |
|---|---|
| ggcacaacat cctagaattt atactggaga gaaaccttac aagtgtaatg agtctggcaa | 2460 |
| agccttaatg agcagtcaac acttactcac catcaggcaa tccatggtga aggaaacttg | 2520 |
| actaatgtaa tgattgtcac caagtcttca gtaacgctac aaccattgca atcattgga | 2580 |
| gaacccataa ggaagagaga tcatacaagt gtaataatcg gcaaattttt cagacatcgt | 2640 |
| ccatacctctg cagttcattg gcgaactcat actggagaca aaccttataa atgtcatgat | 2700 |
| tgaggcaagg tcttcagtca agcttcatcc tatgcaaaac ataggagaat tcatacagga | 2760 |
| gagaaacctc acgtgtgatg attgtggcaa agcctttact tcacgttcac acctccttag | 2820 |
| acatcagaga atgcacactg gacggaaatc ttacaaatgt catcagtgtg gcaaggtttt | 2880 |
| cagtctgact tcactccttg cagaatatca gaaaattcat tttgagataa ttgttccaaa | 2940 |
| tgcaatgagt agagcaaacc atcaagcagt aattgacatt aaagtgttta tgttaagagg | 3000 |
| attgggccag gtacagtgtc tcacacctgt aatcccagca ctttgggagg ccaaggcggg | 3060 |
| tagatcactt gaggtcagga gtttcagatc agtctggcca acaaacatga gccacttttc | 3120 |
| ccagtttgct ttttgttctt taacaaaaac tgatagggat ttttatgggt accgtgttga | 3180 |
| atctaaatca cattgggtta tataatcatt taacaatatt aattttttcca atccatcaat | 3240 |
| atgggttata tgtctgtata tgttttttaat catattgatg tatatttgta gatttcaagg | 3300 |
| tacaaacttc tcacctttt acttttattt ctatttcttt aagttctcta gcaaatggaa | 3360 |
| gtgttttta attttctttt aaaattgttt attgttacaa acttctcatc tttttgcttt | 3420 |
| tattcctaag tatttcttac tttaagttct ctagcaaatg gaagtgtttt taaattttct | 3480 |
| tttaaaattg tttattgtta atgtatggaa attcagctaa tttttggtgc tgatattgta | 3540 |
| ctgtgcagat acactgaatc tgtttattac ttccagtagt attttggttg agtctttgtg | 3600 |
| attttctaca cagaagatca tgtcatctac aaacacatat aatttttactt ctttcttttct | 3660 |
| gatttggatg ggtttgattt cttttgctat ttcattgctc tggctaggac agccagtatt | 3720 |
| tattgaatag aaggggtgag agcattcttc catcatgtga atcctacag gaaaatcatt | 3780 |
| ccatgttccc tgcttcgtta tctactcgtt ggtcatttca tggatggcct ttctattgtt | 3840 |
| gaggtaaatt tccttttctg tctattttgt tcagaatttc tatgatgagt ggattttgaa | 3900 |
| ttttgtgaaa tacttttttct ccatctattg agatgatgtg gttttcatct ttcattctgt | 3960 |
| tcaagtggca tatcacattg atttgcttga ctatgttgaa ccatccttgc atcccagaaa | 4020 |
| taagtggcac ttgagtatct acagtccttt ttacatcctc ttgaatacag ctttttagta | 4080 |
| caaggggtct tcaagaagtt catggaaaaa tacatatttt gcatattatg agaaaattgt | 4140 |
| gtatgaattt cccagttttt gcaccaaaat aaactggtac gaatctgt | 4188 |

<210> SEQ ID NO 6
<211> LENGTH: 2500
<212> TYPE: DNA
<213> ORGANISM: Homo Sapiens

<400> SEQUENCE: 6

| | |
|---|---|
| cccaggcgca gccaatggga agggtcggag gcatggcaca gccaatggga agggccgggg | 60 |
| caccaaagcc aatgggaagg gccggagcg cgcggcgcgg gagatttaaa ggctgctgga | 120 |
| gtgaggggtc gcccgtgcac cctgtcccag ccgtcctgtc ctggctgctc gctctgcttc | 180 |
| gctgcgcctc cactatgctc tccctccgtg tcccgctcgc gcccatcacg gacccgcagc | 240 |
| agctgcagct ctcgccgctg aagggggctca gcttggtcga caaggagaac acgccgccgg | 300 |
| ccctgagcgg gacccgcgtc ctggccagca agaccgcgag gaggatcttc caggagccca | 360 |

```
cggagccgaa aactaaagca gctgcccccg gcgtggagga tgagccgctg ctgagagaaa      420 accccccgccg ctttgtcatc ttccccatcg agtaccatga tatctggcag atgtataaga     480
aggcagaggc ttccttttgg accgccgagg aggttgacct ctccaaggac attcagcact      540
gggaatccct gaaacccgag gagagatatt ttatatccca tgttctggct ttctttgcag      600
caagcgatgg catagtaaat gaaaacttgg tggagcgatt tagccaagaa gttcagatta      660
cagaagcccg ctgtttctat ggcttccaaa ttgccatgga aaacatacat tctgaaatgt      720
atagtcttct tattgacact tacataaaag atcccaaaga agggaattt ctcttcaatg       780 ccattgaaac gatgccttgt gtcaagaaga aggcagactg ggccttgcgc tggattgggg      840
acaaagaggc tacctatggt gaacgtgttg tagcctttgc tgcagtggaa ggcattttct      900
tttccggttc ttttgcgtcg atattctggc tcaagaaacg aggactgatg cctgcctca      960 cattttctaa tgaacttatt agcagagatg agggtttaca ctgtgatttt gcttgcctga     1020
tgttcaaaca cctggtacac aaaccatcgg aggagagagt aagagaaata attatcaatg     1080
ctgttcggat agaacaggag ttcctcactg aggccttgcc tgtgaagctc attgggatga     1140
attgcactct aatgaagcaa tacattgagt ttgtggcaga cagacttatg ctggaactgg     1200
gttttagcaa ggttttcaga gtagagaacc catttgactt tatggagaat atttcactgg     1260
aaggaaagac taacttcttt gagaagagag taggcgagta tcagaggatg ggagtgatgt     1320
caagtccaac agagaattct tttaccttgg atgctgactt ctaaatgaac tgaagatgtg     1380
cccttacttg gctgattttt tttttccatc tcataagaaa aatcagctga agtgttacca     1440
actagccaca ccatgaattg tccgtaatgt tcattaacag catctttaaa actgtgtagc     1500
tacctcacaa ccagtcctgt ctgtttatag tgctggtagt atcaccttt gccagaaggc      1560 ctggctggct gtgacttacc atagcagtga caatggcagt cttggcttta aagtgagggg     1620
tgacccttta gtgagcttag cacagcggga ttaaacagtc ctttaaccag cacagccagt     1680
taaaagatgc agcctcactg cttcaacgca gattttaatg tttacttaaa tataaacctg     1740
gcactttaca aacaaataaa cattgttttg tactcacggc ggcgataata gcttgattta     1800
tttggtttct acaccaaata cattctcctg accactaatg ggagccaatt cacaattcac     1860
taagtgacta agtaagtta aacttgtgta gactaagcat gtaatttta agttttattt       1920 taatgaatta aaatatttgt taaccaactt aaagtcagt cctgtgtata cctagatatt      1980
agtcagttgg tgccagatag aagacaggtt gtgttttat cctgtggctt gtgtagtgtc      2040
ctgggattct ctgcccctc tgagtagagt gttgtgggat aaaggaatct ctcagggcaa      2100
ggagcttctt aagttaaatc actagaaatt tagggtgat ctgggccttc atatgtgtga      2160
gaagccgttt catttatt ctcactgtat tttcctcaac gtctggttga tgagaaaaaa        2220
ttcttgaaga gttttcatat gtgggagcta aggtagtatt gtaaaatttc aagtcatcct     2280
taaacaaaat gatccaccta agatcttgcc cctgttaagt ggtgaaatca actagaggtg     2340
gttcctacaa gttgttcatt ctagttttgt ttggtgtaag taggttgtgt gagttaattc     2400
atttatattt actatgtctg ttaaatcaga aatttttat tatctatgtt cttctagatt      2460
ttacctgtag ttcataaaaa aaaaaaaaa aaaaaaaaa                             2500
```

<210> SEQ ID NO 7
<211> LENGTH: 279
<212> TYPE: DNA
<213> ORGANISM: Homo Sapiens

```
<400> SEQUENCE: 7
tttttttaaa tttaaatgct tttattaaca atcttcttac attacaagga taatatgaca    60
aaaagaaagt ttctgcgtac atattatgat aaaccaacat agctctatttt gtatccagtg  120 ttctaggtcc cgtcacacag gtactataaa gcgtagtctg caaaataata acatcaagag   180 gttttttttta aagaaagtat taacatatta atatgtatgt gataatagac tcctaggtat  240
ttccccccat ccccacttat ttttcctttg tgattgaca                          279

<210> SEQ ID NO 8
<211> LENGTH: 1166
<212> TYPE: DNA
<213> ORGANISM: Homo Sapiens

<400> SEQUENCE: 8
atgcgcataa cctcaggata taaataatgc tgaagcagag ttacgttttt tttgttgttg    60
ttttttttgt ttttgttttt ttaggtttcc gtgtgtttct attgagctgc tcagtgcccg   120
gcttagaaga ccaggaaaag gagtcacagg tcgtatgctg gaggcttgag ccgcggcacc   180
gtggcgcggc tcgcctcgct gcggttggtg gtggcggtgg acattgcagc gcggctggag   240
gggtgagata ttcctgcaca tcctctggtg accccagaat gaggggggact cgctggtgaa   300 ttgcctcggg cttcacgtcc agtacaggct gggtccccgt ggtcgccaag cctcctgcct   360
gctcaatgat gtaggccacg ggattgcatt catacaggag ccggagctgt ggaggaacag   420
aggcaggaca aattcaccaa gagcctagca acatgaagag agatgccagg aagaagagag   480
aagccaggaa acagaagcca accgcacaat ccccacatca gagcaggaga gatgggggc    540 ctgctggcag agctggggct tggctgtggt cactctgagc ctgctctttg gtgttttcat   600
gagtggtggg aagaataggg accatatgga gcccacacag gaagctctag cagtaacaca   660
gcaagcagga agacaattct aaggaagcag cccatagtct tctttctttt cctgtgcatc   720
ttccactgtc agtgaggctc ctcatttatg gtgaacccaa ctgtgtgtat ctcccaagtt   780 ctcacccca gattaatgtt ttcaggaaga taggccatca acagtgagag gaagaagtta    840
cattgtcgta tgagggatgc atttttaacca ttaatttgtg gtacaggctg ggcgcagtgg   900
cttacgcatg taatcccagc actttgggag gccgaggcgg gtggatcacg aggtcaggag   960
attgagacca tcctggctaa catggtgaaa ccccgtctttt gctaaatata caaaaaattg   1020
gccaggcgtg gtggtgggca cctgtagtcc cagctactcg gggggctgag gcaggagaat  1080
ggtgtgaacc cgggaggcag agcttgcagt gagccgagat cgcgccactg cactccagcc  1140
tggatgacag agcaagactc catctc                                       1166

<210> SEQ ID NO 9
<211> LENGTH: 2383
<212> TYPE: DNA
<213> ORGANISM: Homo Sapiens

<400> SEQUENCE: 9
gctgctgcga cagtccacta ccttttttcga gagtgactcc cgttgtccca aggcttccca    60
gagcgaacct gtgcggctgc aggcaccggc cgtcgagtt tccggcgtcc ggaaggaccg    120
agctcttctc gcggatccag tgttccgttt ccagccccca atctcagagc cgagccgaca   180
gagagcaggg aaccggcatg gccaaagccg cggcgatcgg catcgacctg ggcaccacct   240
actcctgcgt gggggtgttc caacacggca aggtggagat catcgccaac gaccagggca   300
accgcaccac ccccagctac gtggccttca cggacaccga gcggctcatc ggggatgcgg   360
```

```
ccaagaacca ggtggcgctg aacccgcaga acaccgtgtt tgacgcgaag cggctgatcg      420
gccgcaagtt cggcgacccg gtggtgcagt cggacatgaa gcactggcct ttccaggtga      480
tcaacgacgg agacaagccc aaggtgcagg tgagctacaa gggggacacc aaggcattct      540
accccgagga gatctcgtcc atggtgctga ccaagatgaa ggagatcgcc gaggcgtacc      600
tgggctaccc ggtgaccaac gcggtgatca ccgtgccggc ctacttcaac gactcgcagc      660
gccaggccac caaggatgcg ggtgtgatcg cggggctcaa cgtgctgcgg atcatcaacg      720
agcccacggc cgccgccatc gcctacggcc tggacagaac gggcaagggg gagcgcaacg      780
tgctcatctt tgacctgggc gggggcacct tcgacgtgtc catcctgacg atcgacgacg      840
gcatcttcga ggtgaaggcc acggccgggg acacccacct gggtggggag gactttgaca      900
acaggctggt gaaccacttc gtggaggagt tcaagagaaa acacaagaag gacatcagcc      960
agaacaagcg agccgtgagg cggctgcgca ccgcctgcga gagggccaag aggaccctgt     1020
cgtccagcac ccaggccagc ctggagatcg actccctgtt tgagggcatc gacttctaca     1080
cgtccatcac cagggcgagg ttcgaggagc tgtgctccga cctgttccga agcaccctgg     1140
agcccgtgga gaaggctctg cgcgacgcca agctggacaa ggcccagatt cacgacctgg     1200
tcctggtcgg gggctccacc cgcatcccca aggtgcagaa gctgctgcag gacttcttca     1260
acgggcgcga cctgaacaag agcatcaacc ccgacgaggc tgtggcctac ggggcggcgg     1320
tgcaggcggc catcctgatg ggggacaagt ccgagaacgt gcaggacctg ctgctgctgg     1380
acgtggctcc cctgtcgctg gggctggaga cggccggagg cgtgatgact gccctgatca     1440
agcgcaactc caccatcccc accaagcaga cgcagatctt caccacctac tccgacaacc     1500 aacccgggt gctgatccag gtgtacgagg gcgagagggc catgacgaaa gacaacaatc     1560
tgttggggcg cttcgagctg agcggcatcc ctccggcccc caggggcgtg ccccagatcg     1620
aggtgacctt cgacatcgat gccaacggca tcctgaacgt cacggccacg gacaagagca     1680
ccggcaaggc caacaagatc accatcacca acgacaaggg ccgcctgagc aaggaggaga     1740
tcgagcgcat ggtgcaggag gcggagaagt acaaagcgga ggacgaggtg cagcgcgaga     1800
gggtgtcagc caagaacgcc ctggagtcct acgccttcaa catgaagagc gccgtggagg     1860
atgaggggct caagggcaag atcagcgagg ccgacaagaa gaaggtgctg gacaagtgtc     1920
aagaggtcat ctcgtggctg gacgccaaca ccttggccga aaggacgag tttgagcaca     1980 agaggaagga gctggagcag gtgtgtaacc ccatcatcag cggactgtac cagggtgccg     2040
gtggtcccgg gcctggggc ttcggggctc agggtcccaa ggagggtct gggtcaggcc     2100 ccaccattga ggaggtagat taggggcctt ccaagattg ctgttttgt tttggagctt     2160 caagactttg catttcctag tatttctgtt tgtcagttct caatttcctg tgtttgcaat     2220
gttgaaattt tttggtgaag tactgaactt gcttttttc cggtttctac atgcagagat     2280
gaatttatac tgccatctta cgactatttc ttcttttaa tacacttaac tcaggccatt     2340
ttttaagttg gttacttcaa agtaaataaa cttaaaatt caa                        2383
```

<210> SEQ ID NO 10
<211> LENGTH: 5661
<212> TYPE: DNA
<213> ORGANISM: Homo Sapiens

<400> SEQUENCE: 10

```
ggcacgtgga ctccctttaa tccagtgact gtcaggtcga tcatatgccg aggacgatga       60
```

```
tcccgccggg ggagtgcacg tacgcgggcc ggaagcggag gaggcccctg cagaaacaga    120
ggcccgccgt gggggcagag aagtccaacc cctccaagcg acaccgggac cgcctcaacg    180
ccgagttgga ccacctggcc agcctgctgc cgttcccgcc tgacatcatc tccaagctgg    240
acaagctttc tgtcctgcgc ctcagtgtca gttacctccg ggtgaagagc ttcttccaag    300
tcgtgcagga gcagagctca cggcagcctg cggccggcgc cccctcgccc ggagacagct    360
gtcctcttgc agggtctgcc gtgctggagg aaggctgct gttggagtct cttaatggct    420
ttgctctggt cgtgagtgca aagggacga tatttatgc atcagcaacg atcgtggact    480
atctgggctt ccatcagacg gatgtaatgc accagaacat ttatgactac atccacgtgg    540
acgaccgcca ggacttctgc cggcagctcc actgggccat ggaccctccc caggtggtgt    600
ttgggcagcc cccgcccttg gagacaggag atgatgctat cctggggagg ctgctcaggg    660
cccaggagtg gggcacaggc acgcccaccg agtactcggc cttcctgacc cgctgcttca    720
tctgccgtgt gcgctgcctg ctggacagca cctcgggctt cctggcccgg ggtcacagg    780 cttggcagct gcggctctgc tgtcccgagc cactcatgac gatgcagttt caaggaaaac    840
taaaattcct gtttggacag aagaagaagg cgccgtcagg agccatgctc ccgccgcggc    900
tgtcgctgtt ctgcattgcg gcacccgttc tcctcccctc cgcagcggag atgaaaatga    960
ggagcgcgct cctgagggca aaacccagag cagacaccgc agccaccgcg gatgcaaaag   1020
taaaagccac caccagtctg tgcgaatcgg aactgcatgg aaaacccaat tactcagcag   1080
gaaggagcag cagagagagc ggcgttttgg tgctcaggga acagactgac gctggccgat   1140
gggcacaggt tccgccagg gccccatgcc tgtgcctccg gggtggccct gaccttgtcc   1200
ttgaccccaa gggggctca ggggacaggg aggaggagca gcacaggatg ctgagcaggg   1260
cctctggagt gacagggcgg agggagactc caggacccac aaagccctg ccctggacag   1320 cgggaaagca cagtgaggat ggtgccaggc cgaggctgca gcccagcaag aatgacccgc   1380 cctcccctgcg ccccatgccc cgcggctcct gcctgccctg ccgtgtgtc cagggcactt   1440 tcaggaactc gcccatctct cacccgccga gcccgtcccc cagtgcctac tccagccgga   1500
ccagcagacc catgcgggat gtcggtgagg accaggtgca ccctccctc tgccactttc   1560 cccagaggag cctgcagcac cagctcccctc agcctggagc tcagcgtttt gccacgaggg   1620
gctatcccat ggaggacatg aagctgcaag gtgtaccgat gcctccgggg gacctgtgtg   1680
gtccgacgct gctgctagat gtgtccatca agatggagaa ggactctggg tgtgagggtg   1740
ctgcagacgg ctgtgtgccc agccaggtgt ggctgggggc cagtgacagg agccacccag   1800
ccaccttccc taccaggatg cacctgaaaa cagagccaga ctctcggcaa caggtgtaca   1860
tctcgcacct ggggcacggc gtgcgggggg ctcagcccca tgggagggcc actgctgggc   1920
gcagcaggga gctgaccct ttccaccctg cacactgtgc ctgcctggag cccacagacg   1980
gccttcccca gtcggagcct cccaccagc tctgtgcacg gggccgaggt gaacagtcct   2040
gcacctgcag agctgctgag gccgcccctg tggtcaagcg ggagcccttg gactcaccc   2100 agtgggctac tcacagccag ggaatggtgc ccgggatgtt gcccaaaagt gccttggcca   2160
cgctggtccc gccccaagct tcggggtgca cattcctgcc atagcgcagt gaccaccatc   2220
caagctcaga tctgtgtgtc tacgctcaga tgcgtcggtg gctgggctgc cctgctcctg   2280
gtcaggccgg agcccgtcct aagacacacg ctttgcagag ctgtgcatgc gcagtctgct   2340
agtgtgtgtg tgcagcatac gcaggagcct atcctgaatt ttgtaaaata tcccaacagt   2400
tcttaaatga aaactggcct taagtctatt caagcatgac agcatttctc tttgaggaat   2460
```

```
taaaatcttt aggaaagtga tcatggctgg acagcttcat gccccagagg cagcgagcac   2520
ccgtcccatg gctgccaagt ccacagtcgg ggatgaagca gtcgggtgat gctcccaagt   2580
ccgcagtcgg ggatgaagcg gtcgggtgat gctcccaagt ccgcagtcgg ggatgaagcg   2640
gtcgggtgac acacctagct cagccctccc aggccacctg cagctcccag cctgtgctgt   2700
gcaggcaggg tcagcccatc gccacagtgc actgtagagg ccagcacacg gcaaattaga   2760
aatacaacac gcggagaaag gggtccgtga gcccactcat agaggaatct agaacgttcc   2820
aggcagcaga ggctggcagc gtgggtccca cactgcccca caccgtgcgg caggtgctcc   2880
atggcgccat gacagagtct gaggccgac ctggactgga attgacagca taacccctgt   2940
tccttctgga catctcccga gttctcagtg ggtctctgcg gacggttctt cctaatctgc   3000
ctcttggtac atcacgtaat acagagttca cagactccgg gtttggaagt acagagaaac   3060
acacaacgta gagagaagac acaggaaact gcgctgcctg tggggttttc tctctggctg   3120
gctgtacagt tcactcaaat gagggttccc attgccatcc taggagaata attagggaca   3180
agacagacaa gtattaatag cattaaaaca gttgtaaagg cgatattttc tgagagtagg   3240
aaatttggat acaaaagcat aagtcagaaa gtgaaggtca ccaatccacc aacccgagaa   3300
cctacagctg atggtgcatt tcaggcttct tccacggtct ggcctggaac cccacccggc   3360
tggtgcaggc atcagatcag ggtgtagaag tcaccccaag caagaggaag ccaggcagtg   3420
aggccctggg gtgtggctgc agctgggccc acctgtgcgg gggtgggaag gccccatcct   3480
cagggagagg gcatcggcgc cctgacgtca gctccactgg gagtggcagg agctgtggga   3540
gcccatgggt gagggaccca ccaccccgct gcactgtgca ttgtgcctcc cgtgtggacg   3600
ccctctctgt tgttggcccg cgggtgaggg acccaccacc cctagggacc caccaccccg   3660
ccgcactgtg cattctgcct cctgtgtgga cgccctctct gttgtcagtg gctttgaggt   3720
gtcagtgctt acttagatgc tggtttaatg ctggacccat tgttaaacg caccttcact   3780
ttgtcaaaac ccaggtttgg ttggcaggac tgggtcttct gcccaatgcc aggtgcctgc   3840
gcctctcagt ggcctggttc ttggacagtt gcccccatg tggcagggat agggataagg   3900
atctcctctc agtactggaa gagaacagcc aaccatctga gcccagagtc acagatccat   3960
cgtggccccc tatgaccccc aagccctacc gaggggcac tcactctctg cttagccagg   4020
gggcgtcttt caaaaggtga cctccatgct gtgctgtcgt gggtgtgaga cgtgctcatg   4080
gccttccact gccatctctc ccttatctga tgcctaaagt cacgatgggg acagagctac   4140
ccaggggcca gccatggggt gaccagccac ctgagggtca gtcacctgtg gagagcaggc   4200
acctgtgaag accaggcacc tgaggactgg cgcctacttc ccactttggc cctacactgg   4260
cacagagccc ctctttattc atttctcatg ctgagcatgg cacacttctg gcctctgggc   4320
atttatggat ttaagaccag gatggtattt cagaagcttc ccacttcctt cctattctaa   4380
ccgagtgccc agctcctttg ctgatcatgg aaagaccctt aataattagg cctgcaggcc   4440
aggcgcagtg gctcatgcct ataatcccag cactttagga ggtcaaggta ggaggatcgc   4500
ttaagcccag gagttcaaga ccagcctggg caacacagga agaatgtgtc tctacaaaaa   4560
ataattaaaa atcagatctg ctgtatccct gaaaagtct caatcaacat gcatgttcca   4620
ctcttggagt tccctgttct gagggccagc cacgtcctgt gtcctggagc ttagccctca   4680
gcagctccct tcagcctggg cgccgcctgg gtcccaaacg tggcagctgc tcttccagtc   4740
tcggggccga ggagggcagg gagctcagtg actgagagtc ttgtgtatca catgtcttga   4800
```

```
gtgtcctgga gccaacggct gtcactggga aaaacaccag gccccaaaga tcgaatcaga      4860
gacgtggctg cgtgtttgcg attgtagcca ggcccttcag tgtcatcaaa ggagcactgg      4920
ggcctcctta agcacagacg gcagccctg cccaggaggc ttcttcacca cgtcctgccc       4980
tgcagcctcc cagaccttta gatgcgcccc tgcccaaggc cctcctggtg acaggtgcca      5040
gattgagtgg tgggttgctg ccaggcaggc cacgctgtgt tgacgctgca ctcagcacgt      5100
gggtgttggc tctgccggtt tgtggtgtg gggaccctac aggaggctgc ggccctgaga       5160
gcctgggatc agcgaggtgt ccgacatccc ttcctcaacg gcaacaaaaa ctccccaagt      5220
cagcactttg gttattttat agccacaacc ctcttggaaa acagtgggga agactatgga      5280
acatagaaag tgtggatgta tcacttctct ctaaaatgtc attgttagca ctaattacag      5340
gttcatgttt ttctgtgtat gtagcttttc cctatatagc tgaaaaagta ttaaagtcaa      5400
atataaggtg ggaatgggat ggaagggagg agatcaatac aacttatatt tttgcagttt      5460
ctactggaag aaaaaagttt tcaataccta gaccaacttg ttgaattttt aaaacttatg      5520
cactataaat gcaactttct ctactgcttt ctcagtgcct ttaggaagct ttcaaatttt      5580
tttgtactgt ggtttgtatt aaatttgcaa tattgatgta aaatacatga catgctagta      5640
catgtttaac aaaaatttaa a                                               5661

<210> SEQ ID NO 11
<211> LENGTH: 1415
<212> TYPE: DNA
<213> ORGANISM: Homo Sapiens

<400> SEQUENCE: 11
agtactatgt tgaagaagag tggtgagagt gggctcctcg tcttgttcca gttctcaaag        60
ggaatgcttt caccatttcc ccattcagta ttatgttggc tgtgggtttg tatagatggc       120
ttttattaca ttaagggatc atggcacaag ttgcagtttc caccctgccc atggaagatg       180
agaagtccat ggaagatgag gagtccattg aagatgagga gtctgttgaa gatgattccg       240
tggagagcag gatggtggtg acattgctca tatcagctct cgagtccacg atgttggaat       300
tcctgatgaa tctgcagtca gcattttgca tgaactgtgt gtggattcat tgcctacatt       360
ggatgatgaa gacttgagtg ttgctactaa gtgtgtcccc gagaaagtgt cagagccttt       420
acgtggacct tctcatgaaa aaggaaacag aatagtcaat ggaaaaggaa aagggcctcc       480
tgcaaaacat ccttccttga agcctagcac tgaagtggaa gatcctgctg tgaaaggagc       540
agtacaaaga aagaatgtac agacattgag agcagaacaa accttaccag tggctttaga       600
ggaagagcaa gaaaggtgtg aaagaagtga aagaagcaa tcacaggtca agaaggaaa        660 taatacaaac aaaagtgaaa aaatacaact atcagaaaat gtatgtcata gtacatcttc       720
tgctgctgct gacagattaa ccaaagaaag aaagattggg aaaacatatc ctcagcaatt       780
tcccaagaaa ctgaaggaag agcatgatag atgcatctta agacaagaaa gtgaagaaaa       840
aacaaatgtt aatatgctgt acaaaaaaat agagaagaat tagaaaggaa agagaaacaa       900
tataagaaag aagttgaagc aaaacaactt gaaccaacta ttgaatcact agagatgaaa       960
ccgaagacta caagaaatac tccaaatcag ataaatcaat ctttggattt tcataatcag      1020
gaagaaatga agatctgat ggatgaaaat tgcattttga gacagatat tgctatactc        1080 cgacaggaaa tatgcacaat gaaaaatgac aacctggaaa aagaaaataa atatcttaag      1140
gacgctaaaa ttgttaaaaa aacaaatgtt gcccttgaaa agtatataaa actcaatgag      1200
gaattgataa caaaaacagc attccggtat caacaagagc ttaatgatct caaagctgag      1260
```

-continued

| | | |
|---|---|---|
| aatacaaggc tcaattccga actgttgaag gaagaagaaa gcaacaaaag actggaagct | 1320 |
| gaaattgaat catcagtcta gactgactgc tgctataagt aagcacagtg aaagtgtgaa | 1380 |
| aacagaaaaa aaaaaaaaaa aaaaaaaaaa aaaaa | 1415 |

<210> SEQ ID NO 12
<211> LENGTH: 3205
<212> TYPE: DNA
<213> ORGANISM: Homo Sapiens

<400> SEQUENCE: 12

| | | |
|---|---|---|
| agcgggagtc tttcgttctg ggaggcccag gcggcttcgc gttctgagaa taaacagaac | 60 |
| ctctgttgct ctgcgacttg caggcactgg gagattcgta gctaagacgc cagggcatcc | 120 |
| cggaagctgg gaaatgggac tgttgacatt cagggatgtg gccgtagaat tctctttgga | 180 |
| ggagtgggaa cacctggaac cagctcagaa gaatttgtat cagaatgtga tgttagaaaa | 240 |
| ctacagaaac ctggtctctc tgggtcttgt tgtctctaag ccggacctga tcaccttttt | 300 |
| ggaacaaagg aaagagcctt ggaatgtgaa gagtgaggag acagtagcca tccagccaga | 360 |
| tgtgttttcg cattataaca aggacctgtt gacagagcac tgcacagaag cttcattcca | 420 |
| aaaagtgata tcgaggagac atgggagctg tgatcttgag aatttacatt taagaaaaag | 480 |
| gtggaaaagg gaggagtgtg aagggcacaa tggatgttat gatgaaaaga cttttaaata | 540 |
| tgatcaattt gatgaatcct ctgttgaaag tttgtttcac cagcaaatac tttcttcttg | 600 |
| tgccaaaagc tataactttg atcaatatag gaaggtcttt actcattcat cattgcttaa | 660 |
| tcaacaagag gaaatagata tttggggaaa acatcacata tatgataaaa cttcagtgtt | 720 |
| atttaggcag gtctctactc taaatagtta ccgaaatgtt tttattggag agaaaaatta | 780 |
| tcattgcaat aattctgaaa aaaccttgaa ccaaagctca agccctaaaa atcatcagga | 840 |
| aaattatttt ctagaaaaac aatacaaatg taaagaattt gaggaagtct ttcttcagag | 900 |
| tatgcatggg caagagaaac aagaacagtc ttacaaatgt aataaatgtg tagaagtttg | 960 |
| tacccagtca ttaaaacata ttcaacatca gaccatccat atcagagaaa actcatatag | 1020 |
| ctataacaaa tatgataaag atcttagtca gtcatcaaat cttagaaagc agataatcca | 1080 |
| taatgaagag aaaccataca aatgtgaaaa atgtggggat agcttaaacc atagtttgca | 1140 |
| ccttactcaa catcagatca ttcctaccga agagaaaccc tataaatgga agaatgtgg | 1200 |
| caaggtcttt aaccttaact gtagtttata ccttactaaa cagcagcaaa ttgatactgg | 1260 |
| agaaaacctt tacaaatgta aagcatgtag caaatctttt actcgttcct ccaatcttat | 1320 |
| tgtgcatcag agaattcaca ctggagagaa accatacaaa tgtaaagaat gtggcaaagc | 1380 |
| cttcgctgt agttcatacc ttactaaaca taagcgaatt catactggag agaaacctta | 1440 |
| taaatgtaaa gaatgtggaa aagcttttaa ccgtagttca tgccttactc aacatcagac | 1500 |
| aactcataca ggagaaaaac tttacaaatg taaagtatgt agcaaatctt atgctcgttc | 1560 |
| ttcaaatctt attatgcatc agagagttca tactggagag aagccttata atgtaaagaa | 1620 |
| atgtggcaaa gtcttttagcc gtagttcttg ccttactcaa catcggaaaa ttcatactgg | 1680 |
| agaaaatctt tacaaatgca agtatgtgc taaacctttt acttgtttct caaatcttat | 1740 |
| tgtgcatgag agaattcata ctggagagaa accctataaa tgtaaagaat gtggcaaagc | 1800 |
| ctttccttat agttcacacc ttattcgaca tcatcgaatt catactggag aaaaaccata | 1860 |
| caaatgtaaa gcatgtagca aatcttttag tgactcctca ggtcttactg tgcatcggcg | 1920 |

```
aactcatact ggagagaaac cctatacatg taaagaatgt ggcaaagcct ttagttatag    1980
ttcagatgtt attcagcatc ggagaattca tactggccag agaccctaca aatgtgaaga    2040
atgtggcaaa gccttcaact ataggtcata cctcactaca catcagagaa gtcatactgg    2100
agagagaccc tacaaatgtg aagaatgtgg caaagccttc aactctaggt catacctcac    2160
tacacatcgg agaagacata ctggagagag accctacaaa tgtgatgaat gtggtaaagc    2220
cttcagctat aggtcatacc tcactacaca tcggagaagt catagtggag agagacccta    2280
caaatgtgaa gaatgtggca agcctttaa ctctaggtca tacctcattg cacatcagag     2340
aagtcatact agagaaaaac tttaaaaatg taaacatgg agcagatttt ttacttgtta     2400
cccatgtctt attgtgcatc agataattta tgggagtg aaaccctaca aatgttaaga      2460
atgtggcata acctttaact attttcaagc cttacacaat agcagagaat ataaactgaa    2520
aaaatccata caaatattaa aaatgtggca aattatttta aactgtgctc aacccttact    2580
caagataatc catactagag aaacactata atgtaaaaa tgtgaaaagt tttattcaaa     2640
atatcaaact tatgagtcac ctaggggttc atagaaaaag gaagtttgca gatgcaataa    2700
atgtgaggaa gtatttaata aaaaatgaag tctaaatgtg tcagagaatt tatgtgagaa    2760
aggactaaag cacagacact ttcagccttt atactaaata agagtatttt ttgtacagaa    2820
taatctaaag gcaaaataat tagataattt atttgcttat atgttttaaa gtagcaagaa    2880
cattgatgtt ttgacaggta tatttcatag atacttcatt tgtatttaca gtatttgagg    2940
tttttggaaa gcaaatatta tttatataat tcagctttca aatctgttgc tgcttttcct    3000
taatccgtgg tgttcatgtg aaaatatgtg ttctgttttt ttttctgcat cagaacaatg    3060
tgaggtcatt ctacgttaat atcattaata tcagcatttt tcatggaagt ttaatgccaa    3120
atgtaaaaca catgaaaatt tttaaaaata tgctctttgt gtttgaataa agtagtaatg    3180
cacgtaaaca aaaaaaaaaa aaaaa                                          3205
```

<210> SEQ ID NO 13  
<211> LENGTH: 2357  
<212> TYPE: DNA  
<213> ORGANISM: Homo Sapiens

<400> SEQUENCE: 13

```
gagccgggct actctgagaa gaagacacca agtggattct gcttccctg ggacagcact       60 gagcgagtgt ggagagaggt acagccctcg gcctacaagc tctttagtct tgaaagcgcc    120
acaagcagca gctgctgagc catggctgaa ggggaaatca ccaccttcac agccctgacc    180
gagaagttta atctgcctcc agggaattac aagaagccca aactcctcta ctgtagcaac    240
gggggccact tcctgaggat ccttccggat ggcacagtgg atgggacaag gacaggagc     300 gaccagcaca ttcagctgca gctcagtgcg gaaagcgtgg gggaggtgta tataaagagt    360
accgagactg gccagtactt ggccatggac accgacgggc ttttatacgg ctcacagaca    420
ccaaatgagg aatgtttgtt cctggaaagg ctggaggaga accattacaa cacctatata    480
tccaagaagc atgcagagaa gaattggttt gttggcctca agaagaatgg gagctgcaaa    540
cgcggtcctc ggactcacta tggccagaaa gcaatcttgt ttctcccct gccagtctct    600 tctgattaaa gagatctgtt ctgggtgttg accactccag agaagtttcg aggggtcctc    660
acctggttga cccaaaaatg ttcccttgac cattggctgc gctaacccc agcccacaga    720 gcctgaattt gtaagcaact tgcttctaaa tgcccagttc acttctttgc agagccttt     780 accctgcac  agtttagaac agagggacca aattgcttct aggagtcaac tggctggcca    840
```

-continued

```
gtctgggtct gggtttggat ctccaattgc ctcttgcagg ctgagtccct ccatgcaaaa      900
gtggggctaa atgaagtgtg ttaaggggtc ggctaagtgg acattagta actgcacact       960
atttccctct actgagtaaa ccctatctgt gattccccca acatctggc atggctccct     1020
tttgtccttc ctgtgccctg caaatattag caaagaagct tcatgccagg ttaggaaggc    1080
agcattccat gaccagaaac agggacaaag aaatccccc ttcagaacag aggcatttaa     1140
aatgaaaag agagattgga ttttggtggg taacttagaa ggatggcatc tccatgtaga     1200
ataaatgaag aaagggaggc ccagccgcag gaaggcagaa taaatccttg ggagtcatta    1260
ccacgccttg accttcccaa ggttactcag cagcagagag ccctgggtga cttcaggtgg    1320
agagcactag aagtggtttc ctgataacaa gcaaggatat cagagctggg aaattcatgt    1380
ggatctgggg actgagtgtg ggagtgcaga gaaagaaagg gaaactggct gaggggatac    1440
cataaaaaga ggatgatttc agaaggagaa ggaaaaagaa agtaatgcca cacattgtgc    1500
ttggcccctg gtaagcagag gctttgggt cctagcccag tgcttctcca acactgaagt     1560
gcttgcagat catctgggga cctggtttga atggagattc tgattcagtg ggttggggc     1620
agagtttctg cagttccatc aggtcccccc caggtgcagg tgctgacaat actgctgcct    1680
tacccgccat acattaagga gcagggtcct ggtcctaaag agttattcaa atgaaggtgg    1740
ttcgacgccc cgaacctcac ctgacctcaa ctaacccta aaaatgcaca cctcatgagt    1800
ctacctgagc attcaggcag cactgacaat agttatgcct gtactaagga gcatgatttt    1860
aagaggcttt ggccaatgcc tataaaatgc ccatttcgaa gatatacaaa acatacttc    1920
aaaaatgtta aaccccttacc aacagctttt cccaggagac catttgtatt accattactt   1980
gtataaatac acttcctgct taaacttgac ccaggtggct agcaaattag aaacaccatt   2040
catctctaac atatgatact gatgccatgt aaaggccttt aataagtcat tgaaatttac    2100
tgtgagactg tatgtttta ttgcatttaa aaatatatag cttgaaagca gttaaactga     2160
ttagtattca ggcactgaga atgatagtaa taggatacaa tgtataagct actcacttat    2220
ctgatactta tttacctata aaatgagatt tttgttttcc actgtgctat tacaaatttt    2280
cttttgaaag taggaactct taagcaatgg taattgtgaa taaaaattga tgagagtgtt   2340
aaaaaaaaaa aaaaaaa                                                   2357
```

<210> SEQ ID NO 14
<211> LENGTH: 2380
<212> TYPE: DNA
<213> ORGANISM: Homo Sapiens

<400> SEQUENCE: 14

```
tcggccaccg ctcgcttcaa tatgctgcc cccagggaga gacgaggcta ccatgaagga       60
gccgagcgca gaccctgagt ccgtcaccca tggatcgcag cgcggagttc aggaaatgga     120
aggcgcaatg tttgagcaaa gcggacctca gccggaaggg cagtgttgac gaggatgtgg    180
tagagcttgt gcagtttctg aacatgcgag atcagttttt caccaccagc tcctgcgctg    240
gccgcatcct actccttgac cggggtataa atggtttttga ggttcagaaa caaaactgtt    300
gctggctact ggttacacac aaactttgtg taaaagatga tgtgattgta gctctgaaga    360
aagcaaatgg tgatgccact ttgaaatttg aaccatttgt tcttcatgtg cagtgtcgac    420
aattgcagga tgcacagatt ctgcattcca tggcaataga ttctggtttc aggaactctg    480
gcataacggt gggaaagaga ggaaaaacta tgttggctgt ccggagtaca catggcttag    540
```

| | |
|---|---|
| aagttccatt aagccataag ggaaaactga tggtgacaga ggaatatatt gacttcctgt | 600 |
| taaatgtggc aaatcaaaaa atggaggaaa acaagaaaag aattgagagg ttttacaact | 660 |
| gcctacagca tgctttggaa agggaaacga tgactaactt acatcccaag atcaaagaga | 720 |
| aaaataactc atcatatatt cataagaaaa aagaaaccc agaaaaaaca cgtgcccagt | 780 |
| gtattactaa agaaagtgat gaagaacttg aaaatgatga tgatgatgat ctaggaatca | 840 |
| atgttaccat cttccctgaa gattactaag ctttggttct gatgtgtctt ggccgtaatg | 900 |
| tttctagtag gttttataaa gctgctcttc ataagagtat tttagtttgt tgagtgtatc | 960 |
| agccattcat aagccagtaa tgacaagtgc agagcttcaa actataactt tgttgcccag | 1020 |
| aggatgtgca gttgtcatct aagctctcag cagtacccgg cttatcctac gacttcacct | 1080 |
| gaaatgctat agttatccct acttttttac cagtttctcc cagaagcacc tgcttaataa | 1140 |
| atcaaagatg tttgaatggt gtcttattct gaaataacct gacctaagac aggtatttag | 1200 |
| attattttgg atacattttg aaagggata gcataaatat tttaagtaaa aagaccttta | 1260 |
| ttttaaataa tagtggatat tttaatgctg gaaattagca ttatagttga tatgccagaa | 1320 |
| attatatctt tggttgtgat ttaaacttat gctataaact aaattaatga tgtaaataca | 1380 |
| tagttttaaa cattcttta gggacatgta acttttaagt atcacttcaa taatacgtat | 1440 |
| tattatagga acaaagattt gggaataatt gattacaggt gaggaagtac tggaattcca | 1500 |
| gttcaaggag ataccatttc atttaggact aaaaggacaa gatacaagtt cacatgatgg | 1560 |
| gaaaaatcag aaaacctctc gcagacaaag ggtatataat ggatatgagg catcaaaaag | 1620 |
| catggtatat tcagtgatgg ggaatagtcc agaaaggctg aaacacagca tgtgatgcga | 1680 |
| gtcaaggtag ttgatgccca actgtgaagg gccgttctaa tctagcatgg aggtagacag | 1740 |
| tgtttcctta atatggctgc atatcagaat tacctaggtc aggacgaggc atggagatgc | 1800 |
| tactttaata ggccctgccg cagatcttcc aaaccagaat cttaatcctg gagtctagga | 1860 |
| atctttattt ttcacacaac tcatccaagt ggttctgata aaatcagtcc agcacttta | 1920 |
| gaacccactg ataacagact tattcctgga gacagcattt gaggaggaat tgaagatttt | 1980 |
| tctaatgaaa agaaaaggg tcacatgaac agatgttgca gtgtacctgt gccagggatt | 2040 |
| tcatgtgtac actttatagg agaataagca agagcttagg taagttatag tccttaccat | 2100 |
| tgggtctaag gcagtttcca ggaaagcatg gcaactcgtt cagctatgta agttgaactc | 2160 |
| tgtaccactt gggagggaac attcccctag atgacaatgt cagtggcact cgaagttgtg | 2220 |
| cagtgcacat tcttatctac caacatatac agcagtcctt ctgggaagga aatttgggca | 2280 |
| ggaaagggaa ctcacagtgt cggaatgcct ggagcatttc ttctagtctg gtggacagaa | 2340 |
| tatgaaagta tctgcctggc agtgcagtaa atgaaaagag | 2380 |

<210> SEQ ID NO 15
<211> LENGTH: 2122
<212> TYPE: DNA
<213> ORGANISM: Homo Sapiens

<400> SEQUENCE: 15

| | |
|---|---|
| tctgatgttc caaaaagtag aatatatata gagatcaaac attcaaaaga tacattctct | 60 |
| cctaagctca aaggttatat ttttattggg tagaacagta taggtaagtt gacatgaaat | 120 |
| tgcatcctgc accatgacca cattagtaat atcagaactt ttgagaaata ctggattttg | 180 |
| aatggtttga gactaattct ttaaaaatta ggctgagcaa cactcacaat ccaaaaatat | 240 |
| tcatattaag acttacacat ttgaagaatg gtacattttg tataaaatca tatttgatac | 300 |

```
cattatttcc acatacctac ttttcatctg ttgcttaatt ttttctttt   agagttcttg    360 ctcaacttta tatggaacaa gtcttattat ttttgaaaga gtgtttagta ccttgtatta    420
agaaacttgg ccaagcgtgg tggttcactc ctgtaatccc agcactttgg gaggtcgagg    480
cgggcagatt gcttgaggcc aggagattga gaccagcctg gcaacatggt gaaatcctg    540 tctctaaaat ttaaaaaaaa gaagaagaag aaactcgaga ccacatcttc aaaaaacaac    600
tttgcagtat ttgaatttta cattatactg cccttcattt ctgacagcca ataaacttta    660
ttgatattta ttgcttttgt agttgttata actaataatt tctttgaaaa tgtgttgtag    720
tttatgtttt tcaaagggtt ttggtagtgt tgtgataga  atggttttgc atatgattat    780
tataggggat atatttatag agctctactt gtatactttg tgacttacat tatgaaaact    840
tcaaagttct caatccatac agttagtatt tgtatccaga gtgtttaaga aaaaaatctg    900
tcttatattt ttagtatata ggagccagtg ttgcttctat ttgttttgaa tacaaattcc    960
agttttcttt gcatattaga tcccacatgt aagaaacaac cttaaacaat aatttgtatg   1020
ctggtaatat ttggacaagt gccataaatt aatgtatatt gtactttctg aatagatttt   1080
ctctaatcat agcaaaattt atttcaaaac tacaactctt tgaattattc cgctataata   1140
aaatttagtt ataaaattat gtggcactac tgaaaatcta aaggataatc tgaagaatga   1200
gtaagacaga tattgataga aattttagt  attttcagaa tgtttgggtt catacacata   1260
agtgaaatca ttttaaaaac taggggctgg gcacagtggc tcacaccagt aatcctagca   1320
ctttgggagg ccaaggcagg aggattgctt gagcccagga gtttgagacc agcctgggca   1380
acatagcaag ccccttat  ctataaaat  aataataact aggtaccatt gtgaaaata    1440 ataactaggg attgattata gtatctttac tctgtattca caaatctctg tattcctgaa   1500
catatttaat cctttgattt acctctgact aggtttgtca ttgtaatccc tgggctgctt   1560
aggaggatac catttggttt gatgaaaaag ctggaatgat aatagctcaa actcttttga   1620
gcatttagta catgcttggc actgttctat atgtcttaag ttattcactc ttgtatttaa   1680
ccatcaacac tcttatgagg taaatatccc gcaattactt ttgcgccaac ctagtaccac   1740
tacagacaag gaaacagatg cagagaggct aagttacaag ggcacacagc cataaacttt   1800
ggatctgtgg agtgactggg cttcagagtc ctcttcctga ctgctgttcc tatgtctttt   1860
gcaaagagaa gtctttgaca ggtatatgct ttattaaaat catgtttaga aagaaatgag   1920
agaatagaat tagaaaaagg aatgactgta ggcttcgatg aaaatgactt tgtgactag    1980 gtgaaaattg tttggctggg tatcctggaa aattgtcttc tgggaatatc tatattccag   2040
ggttcacttt tgtcatagaa ttgtttcttg gcccatttaa gagagatact tgtttatta    2100 ataaatcaaa cgttttaatt tt                                             2122

<210> SEQ ID NO 16
<211> LENGTH: 2253
<212> TYPE: DNA
<213> ORGANISM: Homo Sapiens

<400> SEQUENCE: 16
attcattaag ataataggat catgattttt cattaactca tttgattgat attatctcca     60 tgcattttt  atttctttta gaaatgtaat tatttgctct agcaatcatt gctaacctct    120
agtttgtaga aaatcaacac tttataaata cataattatg atattatttt tcattgtatc    180
actgttctaa aaataccata tgattatagc tgccactcca tcaggagcaa attcttctgt    240
```

| | |
|---|---|
| taaaagctaa ctgatcaacc ttgaccactt ttttgacatg tgagatcaaa gtgtcaagtt | 300 |
| ggctgaggtt ttttggaaag ctttagaact aataagctgc tggtggcagc tttgtaacgt | 360 |
| atgattatct aagctgattt tgatgctaaa ttatcttagt gatctaaggg gcagtttagt | 420 |
| gaagatggaa tcttgtattt aaaatagcct tttaaaattt gttttgtggt gatgattttg | 480 |
| acaacttcca tctttaggag ttatataatc accttgattt tagtttcctg atgtttggac | 540 |
| tatttataat caaggacacc aagcaagcat aagcatatct atatttctga ctggtgtctc | 600 |
| tttgagaagg atgggaagta gaaaaaaaaa aagaaagaa aggaaaggaa gagaggagag | 660 |
| aagaaggcag ggatctccac tatgtatgtt tcactttag aactgttgag cccatgctta | 720 |
| attttaatct agaagtcttt aaatggtgag acagtgactg gagcatgcca atcagagagc | 780 |
| atttgtcttc agaaaaaaaa aaaatctgag tttgagacta gcctggccaa catgttgaaa | 840 |
| ccccatatct actaaaaata caaaaattag cctggtgtgg tggcgcacgc ctgtagtccc | 900 |
| agctactctg gagcctgagg aacgtgaatc gcttgaaccc agaagacaga ggttgcagtg | 960 |
| agctgagatg gcactattgc actccagcct gggtgacaca gcaagactct gtctcaaaaa | 1020 |
| aaaaaaaaaa aaaaaaggaa aaaaaagaaa gaaagaaagt cccagcacac ctagataatt | 1080 |
| taccgagctc ttcagcaaaa accatgttac atacagcata ttccaaagaa atgaactctt | 1140 |
| ctgcaattta aattataagt aatatgttat tttggatcct agagaaacca tttctctac | 1200 |
| atttcatgag catggttaga aaagagttta caagaattag gaagagggaa caattttaat | 1260 |
| ggtcagaaaa gaataaaatt tattctagtt caagaagtgc acacaaagaa tatgcattaa | 1320 |
| tctaacaact atgagattaa atctttcaaa aaggtcaaag gaggattgag aagtttacag | 1380 |
| agatgtccac ggcatttat atcaatctca aaggtaaggt ctgcattttt ataaaccaac | 1440 |
| ttaaacttct gttgagatag gatattttgt tttcaagcca gaattaccat taatcaaata | 1500 |
| tgttttaatt atctgattta gatgatctac tttttatgcc tggcttactg taagttttt | 1560 |
| attctgatac acagttcaaa catcattgca acaaagaagt gcctgtattt agatcaaagg | 1620 |
| caagactttc tatgtgtttg ttttgcataa taatatgaat ataatttaag tctatcaata | 1680 |
| gtcaaaacat aaacaaaagc taattaactg gcactgttgt cacctgagac taagtggatg | 1740 |
| ttgttggctg acatacaggc tcagccagca gagaaagaat tctgaattcc ccttgctgaa | 1800 |
| ctgaactatt ctgttacata tggttgacaa atctgtgtgt tatttctttt ctacctacca | 1860 |
| tatttaaatt tatgagtatc aaccgaggac atagtcaaac cttcgatgat gaacattcct | 1920 |
| gattttttgc ctgattattc tctgttgagc tctacttgtg gtcattcaag attttatgat | 1980 |
| gttgaaagga aaagtgaata tgacctttaa aaattgtatt ttgggtgatg atagtctcac | 2040 |
| cactataaaa ctgtcaatta ttgcctaatg ttaaagatat ccatcattgt gattaattaa | 2100 |
| acctataatg agtattctta atggagaatt cttaatggat ggattatccc ctgatctttt | 2160 |
| ctttaaaatt tctctgcaca cacaggactt ctcattttcc aataaatggg tgtactctgc | 2220 |
| cccaatttct agggaaaaaa aaaaaaaaa agg | 2253 |

<210> SEQ ID NO 17
<211> LENGTH: 5243
<212> TYPE: DNA
<213> ORGANISM: Homo Sapiens

<400> SEQUENCE: 17

| | |
|---|---|
| agcgtgagac tcgcgccctc cggcacggaa aaggccaggc gacaggtgtc gcttgaaaag | 60 |
| actgggcttg tccttgctgg tgcatgcgtc gtcggcctct gggcagcagg tttacaaagg | 120 |

```
aggaaaacga cttcttctag atttttttt cagtttcttc tataaatcaa aacatctcaa      180
aatggagacc taaaatcctt aaagggactt agtctaatct cgggaggtag ttttgtgcat      240
gggtaaacaa attaagtatt aactggtgtt ttactatcca aagaatgcta attttataaa      300
catgatcgag ttatataagg tataccataa tgagtttgat tttgaatttg atttgtggaa      360
ataaaggaaa agtgattcta gctggggcat attgttaaag cattttttc agagttggcc       420 aggcagtctc ctactggcac attctcccat tatgtagaat agaaatagta cctgtgtttg      480
ggaaagattt taaatgagt gacagttatt tggaacaaag agctaataat caatccactg        540
caaattaaag aaacatgcag atgaaagttt tgacacatta aaatacttct acagtgacaa      600
agaaaaatca agaacaaagc tttttgatat gtgcaacaaa tttagaggaa gtaaaaagat      660
aaatgtgatg attggtcaag aaattatcca gttatttaca aggccactga tattttaaac      720
gtccaaaagt ttgtttaaat gggctgttac cgctgagaat gatgaggatg agaatgatgg      780
ttgaaggtta cattttagga aatgaagaaa cttagaaaat taatataaag acagtgatga      840
atacaaagaa gattttttata caatgtgta aaattttttgg ccagggaaag gaatattgaa      900
gttagataca attacttacc tttgagggaa ataattgttg gtaatgagat gtgatgtttc      960
tcctgccacc tggaaacaaa gcattgaagt ctgcagttga aaagcccaac gtctgtgaga      1020
tccaggaaac catgcttgca aaccactggt aaaaaaaaaa aaaaaaaaaa aaaaagcca     1080 cagtgacttg cttattggtc attgctagta ttatcgactc agaacctctt tactaatggc      1140
tagtaaatca taattgagaa attctgaatt ttgacaaggt ctctgctgtt gaaatggtaa      1200
atttattatt ttttttgtca tgataaattc tggttcaagg tatgctatcc atgaaataat      1260
ttctgaccaa aactaaattg atgcaatttg attatccatc ttagcctaca gatggcatct      1320
ggtaactttt gactgtttta aaaataaat ccactatcag agtagatttg atgttggctt       1380
cagaaacatt tagaaaaaca aaagttcaaa aatgttttca ggaggtgata agttgaataa      1440
ctctacaatg ttagttcttt gagggggaca aaaaatttaa aatctttgaa aggtcttatt      1500
ttacagccat atctaaatta tcttaagaaa attttttaaca aagggaatga aatatatatc      1560
atgattctgt ttttccaaaa gtaacctgaa tatagcaatg aagttcagtt ttgttattgg      1620
tagtttgggc agagtctctt tttgcagcac ctgttgtcta ccataattac agaggacatt      1680
tccatgttct agccaagtat actattagaa taaaaaaact taacattgag ttgcttcaac      1740
agcatgaaac tgagtccaaa agaccaaatg aacaaacaca ttaatctctg attatttatt      1800
ttaaatagaa tatttaattg tgtaagatct aatagtatca ttatacttaa gcaatcatat      1860
tcctgatgat ctatgggaaa taactattat ttaattaata ttgaaaccag gttttaagat      1920
gtgttagcca gtcctgttac tagtaaatct ctttatttgg agagaaattt tagattgttt      1980
tgttctcctt attagaagga ttgtagaaag aaaaaaatga ctaattggag aaaaaattggg      2040 gatatatcat atttcactga attcaaaatg tcttcagttg taaatcttac cattattta       2100 cgtacctcta agaaataaaa gtgcttctaa ttaaaatatg atgtcattaa ttatgaaata     2160
cttcttgata acagaagttt taaaatagcc atcttagaat cagtgaaata tggtaatgta      2220
ttattttcct cctttgagtt aggtcttgtg ctttttttc ctggccacta aatttcacaa       2280
tttccaaaaa gcaaataaa catattctga atatttttgc tgtgaaacac ttgacagcag      2340
agctttccac catgaaaaga agcttcatga gtcacacatt acatctttgg gttgattgaa      2400
tgccactgaa acattctagt agcctggaga agttgaccta cctgtggaga tgcctgccat      2460
```

```
taaatggcat cctgatggct aatacacat cactcttctg tgaagggttt taattttcaa    2520
cacagcttac tctgtagcat catgtttaca ttgtatgtat aaagattata caaaggtgca    2580
attgtgtatt tcttccttaa aatgtatcag tataggattt agaatctcca tgttgaaact    2640
ctaaatgcat agaaataaaa ataataaaaa attttcatt ttggcttttc agcctagtat     2700
taaaactgat aaaagcaaag ccatgcacaa aactacctcc ctagagaaag gctagtccct    2760
tttcttcccc attcatttca ttatgaacat agtagaaaac agcatattct tatcaaattt    2820
gatgaaaagc gccaacacgt ttgaactgaa atacgacttg tcatgtgaac tgtaccgaat    2880
gtctacgtat tccactttc ctgctggggt tcctgtctca gaaaggagtc ttgctcgtgc     2940
tggtttctat tacactggtg tgaatgacaa ggtcaaatgc ttctgttgtg gcctgatgct    3000
ggataactgg aaaagaggag acagtcctac tgaaaagcat aaaaagttgt atcctagctg    3060
cagattcgtt cagagtctaa attccgttaa caacttggaa gctacctctc agcctacttt    3120
tccttcttca gtaacaaatt ccacacactc attacttccg ggtacagaaa acagtggata    3180
tttccgtggc tcttattcaa actctccatc aaatcctgta aactccagag caaatcaaga    3240
tttttctgcc ttgatgagaa gttcctacca ctgtgcaatg aataacgaaa atgccagatt    3300
acttactttt cagacatggc cattgacttt tctgtcgcca acagatctgg caaaagcagg    3360
cttttactac ataggacctg agacagagt ggcttgcttt gcctgtggtg aaaattgag      3420
caattgggaa ccgaaggata atgctatgtc agaacacctg agacattttc ccaaatgccc    3480
atttatagaa aatcagcttc aagacacttc aagatacaca gtttctaatc tgagcatgca    3540
gacacatgca gcccgcttta aaacattctt taactggccc tctagtgttc tagttaatcc    3600
tgagcagctt gcaagtgcgg ttttttatta tgtgggtaac agtgatgatg tcaaatgctt    3660
ttgctgtgat ggtggactca ggtgttggga atctggagat gatccatggg ttcaacatgc    3720
caagtggttt ccaaggtgtg agtacttgat aagaattaaa ggacaggagt tcatccgtca    3780
agttcaagcc agttaccctc atctacttga acagctgcta tccacatcag acagcccagg    3840
agatgaaaat gcagagtcat caattatcca ttttgaacct ggagaagacc attcagaaga    3900
tgcaatcatg atgaatactc ctgtgattaa tgctgccgtg gaaatgggct ttagtagaag    3960
cctggtaaaa cagacagttc agagaaaaat cctagcaact ggagagaatt atagactagt    4020
caatgatctt gtgttagact tactcaatgc agaagatgaa ataagggaag aggagagaga    4080
aagagcaact gaggaaaaag aatcaaatga tttattatta atccggaaga atagaatggc    4140
acttttcaa catttgactt gtgtaattcc aatcctggat agtctactaa ctgccggaat    4200
tattaatgaa caagaacatg atgttattaa acagaagaca cagacgtctt tacaagcaag    4260
agaactgatt gatacgattt tagtaaaagg aaatattgca gccactgtat tcagaaactc    4320
tctgcaagaa gctgaagctg tgttatatga gcatttattt gtgcaacagg acataaaata    4380
tattcccaca gaagatgttt cagatctacc agtggaagaa caattgcgga gactacaaga    4440
agaaagaaca tgtaaagtgt gtatggacaa agaagtgtcc atagtgttta ttccttgtgg    4500
tcatctagta gtatgcaaag attgtgctcc ttctttaaga aagtgtccta tttgtaggag    4560
tacaatcaag ggtacagttc gtacatttct ttcatgaaga agaaccaaaa catcgtctaa    4620
actttagaat taatttatta aatgtattat aactttaact tttatcctaa tttggtttcc    4680
ttaaaatttt tatttatta caactcaaaa aacattgttt tgtgtaacat atttatatat     4740
gtatctaaac catatgaaca tatatttttt agaaactaag agaatgatag gcttttgttc    4800
ttatgaacga aaaagaggta gcactacaaa cacaatattc aatcaaaatt tcagcattat    4860
```

```
tgaaattgta agtgaagtaa aacttaagat atttgagtta acctttaaga attttaaata    4920
ttttggcatt gtactaatac cgggaacatg aagccaggtg tggtggtatg tgcctgtagt    4980
cccaggctga ggcaagagaa ttacttgagc ccaggagttt gaatccatcc tgggcagcat    5040
actgagaccc tgccttttaaa aacaaacaga acaaaaacaa acaccaggg acacatttct     5100 ctgtcttttt tgatcagtgt cctatacatc gaaggtgtgc atatatgttg aatgacattt    5160
tagggacatg gtgtttttat aaagaattct gtgagaaaaa atttaataaa gcaacaaaaa    5220
ttactcttaa aaaaaaaaaa aaa                                            5243

<210> SEQ ID NO 18
<211> LENGTH: 425
<212> TYPE: DNA
<213> ORGANISM: Homo Sapiens

<400> SEQUENCE: 18
gctctgagga tcccccgtat agcaccggga atctggcta gagttgatcg cagatgtact       60
tgttttggga atatatgaga aagaaactg ctgagcaggt cagtaaagaa cagtccattt      120
cagctgcagg acagttctct ttcccgggac aagcctacat agcctccaag ggagccaaac     180
tatcccttcc atgcaacaag acaccttgca tggatactct agccatgact tgcttttgga    240
caaaaatcaa ctgctaacgt ttttcatctc taatatcatt aacaccatgg agaaaaaaga    300
aaaaaattca accctagaaa acttgacaac gagaataaga aaatccacaa ggaaaggtca    360
tgctaaaact gatttgacag ttgttccatc accgcctacc acggtgctat aacggggtac    420
cgagc                                                                425

<210> SEQ ID NO 19
<211> LENGTH: 1958
<212> TYPE: DNA
<213> ORGANISM: Homo Sapiens

<400> SEQUENCE: 19
actggtgctg caagtcgctg agctgacagt tgtgccgagg actgtcacca ttgggcaggc     60
atggtggcca gctcctcact tggctgaggt ccagggatgg acacaggttc gctgaacgcg    120
gccagcctga gggaggagca gctccacctg tccttgctgg tgtccagcgg ctggagaaca    180
atcagcttcc acgtggtgcc cgtggtgaga aggaagcttg gggcgcctgc cctgaggggg    240
gtgcagcaga tgcccggatt ccctgagggc agcttgagaa ggatcctcag ccaaggggtg    300
gacctggtgc cggccagcgc ccagctctgg aggacctcca ctgactacct gctcacgagg    360
ctgctggggg agctgggctc cctgcagggt catcgcctgg acagcctctc catcctcgac    420
cgggtcaacc acgagagctg gcgtgacagt ggccagactg acggcctgac ctttggccac    480
ctgaagatgg tgctgctgtg ggcctctgtg ctcttcctgg cgcccgagga ctgggcagaa    540
ctgcagggcg ccgtgtaccg cctgctggtg gtgctgctct gttgcctggc cacgcggaag    600
ctgccccact tcctccaccc gcagcgcaac ctgctgcagg cagcggcct ggaccttggt     660 gccatctacc agcgcgtgga gggcttcgcc agccagcccg aggcggccct gcgcatccac    720
gccacccacc tgggccgcag ccccgcgcg cgcatcggct ccgggctcaa ggcgctcctg      780
cagctgccag ccagtgaccc cacttactgg gccactgcct acttcgacgt cctgctggac    840
aagttccagg tcttcaacat ccaggataag gaccggatcc tgccatgca gagcatcttc      900 cagaagacca ggactctggg aggcgaggag agctgagctg ggccacctgg tctcagccac    960
```

-continued

| | |
|---|---|
| ctgttcttgg ctccccaaca gactctgcac tgcaccatgg gaggctcctg ggatgtttgg | 1020 |
| aagaagaaac gggcttctcc ttgagggggt agtggaggga ttttgtcccc agcagtggcc | 1080 |
| tctgagagtc tttcagtgcc tggtggggca gggcaggcct cttggagcac ctcctccctg | 1140 |
| ggtcagggcc tggatgcagg tgccaagctc tccatgtggt gcatgttgac ccagccacgt | 1200 |
| ggtgttgtca agcaaacagc atcggcagga gacctggagc tgaggacttg ccctgcctg | 1260 |
| cactgtatgc cattccttgg tgacgaaatg ctgtatattt ggttttgaaa aaatgaatgt | 1320 |
| gctgggtata cacagcagaa agggtactgt ccacttttg tatatcagtg tggaaaatat | 1380 |
| ttcccctaga agtagaaaag gctcatgtgc tgatggataa ttttgagtct tctccattct | 1440 |
| ctgtgaatga ccccttccc caggcatccc cacctcctac ctcgttctta gagcaaacta | 1500 |
| aagccaactg agggtgcaca cacagccatg agcccacctg cccaggacta ctcccatctg | 1560 |
| cttcttcccg tccccgtgga agtggcccct gatatggatt gtatctgtat ccccacccaa | 1620 |
| atctcaggta gaattggatc tgtgtcccca cccaagtctc aggtagactt gtaatcccca | 1680 |
| gtgttggagg aggggcccag tgggaggtga ttggatcatg gggtggatt tctcccttac | 1740 |
| tgttctcatg atagtgagtg agttctcatg agatctggtt ttttgagtgt gtggcccctc | 1800 |
| cccctctcct tttgctctct tcctctttct ccggccatgt aagatatgcc tccttctcct | 1860 |
| tcaccttcca ccatgattgt cagtttcctg aggcctccca gccatgcttc ctgtatagcc | 1920 |
| tgcgggactg tgagtcaatt aaacctcttt attcatta | 1958 |

<210> SEQ ID NO 20
<211> LENGTH: 3347
<212> TYPE: DNA
<213> ORGANISM: Homo Sapiens

<400> SEQUENCE: 20

| | |
|---|---|
| agcctcggcg tgcccccagg accggtaaag ttcctctcgc cagccgcatc catgcttctg | 60 |
| gcgcggatga acccgcaggt gcagcccgag aacaacgggg cggacacggg tccagagcag | 120 |
| ccccttcggg cgcgcaaaac tgcggagctg ctggtggtga aggagcgcaa cggcgtccag | 180 |
| tgcctgctgg cgccccgcga cggcgacgcg cagccccggg agacctgggg caagaagatc | 240 |
| gacttcctgc tgtccgtagt cggcttcgca gtggacctgg ccaacgtgtg gcgcttcccc | 300 |
| tacctctgct acaagaacgg cggcggtgcc ttcttgatcc cgtacacact gttccttatc | 360 |
| atcgcgggga tgcccctgtt ctacatggag ctggctctgg acagtacaa ccgggagggg | 420 |
| gctgccaccg tttggaaaat ctgcccattc ttcaaaggcg ttggctatgc tgtcatcctg | 480 |
| atcgccctgt acgttggctt ctactacaac gtcatcatcg cctggtcact ctactacctc | 540 |
| ttctcctcct tcaccctcaa cctgccctgg accgactgtg ccacacctg aacagcccc | 600 |
| aactgtaccg accccaagct cctcaatggc tccgtgcttg caaccacac caagtactcc | 660 |
| aagtacaagt tcacgccggc agccgagttt tatgagcgtg gtgtcctgca ccttcacgag | 720 |
| agcagcggga ttcatgacat cggcctgccc cagtggcagc tcttgctctg tctgatggtc | 780 |
| gtcgtcatcg tcttgtattt tagcctctgg aaaggggtga agacatcagg aaaggtggtg | 840 |
| tggatcacag ccacgctgcc ttacttcgtg ctgttcgtgc tcctggtcca tggcgtcacg | 900 |
| ctgcccggag cctccaatgg catcaatgcc tacctgcaca tcgacttcta ccgcttgaaa | 960 |
| gaggccacgg tatggattga tgccgcaact cagatatttt tttccttggg ggctggattt | 1020 |
| ggagtattga ttgcatttgc cagttacaac aaatttgaca caactgttta cagggatgcc | 1080 |
| ctgctgacca gcagcatcaa ctgtatcacc agcttcgtct ctgggttcgc catcttctcc | 1140 |

```
atccttggtt acatggccca tgaacacaag gtcaacattg aggatgtggc cacagaagga    1200
gctggcctag tgttcatcct gtatccagag gccatttcta ccctgtctgg atctacattc    1260
tgggctgttg tgttttttcgt catgctcctg gcgctgggcc ttgacagctc aatgggaggc    1320
atggaggctg tcatcacggg cctggcagat gacttccagg tcctgaagcg acaccggaaa    1380
ctcttcacat ttggcgtcac cttcagcact ttccttctcg ccctgttctg cataaccaag    1440 ggtgaattt acgtcttgac cctcctggac acctttgctg cgggcacctc catccttttt    1500
gctgtcctca tggaagccat cggagtttcc tggttttatg gagtggacag gttcagcaac    1560
gacatccagc agatgatggg gttcaggccg ggtctatact ggagactgtg ctggaagttc    1620
gtcagtcctg ccttcctcct gttcgtggtt gtggtcagca tcatcaactt caagccactc    1680
acctacgacg actacatctt cccgccctgg gccaactggg tggggtgggg catcgccctg    1740
tcctccatgg tcctggtgcc catctacgtc atctataagt tcctcagcac gcagggctct    1800
ctttgggaga actgccta tggcatcacg ccagagaacg agcaccacct ggtggctcag    1860
agggacatca gacagttcca gttgcaacac tggctggcca tctgagcctg cctggaggag    1920
aaggaggaac cccatgcca atgtccaggt cacaggcatc cgctgcgctc ccacctcgga    1980
caccatcttg ggattcctcc cctggaagtt gtcctttctg atcctctctt cttttcccat    2040
ttacaaatga tttcgtgact gtagtttttg ttcaccttct gtgcatctgg cctgggggct    2100
gttagctcag aggagaggag caaacaggaa aatgacttct gttctgtccc cgctgttttg    2160
ggggaagtct ctcccacttt gggatcctgc tgaagctagg ttcatgaggt cggaaatccc    2220
caccacattt gcctagactt tgggcacagg agttcttagt ccaccaaatc agagagagga    2280
tgggcttttg atcagatacc cctcccaaaa aaaaaaaaa ctaaaactaa agcaaaaatc    2340
aaacaaaatc tggctgagtt tagtggggtg gttggggaag gtacatagac cctcctcttg    2400
cccaccctag acagccctct catgtctgaa cctcagcctg ggagttagat ttatttgtct    2460
ctaaaatgaa gtcagtggat agatgctttg agggattttg agtagaaaca ttcatagtta    2520
attttcactc tggccaatct gagtttgatg tgtgtgttct ggaacattcc tccagctttt    2580
ggtggtcaga tggcccagag atatggggga caggaggaag agggtaaatg aaccacagtg    2640
agcaggttct aggaggtacc tgcatcagac aagctggtgg aggccacgtg gcaagccaca    2700
tctactgagg cctcatgctg ctcttgctct gtaagcacg gagcccagaa acccatctgc    2760
acttcctgag acctgcctgg ggaaacgggg gcagggacca agtgaggcct catgtgtgtc    2820
ttcaccgtgc tgtcctcaca aggccaggtg ggtgcccaaa gggagcctga caggctgttg    2880
tgttaattta ttgttcttgc acacctgcac agcctccctc tggggatccc acctggagtg    2940
gaccaggggt cttgagaaat ggagagttgg ctgcaaaaac tctcatgcac tagatgtggc    3000
accttggagg gcagggtgag acaagcagcc cagaaatact ctctcaagtg gaggggagaa    3060
ttttgagagt ggatgaaca gtttggtggt ttcagagaat ttctaggttt ctacttggat    3120
ctacttctga tacaaacttg cacttggtgc cctctggtgg tgtttagttt tagttccgta    3180
agagaaatga ttcctagttt gctaaattgg tggcatcttt gggaggggtt tctgtttatg    3240
gttagagtct cttacacccct tgttggaggg attcttattc tgactgtggg agctcctgtt    3300
gcgggatctt gggaaaaaat aaagaagccg ctgcattcgc acgtcaa           3347
```

<210> SEQ ID NO 21
<211> LENGTH: 11876
<212> TYPE: DNA

<213> ORGANISM: Homo Sapiens

<400> SEQUENCE: 21

```
gggctgggcc tccctteccc ataacactga gctgctctgc tgggccaacc gtgctcctgg      60
gccagccaga ggaccccat gaggcggcat gcaggcgggg agcaggccac agaacgcagg      120
gtgaaaccca aggcgctcta gaggagatga attatggatc cgccctcccg gaatcctggc      180
tcggccctcc ccacgccacc cagggccagt cgggtctgct cacagcccga ggaggccgcg      240
tgtccagccg cgggcaagag acagagcagg tccctgtgtc tccaagtccc tgagcccgtg      300
acaccggccc caggccctgt agagagcagg cagccaccat ggcgaaggag gaagatgagg      360
agaagaaagc caagaaaggg aagaagggga agaaggcacc ggagccggag aagcccaaac      420
ggagcctgaa ggggacgtcg cggctgttca tgggcttccg cgaccgtaca cccaagatct      480
ccaagaaggg ccagttccgc agcgcctcgg ccttcttctg gggcctccac accggccccc      540
agaagaccaa gcgcaagagg aaggcccgca ccgtgctcaa gtccacgtca aagctcatga      600
cgcagatgcg catgggcaag aagaagcggg cgatgaaggg caagaagccg tccttcatgg      660
tgatccgctt cccaggccgc cgtggctacg gccgcctgcg gccgcgcgcc cggtcactca      720
gcaaagcgtc cacggccatc aactggctca caaaaaagtt cctcctcaag aaggccgagg      780
agtcgggcag cgaacaggcc acagtggacg cctggctgca gcgctcgagc tcccgcatgg      840
gctccccgcaa actcccettc ccgtcgggtg ccgagatcct gcggcctggg ggccggctcc      900
ggaggttccc ccgcagccgc agcatctacg cgtcaggcga ccccctgggc ttcctgccct      960
tcgaggacga ggcccattc catcactcgg gctcccgcaa gtcgctgtac gggcttgagg     1020
gcttccagga cctgggcgag tattatgact atcaccgcga cggcgacgac tactacgacc     1080
ggcagtcact ccaccgctac gaggagcagg aaccctacct ggcgggcctc ggccccctaca     1140
gcccggcctg ccacccctac ggcgaccact actacgggta cccgcccgag gatccctacg     1200
actactacca ccccgactat tacggtggcc cctttgatcc ggggtacacc tacggctacg     1260
gctacgacga ttacgaaccc ccatatgcgc ccccgtcggg gtactcgtct ccttacagct     1320
accacgatgg gtacgagggc gaggcgcacc cttatggcta ctacctggat ccctatgcgc     1380
cgtacgacgc gccatacccca ccctatgacc tcccatacca cactccctac gatgtaccct     1440
actttgatcc ctacggagtc cactacaccg tccctatgc cgaaggcgtc tatggcggtg     1500
gggacgaggc catctacccc cccgaggtgc cctatttta cccggaggag tcggcttcgg     1560
cctttgtgta ccctgggta ccaccgccca tcccgtcgcc ccacaacccg tatgcccacg     1620
ccatggatga catcgccgag ctggaggaac cagaggacgc gggcgtagag cgtcagggga     1680
cctccttccg cctgcccagc gccgccttct tcgagcagca aggcatggat aagcccgcca     1740
ggtccaagct gtccctcatc cgcaagttcc gcctcttccc gcgaccccag gtgaagctgt     1800
ttggaaagga gaagctggag gtgccccttg caccctctct ggacattcct ctccccttgg     1860
gggatgcgga cgaagaagag gacgaggagg agctgccccc ggtttccgct gtgccctacg     1920
gccacccttt ctggggcttc ctcacgccgc gccagcgcaa cctccagcgc gcgctgtcgg     1980
ccttcggcgc ccaccggggc ctgggcttcg gcctgagtt tggccgcccc gtgcctcgcc     2040
ctgccacctc gcttgcgcgg ttcctcaaga gacgctgtc ggagaagaag cccatcgcgc     2100
ggctcagggg cagccagaag gcccgggcgg gcggccctgc tgtcagggag gcggcctaca     2160
aacgcttcgg ctacaagctg gctggcatgg accccgagaa gccccgcacg cccatcgtgc     2220
tgaggagggc ccagccacgc gctcgcagca gcaacgacgc gcgccgccccg cccgcgccac     2280
```

```
agcccgcgcc caggaccctc tcccactgga gcgcgctcct gtctccgccc gtgccccgc   2340 ggcccccaag ctccgggccc ccgcccgcgc cgccgctctc cccggcgctc tcgggcctgc   2400
cccggccggc ctcgccctac ggctccctcc gccgccaccc gccgcctgg gccgccccag    2460 cgcacgtgcc accggcgccg caggccagct ggtgggcctt cgtggagccc ctgccgtga    2520 gcccggaggt gccccccgac ctactagcct tcccagggcc ccgaccctcg ttcaggggct   2580
cccgccggag aggggcggct ttcggcttcc ccggggcctc tccacgggcg tcgcggaggc   2640
gagcttggtc accgctggcc tcgcccagc cctcgctgag gagctcgccg ggcctcggct    2700
actgctcacc cttggcgccc ccgtcgcctc agctgtcctt cgcacgggcc ccttccagc    2760 cgcccttcct gccccggcc cgccggcccc gctcgctgca ggagtcccca gccacgcc     2820 gagccgctgg gcgcctgggc ccacccggct cgccgctgcc gggctcaccc aggccgccct   2880
cgccgcccct ggggctctgc cacagcccgc ggcgcagctc cctgaatctg ccctcgcgcc   2940
tcccgcacac gtggcggcgc ctcagcgagc cacccactcg ggctgtgaag ccgcaagtgc   3000
gcctgccctt ccaccgaccg cccagggccg gggcctggcg ggcgcccctg aacaccggg    3060 agagcccgcg agaacccgag gactcagaga cgccctggac tgtgccccca ctggccccca   3120
gctgggacgt ggacatgcct cccacccaac gcccaccctc cccctggcca ggaggtgcag   3180
gcagccgccg aggcttttcc aggccacccc ctgtgccgga aaacccctt ctccagctcc    3240 tgggccctgt gccatccccc accctccagc ctgaggatcc agctgctgat atgaccaggg   3300
tcttcctggg cagacaccat gagccggggc ctggacagct caccaaatca gctggcccaa   3360
cccctgagaa gcctgaagaa gaggccaccc tgggggaccc ccagctgcca gcagagacca   3420
agcctccaac cccagcacct cccaaggatg tcactccccc caaggatatc actcccccca   3480
aggatgtcct cccagagcaa aagacattaa ggcccagcct ctcatcccca ctggctgcgt   3540
gtgaccagac cagggccaca tggccaccat ggcaccgctg ggaacactg ccccaagccg     3600 cagccccctt ggcgcccatc agggcccag agccctgcc caagggggt gaacggcgcc     3660 aggcagcccc tgggcgtttt gctgtggtca tgcctcgtgt gcagaagctg agctcttcc     3720 agcgagttgg gcctgcaacc ctgaagcctc aagtccagcc cattcaggac cccaagccaa   3780
gagcctgtag tcttcgctgg tcctgcctct ggcttcgggc agatgcctat ggaccctggc   3840
cacgagtaca cacccatccc cagtcctgcc acctgggccc tggagctgcc tgcctgtccc   3900 ttagggctc ctgggaggag gtcggcccgc caagctggcg gaacaagatg cactccatcc     3960
gcaacctgcc atccatgcgg ttccgtgagc agcacgggga ggatggtgtg gaggacatga   4020
cacagctgga agacctccag gaaaccactg tgctgtccaa cctcaagatt agatttgaac   4080
ggaacctcat ctacacatac attgggagca tcctggtgtc ggtgaaccca taccaaatgt   4140
ttggaatcta tgggccggag caggtgcagc agtacaacgg acgggccctg ggagagaatc   4200
ccccgcacct ctttgctgtt gcaaatctcg ccttcgccaa aatgctcgat gccaaacaga   4260
accagtgcat aatcattagt ggagagagcg gctctggcaa aactgaggcc accaagctga   4320
ttctgcgcta cctggccgcc atgaaccaga aacgggaggt catgcagcag ataaagatcc   4380
tggaggcaac accctcttg gagtccttcg gtaatgccaa aaccgtcagg aacgacaact     4440
ccagccgctt tgggaagttt gtggaaatct ttctggaagg gggcgtgatc tctggtgcca   4500
taacctccca gtacctgctt gagaaatcca ggatcgtgtt tcaggccaaa aacgagagga   4560
attaccacat cttctacgag ttgctggccg ggttgcctgc ccagctcagg caggccttta   4620
```

```
gcctgcaaga ggctgagacc tactactatc tgaaccaggg tgggaactgt gagatagcag    4680
gaaagagcga tgcagatgac tttcgccggc tcctggctgc catggaggtg ttgggcttca    4740
gcagtgagga ccaggacagc atcttccgca tcctggcctc catcctgcac ctgggcaacg    4800
tctactttga gaagtatgag acggatgcac aggaggtggc ctcagtggtg agtgcccgag    4860
agatccaggc cgtggcagag ctgctgcaga tctcccctga gggcctgcag aaggccatca    4920
ccttcaaagt gaccgagaca atgcgagaga agatcttcac gccoctaact gtggagagcg    4980 ctgtggatgc cagggacgcc atcgccaagg tcttgtatgc actgctgttc agctggctca    5040
tcaccagggt caacgcgctg gtgtccccaa ggcaggacac actgtccatc gccatcctgg    5100
acatctatgg tttcgaggac ctgagcttca acagctttga gcagctgtgt attaactacg    5160
caaacgagaa ccttcagtac cttttcaaca agatcgtctt ccaggaggag caggaggagt    5220
acatccgtga gcagatagac tggcaggaga tcaccttt gc tgacaaccag ccctgcatca    5280
acctcatctc actgaagcct tatggcatcc tgcggatcct tgacgaccag tgttgctttc    5340
cccaggctac agaccacacc ttcctacaga agtgccacta ccatcatggc gccaacccgc    5400
tctattccaa acccaagatg ccgctgcctg agttcaccat caagcactat gcaggcaagg    5460
tcacctacca ggtgcacaag ttcctggaca agaaccacga ccaagtgcgc caggatgtgc    5520
tggacctgtt cgtacggagc cggacacggg tggtggcaca cctcttctcc agccatgccc    5580
cacaggctgc ccctcagcgc ctgggcaaga gcagctccgt cactcggctc tacaaggcgc    5640
acactgtggc cgccaagttc cagcagtcac tcctggatct ggtggaaaag atggagaggt    5700
gcaacccctt gttcatgcgt tgcctgaagc ccaaccacaa gaaggagcca ggtctctttg    5760
agccagatgt ggtaatggca caattacgct attcaggggt gctggagacc gtgaggatcc    5820
gcaaggaggg atttccagtg cgcctgcctt tccaggggtt catcgacagg tactgctgtc    5880
tagtggccct caagcatgac ctgccggcta atggggacat tgtgtgtca gtgctgagtc    5940 gcctgtgcaa agtcatgcca aacatgtacc gtgttgggt cagcaagctg ttccttaagg    6000
aacacctata ccagctgctg gagagtatgc gagagcatgt cctgaatctg cagccctca    6060 ctctgcagcg ctgcctccgt ggcttcttca ttaagcggcg attccgctct ctgcgccaca    6120
agatcatcct gctgcaaagc cgggcccgtg ctaccttgc caggcaacgc tatcagcaga    6180
tgaggaggag tctggtgaag ttccggtccc tggtacacgc atacgtgagc cgccgacgct    6240
atctcaagct gagggcagag tggaggtgcc aggtggaggg ggcgctgctg tgggagcagg    6300
aggagctgag caagcgggag gtagtcgctg tggggcacct ggaggtaccg gctgagctgg    6360
ctgggctctt gcaagcagtg gcaggcctcg ggctggccca ggtgcctcag gtggcccctg    6420
tgaggactcc tcgactccag gctgagcccc gtgtcacact gccccctggac atcaacaact    6480 atcctatggc caagtttgtc cagtgccact tcaaggaacc tgccttggg atgctgacag    6540 tgcccctgag gacacccctc acgcagctgc cagccgagca ccatgcagaa gccgtgagca    6600
tcttcaagct gatcctgcgc ttcatgggcg acccccacct gcatggtgcc cgggagaaca    6660
tcttcgggaa ctacatcgtg cagaagggc tggcggtgcc tgagctgcgg gatgagatcc    6720
tggcacagct ggccaatcag gtgtggcaca atcacaatgc ccacaatgct gagcggggct    6780
ggctgctgct ggccgcctgc ctcagtggct ttgcaccttc cccgtgcttc aacaagtacc    6840
ttctcaagtt tgtgtctgat tatgggcgga atggcttcca ggctgtgtgt cagcaccgcc    6900
tcatgcaggc catgggccgg gcccaacagc agggctcggg ggctgccgc accttaccc    6960 cgacccagct cgagtggaca gcgacctatg agaaggccag catggcgctg gacgtgggct    7020
```

```
gcttcaatgg tgaccagttc tcctgcccgg tgcactcctg gagtacgggg aagaggtgg    7080 ctggagacat tctgaggcac aggggctgg cagatggctg gcgcggctgg accgtggcca    7140
tgaagaatgg tgtccagtgg gcagagctgg ctggccacga ctacgtgtta gacctggtgt    7200
cggacctgga gctgctcagg gacttccctc gacagaagtc ctacttcatt gtgggcacag    7260
aggggcctgc agccagcagg ggaggcccca aagtggtgtt tgggaacagc tgggactcgg    7320
atgaggacat gtccactaga ccccagcccc aggagcacat gcccaaagta cttgactctg    7380
atgggtacag cagccacaat caggacggta caaatgggga gactgaggcc caagaggga    7440 cagcaaccca ccaagagtca gacagtcttg gagagcctgc tgtgccccac aaggggctgg    7500
actgctacct ggatagcctc tttgaccctg tgctgtccta cggggatgcg gacctggaga    7560
agccaacagc cattgcctac cgcatgaaag gggaggcca gcccggtgga ggcagcagta    7620
gtggtactga agacaccccc aggagacccc cagagccaaa gccaatccca ggcctggatg    7680
cctccacatt ggctctgcag caagccttca tccacaaaca ggccgtgctg ctggcccggg    7740
agatgaccct gcaggccacg gcactccagc agcagcccct gagtgctgcc ctgagatcct    7800
tgcccgcaga gaaaccccca gcaccagagg cacagccgac gtctgtaggc accggtcccc    7860
ctgccaaacc cgtgctcctg cgtgccactc caaagccctt ggccccagcc cctctggcca    7920
aggctccaag gctcccccatc aagcctgtgg ctgcccctgt tctagctcag gatcaggctt    7980
ctccagaaac cacttcaccc tccccagagc tggtccggta ctctacgctc aactctgagc    8040
acttcccaca gcccacacag cagatcaaga atattgtcag gcagtaccag cagccgttcc    8100
ggggaggccg gcctgaggcc ctcaggaagg atggcgggaa agtgttcatg aagcggccag    8160
accctcatga ggaggccctg atgatcctga aagggcagat gacccacctg gcagctgcac    8220
ctggcaccca ggtgtccaga gaggccgtgg ccctggtgaa gccgtgacc agtgcaccaa    8280 ggccatccat ggcaccccact tcagctctgc cctcgcgatc gctggagccc ctgaggaac    8340 tcacgcagac gcggctgcac cgcctcatca atcccaactt ctacggctat caggacgccc    8400
cctggaagat cttcctgcgc aaagaggtgt tttaccccaa ggacagctac agccatcctg    8460
tgcagcttga cctcctgttc cggcagatcc tgcacgacac gctctccgag gcctgccttc    8520
gcatctctga ggatgagagg ctcaggatga aggccttgtt tgcccagaac cagctggaca    8580
cacagaagcc tctggtaacg gaaagcgtga agcgggccgt ggtcagcact gcacgagaca    8640
cctgggaggt ctacttctcc cgcatcttcc ccgccacggg cagcgtgggc actggtgtgc    8700
agctcctagc tgtgtcccac gtgggcatca aactcctgag gatggtcaag ggtggccagg    8760
aggccggcgg gcagctgcgg gtcctgcgtg catacagctt tgcagatatc ctgtttgtga    8820
ccatgccctc ccagaacatg ctggagttca acctggccag tgagaaggtc atcctcttct    8880
cagcccgagc gcaccaggtc aagaccctgg tagatgactt catcttggag ctgaagaagg    8940
actctgacta cgtggtcgct gtgaggaact tcctgcctga ggaccctgcg ctgctggctt    9000
tccacaaggg tgacatcata cacctgcagc ccctagagcc acctcgagtg gctacagtg    9060 ctggctgcgt ggttcgcagg aaggtggtgt acctggagga gctgcgacgt agaggccccg    9120
actttggctg gaggttcggg accatccacg ggcgcgtggg ccgcttccct tcggagctgg    9180
tgcagcccgc tgctgccccc gacttcctgc agctgccaac ggagccaggc cgcggccgag    9240
cagccgccgt ggccgctgct gtggcctctg cagccgctgc acaggaggtg ggccgcagga    9300
gagagggtcc cccagtcagg gcccgctctg ctgaccatgg ggaggacgcc ctggcgctcc    9360
```

| | |
|---|---|
| cacccctacac aatgctcgag tttgcccaga agtatttccg agaccctcag aggagacccc | 9420 |
| aggatggcct caggctgaaa tccaaggagc ctcgggagtc cagaaccttg gaggacatgc | 9480 |
| tttgcttcac caagactccc ctccaggaat ccctcatcga actcagcgac agcagcctca | 9540 |
| gcaagatggc caccgacatg ttcctagctg taatgaggtt catgggggat gccccactga | 9600 |
| agggccagag tgacctggac gtgctttgta acctcctgaa gctgtgcggg gaccatgagg | 9660 |
| tcatgcggga tgaatgttac tgccaagttg tgaagcagat cacagacaat accagctcca | 9720 |
| agcaggacag ctgccagcga ggctggaggc tgctgtatat cgtgaccgcc taccacagct | 9780 |
| gctctgaggt cctccaccca cacctcactc gcttcctcca agacgtgagc cggaccccag | 9840 |
| gcctgccctt tcaggggatc gccaaggcct gcgagcagaa cctgcagaaa accttgcgct | 9900 |
| tcggaggtcg tctggagctc cccagcagca tagagcttcg ggccatgttg gcaggccgca | 9960 |
| gttccaagag gcaactcttt cttcttcctg gaggccttga acgccatctc aaaatcaaaa | 10020 |
| catgcactgt ggccctggac gtggtggaag agatatgtgc tgagatggct ctgacacgcc | 10080 |
| ctgaggcctt caatgaatat gttatcttcg ttgtcaccaa ccgtggccag catgtgtgcc | 10140 |
| cactcagtcg ccgtgcttac atcctggatg tggcctcaga gatggagcag gtggacggcg | 10200 |
| gctacatgct ctggttccgg cgtgtgctct gggatcagcc actcaagttc gagaatgagc | 10260 |
| tatatgtgac catgcactac aaccaggtcc tgcctgacta cctgaaggga ctcttcagca | 10320 |
| gtgtgccggc cagccggccc agcgagcagc tgctgcagca ggtgtccaag ctggcttcac | 10380 |
| tgcagcatcg cgccaaggac cacttctacc tgccgagcgt gcgggaagtc caggagtaca | 10440 |
| tcccagccca gctctaccgt acaacggcag gctcgacctg gctcaacctg gtcagccagc | 10500 |
| accggcagca gacacaggcg ctcagccccc accaggcccg tgcccagttt ctgggcctcc | 10560 |
| tcagcgcctt acctatgttc ggctcctcct tcttcttcat ccagagctgc agcaacattg | 10620 |
| ctgtgccagc cccttgcatc cttgccatca accacaatgg cctcaacttt ctcagcacag | 10680 |
| agactcatga attgatggtg aagttccccc tgaaggagat ccagtcgacg cggacccagc | 10740 |
| ggcccacggc caactccagc tacccctatg tggagattgc gctgggggac gtggcggccc | 10800 |
| agcgcacctt gcagctgcag ctggagcagg gactggaact gtgtcgtgtg gtggccgtgc | 10860 |
| acgtggagaa cctgctcagt gcccatgaga agcggctcac attgcccccc agcgagatca | 10920 |
| ccctgctctg acccagcccc cagccctcca gtaccttctg ccagaagact cactgtgtgg | 10980 |
| cctcagagaa atcactgaac ctctcaggat caatgacccc tgtaaggggc cagagccttg | 11040 |
| gaggacacta agaggaggca ggaggagcaa ctcaaatccc caagaacaca agaagaccca | 11100 |
| tcctgaactg ggatggaatg gcagcatgca aacttggatc agatagcagg aggaactttc | 11160 |
| aaaagtctgg cccactgtgc agtggagcag aaggcaggac catgaggcct cctgccatgt | 11220 |
| acccattgca gaccctgccc ctaactcctg cctatgacac agaagcccca caccagttgc | 11280 |
| ccagatgaac tggcctctgc ctttggttta ctcagggtct gatgttggaa tctgctccaa | 11340 |
| ctccacaccc tagcccttac atgtcctcct aaggggcccc tccttgtgct gccagtcagc | 11400 |
| ctggatttct ggtctttggt tatttctgtg caaacaaaag gtgtgcctgg cagccatttc | 11460 |
| tccatggagt tgctaagtgg ccggaaaaca agcctgaggg aggaggcagg agttggagtt | 11520 |
| accttaggcc cctgattcac tgcctatgaa cagaccatcc cccactcctt gggtatcccc | 11580 |
| aaccccagac cccatcact tgatgggcca cacaagtttg agagtggtac aagggagaag | 11640 |
| tttgggaaaa gccttcttgg aaaatgggac attagcattg agttttgaaa gatgagtagg | 11700 |
| agtttgctaa gaatagatgg aagacagcag gataaacatt ccagagaaaa tcatgtttat | 11760 |

```
tccctgctgt atcttccaga acctaggagg atgcctaaca gagagtaagc acttaaaaaa    11820
tatttgtcat atgaatgaaa aaataaacga gtgaatgttg ataaaaaaaa aaaaaa        11876

<210> SEQ ID NO 22
<211> LENGTH: 2258
<212> TYPE: DNA
<213> ORGANISM: Homo Sapiens

<400> SEQUENCE: 22
cacaagctct agagggcttc cgggaggagg cttagggagc tgggaatccg ggagcagatg      60
gtgggttcct accgtcgagg gtgggagaga gggatctgag gccaagtttg aggtaaggac     120
tgtggagctc catcagatcc ccatccccac ctcccctcat ctgcgcaatc ctgcgagaag     180
ccttagacag gttctggctc agagaaccgg agagaggcac aacgcctggc ccccaggact     240
tggccacagc gtccctgacc ttgtctgctc catgacctct cactgaggcc cattaacccc     300
tcagttccct gatgaggctt gatttagcat ccttgatgtc agctcctaag agtctgggaa     360
gtgcatttaa gtcctggagg ttggacaagg cccccctccc acagcacacc tttccatcca     420
cttctatccc aggcatggct tttgctctcc tggcctccgt gccccggtg tttggactct       480 acacttcttt cttccccgtc ctcatctaca gcttgctagg tactgggaga cacctgtcca     540
caggaacttt cgccatactc agcctcatga caggctcggc cgtcgagcgg ctggtgccgg     600
aacccctcgt ggggaatctg agcggaatcg agaaggagca gctggacgct caacgggttg     660
gggtagccgc ggccgtggcc ttcgggagcg gggcgttgat gctggggatg ttcgtgctgc     720
agctcggcgt cttgtccacc ttttttgtccg agcctgtggt caaggcgctg accagcgggg    780
ccgcgctgca cgtgctcttg tcccagctgc cgagcctctt ggggttgtcc ctcccgcgcc     840
agatcggctg cttctctctc ttcaagacgc tggcctcctt gctgactgcg ctgcctcgga     900
gcagtccggc cgaactgacc atctccgcgc tcagcctggc gctgctcgtg ccggtcaagg     960
aattgaacgt gagattccga gaccggctac ccacgccgat cccggggggaa gtcgtcttgg   1020 tgcttctggc ctccgtgctc tgcttcacct cttctgtgga cacaagatac caagtccaga   1080
tagtggggct gttgcctgga ggatttcccc aaccctcct ccccaacctg ctgagctgc       1140 ccaggattct ggctgactcg ctgcccattg cactggttag ttttgcggtg tctgcctccc    1200
tggcctccat ccatgcagac aagtatagct acactattga ctccaaccag gagttcctgg   1260
cacatggtgc ctccaacctc atctcctccc tcttctcttg ctttcccaac tcggctacgc   1320
tggccaccac caatctactg gtggatgctg gtgggaaaac acagctggca ggcctcttct   1380
cctgcacagt ggtcctgtcg gtgctgctgt ggctggggcc cttcttttac tatctgccca   1440
aggctgtcct ggcttgcatc aacatctcca gcatgcgcca ggtgttctgc cagatgcagg   1500
aacttccaca actatggcac atcagccgag tggactttgc tgtgtggatg gtcacctggg   1560
tggcagtagt gaccctgagt gtggatttgg gcctggctgt gggtgtggtc ttctccatga   1620
tgactgtggt ctgccgcacc cggagctcct ccaggtcccg gggctctgca tcctgagcta   1680
tccaacacca ctgtactttg ggacccgtgg gcagtttcgc tgcaacctgg agtggcacct   1740
ggggctcgga gaaggagaaa aggagacttc aaagccagat ggcccaatgg ttgcagttgc   1800
tgagcctgtc agggtggtgg tcctagactt cagtggtgtc accttttgcag atgctgctgg   1860 ggccagagaa gtggtgcagc tggccagccg atgtcgagat gctaggatcc gcctcctcct   1920
ggctcagtgt aatgccttgg tgcaggggac actgacccgg gtaggactcc tggacagggt   1980
```

```
gactccagat cagctgtttg tgagtgtgca ggatgcagct gcttatgccc tggggagcct    2040
gttaaggggc agtagcacca ggagcgggag ccaggaggca ctgggctgcg gcaagtgagg    2100
caggggagct cactgaccca aagatttgca ccgtgtgggt ctgacctcat catgtggagt    2160
gcagagggcc ctgatgacat gtgtgtgatg aggaccatga cccttgaacc cccttaccta    2220
acgtaactaa taaaatgaag ctgagagctt tggaatcc                            2258

<210> SEQ ID NO 23
<211> LENGTH: 2991
<212> TYPE: DNA
<213> ORGANISM: Homo Sapiens

<400> SEQUENCE: 23
ctgcttactg cgcacggcca atcctatgag aactcagcat cccagctcat ctgagcagat      60
cctggaagtg atttctgcag ctcaggattt ttttttttaag ctacattgaa aatataggtt   120
tattttttgt tcaggttttt cttttatatt ttttttctgc acaaaggagg aggattttc    180 acttactcat atcgaggcca gattttaaaa gccagctaag gcagcatcag ctgtgcggga    240
tttaaagcct atagctcagc tgaaaaaaaa ggtgggggc agggaaggga agataaaagg     300
agaggaagct gggagaagac aagcatcatc ttattttgct atgtggtagg aactgtctat    360
aagatagtgt agaattgttt atcttgagca gtttgttctt aacctataag gtattttcc    420 tttttttttt ttttaaacct cccccacccct ttcctgaaa gctttgtttc agagctttgt   480
attgggtttt tttggtgagg aggttgtatt tatttttttg gtgtgtgtgt gtgagtgtgt    540
gtgtgtctgt gtgtgtgttg tggtcccagc tgagtcatca tgtctgctct gacgcctccg    600
accgatatgc caaccccac cactgacaag atcacacagg ctgccatgga gaccatctac      660
ctttgcaaat tccgagtgtc catggatgga aatggctct gcctgcgaga gctggatgac     720
atctcactta cacctgaccc agagcctacc catgaagatc ctaattatct catggctaat    780
gaacgcatga acctcatgaa catggccaag ctgagtatca agggcttgat tgaatcagct    840
ctgaacctgg ggaggactct tgactctgac tatgcacctc tccagcaatt ctttgtggtg    900
atggagcact gtctgaaaca tggcttgaaa gctaaaaaaa cttttctcgg acaaaataaa    960
tccttctggg ggcctctaga actggtagaa aagcttgttc cagaagccgc agagataaca   1020
gcaagtgtta aagatcttcc aggacttaag acaccagtag gtagaggaag agcctggctt   1080
cgtttggcat taatgcaaaa gaaactttca gaatatatga aagctttgat caataagaaa   1140
gaacttctca gtgaattcta cgaacccaat gccctcatga tggaagaaga aggagccata   1200
attgctggtc tgttggtggg tctgaatgtc attgatgcca atttctgtat gaaaggagaa   1260
gacttggact ctcaggttgg agttatagat ttttcaatgt atctcaagga cgggaacagc   1320
agtaaaggta ctgaaggaga cggtcagatt actgcaattc tggaccagaa gaactatgta   1380
gaagaactga acagacattt gaatgctact gtaaacaacc ttcaggcaaa agtagatgca   1440
ttagaaaaat ccaacactaa actgacagag gagcttgcag ttgcaaacaa caggatcatt   1500
accttacaag aagaaatgga acgagttaaa gaggaaagtt cctacatact ggaatccaat   1560
cggaagggtc ccaagcaaga cagaactgca gaagggcaag cactaagtga agcaagaaag   1620
catttaaaag aagagacaca attacgattg gatgttgaga agaactggaa gatgcagatc   1680 agcatgagc aggagatgga attggctatg aagatgctgg agaaggatgt ctgtgagaag   1740
caggatgccc tggtatctct tcggcagcag ctggatgacc tcagagctct caagcatgaa   1800
cttgccttta agctgcagag ttcagactta ggagtaaaac agaaaagtga actaaacagt   1860
```

```
cgcttggaag agaagactaa tcagatggct gctaccatta acaacttga acaaagattg    1920 cgccaggctg agcgaagccg ccaatctgct gagttggaca accggctctt caaacaggac    1980
tttggagaca agatcaacag tctgcagctg gaagtcgagg agctcaccag gcagcggaac    2040
cagcttgagt tagaactaaa acaggaaaaa gaaagaagat tacaaaacga caggagcatc    2100
ccaggaaggg gttcccagaa gtcagaatcc aagatggatg ggaagcacaa aatgcaagag    2160
gaaaatgtta aactaaaaaa gcccctggaa gaaagccaca ggctgcaacc ccaccctatg    2220
gatgaacagg atcagctgct gctctctgaa aagccacagt tgtgtcagct atgccaggaa    2280
gacggcagcc taacaaagaa tgtgtgtaag aactgcagcg gaaccttctg tgatgcctgt    2340
tcaacaaatg aactgcctct tccttcaagt atcaagcttg agcgagtttg caatccctgt    2400
cacaagcatc tgatgaagca atattctacc agcccatcat aagactggag ccaagacct    2460 ggaccaaaac gtttatgcag gctcctctgt acctgtgttt tagctgtcag gatctcatag    2520
agcccagttc ttagagtcaa ctaaagagtt gataggaatt tactaggtcc agggagaaaa    2580
ggcagtggtt ggggttactg gaaattttgc tcattttctc taatgactgt atgaataaaa    2640
gtgaacttac ttgagccttt ctcttctaaa tctaaacaac ctgatattga aggtttgctt    2700
tatagcatat ctttggaaag gcaactcatt tttatgatta gtgatactgg ggtggattta    2760
ataggagaga gaatccaggc agataagaat aaaaaggaaa atgatcatct ccttctatag    2820
catttgcaga ttcaagggggg agaggtagat gctgagatca aaatgacagt tgttacttat    2880
ttttccaggt gctgttagta taaacattgt ttcctcttca cccctgctaa ctacctcttt    2940
aaagtatttc taccaaactg tgaacccaat ctcagggaaa agaaattaaa a              2991
```

<210> SEQ ID NO 24
<211> LENGTH: 2279
<212> TYPE: DNA
<213> ORGANISM: Homo Sapiens

<400> SEQUENCE: 24

```
gcattctagt gcgaccttgt ttacacctcc cctggctcag tcacacagct gtgtggtagg      60
ctactagaag tgtttagtag ttgtcactgg gatcatgctg atgtggcccc atccccgccc     120
ctccctgccc tgtgatatcg gaggaaacct gacagagcaa attggccatg gccaagaaaa     180
aggaaaagaa agagtgccac caaaagcagg gagcctaagg ggagcagtta caggtcctct     240
ttggattcca gcacgacgca tcaaaccata ccatgacgtg actaggaccc aacctagaaa     300
tgaaggaact gaccctacag gactcacaac cctggataat gcagtgtcct cggacggcaa     360
caagctctgg acattacctg ggggatgctg aaggcggcaa ctgaggaggc tgaatgaatc     420
ctgctccaga cacagacacc attcactcca gataatttgt tgcttgctat gctctctgtt     480
gtacattgca actcgcatag ggatgcaaag ccggaataag agcaatgacc accatgcctg     540
acagacctgt tgctgcgcac acctgtactc tccaatgaac aagactgaat gcaaaaaaaa     600
cagaaaatgg ggagatttag gggatcagtc agtgtggttg gaaaattgta agatgaagtt     660
acaggatata gacacaaacc ttcttggaag gccagaaggt ttgcatagct tcagtaaagg     720
atttggctga atcctttttt acctctaatc ccctttacct tgagttgata gcaatagagc     780
aaataacatg ggaatgtggg ggagtttatc tgaatagctt gtttactcat gtggtcctaa     840
gaccaacctt tgattatccg caggtgcatg attgctctct acctggggcc aggggggagtt     900 aattacccac aggtggagct gaagagccag gaggctcaga gtctgcagca gcagcaggac     960
```

| | |
|---|---|
| cagtacctgg gtcatctgca gcagtatgtg gccacctatc agcagcaggt ggtcacctat | 1020 |
| cagcagctga cctctgagga ggaggagctg cacaaccagt tactgctgca gacccagctc | 1080 |
| gtggaccggc tgcagcagca gaaagctcaa agcaaagctg tggccaagat gggctgccaa | 1140 |
| gagttgcggg agacccagga gcacctggaa gctatcagcc agcagaacca gcagcctcag | 1200 |
| gcccagttga gcctcatggc tctccctggg gaaggagatg acagtgagg aggaggagga | 1260 |
| ggtgcctcag cccatgccaa gcatcccgga ggatctagag agccgaagg ccatggtggc | 1320 |
| attttcaac tcagctgtag ctagtgccga ggaggagcag gcacggctat gtgggcagct | 1380 |
| gaaggagtgc actgccagcg cctggctcat ctgttggcct cggcccagaa ggaacctgag | 1440 |
| gcagcagccc cagccccaag aactgggggt gatcccatgt gtggggagac ccaccaggcc | 1500 |
| ctgcaggggg ccatggagaa gctgtgggag agtacatcgc actgtaccag agccagaggg | 1560 |
| cagtgcggaa ggaggaggag tgcatcagca ggctggccca ggacaaggga gaggtgaagg | 1620 |
| tgaagctgct ggagctggcg tggcttgtgg acgactgcaa caagtggcat agcagattcc | 1680 |
| tggcagctgc ccagaaccct gctgatgagc ccactccagg ggcccccgcc cccagtagc | 1740 |
| ttggggctac tgacaagcca gggtagtgag tagagtcctc aggcacagtg ggcacgcagg | 1800 |
| agcagggag ggctcccaca gcaccctgcc tccctctctc caaagatctt tgtgaggtga | 1860 |
| gccttgccag cagtggggag tctgcacaag gagaggcggg gaagcattct ccctgtgaca | 1920 |
| acccccactga gcagcagatc atgcaactgc ttcatgagat gcagaacctc caggagcacc | 1980 |
| caggcttggg cagcagccct tgcattcctt ttttgtacca gactgatgag aacaatgagg | 2040 |
| tgaagatcac catcatctaa aagccggcca ctgtcagcaa aacctgggga agtggggctg | 2100 |
| gaggctctgc ccctaccatg tccctaccac cccttcccag tcaaccctt accctcacag | 2160 |
| tagcaagcat aagaccctg tctaatgtgg ggagacaggt ggagatgagg tgaagatcac | 2220 |
| cataatctaa aaggccacta ataaaaaaa taaaaatt taaaaaaaa aaaaaaaa | 2279 |

<210> SEQ ID NO 25
<211> LENGTH: 2391
<212> TYPE: DNA
<213> ORGANISM: Homo Sapiens

<400> SEQUENCE: 25

| | |
|---|---|
| caggtctccc aggcttcctc agcgtcgacg ccggggagcg ccctgggtt gggagcgccc | 60 |
| ggggcccgcg aaggaggagg tggctcaggt gtcagggcgc accgtgggaa ccggccccgg | 120 |
| gggaggcgtg gaaacgcggg gcctgggact cgaccagccc ctcccgtgcg gatcgcaaaa | 180 |
| tctcggagct gaaacagccc gttgttcgca gcctccctct gacccgccac cctgcacatt | 240 |
| gttttccatt cgcccgggtc gcgggtggga ggagaggcac gccggggttc tggagcttgg | 300 |
| ccgcgcgcca ggcttgtggc cttcgtcccc ctggggccac tggggcggcc acgcctctcc | 360 |
| ggcgggagga gagaacgcgt gggtccgggt ggctgctccg gcccttccgc ctccagctcg | 420 |
| gccatggggt cgcgcagctc ccacgccgcg gtcattcccg acgggacag tattcggcga | 480 |
| gagaccggct tctcccaagc cagcctgctc cgcctgcacc accggttccg ggcactggac | 540 |
| aggaataaga agggctacct gagccgcatg gatctccagc agatagggc gctcgccgtg | 600 |
| aaccccctgg gagaccgaat tatagaaagc ttcttcccg atgggagcca gcgagtggat | 660 |
| ttcccaggct ttgtcagggt cttggctcat tttcgccctg tagaagatga ggacacagaa | 720 |
| acccaagacc ccaagaaacc tgaacctctc aacagcagaa ggaacaaact tcactatgca | 780 |
| tttcagctct atgacctgga tcgcgatggg aagatctcca ggcatgagat gctgcaggtt | 840 |

-continued

```
ctccgtctga tggttggggt acaggtgaca gaagagcagc tggagaacat cgctgaccgc    900
acggtgcagg aggctgatga agatggggat ggggctgtgt ccttcgtgga gttcaccaag    960
tccttagaga agatggacgt tgagcaaaaa atgagcatcc ggatcctgaa gtgactccgt   1020
ttgtgccttg ggcttgctcc tgcaaccagt atctccttgg aattcatcca agcccccat    1080 ggacgcatgg acgcagggcg acaataaact gtattttcgt ttctaactct atttagggcc   1140
aagagaagaa agctggaagg atgtgtacta aagtctagct cagcagtccc caaccttttt   1200
ggcatcaggg acagtttttc cacggatggg tgacagggga tggttttggg atgattcaag   1260
tgcattacat ttattgtgca ctttatttct attatgatta cattgtaata tataatgaaa   1320
taattataca actcaccata atgtagaatc agcaggagcc ctgagcttgt tttcctgcaa   1380
ttagacggtc ccatatggga gtgatgggag acagtgacag atcatcaggc attagattct   1440
cataaggagt gcacaatcta gatccttttgg tgtgcagttc acagtaggat ttgggctcct   1500
atgataatct aatgccactg ctgatctgac aggaggcaga gctcaggcgg taatgcaagc   1560
aatggggagt ggctgtaaat atagatgaag cttcagctcg cctgccgctc accttgtgct   1620
gtgcagcccg gttcctaaca gaccacagac cccacaccag gtctatctca tttggtctca   1680
gagctgtgaa tcagccagca atattttagt tgcaaatcac tgaaaaccca actcaaagtg   1740
acttaagtca gaaagaaatt ttatgaattc aggtaattaa aaagtccaga agtatctgcc   1800
tttaggcaca gctggatcca agggcacaaa tgatgtcatc aggctccagt tattctccat   1860
ctcccagctc agcttttcct gtctgtaagc ctgattttca ggaaggctct ttcctagtga   1920
tggagatgac caccatcagc tccaggcttc tatcctgcta acccagtaac ccagtgggaa   1980
gagatttact tattccaata attccaagtg gagagtgtca ttgacccgtt tggggtctca   2040
tctctacttc taggggaatg aaacactttg agtggccagg cctgtgtcat gtgctaattc   2100
ctagagccag ggaaataagg tctgaggatt caggatgggg tgaaaggtgg ttgcttaaag   2160
gaaaatgaaa tacaattagc agaataaggg gaaacgagtg gtctgctctg ctcgggcaaa   2220
acaagagatg cccattactg tgagggaccc ttgaagtctg gactcttaaa tgggttttg    2280 ctgatttcct gggtgcatgc taggatgatg gggcttgatg cagtagggaa gagacgatgt   2340
aaaaataata aacaatatat accttcaaaa aaaaaaaaa aaaaaaaaa a              2391
```

<210> SEQ ID NO 26
<211> LENGTH: 1787
<212> TYPE: DNA
<213> ORGANISM: Homo Sapiens

<400> SEQUENCE: 26

```
agcaacgagc gacggcctga cgtcggcgga gggaagccgg cccaggctcg gtgaggaggc     60
aagtcctgca gcctcagcat gcgctggccg gatgtaccct gaggtgccct ctcacttcct    120
ccttcaggtt ctgagggac aggctgacct ggaggaccag aggcccccgg aggagcactg    180
aaggagaaga tctgccagtg ggtctccatt gcccagctcc tgcccacact cccgcctgtt    240
gccctgacca gagtcatcat gcctcttgag cagaggagtc agcactgcaa gcctgaagaa    300
ggccttgagg cccgaggaga ggccctgggc ctggtgggtg cgcaggctcc tgctactgag    360
gagcaggagg ctgcctcctc ctcttctact ctagttgaag tcaccctggg ggaggtgcct    420
gctgccgagt caccagatcc tccccagagt cctcagggag cctccagcct ccccactacc    480
atgaactacc ctctctggag ccaatcctat gaggactcca gcaaccaaga agaggagggg    540
```

```
ccaagcacct tccctgacct ggagtctgag ttccaagcag cactcagtag gaaggtggcc        600
aagttggttc attttctgct cctcaagtat cgagccaggg agccggtcac aaaggcagaa        660
atgctgggga gtgtcgtcgg aaattggcag tacttctttc ctgtgatctt cagcaaagct        720
tccgattcct tgcagctggt cttttggcatc gagctgatgg aagtgggacc catcggccac       780
gtgtacatct ttgccacctg cctgggcctc tcctacgatg gcctgctggg tgacaatcag        840
atcatgccca agacaggctt cctgataatc atcctggcca taatcgcaaa agagggcgac        900
tgtgcccctg aggagaaaat ctgggaggag ctgagtgtgt tagaggtgtt tgaggggagg        960
gaagacagta tcttcgggga tcccaagaag ctgctcaccc aatatttcgt gcaggaaaac       1020
tacctggagt accggcaggt ccccggcagt gatcctgcat gctatgagtt cctgtggggt       1080
ccaagggccc tcattgaaac cagctatgtg aaagtcctgc accatatggt aaagatcagt       1140
ggaggacctc gcatttccta cccactcctg catgagtggg ctttgagaga ggggaagag       1200 tgagtctgag cacgagttgc agccagggcc agtgggaggg ggtttgggcc agtgcacctt       1260
ccggggcccc atcccttagt ttccactgcc tcctgtgacg tgaggcccat tcttcactct       1320
ttgaagcgag cagtcagcat tcttagtagt gggtttctgt tctgttggat gactttgaga       1380
ttattctttg tttcctgttg gagttgttca aatgttcctt ttaacggatg gttgaatgag       1440
cgtcagcatc caggtttatg aatgacagta gtcacacata gtgctgttta tatagtttag       1500
gagtaagagt cttgttttt attcagattg ggaaatccat tccatttgt gaattgtgac         1560 ataataatag cagtggtaaa agtatttgct taaaattgtg agcgaattag caataacata       1620
catgagataa ctcaagaaat caaaagatag ttgattcttg ccttgtacct caatctattc       1680
tgtaaaatta aacaaatatg caaaccagga tttccttgac ttctttgaga atgcaagcga       1740
aattaaatct gaataaataa ttaaaaaaaa aaaaaaaaa aaaaaaa                      1787

<210> SEQ ID NO 27
<211> LENGTH: 6218
<212> TYPE: DNA
<213> ORGANISM: Homo Sapiens

<400> SEQUENCE: 27
gttaaatctg tggcctttgc atcgaagcca tgctttcaag atgtaaaacc tatggagctg         60
acaccagggg cccaacagca aggtataaat tatcaagagt tgacttcagg atggcaagat        120
gtgaaatcaa tgatgttggt accagagcca actaggaagt tcccatcagg accactgttg        180
actagtgtca gattttcaaa tttgtctcca gaatcacagc aacaggatgt gaaatctttg        240
gagtttactg tagagccaaa gttgcaaagc gtaaaacatg tgaaattatc ttcagtgtct        300
ctgcagcaaa ctataaaatc tgtggaatta gcaccagggt cactgcctca agagtgaaa        360 tatggggagc aaactccaag aacaaattat caaatcatgg aatcctctga actaatccct        420
agaccagggc atcagtttgc aaaatatgca gagatgatcc cacagccaaa gtatcaaatc        480
cctaaatctg caaatttgat ttcaatacca atttatcacg ccacagaatc ttcagaaatg        540
gcacaaggat tggcatataa aggcatagat actgtagaga atctgtggg gttgacccca         600 aagctaacag gtagagctaa ggaatcctta gggatgctgc tgcagccaga tcttcaggta        660
ccaaaatttg ttgatctgac tccaatggta agggatcaag gctcaaaatt cttaggatta        720
actccagaga aaagctacca aatcctagaa actatggaat tgctctctca gtcacggccc        780
cgagttaagg atgtggggga gttatatatg aagccactgc agcaaactgt ggaatatgaa        840
gggattactc cggaactcaa gcattacttt acagaagcta tggggttgac cgctgaggca        900
```

```
aggatacaag caaatgaatt ctttggaatg accccaaagc caacaagtca agccactgga      960
tttgcagaga gatccccaag gctctgtcct caaaacttag aatgtgtgga ggtgatctct     1020
gagaaaagac tgcaagggga agaatctgtg gtattgattc caaagtcatt acatcacgtc     1080
ccagattctg cttcagggat gacacctggg ttaggacatc gagttcctga atctgtggag     1140
ttgacttcta agtcaggagt gcaggtagag aaaactttgc aattaacccc caaaccacag     1200
catcatgtgg gatctccagg gataatatca gggttaggac atcaagtccc agaatctgta     1260
aatctgacct gtaagcaatg gctacaaatg gaggaatctt tagaggtgcc cctgaagcaa     1320
acaagtcaag ttataggaca tgaagaatct gtagagctca cctctgaggc acggcagcac     1380
agggaggtat caatgggggct aacaaagtca agaatcaaa gtatgaaatc tccagggaca     1440
accccaggac cactgggtcg aattgtagaa tttatgagga ttagtccaga gccactagat     1500
caagtcacag aatctgcaag gacacagctt caagttgctc aatctgaaga ggtaatcctc     1560
atagatgtcc caaagttgt tcaatctgtg aaagtgaccc ctggaccacc atttcaaatt     1620
gtaaagtctg tgacgatacc aaggccaacc cctcaaatgg tagaatatat tgagttgact     1680
ccaaaactgc aatatgtgag accttcagag caccacacag ggccatgttt gcaagatgtg     1740
aaatctacaa aattaatcac aaagccaaaa caccagattt tggaaacagt ggagttgaca     1800
gggtttcaaa ttgtaaaaac tatgttaatc ccagggccat cccttcaaat cgtaaaatct     1860
gaggagttag caccaggacc aattcctcag gttgtagaac aataggagt agccctagaa     1920
tcaggaattg aagcaataaa ttgtgtggat ttacttccaa ggccacatct tcaagaactg     1980
atagtacctg cagaattaac tccaagtcca tgtactcaag tgaagtctgc agaattaacc     2040
tcaccgcaaa catctccatt tgaggaacat acaatattga ctcataaaca agggcttcag     2100
gctgtgaaat ctacagtgat aaaaacagag cctcctaaag ttatggaaac tgaggatttg     2160
aatctaggac acgtgtgtca gaataggggac tgtcagaagt taacatcaga agagttacaa     2220
gtagggactg acttctctag gttcctacaa agctcttcaa ccacactcat ttcaagctct     2280
gtcagaacag catctgaatt aggaggactt tgggattctg ggatacagga agtatccaga     2340
gctttggata taaaaaaccc tgggacagat attttgcagc ctgaagagac ctatatagac     2400
cctactatga tacaatcttt aacttttcct ttggcccttc ataatcaaag ctccgataag     2460
acagctaaca ttgtggaaaa cccatgtcct gagattctag gagtggatgt aatatctaaa     2520
gagacaacta agaggaagca aatggaggag ctagagaact cacttcagag acatctacca     2580
caaagctgga gatcacgatc taggacattc caggcagaat caggggttca gaaaggtctc     2640
atcaagtctt ccccgggcag acaacacaat gtctgggaga gtcatgcctg gaggcagcga     2700
ctaccaagaa aaatatctctc cactatgcta atgctgggga atattttagg gaccactatg     2760
gaaaggaagc tttgttctca acatctttta gcagaaagag ccactgcaga tacctgtcaa     2820
tctattcaga atttatttgg gattccagct gaactgatgg aaccttccca gagcctgcca     2880
gagaagggtc cagttactat ttctcagcct tctgtggtca aaaactatat tcagagacat     2940
acttttttatc atggtcataa gaaaagaatg gccttaagga tatggacacg tggctccaca     3000
tcttccataa tacagcaata ctctgggact agagtgagaa taaagaagac aaaactcaacg     3060
ttcaatggta tatcccaaga agtcattcaa catatgcctg tctcatgtgc aggggggccag     3120
cttcctgtcc tggtaaagtc agagtcttcc ctcagcatat tttacgatag agaagatctt     3180
gttccaatgg aagaaagtga ggactcacag agtgattccc agacaaggat ttctgagtcc     3240
```

```
caacactccc tcaagccaaa ttatctttcc caggccaaga ctgacttctc agaacagttc    3300
cagttgctag aagatctgca gctaaaaata gcagcaaaac tcttaaggag tcaaataccc    3360
cccgatgtgc ctccacctct agcttcaggt ctagtcctaa atacccctat ctgcctacag    3420
tgtggccgat gttcaggact taattgccat cataaattac agaccacttc ggggccttat    3480
cttcttatct atccacagct ccaccttgta cgcactcctg aaggccatgg tgaggttcgg    3540
ttgcatcttg gctttaggct gagaattggg aaaagatccc aaatctcaaa gtatcgtgaa    3600
agagatagac ccgtcatacg gagaagccct atatcaccat cacaaaggaa agctaaaatc    3660
tatactcaag cttccaagag tcctacttcc acaatagatt tgcagtctgg gccttcccag    3720 tccctgctc ctgtacaagt ctacatcagg cgaggacaac gcagcaggcc tgacttagta     3780
gaaaagacaa aaactagagc acctgggcac tatgaattca ctcaagttca caacctacca    3840
gagagtgact ctgaaagcac tcagaatgaa aaacgggcta agtgagaac caaaaagacc     3900 tctgattcaa aatatccaat gaagagaatc accaagcgac ttagaaaaca cagaaagttc    3960
tacacaaaca gtagaaccac aatagagagt ccttctaggg aattagcagc ccatttaaga    4020
aggaagagga ttggagcaac tcagacaagt actgcctctt taaaaagaca acctaagaaa    4080
ccttcccaac ccaagttcat gcaactgctt tttcagagcc taaagcgggc attccaaaca    4140
gcacacagag ttatagcttc tgttgggcgg aagcctgtgg acgggacaag gccagacaat    4200
ttgtgggcaa gcaaaaacta ttatccaaaa caaaatgcca gggactattg cttaccaagc    4260
agtatcaaaa gagacaagag gtcagctgac aagctaacgc cagcaggctc aaccattaag    4320
caggaggaca tattgtgggg aggaacggtc cagtgcagat cagctcaaca gccaagaaga    4380
gcttactctt tccaacccag acctcttcga ctgcccaagc ccacagattc ccaaagtggt    4440
attgctttcc aaactgcctc agtggggcag cctctgagaa ctgttcaaaa ggacagtagt    4500
agcagatcaa agaaaaactt ctatagaaat gaaacctcca gccaggagtc taagaacttg    4560
tccacaccag gaaccagagt tcaggcccga ggaagaatcc tacctggttc ccctgtgaag    4620
agaacctggc accgacatct taaagacaaa ctcacacaca aggagcataa ccaccccagc    4680
ttctataggg agagaacccc acgcggtcct tctgagagaa cccgtcataa cccctcttgg    4740
agaaaccatc gcagtccctc tgagagaagc caacgcagtt ccttggagag aagacatcac    4800
agtccctctc agaggagcca ctgcagtccc tctaggaaaa accattccag tccttctgag    4860
agaagctggc gcagtccgtc tcagagaaat cactgcagtc cccccgagag gagctgtcac    4920
agtctctctg aaaggggcct tcacagtccc tctcagagga gccatcgcgg tccctctcag    4980
agaagacatc acagtccctc agagagaagc catcgcagtc cctcagagag aagccatcgc    5040
agttcctctg agaagacca tcgcagtccc tcccagagga gccatcgcgg tccctcagag    5100
agaagccatt gcagtccctc tgagagaaga catcgcagtc cctctcagag agccatcgt    5160 ggtccctctg agaagacaca tcacagtccc tctaagagaa gccatcgcag tcccgctcgg    5220
aggagccatc gcagtccctc agagagaagc catcacagtc cctctgagag aagccatcac    5280
agtccctctg agaagacaca tcacagtccc tctgagagaa gccattgcag tccctctgag    5340
agaagccatt gcagtccctc tgagagaaga catcgcagtc cctctgagag aagacatcac    5400
agtccctcag agaaaagcca tcacagtccc tctgagagaa gccatcacag tccctctgag    5460
agaagacgtc acagtccctt ggagaggagc cgtcacagtc tcttggagag agccatcgc    5520 agtccctctg agaggagatc tcacaggtcc tttgagagga gccatcgtag gatttctgag    5580
agaagtcaca gtccctcaga gaagagccac ctcagtccct tggaaagaag ccgttgcagt    5640
```

| | |
|---|---|
| ccctctgaga ggagaggaca cagttcctct gggaaaacct gtcacagtcc ctctgagaga | 5700 |
| agccatcgca gtccctccgg gatgaggcaa gggaggacct ctgagaggag ccatcgcagt | 5760 |
| tcctgtgaga gaacccgtca cagtccctct gagatgaggc cagggaggcc ctctgggagg | 5820 |
| aaccattgca gtccctctga gaggagccga cgcagtcccc ttaaggaggg actcaagtac | 5880 |
| agtttccctg gagagaggcc cagccatagt ttgtctagag atttcaagaa tcaaacaact | 5940 |
| ctcctcggga ccacacataa aaatcccaaa gcagggcaag tgtggaggcc tgaagctact | 6000 |
| cgatgaggcg aggtccgccc ctattattca ttgtcctaag tcttcatcgt gctgcccttt | 6060 |
| ccaggcttct ttcctgctca gccactgcct ccaattcctg cgcccccagc gtggaaaggc | 6120 |
| ttccatttct ctctaccggg ggggaggcgg gtgagaatgg gtctgtaatt tctctaagat | 6180 |
| gaataaaggg gcagtaaatg aaaaaaaaaa aaaaaaaa | 6218 |

<210> SEQ ID NO 28
<211> LENGTH: 1404
<212> TYPE: DNA
<213> ORGANISM: Homo Sapiens

<400> SEQUENCE: 28

| | |
|---|---|
| ggcagtgcag ctgtgggaac ctctccacgc gcacgaactc agccaacgat ttctgataga | 60 |
| tttttgggag tttgaccaga gatgcaaggg gtgaaggagc gcttcctacc gttagggaac | 120 |
| tctggggaca gagcgccccg gccgcctgat ggccgaggca gggtgcgacc caggacccag | 180 |
| gacggcgtcg ggaaccatac catggcccgg atccccaaga ccctaaagtt cgtcgtcgtc | 240 |
| atcgtcgcgg tcctgctgcc agtcctagct tactctgcca ccactgcccg gcaggaggaa | 300 |
| gttccccagc agacagtggc cccacagcaa cagaggcaca gcttcaaggg ggaggagtgt | 360 |
| ccagcaggat ctcatagatc agaacatact ggagcctgta acccgtgcac agagggtgtg | 420 |
| gattacacca acgcttccaa caatgaacct tcttgcttcc catgtacagt ttgtaaatca | 480 |
| gatcaaaaac ataaaagttc ctgcaccatg accagagaca cagtgtgtca gtgtaaagaa | 540 |
| ggcaccttcc ggaatgaaaa ctccccagag atgtgccgga gtgtagcag gtgccctagt | 600 |
| ggggaagtcc aagtcagtaa ttgtacgtcc tgggatgata ccagtgtgt tgaagaattt | 660 |
| ggtgccaatg ccactgtgga aaccccagct gctgaagaga caatgaacac cagcccgggg | 720 |
| actcctgccc cagctgctga agagacaatg aacaccagcc cagggactcc tgccccagct | 780 |
| gctgaagaga caatgaccac cagcccgggg actcctgccc cagctgctga agagacaatg | 840 |
| accaccagcc cggggactcc tgccccagct gctgaagaga caatgaccac cagcccgggg | 900 |
| actcctgcct cttctcatta cctctcatgc accatcgtag ggatcatagt tctaattgtg | 960 |
| cttctgattg tgtttgtttg aaagacttca ctgtggaaga aattccttcc ttacctgaaa | 1020 |
| ggttcaggta ggcgctggct gagggcgggg ggcgctggac actctctgcc ctgcctccct | 1080 |
| ctgctgtgtt cccacagaca gaaacgcctg ccctgcccc aagtcctggt gtctccagcc | 1140 |
| tggctctatc ttcctccttg tgatcgtccc atccccacat cccgtgcacc ccccaggacc | 1200 |
| ctggtctcat cagtccctct cctggagctg ggggtccaca catctcccag ccaagtccaa | 1260 |
| gagggcaggg ccagttcctc ccatcttcag gcccagccag gcaggggca gtcggctcct | 1320 |
| caactgggtg acaagggtga ggatgagaag tggtcacggg atttattcag ccttggtcag | 1380 |
| agcagaaaaa aaaaaaaaaa aaaa | 1404 |

<210> SEQ ID NO 29

```
<211> LENGTH: 1173
<212> TYPE: DNA
<213> ORGANISM: Homo Sapiens

<400> SEQUENCE: 29
gcacagagtt gggagtgact ccagagcctc ctgcaagatg ctgttgattc tgctgtcagt        60
ggccttgctg gccctgagct cagctcagaa cttaaatgaa gatgtcagcc aggaagaatc       120
tccctcccta atagcaggaa atccacaagg accatcccca caaggaggca acaagcccca       180
aggcccccca cctcctccag gaaagccaca aggaccaccc ccacaaggag gcaacaaacc       240
tcaaggtccc ccacctccag gaaagccaca aggaccaccc ccacaagggg acaagtcccg       300
aagtccccga tctcctccag gaaaaccaca aggaccaccc ccacaaggag gtaaccagcc       360
ccaaggtccc ccacctcctc caggaaagcc acaaggacca ccccacaag gaggcaacag       420
acctcaaggt ccccccacctc caggaaagcc acaaggacca ccccacaag gagacaagtc       480
ccgaagtccc cgatctcctc caggaaagcc acaaggacca ccccacaag gaggtaacca       540
accccaaggt ccccccacctc ctccaggaaa gccacaagga ccacccccac aaggaggcaa       600
gaaacctcag gtcccccac ctccaggaaa gccacaagga ccacccccac aaggagacaa       660
gtcccgaagt tccaatctc ctccaggaaa gccacaagga ccacccccac aaggaggcaa       720
ccagccccaa ggtcccccac ctcctccagg aaagccacaa ggaccacccc cacaaggagg       780
caacaaacct caaggtcccc cacctccagg aaagccacaa ggaccaccg cacaaggagg       840
cagcaagtcc caaagtgccc gatctcctcc aggaaagcca aggaccac cccaacaaga       900
aggcaacaat cctcaaggtc ccccacctcc agcaggagga atccccagc agcctcaggc       960
acctcctgct ggacagcccc agggaccacc acgccctcct caaggggggca gaccttccag      1020
acctccccag tgcagcctcc ccagtcatc taggattcaa tgacaggaag tgaataagaa      1080
gatgagagtg attcaaatga ttcaaattcc atgacattgg aaaaaggtca tcatagctct      1140
aacttcaata taccaataaa ataatcagct tgc                                    1173

<210> SEQ ID NO 30
<211> LENGTH: 1404
<212> TYPE: DNA
<213> ORGANISM: Homo Sapiens

<400> SEQUENCE: 30
ggcagtgcag ctgtgggaac ctctccacgc gcacgaactc agccaacgat ttctgataga        60
tttttgggag tttgaccaga gatgcaaggg gtgaaggagc gcttcctacc gttagggaac       120
tctggggaca gagcgcccccg gccgcctgat ggccgaggca gggtgcgacc caggacccag       180
gacggcgtcg ggaaccatac catggcccgg atccccaaga ccctaaagtt cgtcgtcgtc       240
atcgtcgcgg tcctgctgcc agtcctagct tactctgcca ccactgcccg gcaggaggaa       300
gttccccagc agacagtggc cccacagcaa cagaggcaca gcttcaaggg ggaggagtgt       360
ccagcaggat ctcatagatc agaacatact ggagcctgta acccgtgcac agagggtgtg       420
gattacacca acgcttccaa caatgaacct tcttgcttcc catgtacagt ttgtaaatca       480
gatcaaaaac ataaaagttc ctgcaccatg accagagaca cagtgtgtca gtgtaaagaa       540
ggcaccttcc ggaatgaaaa ctccccagag atgtgccgga agtgtagcag gtgccctagt       600
ggggaagtcc aagtcagtaa ttgtacgtcc tgggatgata tccagtgtgt tgaagaattt       660
ggtgccaatg ccactgtgga aaccccagct gctgaagaga caatgaacac cagcccgggg       720
actcctgccc cagctgctga agagacaatg aacaccagcc cagggactcc tgccccagct       780
```

```
gctgaagaga caatgaccac cagcccgggg actcctgccc cagctgctga agagacaatg      840
accaccagcc cggggactcc tgcccagct gctgaagaga caatgaccac cagcccgggg       900
actcctgcct cttctcatta cctctcatgc accatcgtag ggatcatagt tctaattgtg      960
cttctgattg tgtttgtttg aaagacttca ctgtggaaga aattccttcc ttacctgaaa     1020
ggttcaggta ggcgctggct gagggcgggg ggcgctggac actctctgcc ctgcctccct     1080
ctgctgtgtt cccacagaca gaaacgcctg ccctgcccc aagtcctggt gtctccagcc      1140
tggctctatc ttcctccttg tgatcgtccc atccccacat cccgtgcacc cccaggacc      1200 ctggtctcat cagtccctct cctggagctg ggggtccaca catctcccag ccaagtccaa     1260
gagggcaggg ccagttcctc ccatcttcag gcccagccag gcaggggca gtcggctcct      1320 caactgggtg acaagggtga ggatgagaag tggtcacggg atttattcag ccttggtcag     1380
agcagaaaaa aaaaaaaaaa aaaa                                            1404
```

<210> SEQ ID NO 31
<211> LENGTH: 2174
<212> TYPE: DNA
<213> ORGANISM: Homo Sapiens

<400> SEQUENCE: 31

```
cgtgatctcg ggtttgtcgg gctgaaatgt ggcgggtctc ggaaggttcc gacctcagta       60
aagagagcta acgtgtattc ttcttttct tagatgctga gatgaatcgt cacctgtgtg       120
tttggctttt tagacatcca tctcttaatg gttacctcca gtgtcacatc cagctccatt      180
ctcatcaatt tagacagata catcttgata caaggctgca agttttaga caaaacagga       240 attgcattct tcatctgtta agtaagaatt ggtccaggag atattgccat caagacacca      300
agatgctctg gaagcataaa gcactacaga aatatatgga gaacctgagt aaggagtacc      360
aaacacttga gcaatgtctg cagcatatcc ctgtgaatga ggaaaaccga aggtccttga      420
acagaaggca tgctgagttg gcacctcttg cagccatttta ccaagaaatt caggagactg     480
aacaagcaat tgaagaatta gaatcaatgt gtaaaagcct aaataaacaa gatgaaaagc      540
agttacaaga acttgcactg gaagaaaggc aaaccattga tcaaaaatc aacatgttgt       600 acaatgagct tttccagagc cttgtgccaa aggagaaata tgacaaaaat gatgttattt      660
tagaggtgac agctggaagg actactggag gtgacatctg ccaacaattt acccgagaaa     720
tatttgacat gtaccagaat tattcgtgct ataaacactg gcaatttgaa cttctgaatt      780
atacaccagc agattatggt ggactacatc atgcagccgc ccgaatttcc ggtgacggtg      840
tctataagca tttgaagtat gagggtggga ttcaccgagt tcagcgcatc cccgaggtgg     900
gcctgtcctc aaggatgcag cgcattcaca caggaacgat gtcggttatt gtccttcctc      960
agccagatga ggtggatgtg aaattggacc ccaaggattt gcgaatagat acattcgag      1020 ccaaaggagc aggagggcag catgttaata aactgatag tgccgtcaga cttgtccaca     1080
tccccacagg gctagtagta gaatgccaac aagaaagatc acagataaaa aataaagaaa     1140 tagccttcg tgtgttgaga gctagactct accagcagat tattgagaaa gacaagcgtc      1200
agcaacaaag tgctagaaaa ctgcaggtgg gaacaagagc ccagtcagag cgaattcgga     1260
catataattt cacccaggat agagtcagtg accacaggat agcatatgaa gttcgtgata     1320
ttaaggaatt tttatgtggt gggaagggcc tggatcagct aattcagaga ctgcttcaat     1380
cagcagatga agaagccatt gctgaacttt tggatgaaca ccttaaatca gcaaaataaa     1440
```

| | |
|---|---|
| tactaactta ttattattta tgattatata aatgaaatgg acctatatca agaggcagac | 1500 |
| tgaagcttgg aaatcattat gaatatttgt aaattacagc tttaagaaca cattacacat | 1560 |
| aaatatatgt tttgtaatta atcgaagtca catttcctga cctaagaatt tatttaggt | 1620 |
| ttcctgtaaa gtacaatcca actcatcaag tagaaaataa gcatgcatca ttgaaaagag | 1680 |
| aaagtattga gaattgattg tgtcatttag gacaagtcac ttgttctctt tatatgcctt | 1740 |
| ttttccccag ccatctatga attaatttaa atatattttt aatctactac ttcaggaaaa | 1800 |
| tatggtaaaa tttagtaaaa tatgaatttt agacttcctt ataaaccttt tatttaaata | 1860 |
| caaagtaccct tggcctatag tggatgctta tgcctgtaat cccagtgctt tgaagggcca | 1920 |
| aaggggaag atctcttgag gtaagaattt gagaccagcc tgggcaaaat agaccccatg | 1980 |
| tctacaaaaa aactcaaaac ataaagaaaa accataatac tgttaatcat gttaaagtta | 2040 |
| agacttagac tgcaactttt aaataaaaat tatgaagaat atgagtcatt caataacaat | 2100 |
| gagcatctgg gtacagacag taaagcccctt tgattgctgt atgaattcca cactatataa | 2160 |
| acaataagct gata | 2174 |

<210> SEQ ID NO 32
<211> LENGTH: 349
<212> TYPE: DNA
<213> ORGANISM: Homo Sapiens

<400> SEQUENCE: 32

| | |
|---|---|
| atggcaggcc aagcgaacat atcttgagaa cagtgctata ttaaggaaag ctctgcaaga | 60 |
| aatcaaaata agattctact agaaaacctg ctaaggagtg cccggggggta ggtgggggaag | 120 |
| tatggaaagg caagaaccga agtctagcta ggcagtgtca ggagacacct ggaagagtgg | 180 |
| tattcagcta gaggaaattg ccacaaaatt agatggaaat tttcagtgtt gagggatcta | 240 |
| aaaaagacca atgtgattca gtccagtgca tagatgcaga actcatactg caaatgtcca | 300 |
| aattgtccctt cctgtctttt cttgtcaaac ttggccttgc catatgcaa | 349 |

<210> SEQ ID NO 33
<211> LENGTH: 1086
<212> TYPE: DNA
<213> ORGANISM: Homo Sapiens

<400> SEQUENCE: 33

| | |
|---|---|
| agtacgcggg ggggctgtgc cgtggctgga agttactgtg aggcggcggc taagaaggcg | 60 |
| gctctggtgg cggcggtgga ggctgaggcg gcggccgagg cggcgacgga ggaaacagaa | 120 |
| gatggcagat tttttgaaag gactgcctgt ctacaacaaa agcaatttta gtcgatttca | 180 |
| cgcggactcc gtgtgcaaag cctcgaaccg acggccctca gtctacctgc ctacccgcga | 240 |
| gtacccgtct gaacagatca tcgtgacaga aaagacaaac atcctcctgc gctacctgca | 300 |
| tcagcaatgg gacaaaaaga acgctgccaa gaagagagac caggagcaag tggagctgga | 360 |
| aggcgagagc tccgcaccctc cccgcaaggt ggcgcggacc gacagcccag acatgcacga | 420 |
| ggacacttaa gactctcaac tccacaggcg cctcctgcca ggtctgctcc tcggtcgccc | 480 |
| acccgccctgc ccgccatgtg taagcacccc gcccgcccgc ctccctgccg gcccatccac | 540 |
| accctgcgtc cacaccactt ccaacctcat aggagccgat gtatttattt tccttgagtt | 600 |
| tttatttatg ctgtaacctg tatcaagcgt tggttaaagg ggacatcaga cccagtagtg | 660 |
| tgatgttggt agatgctttt taaaaaaaac aacattgtcc ccccgacccc cgccttccat | 720 |
| cgggccagtt ccccgattcc tgccccccagt tctccagaga accagagtgt gtctgtgaga | 780 |

```
gtctctagcg ggggctttac tgtggccggg tgacaggggc gggcccgggg tggcctgacc        840
taccaggaca gccgagtggc cttctccccc ccaacaccgg tccaggccat tgagactcgg        900
tcttgtccca cgcttcgccc ggaactttcc catgcccaga cctcactcag cgtgcacgca        960
cgttggggag aagtcggccc ttgggatctt tctcttgagt catttttattt ttatcatgga      1020 ctagtgcgtg ctccgtgtcc accccccaata aagggtcttt tcctaaaaaa aaaaaaaaaa      1080
aaaaaa                                                                  1086

<210> SEQ ID NO 34
<211> LENGTH: 398
<212> TYPE: DNA
<213> ORGANISM: Homo Sapiens

<400> SEQUENCE: 34
ccaatattta tttaatggtg gatcttgacg tggcactata atctggctcc cagtccatga         60
aactgaagtc cagaagcagt tttcctaac ctgggacctg ccaaaaaaca cactatatgt        120 gccctgtag gcatgctggc tgactttatt cccactgtga atcttgaagc agtcctaaaa        180
cccagctcca gtcccaaaac ctacctccag tccctgtcaa ctaaagtctg ggagcagtcc        240
tgcccaccca ggaatctgga gggagaaatg ccatgaagcc agaaacaaac ctgaagactt        300
tggtctcagc tgtgtatcct gaagcagccc tatgaatcag ttccacaccc ccattccccc        360
actccagata aagcttcagt tatatctcaa aaaaaaaa                                398

<210> SEQ ID NO 35
<211> LENGTH: 6093
<212> TYPE: DNA
<213> ORGANISM: Homo Sapiens

<400> SEQUENCE: 35
gcctgccagc tagccggagc cgcgggtgag cgcggcgagc ggcgaccctg gtgaggagcg         60
cggcgcggga ggcacgttcc ttagctccgc cgcggccgtc ctccgcggct cgaggactcc        120
gcttccttcc ctcccctccc ctgcgctccg gcctggggtc tcggcgcggg gagcggaggg        180
aagggacgaa ggaggagtag gtgaaagcgg ggtgaggggc ggaagggtcc cggcgcgggg        240
tgaggcgagg gctgcctctt gttctcccgc cgctgccgcc gtctcctggt cgggtgccgc        300
ggccagaggc gcgcggggct gccgaggcac ccgcactatg caggcagact gccggccgcc        360
gcgatggcga ccgggcggt ggtgagagcc aggcgctgcc cgcagtgtcc ccaagtccgg        420
gccgcggccg ccgcccccgc ctgggccgcg ctccccctct cccgctccct ccctccctgc        480
tccaactcct cctccttctc catgcctctg ttcctcctgc tcttacttgt cctgctcctg        540
ctgctcgagg acgctggagc ccagcaaggt gatggatgtg gacacactgt actaggccct        600
gagagtggaa cccttacatc cataaactac ccacagacct atcccaacag cactgtttgt        660
gaatgggaga tccgtgtaaa gatggagag agagttcgca tcaaatttgg tgactttgac        720
attgaagatt ctgattcttg tcactttaat tacttgagaa tttataatgg aattggagtc        780
agcagaactg aaataggcaa atactgtggt ctggggttgc aaatgaacca ttcaattgaa        840
tcaaaaggca atgaaatcac attgctgttc atgagtggaa tccatgtttc tggacgcgga        900
tttttggcct catactctgt tatagataaa caagatctaa ttacttgttt ggacactgca        960
tccaattttt tggaacctga gttcagtaag tactgcccag ctggttgtct gcttcctttt       1020
gctgagatat ctggaacaat tcctcatgga tatagagatt cctcgccatt gtgcatggct       1080
```

-continued

```
ggtgtgcatg caggagtagt gtcaaacacg ttgggcggcc aaatcagtgt tgtaattagt    1140
aaaggtatcc cctattatga aagttctttg gctaacaacg tcacatctgt ggtgggacac    1200
ttatctacaa gtcttttac atttaagaca agtggatgtt atggaacact ggggatggag    1260
tctggtgtga tcgcggatcc tcaaataaca gcatcatctg tgctggagtg gactgaccac    1320
acagggcaag agaacagttg gaaacccaaa aaagccaggc tgaaaaaacc tggaccgcct    1380
tgggctgctt ttgccactga tgaataccag tggttacaaa tagatttgaa taaggaaaag    1440
aaaataacag gcattataac cactggatcc accatggtgg agcacaatta ctatgtgtct    1500
gcctacagaa tcctgtacag tgatgatggg cagaaatgga ctgtgtacag agagcctggt    1560
gtggagcaag ataagatatt tcaaggaaac aaagattatc caggatgt gcgtaataac    1620
tttttgccac caattattgc acgttttatt agagtgaatc ctacccaatg gcagcagaaa    1680
attgccatga aaatggagct gctcggatgt cagtttattc ctaaaggtcg tcctccaaaa    1740
cttactcaac ctccacctcc tcggaacagc aatgacctca aaaacactac agcccctcca    1800
aaaatagcca aggtcgtgc cccaaaattt acgcaaccac tacaacctcg cagtagcaat    1860
gaatttcctg cacagacaga acaaacaact gccagtcctg atatcagaaa tactaccgta    1920
actccaaatg taaccaaaga tgtagcgctg gctgcagttc ttgtccctgt gctggtcatg    1980
gtcctcacta ctctcattct catattagtg tgtgcttggc actggagaaa cagaagaaa    2040
aaaactgaag gcacctatga cttaccttac tgggaccggg caggttggtg aaaggaatg    2100
aagcagtttc ttcctgcaaa agcagtggac catgaggaaa ccccagttcg ctatagcagc    2160
agcgaagtta atcacctgag tccaagagaa gtcaccacag tgctgcaggc tgactctgca    2220
gagtatgctc agccactggt aggaggaatt gttggtacac ttcatcaaag atctaccttt    2280
aaaccagaag aaggaaaaga agcaggctat gcagacctag atccttacaa ctcaccaggg    2340
caggaagttt atcatgccta tgctgaacca ctcccaatta cggggcctga gtatgcaacc    2400
ccaatcatca tggacatgtc agggcacccc acaacttcag ttggtcagcc ctccacatcc    2460
actttcaagg ctacggggaa ccaacctccc ccactagtgg aacttacaa tacacttctc    2520
tccaggactg acagctgctc ctcagcccag gcccagtatg ataccccgaa agctgggaag    2580
ccaggtctac ctgccccaga cgaattggtg taccaggtgc acagagcac acaagaagta    2640
tcaggagcag aagggatgg ggaatgtgat gtttttaaag aaatcctttg aagatgatgc    2700
tgctttttac aaagcatcgt tttaaagcac atggccttt ttttttaatt attagtggta    2760
gtaatatata gaatgtatta cataactgtc actgaagtgg ttggggaaaa tgtggtgact    2820
gaggtacagg aaactactaa tcttgccatc ttgctttaag gtgttatggt ggcacagtta    2880
ctgctcgcct gttaaattc aaatgtcctg tttgatacta ctgtagaaca ctatttttaa    2940
tacagaaaaa gctccctata atgcacttca gagaaattaa aaatcacaga gtatttatta    3000
ccaatgctgc aggtacatta atgaactcga gatggctctg taagcctgac tgcaataac    3060
gcacggtact gttcttgaaa tacctaatgg cttgaaattc tagtctgttt gtgaaagatg    3120
ggtactatca tgatttcctc ttctattcct atattctttt ctggattttt tttaataatt    3180
agtgatataa gcattgtttt tattgcagcc atatccactt atccatctta agatctgtag    3240
ctgggatttt ctgacttgta atgagcaggg ggattgcttt ttcactttgt gacactcttt    3300
agagcttaa tgcttcacag tatatggcct ggtctcatcc ttgcgtgttc cacttgaggc    3360
cctttggtgt cttgccccat tcttgtgttt ataaatgtt tgagtatttc tgatgagtga    3420
tgcttgcctt agtctcatga attcagatcc cttcatgtcc tttaagtatg ctcctcaatg    3480
```

```
tgtaaacagg aacaacttta tgatttgaaa gctttaaagg agattcttct cccacccca   3540 actttatttg caatgggatt tttcctagga gagttatgaa aagttgaagg cttctaaggg   3600
aatactgtaa acatgaccca cttatattta tcacagtgaa aggcaaaatt attcactcag   3660
aagtaatata aattacctct ttaaaaagta accagaattt gtcctttttg gttttataca   3720
ttcacaaaca tatacatttt tcttgagtct caaggtattt tatatttta gtcagaaaaa   3780 ataattttc atttcagttt tccataaact gttacacaaa atataaacct aacgtgtatt   3840
tttcaggact gcgtgatcgt gcactttgtg tggtaagagg tttgagtagt cctatatgtc   3900
acctagggaa cagacattat agcttactag caaatgaata ttcatgcctt gtttttgata   3960
cctcctggca gcttccatgt caccacttgt tcatacctgc ccagagctag ttttagacat   4020
ggcaaaatag aaatcatctg taatttatta gctaacaatg taaaaccatc ttttaaagcc   4080
ttcagactgt caagacgaca tgagcagctc accatatgat aaaaatacat aaatttgaca   4140
ttccctcttc cataaacctt tgtttgtaga tttaatgttg aacagtactt ttccataaag   4200
ttctagtcac ttctgttggc ctgagccacc agattatgat gttgccagaa ttcactcaat   4260
ttgaataaag atgaacagta tttgtttct tgtttccatg aattatatca gtattctaaa   4320
acatcgcttc agaaagagaa ctgtttattt ctgcaggctt cctgtccttt tgtggtatgg   4380
ttttttggcc ttattttcac tggcttttcc ttctccaaac tttgaggcgt gatttcattc   4440
attgaagaat caatacatat tttgtttcaa aatgtttgaa acaaaagaca tagatggtag   4500 actttttatta aaacatatat ggatgtggaa agcacatata ttaatgcagt catcccttt   4560 caggtgggaa gagagcaaac cagttgattt tttaattcat ccttagtaca cagagaatat   4620
acttttcctc aagtaatata cctgtttgaa gctttaagag atgttttt ggtaactatt   4680 tcattttccc aaagaagttt gctattcttg tgttaattgt gtatacctga ttgttttttc   4740
ctggaggttt tgttgttgt tgtttagttt tgggttttt tttttttaag aggggcaagt   4800
gttttctgaa atgatgcata ttttaagact cgattcatat tgccactgtg ctatccttga   4860
actaccaata atttttataa aatatctagt tttactact tttatataaa ctttacttc   4920 cagatgaaga gctgagcctg attcaaatgg tttttctgct ttatacttct ttttagttca   4980
ttggttttta tagtagaggt tttctatttt tttttttttt tttttacta catttatatg   5040 tctgatacat atacggcttt ggagacaatc aagtaacaac tgaaaatgtg aaagtaaacca   5100 tatctgacaa aattcccttg aattttatc ctttgcttgc aacatttaag actcaaagtc   5160
actggtatat tggattaagt ttttcctgt taatgcaatt atagaaatac atcggagaca   5220
caacaaatgt ggccattaca ggtttcataa aattacactg acttggctgt tacttgatct   5280
taggaaacag cacagtttaa gatattgtga attctgactt atactttatt aaatgctgta   5340
aatctaaata gatcctgttg gatgtgatgg gtctagtcca gtttatttaa gttcatgttt   5400
cactgtttgc actttgcatt gaacaatggg tttattcgct gatgtaaacg gttcgagtga   5460
agaattaatg cagtaagtat gacaacacat acacacttgc ctctccccat ctccagaaga   5520
ggggagcaga gtccgagctt atctaaatat gaatgtggcc acaaagctgt ggaaggtgac   5580
aaagcttaaa caccttgcc ctggctctgc attgtcacct agagagcaag aggtctatag   5640
aaacatcatg tcacatgaaa cgattctctg cttttggtt ctgaacttga agtccctaaa   5700
ctgcaaaatc taagagttgg gtggttatta aaatgctttt aaagtcaact gtggcaccaa   5760
ttctaatgta atccaacttg tgactgtttt tttttgtttt gttttgtttt tgtgtgtgtg   5820
```

| | |
|---|---:|
| tgtgtggcac tgggaaaagt ggaaacaaac atgtattgaa atacatattg gaaataaaaa | 5880 |
| tggtttgagc gtcagtgata ttctcccaga atgtacttat cttacctcgg catgtactgt | 5940 |
| agtcactcag tatttgtata tgttgctaga atttagattg taaaatagtg aaattttaat | 6000 |
| gtgttcattt gttttaatg tatatatgtc ttgctcagat tatttggttt aaataaaaca | 6060 |
| accttgaggt ttgtagcttt tccttatact ata | 6093 |

<210> SEQ ID NO 36
<211> LENGTH: 4710
<212> TYPE: DNA
<213> ORGANISM: Homo Sapiens

<400> SEQUENCE: 36

| | |
|---|---:|
| cgctgccccg tccacgccgc ccgcgccccg cagtcccacc cgcaggaccc ccggccgcgc | 60 |
| cagggtctcg cctgcgcccc ccgcgcccgc ccgcggacta caagtcccgc catgcccgc | 120 |
| cgccgccccc cggcttccgg tgctgcgcag tttccggagc ggatcgcaac ccggagtccg | 180 |
| gatccgatcc cgctctgcac attccaaagg cagccgcgcg ccgccccggt ccagccgcca | 240 |
| tgccgactgt tctttgttac attcgccggc tgcgggcacc gttggcgatc ggagtcaaaa | 300 |
| cccggctgga tttcccggag ccgctccggg atcgccctgc gcgccgcccg ccgccgggg | 360 |
| tcttcgccgc cccggcccgc ggccccgcgg ccccgccgc cgggcggcgt cgtcgccgag | 420 |
| gccccagggg atgtcgttat cccccgccct cgggtacagc ccatgcgggt cgcacggggg | 480 |
| ggtccctgga ccccccaaccc cgcgtttaga gaagctgagt cctggtccca gattgggaac | 540 |
| cagagggtca gtgagcagct cttggaaaca tctctaggga atgaggtgtc cgacactgag | 600 |
| ccactgagcc ctgcgagtgc aggcctgcga cgcaatcctg ccctacctcc tggaccctt | 660 |
| gcacaaaact tttcctgggg gaaccaggaa aatctgcccc cagccctggg gaagattgcg | 720 |
| aacggaggag gaactggggc aggcaaggcc gaatgcggct atgaaactga gtcacacttg | 780 |
| ctagagccgc acgagatacc tttgaacgtg aatacacaca agttcagtga ctgtgagttt | 840 |
| ccatatgagt tttgcacggt ctgctttca cccttcaagc tgctggggat gagcggggtg | 900 |
| gagggcgtgt ggaatcagca ttcaagaagt gccagcatgc acactttcct aaaccactca | 960 |
| gcaacgggca tcagagaagc aggttgcagg aaggacatgc cggtgtcaga gatggctgaa | 1020 |
| gatgggagcg aagagatcat gttcatctgg tgtgaagact gcagccagta ccacgactcc | 1080 |
| gaatgtcccg agctgggccc agtggtcatg gtcaaagact cctttgtgtt aagcagggca | 1140 |
| aggtcttggc ctgccagcgg acacgtgcac acccaggcgg ggcaggggat gcggggttat | 1200 |
| gaggacaggg acagggctga cccacagcag cttccagaag cagtccctgc aggcctggtg | 1260 |
| aggcggctca gtgggcagca gctgccctgc cgttccaccc tcacctgggg gaggctgtgc | 1320 |
| cacctggtgg cccagggcag gtcatcccttt cctcccaact tggagatcag acgactggaa | 1380 |
| gatggagccg aggggtgtt cgccatcact cagctcgtca agcggacaca gttcggtccc | 1440 |
| tttgagtcca ggagggtcgc caaatgggaa aaggagtctg catttcccct gaaggtgttc | 1500 |
| cagaaggacg ggcacccccgt gtgcttcgac acctccaacg aggatgactg caactggatg | 1560 |
| atgctggtgc ggccagcggc ggaggccgag caccagaacc tgacggccta ccagcacggc | 1620 |
| agcgacgtgt acttcaccac ctccagagac atccccccgg gtaccgagct gcgcgtgtgg | 1680 |
| tatgcggccc tctatgccaa gaagatggac aagcccatgc tgaagcaggc cggctctggc | 1740 |
| gtccacgctg caggcacccc agaaaacagc gccccgtgg agtcggagcc cagccagtgg | 1800 |
| gcgtgtaaag tgtgttctgc caccttcctg gagctgcagc tcctcaatga acatctgttg | 1860 |

```
ggccacttag aacaagccaa aagccttcct ccaggcagcc aaagcgaggc agcagctccc    1920
gagaaggagc aggacacacc ccggggggaa cccctgcag tgcccgagag cgagaatgtt    1980
gccaccaaag aacagaagaa aaagcctcga aggggagaa acccaaagt gtccaaagct    2040 gagcagcctc tagtcatcgt ggaagacaag gaacccacag agcaagtggc agagatcatt    2100
accgaggtcc ctccggatga gcctgtgagt gcaacgccag atgagcggat catggagctg    2160
gttctgggga agctggccac caccaccact gacaccagct cggttccaaa gttcaccat     2220 catcagaata acaccatcac gctcaagagg agcttaattc tctcaagcag acacggcatc    2280
cggcgcaagc tcatcaaaca gctcggggag cacaagcggg tttaccagtg caatatctgc    2340
agcaagatct tccagaacag cagcaacctg agcaggcacg tgcgctcgca tggtgacaag    2400
ctgtttaagt gcgaagagtg tgcaaaattg ttcagccgca aagagagcct aaagcagcac    2460
gtttcctaca gcacagcag gaacgaggtg gacggcgagt acaggtaccg ctgcggcact    2520
tgtgagaaga ccttccgcat cgagagcgcg ctggagttcc acaactgcag gacagatgac    2580
aagacgttcc aatgtgagat gtgtttcaga ttcttctcca ccaacagcaa cctctccaag    2640
cacaagaaga agcacggcga caagaagttt gcctgtgagg tctgcagcaa gatgttctac    2700
cgcaaggacg tcatgctgga ccaccagcgc cggcacctgg aaggagtgcg gcgagtgaag    2760
cgagaggacc tggaggccgg tggggagaac ctggtccgtt acaagaagga gccttccggg    2820
tgcccggtgt gtggcaaggt gttctcctgc ggagcaata tgaacaagca cctgctcacc    2880
cacggcgaca gaagtacac ctgcgagatc tgcgggcgca agttcttccg cgtggatgtg    2940
ctcagggacc acatccatgt ccacttcaag gacatcgcgt tgatggatga ccaccagagg    3000
gaagagttta tcggcaagat cgggatctcc tcggaagaaa acgatgacaa ttctgacgag    3060
agcgcagact cggagcctca caagtacagc tgcaagcggt gccagctcac cttcggccgg    3120
gggaaggagt acctgaagca catcatggag gtgcacaagg agaagggcta tggctgcagc    3180
atctgcaacc ggcgctttgc actgaaggcc acctaccacg cccacatggt catccaccgt    3240
gaaaacctgc cggaccccaa cgtgcagaag tacatccacc cctgcgagat ctgcgggcgg    3300
atcttcaaca gcatcgggaa cctggagcgc acaagctca tccacacagg tgtgaagagc    3360
cacgcctgcg agcagtgtgg gaagtccttt gccaggaagg acatgctgaa ggagcacatg    3420
cgtgtgcacg acaatgtccg cgagtacctg tgtgccgagt gtgggaaagg catgaagacc    3480
aagcacgcgc tgcgccacca catgaagctg cacaagggca tcaaggagta cgagtgcaag    3540
gagtgccacc gcaggttcgc gcagaaggtc aacatgctca gcactgcaa gcggcacacg    3600 gggattaaag atttcatgtg tgaattgtgt gggaagacat tcagcgagag gaacaccatg    3660
gagacccaca agctcatcca cagtgggc aagcagtgga cgtgctccgt gtgcgacaag    3720
aagtacgtga ccgagtacat gctgcagaag cacgttcagc tcacacacga caaggtggag    3780
gcgcagagct gccagctgtg cgggaccaag gtgtccacca gggcctccat gagccgacac    3840
atgcggcgca agcaccccga ggtgctcgcg gtgaggatcg atgacctgga ccacctcccg    3900
gagaccacca ccatcgacgc ctcctccatt ggcatcgtcc agcctgagct gactctggag    3960
caggaggatt tggccgaagg gaagcacggg aaagctgcca agcgaagtca agagagaaag    4020
cagaagccag aagaggaggc gggtgctccg gtgcccgagg acgccacctt cagcgaatac    4080
tcagagaaag agacggagtt cacaggcagt gtaggcgacg agaccaattc cgcagtacag    4140
agcattcagc aggtagtggt gaccctgggt gacccaaatg tgaccacacc atcgagctca    4200
```

| | |
|---|---|
| gtcggcttaa ccaacatcac cgtgaccccc atcaccactg cggccgcgac tcagtttacc | 4260 |
| aatctccagc cggtggccgt ggggcacctt accaccctg aacgccagtt acagctggac | 4320 |
| aactcaatcc tgaccgtgac ctttgatacc gtcagcggct ctgccatgtt gcacaaccgc | 4380 |
| caaaatgacg tccagatcca cccccagccg gaagcctcga acccacagtc tgtggcccat | 4440 |
| ttcatcaacc tgacgaccct ggtcaactcc atcacgcccc tggggagcca gcttagtgac | 4500 |
| cagcacccgc tcacgtggcg ggcagtgccc cagactgacg tcttgccacc ctcgcagccg | 4560 |
| caggcacccc cacagcaggc ggcccagccc caggtgcagg cggagcagca gcagcagcag | 4620 |
| atgtacagct actgagctgc gttccgggag actcggggca agaactgcag agggatgttt | 4680 |
| gggatttgtt tagatgtgtt tgctggatac | 4710 |

<210> SEQ ID NO 37
<211> LENGTH: 3140
<212> TYPE: DNA
<213> ORGANISM: Homo Sapiens

<400> SEQUENCE: 37

| | |
|---|---|
| agtcgcatgc aggacagcac cgcgtgcggc agctgctctg gtggcctcct gcttacccgg | 60 |
| ccctccactt taccgttagc acggagtgcg gcaccctgct tgggcctttc ggctctgcct | 120 |
| cccctgcccg tcacggcggg tcacgacatc ggccaggacg cagcagaagg gacaagacac | 180 |
| gcaaagaaga tggcgcaccc acctcggcac cgaaggccag tgcgacctcc cgggagcagg | 240 |
| cgggccagca tgggccttcc cggaggagac agctaagccg agacctggga ctgcagagga | 300 |
| gaaacaagga ggaggcaggc ggggcccggt gccctcctcg tctgccgtgc cgggtggaca | 360 |
| gtctgctcgc ctgtctgcgt gacgaaaccg aggcacagag acgcgctatg ccagcggcgg | 420 |
| gtatagcaag ggctccctcc gcgccacgtg ttgccatcca ccacacagga atgaccgtct | 480 |
| ccgtgtcata gatgggaaac caggacgtgt aggcatcagg gtttctccat tttggccaga | 540 |
| ctggtctgga acttctgagt tcaagcggtc ctcccgtctc agccttccaa agtgctggga | 600 |
| tgacaggtgt gagcagctgc gccctgcagg tgcaggccct ggaagacaag ggaggagcct | 660 |
| gtgagccacc ggcccacgtg aaagtaaatg catgaagttc cctctcgctg aactgaaaag | 720 |
| agcctcaacc tggacctgac accaacttcg ccggtgctgc ctggctggtt gctctagcgc | 780 |
| cctgaaggag aggaatgcag tcatatttca ctgtgatttt cagtgtcatt tccacgaaga | 840 |
| ctaatgatgt tgagcttttt tttctccata atacaggaaa gagacccaaa cccatgaaga | 900 |
| atgagataca tgtacagttt tgattataaa accaaagaat aatggcttca caagatgacg | 960 |
| gctgggctcc tgggctgcct tcagtgtctt taaacagaga tagagtcttg ctatgttgtc | 1020 |
| caggctgaca ctgaactctt gggctccaac gatcctcctg ccccggcctc ctgagtacct | 1080 |
| gggattatag gcacaagtca ccatgcccag ccggaataat ctgaaggaaa gacgggtata | 1140 |
| ttcaagatga ctttgctgct ggaaatatga cagaataatg tggtatcttc ttctgcactt | 1200 |
| ccaagctctt tcacactcag gctcttcctg gcttttctgc ctcagccacc ataaactgtg | 1260 |
| gttgcttctc cagctctgtt acagttcaga cttgagggga ggtgacaaga gctaacatgt | 1320 |
| taccatgggg agcctggctg acatctccga aactgaagac tctatggaag cctcatgcta | 1380 |
| ttgcaatgtg tacatcaaaa gtaaagtacc ccaggttaaa actatgagga agttgccatc | 1440 |
| tttacttcca ggagcaaaga cactgaaact gtcccctgca agccccttaa tttcatacag | 1500 |
| tcctctgact gcccccaac cctggctact tttttttgaa ataaggtctc actctgtcat | 1560 |
| ccaggctgga gtgcagtggc aaaatcacaa taccctgcag ccttgacctc atgggctcaa | 1620 |

```
gcagtcctcc cacctcagcc tcctgggtag ctgggactac aggcttgcac taccacaccc    1680
agcttatttt ttgtagagac agagtttcgt catgttgccc aggctggtct caggagtcac    1740
tcctgagctc aagtgatccg cctgccttgg cctcccacag tgctgggatt acaggagtga    1800
gccaccatgt ctggtcctct gacccttta gcaggaaatc cagcccagcc cctgaacggc    1860
atgttagaca gttcaacaaa gccttctaga agaccaaaga agactcatag gaataagcct    1920
cttgctgatt aatggaaaca tgaccatttg tggagaaagt gcaatctgca ttgaacacct    1980 ttagggaac ctgtcattta agacttcaag cattaccatg aaaacttcct ctgaaacacc    2040
ttacagacat ctctgtaaaa cagatttaaa gagaaacaca tttctgctta atcggtacac    2100
atcaaatggc gatttaagag caaggctagg aaaccagaag atgatatgca tatacataaa    2160
gttgccacta ttccaaatag taaaataaag acaaagtcaa tggtcctagg agagctggtg    2220
ggttgtggag ccaggagaga aaggcagctc ccttcacctt ccctgtacat tccaggaggc    2280
cctagaatga cctagatggt gttacgcaca agccctcct tctcccatcc cgccatcatc    2340
tcaggagcaa atggccacac tcgggtatac ggagcagctc aagcaaccag gtcttcctgc    2400 cattccctg aaagggctgg ttttgccaaa cgccagagcc acattgtgtt aatcagcgcc    2460
catccctaga cacaggggct tgcagccttg tcacacaaat gagccatgga gatgtttccg    2520
actcctcccc tccctgccac tcacaagcag ccagctgccg agccctgcag actcttcctt    2580
tacgacgtcg gttgtatcca cttcccttct ggtcccacac ccaagttcag gaccatttta    2640
gcacgtgcct acattattgc cacagccatt gtcttcatct gttttgtgct gctgtacaag    2700
gaacaaactt atttggcttg tggtttggga ggtgggaaa tccaagatcc agggccacat    2760
ctgctgaagg ccttcctgct gtaccgtaac ataacgggag gcatcactgg tgagagagag    2820
agagcacaag aaagggccaa actcgctttt atagtgaacc cactcctgca ataacaacgt    2880
tcaaatgcta accacctctt cccgtccctg cccctcaaca tggccatgct ggggattaag    2940
tgtccaacac atgagctttg ggatacatgt tccaactaca gccgccacct gctgtcctcc    3000
ttgccttctc cctcttctct acacttctgc cggattctct agttggatta atcttgaaac    3060
atcacttaat tgttaccact ctcccaaaag cagtcaattt taacccattc ccaacaggct    3120
tgagaataaa agtttcagcc                                                3140
```

<210> SEQ ID NO 38
<211> LENGTH: 2785
<212> TYPE: DNA
<213> ORGANISM: Homo Sapiens

<400> SEQUENCE: 38

```
gagagagaga gagagagaga gagagagaga gagcgagaga gcgtgagcgc gcgcaagcta      60
gcgagcaaac cagagagaca gaccgagaga gggaccagga gagagaccca gagagagaag    120
aagaagccag aagccgagct ctgtcagggc tcaacctcca acttgtttca gttcattcat    180
ccttctctcc tttccgctca gactgtagag ctcggtctct ccaagtttgt gcctaagaag    240
atgataatca cacaaacaag tcactgttac atgaccagcc ttgggattct tttcctgatt    300
aatattctcc ctggaaccac tggtcaaggg gaatcaagac acaagaacc cggggacttt    360 gtgaagcagg acattggcgg gctgtctcct aagcatgccc cagatattcc tgatgacagc    420
actgacaaca tcactatctt caccagaatc ttgatcgtc ttctggacgg ctatgacaac    480
cggctgcgac ctgggcttgg agatgcagtg actgaagtga agactgacat ctacgtgacc    540
```

```
agtttggcc ctgtgtcaga cactgacatg gagtacacta ttgatgtatt ttttcggcag    600
acatggcatg atgaaagact gaaatttgat ggcccatga agatccttcc actgaacaat    660
ctcctggcta gtaagatctg gacaccggac accttcttcc acaatggcaa gaaatcagtg    720
gctcataaca tgaccacgcc caacaagctg ctcagattgg tggacaacgg aaccctcctc    780
tatacaatga ggttaacaat tcatgctgag tgtcccatgc atttggaaga ttttcccatg    840
gatgtgcatg cctgcccact gaagtttgga agctatgcct atacaacagc tgaagtggtt    900
tattcttgga ctctcggaaa gaacaaatcc gtggaagtgg cacaggatgg ttctcgcttg    960
aaccagtatg acctttttggg ccatgttgtt gggacagaga taatccggtc tagtacagga   1020
gaatatgtcg tcatgacaac ccacttccat ctcaagcgaa aaattggcta ctttgtgatc   1080
cagacctact tgccatgtat catgactgtc attctgtcac aagtgtcgtt ctggctcaac   1140
agagagtctg ttcctgcccg tacagtcttt ggtgtcacca ctgtgcttac catgaccacc   1200
ttgagtatca gtgccagaaa ttccttacct aaagtggcat atgcgacggc catggactgg   1260
ttcatagccg tctgttatgc ctttgtattt tctgcactga ttgaatttgc cactgtcaac   1320
tatttcacca gcggagttg ggcttgggaa ggcaagaagg tgccagaggc cctggagatg   1380
aagaagaaaa caccagcagc cccagcaaag aaaaccagca ctaccttcaa catcgtgggg   1440
accacctatc ccatcaacct ggccaaggac actgaatttt ccaccatctc caagggcgct   1500
gctcccagtg cctcctcaac cccaacaatc attgcttcac ccaaggccac ctacgtgcag   1560
gacagcccga ctgagaccaa gacctacaac agtgtcagca aggttgacaa aatttcccgc   1620
atcatctttc ctgtgctctt tgccatattc aatctggtct attgggccac atatgtcaac   1680
cgggagtcag ctatcaaggg catgatccgc aaacagtaga tagtggtggc agtgcagcaa   1740
ccagagcact gtatacccccg tgaagcatcc aggcacccaa accccggggc tccccttcgc   1800
gtatttcagg attctccttt ttaccccctct accaagctgt gaccctcaat tcatatttat   1860
gaatctctac gcaaaaaata actacagaaa aattacttgt ccctccaata ttgcccagta   1920 taacccccatc aaagccaaac actgccattt gtccagttgc tcatcttagt ctgccaatct   1980
cccctagctg agggcactgc atgtatttta ttgcactctg cccgctgcaa aaagaacaag   2040
agattctact ctccatagtg gaagccttgg ctgtttgaga ggcccagaac aaggagaatt   2100
gttgactccc atctagatca gatgactcta acttactagg cagccaggtt aggctaggcc   2160
atgtgatcct gcgtgccacc tcccctgcct tcagcaaggc ctactaggca taagtactga   2220
tagcaaaggt gggagccagt tctacacccc caacccattt attggtttgg aaattagtgg   2280
ggacaattgg tactaaccac cgtctaccat gtatggccaa aataaataga actagctctg   2340
ccagcctggc accaagatgg ctggtgccct gccatgtcca gccccctcggg aaaatagtcc   2400 cctccttggt acatctctcc tccagaaaat cttcttcccc cactgccttt ggcacccttg   2460
tagccaactg agcactactt aatttggact cattaccacc tgtaaacttt tcaggaaaaa   2520
atgatcaagc atttttatt tatatcgaaa agttgcaaat agaaacaaag tgatctagat   2580
ttaaaaaaaa catttttta aaatatggga gagatacaaa agtcacctcc ctgccaaggc   2640
aactagccta tactgattg ggtaagaggt ttggagtgga tggtagttga ggattgaagt   2700
ctggctcaaa agagaaggct actggcagat gaaagtcaaa ttcttccttc catacactcc   2760
acattccaca ccctggccca ggcac                                         2785

<210> SEQ ID NO 39
<211> LENGTH: 960
```

<212> TYPE: DNA
<213> ORGANISM: Homo Sapiens

<400> SEQUENCE: 39

```
atggaaagag gaaaccaaac agaagttgga aactttctcc tcctgggatt cgcagaggac    60
tctgacatgc agcttctcct ccatgggctg ttcctctcca tgtacctggt taccatcatc   120
ggaaacctgc tcatcatcct gaccatcagt tcagactccc acctccacac ccccatgtac   180
ttcttcctct ccaacctgtc ctttgctgac atctgtttca catccacgac tgtcccaaag   240
atgctggtga atatccaaac acaaagcaaa atgatcactt ttgcaggctg cctcactcag   300
atatttttt tcattgcatt tggatgcctg acaatttgc tcctgaccat gacggcctat   360
gaccgcttcg tggccatctg ttaccccctg cactacacgg tcatcatgaa ccccggctc   420
tgtggactgc tggttctggg gtcctggtgc atcagtgtca tgggttcctt gcttgagacc   480
ttgaccattt tgaggctgtc cttctgcaca aatatggaaa ttccgcactt ttttgtgat   540
ccttccgaag tcctgaagct ggcctgttct gacaccttca tcaataacat cgtgatgtat   600
tttgtgacca ttgtcctggg tgttttcct ctctgtggaa tcctattctc ttattctcag   660
attttctcct ccgtcctaag agtatctgcc agaggccagc acaaagcctt tccacctgt   720
ggttcccacc tctcagtggt cagcttgttc tatggcactg gccttggggt ctatctcagt   780
tctgcagtta caccaccttc taggacaagt ctggcagcct cggtgatgta caccatggtc   840
accccatgc tgaaccccctt catctacagc ctgaggaaca aggacatgaa ggggtcactg   900
gggagactcc tcctcagggc aacgtctctc aaagagggga ccattgctaa gctctcatga   960
```

<210> SEQ ID NO 40
<211> LENGTH: 1591
<212> TYPE: DNA
<213> ORGANISM: Homo Sapiens

<400> SEQUENCE: 40

```
ccctgcgtct ctgcccgccc cgtggcgccc gagtgcactg aagatggcgg ctgctgtagg    60
acggttgctc cgagcgtcgg ttgcccgaca tgtgagtgcc attccttggg gcatttctgc   120
cactgcagcc ctcaggcctg ctgcatgtgg aagaacgagc ttgacaaatt tattgtgttc   180
tggttccagt caagcaaaat tattcagcac cagttcctca tgccatgcac ctgctgtcac   240
ccagcatgca ccctatttta agggtacagc cgttgtcaat ggagagttca agacctaag   300
ccttgatgac tttaagggga aatatttggt gcttttcttc tatcctttgg atttcacctt   360
tgtgtgtcct acagaaattg ttgcttttag tgacaaagct aacgaattc acgacgtgaa   420
ctgtgaagtt gtcgcagtct cagtggattc ccactttagc catcttgcct ggataaatac   480
accaaggaag aatggtggtt tgggccacat gaacatcgca ctcttgtcag acttaactaa   540
gcagatttcc cgagactacg gtgtgctgtt agaaggttct ggtcttgcac taagaggtct   600
cttcataatt gaccccaatg gagtcatcaa gcatttgagc gtcaacgatc tcccagtggg   660
ccgaagcgtg gaagaaaccc tccgcttggt gaaggcgttc cagtatgtag aaacacatgg   720
agaagtctgc ccagcgaact ggacaccgga ttctcctacg atcaagccaa gtccagctgc   780
ttccaaagag tactttcaga aggtaaatca gtagatcacc catgtgtatc tgcaccttct   840
caactgagag aagaaccaca gttgaaacct gcttttatca ttttcaagat ggttatttgt   900
agaaggcaag gaaccaatta tgcttgtatt cataagtatt actctaaatg ttttgttttt   960
gtaattctgg ctaagaccctt ttaaacatgg ttagttgcta gtacaaggaa tcctttattg  1020
```

| | |
|---|---|
| gtaacatctt ggtggctggc tagctagttt ctacagaaca taatttgcct ctatagaagg | 1080 |
| ctattcttag atcatgtctc aatggaaaca ctcttctttc ttagccttac ttgaatcttg | 1140 |
| cctataataa agtagagcaa cacacattga agcttctga tcaacggtcc tgaaattttc | 1200 |
| atcttgaatg tctttgtatt aaactgaatt ttcttttaag ctaacaaaga tcataatttt | 1260 |
| caatgattag ccgtgtaact cctgcaatga atgtttatgt gattgaagca aatgtgaatc | 1320 |
| gtattatttt aaaaagtggc agagtgactt aactgatcat gcatgatccc tcatccctga | 1380 |
| aattgagttt atgtagtcat tttacttatt ttattcatta gctaactttg tctatgtata | 1440 |
| tttctagata ttgattagtg taatcgatta taaaggatat ttatcaaatc cagggattgc | 1500 |
| attttgaaat tataattatt ttcttttgctg aagtattcat tgtaaaacat acaaaataaa | 1560 |
| catattttaa aacatttgca ttttaccacc a | 1591 |

<210> SEQ ID NO 41
<211> LENGTH: 4472
<212> TYPE: DNA
<213> ORGANISM: Homo Sapiens

<400> SEQUENCE: 41

| | |
|---|---|
| aaagtcggga gtgccatggt gccagctggg gatcaagacc gcgcgccaca caggggaag | 60 |
| ccggcccagg ctggggctcg cacctcacgt gcctcccggg ccctgcgatc ctggaggcgc | 120 |
| tcccaggccg cgcgcgccac ggtcacccac ccacgtgggg ggcacgaccg tgggagtcac | 180 |
| ggggggtacc gtgagggtca caggggggtgc cgcagggatc cacagtgggc ttccgcgggg | 240 |
| cctccacccc tgagcttcac agaggaagtg aaatttgagc tgcgcgccct gaaggactgg | 300 |
| gacttcaaaa tgagcgtccc tgactacatg cagtgtgctg aggaccacca gacgctgctc | 360 |
| gtggtggtcc agcctgtggg catcgtctcc gaggagaact tcttcaggat ctataagagg | 420 |
| atttgctctg tgagtcagat cagcgtgcgg gactcccagc gagtcctcta catccgctac | 480 |
| aggcaccact acccacccga gaacaacgag tggggtgact ccagaccca ccgcaaagtc | 540 |
| gtgggcctca tcaccatcac agactgcttc tcggccaagg actggccaca gacctttgag | 600 |
| aagttccacg tgcagaagga gatctacggc tccacactgt atgactcccg gctcttttgtc | 660 |
| ttcgggctgc aggggagat cgtggagcag ccgcgcaccg acgtggcttt ctaccccaac | 720 |
| tacgaggact gccagacggt ggagaagaga atcgaggact catcgagtc actgttcatc | 780 |
| gtgctggagt ccaagcgtct ggacagagcc acagacaagt ctggggataa gatccccctt | 840 |
| ctctgtgtcc cgttttgagaa aaaggacttt gtaggactgg acacagacag cagacattac | 900 |
| aagaagcggt gccaaggccg catgcggaag cacgtggggg acctgtgcct gcaggcaggg | 960 |
| atgctgcagg actccctggt gcattaccac atgtcggtgg agctgctgcg ttctgtgaat | 1020 |
| gactttctgt ggcttggagc tgccctggaa ggattgtgtt cagcttctgt catctatcac | 1080 |
| tatcctggtg gaactggtgg gaagagtgga gctcggaggt tccagggcag caccccttcct | 1140 |
| gctgaagcag ccaatagaca ccggccaggg gcacaggaag ttctcattga tccaggtgcc | 1200 |
| ctcaccacca atggcatcaa ccctgacacc agtactgaga tcggacgtgc taagaactgc | 1260 |
| cttagccctg aagacataat tgacaagtat aaagaggcga tttcctatta cagcaagtat | 1320 |
| aagaatgcgg gagtgattga gttggaagcg tgcatcaagg ctgtacgtgt ccttgcaatt | 1380 |
| cagaaacgga gcatggaagc atcagaattt cttcagaatg cagtttacat taaccttcga | 1440 |
| cagctttctg aggaagagaa aattcagcgc tacagcatcc tctccgagct ctatgagctg | 1500 |
| atcggcttcc atcgcaagtc tgcgttcttc aagcgcgtgg ccgccatgca gtgcgtggcc | 1560 |

```
ccaagcatcg cggagcctgg gtggagggcc tgctacaaac tcctcctgga aacgctgccc   1620
ggctacagtc tgtcgctgga tcccaaagat ttcagcagag gcacgcacag aggctgggct   1680
gcggtccaga tgcgtttgct ccatgaattg gtctacgcct cccgaaggat ggggaaccct   1740
gccctctctg tcagacacct gtccttcctt ctacagacca tgctggactt cttgtcggat   1800
caggaaaaga aagatgtggc ccaaagccta gagaactata cgtccaagtg tcctgggacc   1860
atggagccca tcgccctccc tggcggcctc accctgccac cggtgccctt caccaagctt   1920
cccgtcgtca ggcatgtgaa actattgaac cttcctgcta gcctccggcc acacaaaatg   1980
aaaagcttgc tgggtcagaa cgtgtcaacc aaaagtcctt tcatctattc accaattatc   2040
gcacacaacc gtggagaaga gcggaacaag aaaatagatt tccagtgggt tcaaggagat   2100
gtgtgtgaag ttcagctgat ggtatataac ccaatgccgt ttgaacttcg agttgaaaac   2160
atggggctgc tcaccagcgg agtggagttc gagtctctcc ctgcggcgct ttctcttccg   2220
gctgaatctg gtctgtaccc agtgacgctc gtcggggtcc cgcagacgac tggaacgatt   2280
actgtgaacg gttaccatac cacggtcttc ggtgtgttca gtgactgttt gctggataac   2340
ctgccgggaa taaaaccag tggctccaca gtggaagtca ttcccgcgtt gccaagactg   2400
cagatcagca cctctctgcc cagatctgca cattcattgc aaccttcttc tggtgatgaa   2460
atatctacta atgtatctgt ccagctttac aatggagaaa gtcagcaact aatcattaaa   2520
ttggaaaata ttggaatgga accattggag aaactggagg tcacctcgaa agttctcacc   2580
actaaagaaa aattgtatgg cgacttcttg agctggaagc tagaggaaac ccttgcccag   2640
ttccctttgc agcctgggaa ggtggccacg ttcacaatca acatcaaagt gaagctggat   2700
ttctcctgcc aggagaatct cctgcaggat ctcagtgatg atggaatcag tgtgagtggc   2760
tttccctgt ccagtccttt tcggcaggtc gttcggcccc gagtggaggg caaacctgtg   2820
aacccacccg agagcaacaa agcaggcgac tacagccacg tgaagaccct ggaagctgtc   2880
ctgaatttca atactctgg aggcccgggc cacactgaag gatattacag gaatctctcc   2940
ctggggctgc atgtagaagt cgagccgtct gtattttca cccgagtcag caccctccca   3000
gcaaccagta cccggcagtg tcacctgctc ctggatgtct tcaactccac cgagcatgag   3060
ctgaccgtca gcaccaggag cagcgaggca ctcatcctgc acgccggcga gtgccagcga   3120
atggctattc aagtggacaa gttcaacttt gagagtttcc cggagtcccc tggggagaag   3180
gggcaatttg caaaccccaa gcagctggag gaagagcggc gggaagcccg aggcctggag   3240
atccacagca agctgggcat ctgctggaga tcccctcccc tgaagcgcag tggcgaggcg   3300
agtgtggaag gactcctgaa ccagctcgtc ctggagcacc tgcagctggc gcctctgcag   3360
tgggatgtgc tggtggacgg acagccatgt gaccgcgagg ctgtggcggc ctgccaggtg   3420
ggcgaccccg tgcgcctgga ggtgcggctg accaaccgga gcccgcgcag cgtagggccc   3480
ttcgccctca ctgggtccc cttccaggac accagaacg cgtgcacaa ctacgacctg   3540
cacgacaccg tctccttcgt gggctccagc accttctacc tcgacgcggt gcagccgtcc   3600
ggccagtcgg cctgcctcgg ggccctcctc ttcctctaca cgggagactt cttcctccac   3660
atccggttcc acgaggacag caccagcaag gagctgccac cctcttggtt ctgcctgccc   3720
agtgtgcacg tgtgtgccct ggaggcgcag gcctgagccc gcctacttcc gtccctcttt   3780
ctgcagggcc agaggtgacc ctgcctggcc tcccacaccc cctgcaatga gcaaggcctt   3840
cactgcagcc ccatctcctc ctcctccccc agacccctcc cagccctctc ctcctgttcc   3900
```

| | |
|---|---|
| tcctgtagca tctttgctgg gctacgcaga agccccggac atggcagccc cacccccatgc | 3960 |
| cacgccccTT cctacactgt tccctggacc atacacaggc tgaagcagag gaaatcccaa | 4020 |
| agcgggtgcc catccagccc aggtcccagg atccctgcac ccatttctgt gacctggggc | 4080 |
| cccagccgtg ctgtgctgct catcccagca gagggacctc cctcgtccag cgacttccct | 4140 |
| ttggccatag aaagaaatgg tgagcatgag actgggcaca gcctgagggc gtgggcagct | 4200 |
| tcccacccTC cctgggcctt ggaatccccc aaggctggtt ttcttcctgg agaccccat | 4260 |
| gggcaacttg gcaggagaga tggtgccgta ggaggtcgtg gatggttgat gccaagagag | 4320 |
| gccctccacc cgtggtgggc aaatgtccag gcctgggctg gcagcccagg gctgtttctg | 4380 |
| ggtgctccct ggccccaggg tggcgtctgg ttaccatggc tgtgtgtgtc catgtctgca | 4440 |
| agcagttctt caataaatgg cctgcctccc cc | 4472 |

<210> SEQ ID NO 42
<211> LENGTH: 1302
<212> TYPE: DNA
<213> ORGANISM: Homo Sapiens

<400> SEQUENCE: 42

| | |
|---|---|
| gagacagccc gccggccgcc cggatctcca cctgccaccc cagagctggg acagcagccg | 60 |
| ggctgcggca ctgggaggga gaccccacag tggcctcttc tgccacccac gcccccaccc | 120 |
| ctggcatggc cgaccagctg actgaggagc aggtcacaga attcaaggag gccttctccc | 180 |
| tgtttgacaa ggatggggac ggctgcatca ccacccgcga gctgggcacg gtcatgcggt | 240 |
| ccctgggcca gaaccccacg gaggccgagc tgcgggacat gatgagtgag atcgaccggg | 300 |
| acggcaacgg caccgtggac ttccccgagt tcctgggcat gatggccagg aagatgaagg | 360 |
| acacggacaa cgaggaggag atccgcgagg ccttccgcgt gttcgacaag gacggcaacg | 420 |
| gcttcgtcag cgccgccgag ctgcgacacg tcatgacccg gctggggag aagctgagtg | 480 |
| acgaggaggt ggacgagatg atccgggccg cggacacgga cggagacgga caggtgaact | 540 |
| acgaggagtt tgtccgtgtg ctggtgtcca agtgaggccg gcgcccacca tgctcctggg | 600 |
| cgcccacgcg gcccacaggg caagaacccg gggcctcccg cctcctcccc catcccctg | 660 |
| cctcccctgg gcactgtggc ttcctcctgc gcctggttga ttcagcccac ctctctgcat | 720 |
| cccgcttccc gcgtctcttc tctgcactcc tgccgacctt cccacctgct catctgaatg | 780 |
| acacggaacg ctcccactgc aggcaaaccg tgacgccctc cccactcggg agaagcagag | 840 |
| ctgaccttag gaccgagcac cagggcaggt tgcgctgact ctgcggccct ccaggacgga | 900 |
| caccgggtga ccccttaggg cacccaggca agatccctaa gaggcaccca atgcccaggc | 960 |
| cagggggct gcagccctca gccccgcca ggattcccgc aggctcctgg actggaagct | 1020 |
| ccctccgcgg tcggattctg gagggtggga ggcatcttgg cctgcagtaa gcggtgctga | 1080 |
| cggggactct ggccacagag gtcaggcctc ctgaaaacag cactgccttc cgcgctgccc | 1140 |
| cagcttgccc cattccttgt ccgccaaccc accgtgattc atcttctgaa gctgggagtg | 1200 |
| aaactgggtc agctgtaacc tgttcctatt catctggaag gagggaggct tggatgagca | 1260 |
| ggggatgaga gctgcaggga aataaatgag atattcgtcc tt | 1302 |

<210> SEQ ID NO 43
<211> LENGTH: 1859
<212> TYPE: DNA
<213> ORGANISM: Homo Sapiens

<400> SEQUENCE: 43

```
ggaagtctat ccgggctttc gcgtcaccac cctgcccacc tgggtggcgc gtggcttacg      60
caacggtcac tgggctcctg ggccgctccc gggccagcga gggctgcgaa agaagttgta     120
gcatgcatac cacagaatca aaaaatgaac atttggagga tgaaaacttc caaacatcta     180
caactcctca gagtctcatt gatcctaata atactgcaca tgaagaaact aaaactgtct     240
tatcagatac agaagaaata aaaccacaga caaaaaagga gacatacatt tcttgtcctc     300
taagaggagt attgaatgta attattacaa atggagttat actgtttgtg atatggtgta     360
tgacctggtc aatcttaggc tctgaagctc tccctggtgg aaatttattt gggttgttca     420
ttatttttta tagtgccatt attgggggaa aaatttttaca actcattaga ataccctttag    480 tgcctccact tccacctctt cttgggatgt tactggctgg ttttacgatt aggaatgttc     540
cattcatcaa tgaacatgtc catgttccta acacatggtc ttcaattta agaagcattg      600 cccttaccat tattctaata agagctgggc ttggactcga tccacaggct ttgaggcatt     660
tgaaggtcgt tgtttcaga ttggctgtag gtccatgcct tatggaggca agtgcagctg      720
ctgttttttc acacttcatt atgaaatttc cctggcaatg ggcatttcta ttaggttttg     780
ttctaggtgc tgtctctcct gctgttgttg tcccttacat gatggtgctg caagaaaatg     840
gatatggtgt tgaggaaggc attccaacct tattaatggc tgctagcagt atggatgaca     900
ttctggctat cactggattc aatacatgct tgagcatagt cttttcctca ggtggtatac     960
ttaataacgc catagcctct ataaggaacg tatgtattag tctgctggca ggaattgttt    1020
tgggattttt tgttcgatat tttccaagtg aagaccagaa aaaacttaca ttgaagagag    1080
gattccttgt tttgactatg tgtgtttctg ccgtcttagg cagccaacgt attggtttac    1140
atggatctgg aggattatgc acactagtgt tgagtttcat tgcagggaca aaatggtccc    1200
aagaaaagat gaaagtccaa aagattatta cgactgtatg ggatattttt caaccacttc    1260
tttttggttt agttggagca gaagtatctg tttcatcgct tgaatcaaat attgttggca    1320
tatctgttgc cactctaagt ttggcattat gtgttcgaat tttaaccaca tatctattga    1380
tgtgctttgc tggttttagt tttaaggaga aaatatttat tgcttttagca tggatgccca    1440 aagctacagt acaggctgtg ttaggtcctc tggctctaga aacagcaaga gtctccgcac    1500
cccacttgga accatatgcg aaggatgtga tgacagtagc atttttagcc atcttgatca    1560
cagctccaaa tggagctcta cttatgggca ttctggggcc taaaatgctt acacgccatt    1620
atgatccaag caaaataaaa ctgcagttgt caacattaga acatcattaa aaagtttacc    1680
tgtcatcatc tgcctgcttc ttttaatgaa ttatttcaca tgcacagaaga attttaaagt    1740 agaaatatgt ggggactgta cagagaatcc aggatttagt aaacatgtga tttcagtaca    1800
gggcttttct tggacttttt actccaaagt taatttaata aaaataatat taaatggaa     1859
```

<210> SEQ ID NO 44
<211> LENGTH: 1035
<212> TYPE: DNA
<213> ORGANISM: Homo Sapiens
<220> FEATURE:
<221> NAME/KEY: misc_feature
<222> LOCATION: 30, 32, 86
<223> OTHER INFORMATION: n = A,T,C or G

<400> SEQUENCE: 44

```
ycactcccc aaatcyccwa tttatcaggn gntcactgaa ataaaaata caattgagct      60 cccatcatca gtkckagtcr atgggnaatg cgcctttaag agaaaactgg tcagatgaat    120
```

| | |
|---|---|
| attattgctt cccattttca accagtaaat agttgccact gagaaactga cagccaggag | 180 |
| tctgtcaaga atgctcaaga tatgttatat aatacaacat gcctgttcac aggggggaaaa | 240 |
| atcctaggaa ataacttatg tgtacttctt gatttcatca tacaagacaa gcacaaaagc | 300 |
| accacccatg cctctgagaa cattggacca tgcacccttg aaaaaagctt tgcctccttc | 360 |
| atcacgagcm atcttccgcc agcagtcaag cgtgcctgtg tacatgatgt cagttccttt | 420 |
| gcgccctgac tgcatcatca tgcggcggcg aacggtgtca aatggatagg aagtcaaccc | 480 |
| ggcaacagca gtgacagtct gtgcgatcat ccagctgatg acgatgtgag tgttcttggg | 540 |
| atccggaagc attcccttg cagtgtcata gataccgaag taggcggctc ggtagatgat | 600 |
| aatacccctgc acagacacgt taaagccttg gtacaggccc ttaatcccat cagatttgta | 660 |
| gatcttaacc aggcagtcac cgaggcctcg gaattcccctt tcagctccag ctttacccac | 720 |
| atcagctgct agacgggtac gggcaaaatc aagagggtac acaaaacaca gggatgtggc | 780 |
| ccctgcggca ccacccgatg ccagattccc tgcaaagtag cgccaaaact gggttctctt | 840 |
| gtccacacca cccaggaaga tctgcttgta tttatctttg aaggcgaagt taagagcctg | 900 |
| ggtggggaag tatctgatga cattggccag gttaccgcgc cagaaggaca gaactccctg | 960 |
| ctccttggga atacgaccca cgcagtctat aatgcctttg tattgcttat ctgcagtgat | 1020 |
| ctgcttgcck gcatg | 1035 |

<210> SEQ ID NO 45
<211> LENGTH: 2031
<212> TYPE: DNA
<213> ORGANISM: Homo Sapiens

<400> SEQUENCE: 45

| | |
|---|---|
| gagcgcgcgc gccgccgccg ttgccgccgg gctgagagaa gagcttgcgg ggtttgcggt | 60 |
| tgatggcccc gactgaaggg ctggaggcgg tgtatgccgc tgttcttgct gtcgctcccg | 120 |
| acacctccgt ccgcttctgg tcatgagagg agacagaggc ctgaagcaaa gacatctggg | 180 |
| tcagagaaaa agtatttaag ggccatgcaa gccaatcgta gccaactgca cagtcctcca | 240 |
| ggaactggaa gcagtgagga tgcctcaacc cctcagtgtg tccacacaag attgacagga | 300 |
| gagggttctt gccctcattc tggagatgtt catatccaga taaactccat acctaaagaa | 360 |
| tgtgcagaaa atgcaagctc cagaaatata aggtcaggtg tccatagctg tgcccatgga | 420 |
| tgtgtacaca gtcgcttacg gggtcactcc cacagtgaag caaggctgac tgatgatact | 480 |
| gccgcagaat ctggagatca tggtagtagc tccttctcag aattccgcta tctcttcaag | 540 |
| tggctgcaaa aaagtcttcc atatattttg attctgagcg tcaaacttgt tatgcagcat | 600 |
| ataacaggaa tttctcttgg aattgggctg ctaacaactt ttatgtatgc aaacaaaagc | 660 |
| attgtaaatc aggtttttct aagagaaagg tcctcaaaga ttcagtgtgc ttggttactg | 720 |
| gtattcttag caggatcttc tgttctttta tattacccct tcattctca gtcactttat | 780 |
| tacagcttaa ttttttttaaa tcctactttg gaccatttga gcttctggga agtattttgg | 840 |
| attgttggaa ttacagactt cattctgaaa ttctttttca tgggcttaaa atgccttatt | 900 |
| ttattggtgc cttctttcat catgcctttt aaatctaagg gttactggta tatgctttta | 960 |
| gaagaattgt gtcaatacta ccgaactttt gttcccatac cagtttggtt tcgctacctt | 1020 |
| ataagctatg gggagtttgg taacgtaact agatggagtc ttgggatact gctggcttta | 1080 |
| ctctacctca tattaaaaact tttggaattt tttgggcatc tgagaacttt cagacaggtt | 1140 |
| ttacgaatat ttttttacaca accaagttat ggagtggctg ccagcaagag acagtgttca | 1200 |

```
gatgtggatg atatttgttc aatatgtcaa gctgaatttc agaagccaat tcttctcatt    1260
tgtcagcata tattttgtga agagtgcatg accttatggt ttaacagaga gaaaacatgt    1320
ccactctgca gaactgtgat ttcagaccat ataaacaaat ggaaggatgg agccacttca    1380
tcacaccttc aaatatatta agttgtataa actatcaagg ccacaaaata ctaatgtcat    1440
ttggtcataa tgactactga taaggcatca gaatggattt tcagggctac cagaaaaatg    1500
tttccagatg gttttagaat gtaggactta tgatccaatt caccaaaaga ttaaatgaaa    1560
ccaccctgtg ttttaaaata tatataatgt tcaacctaat gtatatgcaa catttattct    1620
attctaatta tttgacaggt aactgcagtg ttaaattgta aatgtgtttt ctttatgtta    1680
ccaaaacagc aatttgaaat tagaactagt ggttttagag aactcaggta ttctttcctg    1740
acattgtttt cagaataaag aatatttttc ataatatttt aagatacata ctatctaaaa    1800
gtagaatttt gttcagcatt gacttttata attcccatcc taaaaattct taatattttc    1860
ataaaatttg tattttaaa tgaaaattct aaatgttgta ttttatcagt aacattttct    1920
aagtgaagat taatttactg aggatgatac attatagtat tgtattattc tctgtagtaa    1980
gattagtaat aagtgaaaat aaatgattta aattcaaaaa aaaaaaaaa a              2031
```

<210> SEQ ID NO 46
<211> LENGTH: 1074
<212> TYPE: DNA
<213> ORGANISM: Homo Sapiens

<400> SEQUENCE: 46

```
gatcaacaca tttcatctgg gcttcttaaa tctaaatctt taaaatgact aagttttctt      60
ccttttctct gttttttccta atagttgggg cttatatgac tcatgtgtgt ttcaatatgg    120
aaattattgg agggaaagaa gtgtcacctc attccaggcc atttatggcc tccatccagt    180
atggcggaca tcacgtttgt ggaggtgttc tgattgatcc acagtgggtg ctgacagcag    240
cccactgcca atatcggttt accaaaggcc agtctcccac tgtggtttta ggcgcacact    300
ctctctcaaa gaatgaggcc tccaaacaaa cactggagat caaaaaattt ataccattct    360
caagagttac atcagatcct caatcaaatg atatcatgct ggttaagctt caaacagccg    420
caaaactcaa taaacatgtc aagatgctcc acataagatc caaaacctct cttagatctg    480
gaaccaaatg caaggttact ggctggggag ccaccgatcc agattcatta agaccttctg    540
acaccctgcg agaagtcact gttactgtcc taagtcgaaa actttgcaac agccaaagtt    600
actacaacgg cgacccttt atcaccaaag acatggtctg tgcaggagat gccaaaggcc    660
agaaggattc ctgtaagggg gactcagggg gccccttgat ctgtaaaggt gtcttccacg    720
ctatagtctc tggaggtcat gaatgtgtgt tgccacaaa gcctggaatc tacaccctgt    780
taaccaagaa ataccagact tggatcaaaa gcaaccttgt cccgcctcat acaaattaag    840
ttacaaataa ttttattgga tgcacttgct tcttttttcc taatatgctc gcaggttaga    900
gttgggtgta agtaaagcag agcacatatg gggtccattt ttgcacttgt aagtcatttt    960
attaaggaat caagttcttt ttcacttgta tcactgatgt atttctacca tgctggtttt   1020
attctaaata aaatttagaa gactcaaaaa aaaaaaaaa aaaaaaaaaa aaaa          1074
```

<210> SEQ ID NO 47
<211> LENGTH: 1518
<212> TYPE: DNA
<213> ORGANISM: Homo Sapiens -continued

```
<400> SEQUENCE: 47
cacttccctt cccgcgatgg cggcacaggg agctgctgcg gcggttgcgg cggggacttc      60
aggggtcgcg ggggagggcg agcccgggcc cggggagaat gcggccgctg aggggaccgc     120
cccatccccg ggccgcgtct ctccgccgac cccggcgcgc ggcgagccgg aagtcacggt     180
ggagatcgga gaaacgtacc tgtgccggcg accggatagc acctggcatt ctgctgaagt     240
gatccagtct cgagtgaacg accaggaggg ccgagaggaa ttctatgtac actacgtggg     300
cttttaaccgg cggctggacg agtgggtaga caagaaccgg ctggcgctga ccaagacagt     360
gaaggatgct gtacagaaga actcagaaa gtacctgagc gagctcgcag agcagcctga     420
gcgcaagatc actcgcaacc aaaagcgcaa gcatgatgag atcaaccatg tgcagaagac     480
ttatgcagag atggaccca ccacagcagc cttggagaag gagcatgagg cgatcaccaa     540
ggtgaagtat gtggacaaga tccacatcgg gaactacgaa attgatgcct ggtatttctc     600
accattcccc gaagactatg gaaacagcc caagctctgg ctctgcgagt actgcctcaa     660
gtacatgaaa tatgagaaga gctaccgctt ccacttgggt cagtgccagt ggcggcagcc     720
ccccgggaaa gagatctacc gcaagagcaa catctccgtg cacgaagttg atggcaaaga     780
ccataagatt tactgtcaga acctgtgtct gctggccaag cttttcctgg accataagac     840
actgtacttt gacgtggagc cgttcgtctt ttacatcctg actgaggtgg accggcaggg     900
ggcccacatt gttggctact tctccaagga gaaggagtcc ccggatggaa acaatgtggc     960
ctgcatcctg accttgcccc cctaccaacg ccgcggctac gggaagttcc tcatcgcttt    1020
cagttatgag ctctccaagc tggagagcac agtcggctcc ccggagaagc cgctgtctga    1080
cctgggcaag ctcagctacc gcagctactg gtcctgggtg ctgctggaga acctgcggga    1140
cttccggggc acactgtcca tcaaggacct cagccagatg accagtatca cccaaaatga    1200
catcatcagt accctgcaat ccctcaatat ggtcaagtac tggaagggcc agcacgtgat    1260
ctgtgtcaca cccaagctgg tggaggagca cctcaaaagt gcccagtata gaaaaccacc    1320
catcacagtg gactccgtct gcctcaagtg ggcacccccc aagcacaagc aagtcaagct    1380
ctccaagaag tgagcagcct ggcccctgct gccggacctg agcctcctgg ctcccagcct    1440
gtaaatatgt atagacctgt tttgtcattt ttttaataaa gtcagttctg gtggccctgg    1500
actttggagg ggaaggggg                                                  1518

<210> SEQ ID NO 48
<211> LENGTH: 2014
<212> TYPE: DNA
<213> ORGANISM: Homo Sapiens

<400> SEQUENCE: 48
aaaccctgaa gagcccaagc aatgtggttg taaaatttgc aaaataagat taaatcttaa      60
ctgcaatctg ttaacactgc tgtctccttt cactctttct cctatatcac actttcccac     120
atgttggatg gccttggagt ggtagccata agcattttg gaattcaact aaaaactgaa     180
ggatccttga ggacggcagt acctggcata cctacacagt cagcgttcaa caagtgtttg     240
caaaggtaca ttggggcact gggggcacga gtgatctgtg acaatatccc tggtttggtg     300
agccggcagc ggcagctgtg ccagcgttac ccagacatca tgcgttcagt gggcgagggt     360
gcccgagaat ggatccgaga gtgtcagcac caattccgcc accaccgctg gaactgtacc     420
accctggacc gggaccacac cgtctttggc cgtgtcatgc tcagaagtag ccgagaggca     480
gcttttgtat atgccatctc atcagcaggg gtagtccacg ctattactcg cgcctgtagc     540
```

```
cagggtgaac tgagtgtgtg cagctgtgac ccctacaccc gtggccgaca ccatgaccag    600
cgtggggact ttgactgggg tggctgcagt gacaacatcc actacggtgt ccgttttgcc    660
aaggccttcg tggatgccaa ggagaagagg cttaaggatg cccgggccct catgaactta    720
cataataacc gctgtggtcg cacggctgtg cggcggtttc tgaagctgga gtgtaagtgc    780
catggcgtga gtggttcctg tactctgcgc acctgctggc gtgcactctc agatttccgc    840
cgcacaggtg attacctgcg cgacgctat gatgggctg tgcaggtgat ggccacccaa    900
gatggtgcca acttcaccgc agcccgccaa ggctatcgcc gtgccacccg gactgatctt    960
gtctactttg acaactctcc agattactgt gtcttggaca aggctgcagg ttccctaggc   1020
actgcaggcc gtgtctgcag caagacatca aaaggaacag acggttgtga atcatgtgc    1080 tgtggccgag ggtacgacac aactcgagtc accgtgtta cccagtgtga gtgcaaattc    1140
cactggtgct gtgctgtacg gtgcaaggaa tgcagaaata ctgtggacgt ccatacttgc   1200
aaagccccca agaaggcaga gtggctggac cagacctgaa cacacagata cctcactcat   1260
ccctccaatt caagcctctc aactcaaaag cacaagatcc ttgcatgcac accttcctcc   1320
accctccacc ctgggctgct accgcttcta tttaaggatg tagagagtaa tccataggga   1380
ccatggtgtc ctggctggtt ccttagccct gggaaggagt tgtcagggga tataagaaac   1440
tgtgcaagct ccctgatttc ccgctctgga gatttgaagg gagagtagaa gagataggg    1500 gtctttagag tgaaatgagt tgcactaaag tacgtagttg aggctccttt tttctttcct   1560
ttgcaccagc ttcccgacac ttcttggtgt gcaagaggaa gggtacctgt agagagcttc   1620
tttttgtttc tacctggcca agttagatg ggacaaagat gaatggcatg tcccttctct    1680
gaagtccgtt tgagcagaac tacctggtac cccgaaagaa aaatcttagg ctaccacatt   1740
ctattattga gagcctgaga tgttagccat agtggacaag gttccattca catgctcata   1800
tgtttataaa ctgtgttttg tagaagaaaa agaatcataa caatacaaac acacattcat   1860
tctctctttt tctctctacc attctcaacc tgtattggac agcactgcct cttttgctta   1920
cttgctgcct gttcaaactg aggtggaatg cagtggttcc catgcttaac agatcattaa   1980
aacaccctag aacactccta ggatagatta atgt                               2014

<210> SEQ ID NO 49
<211> LENGTH: 3258
<212> TYPE: DNA
<213> ORGANISM: Homo Sapiens

<400> SEQUENCE: 49
aaggctgtgg accccagaga aggtggcagg tggccccccct aggagagctc tgggcacatt    60
cgaatcttcc caaactccaa taataaaaat tcgaagactt tggcagagag tgtgtgtgtg   120
tgtgtatggt tgttgggcgt aggacaggtt tcggggatgc gcggtacgcg gtaccacccc   180
tcggaggccc ccaccccccag acgcccaggc cgcctcccca ctcccccctca agcagcccca   240 gccgggggact ttccgtcgcg gggaaggggc ggggaccctg agcgaaaggt gcggaggcgg   300
cctgccgggg tggttcggct tcccgttgcc gcctcgggcg ctgtacccag agctcgaaga   360
ggagcagcgc ggccgcgcgg acccggcaag gctgggccgg actcggggct cccgagggac   420
gccatgcggg gaggcagggg cgccccttc tggctgtggc cgctgccaa gctggcgctg    480 ctgcctctgt tgtgggtgct tttccagcgg acgcgtcccc agggcagcgc cgggccactg   540
cagtgctacg gagttggacc cttgggcgac ttgaactgct cgtgggagcc tcttggggac   600
```

```
ctgggagccc cctccgagtt acacctccag agccaaaagt accgttccaa caaaacccag    660
actgtggcag tggcagccgg acggagctgg gtggccattc ctcgggaaca gctcaccatg    720
tctgacaaac tccttgtctg ggcactaag gcaggccagc ctctctggcc cccgtcttc    780 gtgaacctag aaacccaaat gaagccaaac gccccccggc tgggcccctga cgtggacttt    840 tccgaggatg accccctgga ggccactgtc cattgggccc acctacatg gccatctcat    900 aaagttctga tctgccagtt ccactaccga agatgtcagg aggcggcctg gaccctgctg    960
gaaccggagc tgaagaccat acccctgacc cctgttgaga tccaagattt ggagctagcc   1020
actggctaca aagtgtatgg ccgctgccgg atggagaaag aagaggattt gtggggcgag   1080
tggagcccca ttttgtcctt ccagacaccg ccttctgctc caaaagatgt gtgggtatca   1140 ggaacctct gtgggacgcc tgaggagag gaacctttgc ttctatgaa ggccccaggg   1200 ccctgtgtgc aggtgagcta caaagtctgg ttctgggttg gaggtcgtga gctgagtcca   1260
gaaggaatta cctgctgctg ctccctaatt cccagtgggg cggagtgggc cagggtgtcc   1320
gctgtcaacg ccacaagctg ggagcctctc accaacctct ctttggtctg cttggattca   1380
gcctctgccc cccgtagcgt ggcagtcagc agcatcgctg ggagcacgga gctactggtg   1440
acctggcaac cggggcctgg ggaaccactg gagcatgtag tggactgggc tcgagatggg   1500
gaccccctgg agaaactcaa ctgggtccgg cttccccctg ggaacctcag tgctctgtta   1560
ccagggaatt tcactgtcgg ggtccctat cgaatcactg tgaccgcagt ctctgcttca   1620
ggcttggcct ctgcatcctc cgtctggggg ttcaggagg aattagcacc cctagtgggg   1680
ccaacgcttt ggcgactcca agatgcccct ccagggaccc ccgccatagc gtggggagag   1740
gtcccaaggc accagcttcg aggccacctc acccactaca ccttgtgtgc acagagtgga   1800 accagccct ccgtctgcat gaatgtgagt ggcaacacac agagtgtcac cctgcctgac   1860
cttccttggg gtccctgtga gctgtgggtg acagcatcta ccatcgctgg acagggccct   1920
cctggtccca tcctccggct tcatctacca gataacaccc tgaggtggaa agttctgccg   1980
ggcatcctat tcttgtgggg cttgttcctg ttggggtgtg gcctgagcct ggccacctct   2040
ggaaggtgct accacctaag gcacaaagtg ctgccccgct gggtctggga aaagttcct   2100 gatcctgcca acagcagttc aggccagccc cacatggagc aagtacctga ggcccagccc   2160 cttgggggact tgcccatcct ggaagtggag gagatggagc cccgccggt tatggagtcc   2220 tcccagcccg cccaggccac cgccccgctt gactctgggt atgagaagca cttcctgccc   2280
acacctgagg agctgggcct tctggggccc cccaggccac aggttctggc ctgaaccaca   2340
cgtctggctg ggggctgcca gccaggctag agggatgctc atgcaggttg caccccagtc   2400
ctggattagc cctcttgatg gatgaagaca ctgaggactc agagaggctg agtcacttac   2460
ctgaggacac ccagccaggc agagctggga ttgaaggacc cctatagaga agggcttggc   2520
ccccatgggg aagacacgga tggaaggtgg agcaaaggaa aatacatgaa attgagagtg   2580
gcagctgcct gccaaaatct gttccgctgt aacagaactg aatttggacc ccagcacagt   2640
ggctcacgcc tgtaatccca gcactttggc aggccaaggt ggaaggatca cttagagcta   2700
ggagtttgag accagcctgg gcaatatagc aagacccctc actacaaaaa taaaacatca   2760
aaaacaaaaa caattagctg ggcatgatgg cacacacctg tagtccgagc cacttgggag   2820
gctgaggtgg gaggatcggt tgagcccagg agttcgaagc tgcagggacc tctgattgca   2880
ccactgcact ccaggctggg taacagaatg agaccttatc tcaaaaataa acaaactaat   2940
aaaaagcaaa aaaaaaaaa aaagaaaaga aaaacactg catttgggca ccatctcagc   3000
```

```
tcccttgcat ccaggtgcag catggactga gttcttgaca acagaatgtg gtcagaagtg    3060
acatatgcca acacggggtc tgggtggggg ctcccccaca tcctttcctt gcctatgagc    3120
tggaacataa cacatgccta tgatccagct ttggtcatac caaggggaa ggtggagcaa     3180 gaaatgaaaa ggaacctgaa tccctgaatg actgcatgga tagaaccact aagaaaaata    3240
aacttttata tttttata                                                  3258

<210> SEQ ID NO 50
<211> LENGTH: 4359
<212> TYPE: DNA
<213> ORGANISM: Homo Sapiens

<400> SEQUENCE: 50
gttgtaaact tcacctcccg ggggctcttc cccttctgta cccctttgct gtttgtcccc      60
ctcctcccgg gtcctggagt ccgtcgtgtt ccaacagttt ttgctcttat tcccgtgggc     120
tgcctgggcc tcctttcacc cgtgagactt ggagcggccc ctgggtctt gggtgtgcag      180 cacggatcac gcgagacccc tgagacctca aatcatctaa cgtgaagcca cagacatctt     240
gggcaatttt aatcatcaag aaagaaatat gtcattaaga aatagcaggg tattttgaaa     300
gagttggaaa acatcatgaa tttgaatact tcaagtaata ctggtgatac ccaaaggttg     360
aagattgcct cattggatgt aaaacaaata cttaaaaatg aaacagagtt ggatattact     420
gataatctca ggaagaaact ccattgggct aaaaagaaa agttagaaat aacaaccaaa      480
cacaatgcag agctggcaag ctatgagagc cagattgcca agctacggtc cgaggttgaa     540
aagggagaag cattgcgaca aagtctggaa tatgacctag ctgttgctag aaaggaagct     600
ggtcttggaa gacgggctgc tgaagaaaga ttagccgagg cacataggat ccaagaaaaa     660
ctctgtgcac agaattcaga acttcaagca aagacaaatg agactgagaa agcatttcag     720
acttctcagc aaaaatggaa agaagaatgc agaagatttg aacatgattt ggaggaaaga     780
gacaatatga tccaaaattg caatcgagaa tatgatttac ttatgaaaga aaaaagcaga     840
ctagagaaaa ctctacagga agcgttggaa aaacatcaac gggagaagaa tgagatggag     900
tctcatatca gggagacagc attggaggag tttagattac aagaagaaca atgggaagca     960
gaaagaagag aattacaatt tatagtacag gagcaagata ctgctgtgca aaatatgcat    1020
aagaaagtag aaaaattaga aacagaacat atggactgct ctgacctttt acggcgacaa    1080
acaagtgaac ttgaatttag cactcaacga gaggaacgcc ttagaaaaga atttgaggca    1140
actactctaa gagtgaggaa attagaagaa acattgaag cagaaagagc agcgcatttg      1200
gaatcaaaat ttaattctga aattattcag ttacggattc gagaccttga aggagctttg    1260
caagtagaga aggccagtca agcagaagct gttgctgatt tggaaattat caagaatgaa    1320
ttcaaagaag ttgaaagtgc atatgagcga gaaaagcata atgcacaaga gagctttgca    1380
aaactaaatt tattagaaaa agagtatttc tccaaaaata agaaactaaa tgaagacatc    1440
gaggaacaga agaaagtaat tatagaacctt tcaaagagac tccagtataa tgaaaaaagt    1500
tgcagtgaat tacaggaaga actagtaatg ctaagaagc accaggcctt cctagtagag      1560
acatgtgaaa ataacgtgaa agaattggaa tcgatcttgg acagctttac tgtgtcgggc    1620
cagtggacat caggcatcca caaggacaaa gataaacctc ccagcttctc tgttgtcctt    1680
gagagattga ggcgtaccct gacagattac cagaacaagc tggaagatgc atctaatgag    1740
gaaaaggcat gtaatgaact tgattctacg aaacagaaga tagactctca cactaaaaat    1800
```

```
ataaaggaac ttcaggataa actggctgat gttaataaag agttaagtca tttacacact    1860
aaatgtgcag accgagaggc tttaataagc actttaaaag tggaactaca aaatgtgctg    1920
cactgttggg agaaagaaaa ggctcaggca gcccagtctg aaagtgaact gcagaagctt    1980
tcccaggctt tccataagga tgcagaggag aagctaacct tccttcacac cttatatcag    2040
cacttggtag caggctgtgt gctcataaaa caaccagaag gcatgctgga taaattctct    2100
tggtctgagc tttgtgcagt cttacaggag aatgttgatg ccctgattgc agacctcaac    2160
agggctaatg agaagataag gcatctagag tatatctgta aaacaagtc tgacacgatg     2220
agagagcttc agcagactca ggaagacacc tttaccaaag tggcagaaca gatcaaagcc    2280
caagagagct gctggcacag acaaaagaag gaactagagc tgcagtattc tgaactcttc    2340
ctggaggtgc agaagagggc acagaaattt caagaaattg ctgaaaaaaa catggaaaaa    2400
ttgaaccata ttgagaagtc acatgaacag ttggttcttg aaaattcgca cttcaaaaaa    2460
ctgttatcac agactcaaag ggaacagatg tccttgctgg cagcctgtgc attaatggct    2520
ggtgccttat atcccctcta tagccgatca tgcgccttgt ctacacagag agattttctc    2580
caggagcagg tcaacacctt tgagttgttc aaactggaaa ttagaactct agcccaggct    2640
ttgtcaactg tagaggaaaa gaagcaagag gaagccaaga tgaaaagaa acattcaaa     2700
ggattgatac gtatatttcg gaaaggtgtt attgctgttt tggcagcaaa cagactcaag    2760
attttgggcc aatcatgtgc ctctcttttt acctggatgg agagtttcaa agaaggcata    2820
ggcatgttag tgtgcacagg agagccccaa gacaagcata aatttccaaa acatcaaaag    2880
gagcagttgc gttgtttaca agcgctcagt tggctcacca gttctgacct tcttgctgca    2940
ataatcagtt ctatggctga attacaagac gtcattggta aagcagatcc aaattccaga    3000
atttgtggac atttactcat aggtgcagcc aagaattctt ttgcaaaact catggataaa    3060
attagtctgg taatggaatg tatacctctg cacagtagca ggagtattac atatgtagaa    3120
aaagattccc tggttcagag gctggcccat ggacttcata agtaaacac actggccctg     3180
aaatatggtt tgcgtggcca tgtgcccatt acgaaaagca cagcatcgtt gcagaagcaa    3240
atacttggat ttacacaaag actgcatgct gcagaagtgg agcgccgctc actacgctta    3300
gaggtcacag aattcaaacg aagtgtgaat gaaatgaaaa aggagcttga caaagcccag    3360
ggtctgcaaa tgcaattaaa tgaatttaag cagtctaaat tgatcaccca tgagaagttt    3420
gaaagtgcat gtgaagaact aaataatgca ttacttcggg aagagcaggc acaaatgcta    3480
ttgaatgaac aggcacaaca actacaggaa ttgaattata aacttgaatt gcactccagt    3540
gaggaagctg acaaaaacca aactcttgga gaagctgtta agagtctctc cgaggcaaag    3600
atggagctga agaaaaaga tcaatctctg cgtcagctca atagacatct tacccagctg    3660
gagcaggaca agcgtcgact ggaggagaac atccatgatg cagagagtgc cctccgcatg    3720
gcagccaaag acaaagaatg tgttgctaat cacatgagag cagtagaaaa tacgcttcac    3780
aaggtcagag atcagatctc gctgtcatgg tctgcggcaa gtaggaatga cttcacccta    3840
cagctaccca aactgcacct ggagaccttt gcaatggagg ggctcaaggg cgggccagag    3900
gtggtagcat gccaggctat gattaaaagt ttcatggatg tctaccagct tgcaagcact    3960
agaatcatga cattagagaa ggaaatgaca tctcatcgaa gtcacattgc agccttgaaa    4020
tcagaacttc acacagcttg tttacgtgaa aatgcaagtt tacaatcaat aggatcacga    4080
gaccattcaa atctctccat tccttcaaga gctcctcttc ctgctgacac aactggtatt    4140
ggggatttct taccattgaa agctgaactt gatactactt acactttctt aaaggagaca    4200
```

```
tttataaata ctgtgcccca tgctctgaca tcatctcact cctctccagt gactatgtct    4260
gctaatgcca acagaccaac tcagattgga ttatgacttc atgaaattaa aaaatggagg    4320
aagagttaac agtacaatta aaattgtttt gaatgggaa                           4359
```

CYTOMEGALOVIRUS VACCINES AND METHODS OF PRODUCTION

Pursuant to 35 U.S.C. §202(c), it is acknowledged that the United States government may have certain rights in the invention described herein, which was made in part with funds from the National Institutes of Health under Grant Nos.: CA85786, CA82396. AI54430 and GM71508.

This application is the U.S. National Stage of International Application No. PCT/US2008/079494, filed Oct. 10, 2008, which designates the U.S., published in English, and claims the benefit of U.S. Provisional Application No. 60/998,426, filed Oct. 10, 2007, the entire contents of which are incorporated by reference herein.

INCORPORATION BY REFERENCE OF MATERIAL IN ASCII TEXT FILE

This application incorporates by reference the Sequence Listing contained in the following ASCII text file:
a) File name: 45611000002SUBSEQLIST6222016; created Jun. 22, 2016, 161 KB in size.

FIELD OF THE INVENTION

The invention relates generally to the field of vaccine development. More specifically, the invention relates to methods of increasing diversity in cytomegalovirus vaccines through the selection of cell type in which the virus is propagated, and to the use of cytomegalovirus produced by those methods in the development of vaccine compositions.

BACKGROUND OF THE INVENTION

Various publications, including patents, published applications, technical articles and scholarly articles are cited throughout the specification. Each of these cited publications is incorporated by reference herein, in its entirety. Full citations for publications referenced by numbers in parentheses or otherwise not cited fully within the specification are set forth at the end of the specification.

Cytomegalovirus (CMV) is a herpes virus classified as being a member of the beta subfamily of herpesviridae. According to the Centers for Disease Control and Prevention, CMV infection is found fairly ubiquitously in the human population, with an estimated 40-80% of the United States adult population infected. The virus is spread primarily through bodily fluids, and is frequently passed from pregnant mothers to the fetus or newborn. In most individuals. CMV infection is latent, although virus activation can result in high fever, chills, fatigue, headaches, nausea, and splenomegaly.

Although most human CMV infections are asymptomatic. CMV infections in immunologically immature or immunocompromised individuals, such as newborns, HIV-positive patients, allogeneic transplant patients and cancer patients, can be particularly problematic. CMV infection in such individuals can cause severe morbidity, including pneumonia, hepatitis, encephalitis, colitis, uveitis, retinitis, blindness, and neuropathy, among other deleterious conditions. In addition, CMV is a leading cause of birth defects. At present, there is no cure or preventive vaccine for CMV infection.

The entry of herpesviruses into cells is a complex process initiated by adsorption and receptor binding and followed by fusion of the virus envelope with a cell membrane. Fusion occurs at either the plasma membrane or an endosomal membrane. For instance, Epstein-Barr virus (EBV) enters primary B cells via receptor-mediated endocytosis (1, 2), yet it infects epithelial cells or transformed B cells by fusion of the virion envelope with the plasma membrane (1). Herpes simplex virus fuses with the plasma membrane of some cell types, but enters others by endocytosis (3-6). Human cytomegalovirus (HCMV) infects multiple cell types in vivo, including epithelial cells, endothelial cells and fibroblasts (7). It fuses with the plasma membranes of fibroblasts (8), but enters retinal pigmented epithelial cells and umbilical vein endothelial cells via endocytosis (9, 10).

The mechanism by which herpesviruses 'choose' their route of entry remains unclear. It is generally assumed that entry pathways are mainly determined by the host cell, but there is precedent for tropic roles of virion glycoproteins (11). EBV virions contain two gH complexes, gH/gL and gH/gL/gp42 (12, 13), which have mutually exclusive functions (11). Fusion with the plasma membrane of B cells is mediated by gH/gL/gp42 (14-16), but entry into epithelial cells is triggered by gH/gL (11, 12, 17). The cell type in which EBV is produced can alter its tropism. B-cell-derived EBV virions contain less gH-gL-gp42 than epithelial-cell-derived virions. As a result, B-cell-generated virus is more infectious for an epithelial cell and epithelial cell-derived virus is B cell tropic (18).

HCMV also encodes two gH/gL complexes: gH/gL/gO and gli/gL/pUL128/pUL130/pUL131 (19, 20). The gO-containing complex is sufficient for fibroblast infection, whereas the pUL128/pUL130/pUL131-containing complex is required to infect endothelial and epithelial cells (19-21). The AD169 laboratory strain contains only the gli/gL/gO complex in its virions (19). The absence of the second gH/gL complex is responsible for the loss of epithelial and endothelial cell tropism in HCMV laboratory strains (19-22).

There is a need for variety and diversity of CMV vaccines, and for effective means to control the spread and activation of the virus, particularly in immunocompromised individuals and pregnant women. The present invention addresses that need.

SUMMARY OF THE INVENTION

One aspect of the present invention features a method of making a cytomegalovirus (CMV) vaccine. The method comprises propagating strains or isolates of CMV in cultured cells of a selected cell type, thereby producing a cell type-conditioned CMV, and producing a CMV vaccine from the cell type-conditioned CMV. In certain embodiments, the CMV strain or isolate is a human CMV (HCMV) strain or isolate. A wide variety of cell types are suitable for the method, including but not limited to epithelial cells, endothelial cells, fibroblasts, neuronal cells, smooth muscle cells, macrophages, dendritic cells and stromal cells. In a specific embodiment, the selected cell type is an epithelial cell.

The aforementioned method can further comprise producing the cell type-conditioned CMV in two or more different selected cell types and combining those CMV to produce the CMV vaccine. Alternatively or additionally, the method comprises providing two or more CMV strains or isolates, growing each of the strains or isolates in the cultured cells comprising the selected cell type or two or more different selected cell types, and combining all the CMV produced therefrom to make the CMV vaccine.

In certain embodiments, the method comprises producing a live attenuated CMV vaccine. In other embodiments, it comprises producing an inactivated or killed CMV vaccine. In still other embodiments, it comprises producing combination vaccines comprising one or more live attenuated viruses, inactivated viruses and other immunogenic components, e.g., immunogenic CMV proteins and peptides, and the like.

CMV vaccines produced by the aforementioned methods are also within the scope of the present invention.

Another aspect of the invention features kit for practicing the methods of the invention. Such kits typically include a package in which is contained one or CMV strains or clinical isolates, cultured cells of one or more selected cell types, and instructions for using the cultured cells and the CMV strains or isolates to produce cell type-conditioned CMV for use in a CMV vaccine.

Another aspect of the invention features a vaccine composition comprising a cytomegalovirus (CMV) population or virion components thereof, admixed with a suitable pharmaceutical carrier or adjuvant, wherein the CMV population is isolated from an cultured cells of a selected cell type. In one embodiment, the selected cell type is an epithelial cell type. In one embodiment, the vaccine composition comprises HCMV.

In various embodiments of the vaccine composition, the CMV population isolated from epithelial cell cultures is characterized by one or more features in subsequently infected host cells including but not limited to: (a) entry into the host cells by fusion with host cell plasma membranes; (b) greater virion-mediated cell-cell fusion of the host cells as compared with an equivalent CMV population isolated from cultured fibroblasts: (c) accelerated virus growth in the host cells as compared with an equivalent CMV population isolated from culture fibroblasts: (d) elicitation of a cellular response involving changes in expression greater than or equal to 2.5 fold of about two thirds fewer genes than a response elicited by an equivalent CMV population isolated from culture fibroblasts at 10 hours post-infection: or (e) elicitation of a cellular response involving a change in expression of one or more genes as shown in Table 2 and Table 4 herein, the latter being represented by GenBank Accession Nos: AK094860, NM_145023, NM_133492, NM_001039580, NM_001004301, NM_001034, AI369525, AK123066, NM_005345, NM_020731, BC071797, NM_003414, NM_000800, NM_138467, AK090803, AL133118, NM_001165, BG001037, NM_024861, NM_001043, NM_016239, NM_001018084, NM_001037442, NM_017600, NM_022097, NM_175868, NM_032266, NM_003841, NM_005039, NM_145051, NM_004294, AW856073, NM_024050, AF085968, NM_080927, NM_022115, AK056703, NM_000808, NM_012377, NM_006793, NM_031466, NM_005185, NM_139173, BX360933, NM_016125, NM_002104, NM_032188. NM_004185, NM_004843 or NM_173550.

In certain embodiments, the vaccine composition comprises a CMV population or virion components thereof isolated from a cell culture of two or more different selected cell types. For instance, the CMV population may be isolated from as an epithelial cells and cells of another cell type, such as a fibroblast cell type. In other embodiments, the CMV population comprises two or more CMV strains or clinical isolates grown in the selected cell type. Certain embodiments can comprise a plurality of CMV strains or clinical isolates grown in cell cultures of a plurality of different cell types.

In one embodiment, the vaccine composition comprises a live attenuated CMV vaccine. In another embodiment, it comprises an inactivated CMV vaccine. In still other embodiments, the vaccine composition can be a combination vaccine comprising one or more strains of live attenuated virus or components thereof, inactivated virus or components thereof, and/or other immunogenic CMV peptides or proteins.

Another aspect of the invention features a method of immunizing an individual against CMV, comprising administering to the individual a CMV vaccine composition produced by the aforementioned methods and/or comprising the aforementioned features. In one embodiment, the individual to be immunized is a human.

Other features and advantages of the invention will be understood by reference to the drawings, detailed description and examples that follow.

DETAILED DESCRIPTION OF ILLUSTRATIVE EMBODIMENTS

Figure 1:
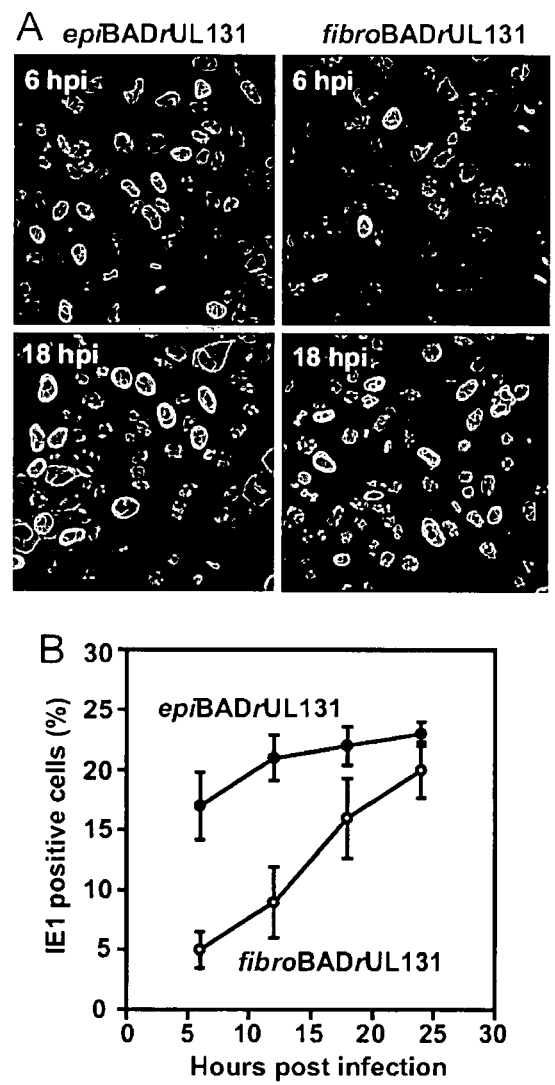
FIG. 1. Kinetics of HCMV IE1 expression in ARPE-19 cells. (A) Infected cells (0.1 pfu/cell) were fixed at indicated times, and stained for IE1 (green in color photo, light gray in black and white photo), Sp100 (red in color photo, very dark gray in black and white photo) and DNA (blue in color photo, dark gray in black and white photo). (B) At various times after infection (0.1 pfu/cell), the percentage of IE1-expressing cells was quantified; results are shown on the graph.

Various terms relating to the methods and other aspects of the present invention are used throughout the specification and claims. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is to be understood that the terminology used herein is for the purpose of describing particular embodiments only, and is not intended to be limiting.

DEFINITIONS

As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "amplifying," "propagating," and "growing," or "amplification," "propagation," and "growth" are used interchangeably herein to refer to the general process of introducing virus into cultured cells or infecting cells with virus under conditions permitting the virus to replicate and multiply within the cells, in accordance with methods well known to virologists and medicinal biologists. In particular, these terms are used herein to refer to the step of the inventive method in which the CMV is "conditioned" by propagation on a selected cell type, as the step prior to using the conditioned CMV for the production of a vaccine.

"Biomolecules" include proteins, polypeptides, nucleic acids, lipids, polysaccharides, monosaccharides, and all fragments, analogs, homologs, conjugates, and derivatives thereof.

"Cell culture" refers generally to cells taken from a living organism and grown under controlled conditions ("in culture" or "cultured"). A "primary cell culture" is a culture of cells, tissues, or organs taken directly from an organism(s) before the first subculture. A "cell line" is a population of cells formed by one or more subcultivations of a primary cell culture.

A "coding region" of a gene consists of the nucleotide residues of the coding strand of the gene and the nucleotides of the non-coding strand of the gene which are homologous with or complementary to respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

The terms "conditioned virus," "cell type-conditioned virus," "conditioned CMV" or "cell type-conditioned CMV" refer to CMV that has been propagated in a selected cell type prior to its use in vaccine production, in accordance with the methods described herein. These terms are intended to be analogous to the term "conditioned medium," which describes culture medium in which a particular cell type or cell line has been grown and then removed, and which contains components or factors produced by the cells, thereby altering the functionality of the medium. For purposes of the present application, the term "conditioned virus" similarly refers to virus that has been grown in a selected cell type and then removed from those cells, wherein the virus thereafter exhibits one or more altered functional features resulting from its growth in that cell type.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e. rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to the inhibition of virus infection as determined by any means suitable in the art.

As used herein "endogenous" refers to any material from or produced inside an organism, cell, tissue or system. "Exogenous" refers to any material introduced from or produced outside an organism, cell, tissue or system.

The term "expression" as used herein is defined as the transcription and/or translation of a particular nucleotide sequence driven by its promoter.

As used herein, "immunization" or "vaccination" are use interchangeably herein and are intended for prophylactic or therapeutic immunization or vaccination. "Therapeutic vaccination" is meant for vaccination of a patient with CMV infection.

"Isolated" means altered or removed from the natural state. For example, a nucleic acid or a peptide naturally present in a living animal is not "isolated." but the same nucleic acid or peptide partially or completely separated from the coexisting materials of its natural state is "isolated." An isolated nucleic acid or protein can exist in substantially purified form, or can exist in a non-native environment such as, for example, a host cell. Unless it is particularly specified otherwise herein, the proteins, virion complexes, antibodies and other biological molecules forming the subject matter of the present invention are isolated, or can be isolated.

The terms "patient," "subject," "individual," and the like are used interchangeably herein, and refer to any animal, or cells thereof whether in vitro or in situ, that can be infected with CMV. In certain non-limiting embodiments, the patient, subject or individual is a human.

"Parenteral" administration of an immunogenic or vaccine composition includes. e.g. subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means. i.e. the cloning of nucleic acid sequences from a recombinant library or a cell genome, using ordinary cloning and amplification technology, and the like, and by synthetic means.

As used herein, the terms "peptide," "polypeptide." and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A "single package" can also include virtual components. For instance, a kit may contain abbreviated physical instructions contained within the physical package, and instructions for accessing more detailed instructions from a virtual environment, such as a website for example.

The term "therapeutic" as used herein means treatment and/or prophylaxis. A therapeutic effect is obtained by avoidance, delay, suppression, remission, or eradication of a disease state associated with CMV infection.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes for instance, prevention of CMV propagation to uninfected cells of an organism. The phrase "diminishing CMV infection" is sometimes used herein to refer to a treatment method that involves reducing the level of infection in a patient infected with CMV, as determined by means familiar to the clinician.

DESCRIPTION

Cytomegalovirus (CMV) infects multiple cell types in vivo, including epithelial cells, endothelial cells and fibroblasts. As summarized above in the background material, various studies have reported that the virus fuses with the plasma membranes of fibroblasts, but enters retinal pigmented epithelial cells and umbilical vein endothelial cells via endocytosis. Due to the relative ease of propagating CMV in cultured fibroblasts as compared with epithelial or endothelial cell cultures, studies such as the above-summarized studies have been conducted using fibroblast-propagated CMV strains. Likewise, cultured fibroblasts are typically the cell type of choice in propagating CMV for clinical applications, such as the development of attenuated virus strains for vaccines.

It has now been demonstrated in accordance with the present invention that the cell type in which CMV particles are produced has a profound influence on their behavior in subsequent rounds of infection. Thus, for example, while it was heretofore reported that that CMV enters epithelial cells by endocytosis, the present inventors have demonstrated that this is the mode of entry for CMV propagated in fibroblasts, but not for CMV propagated in cultured epithelial cells. Epithelial cell-propagated CMV enters epithelial cells predominantly via fusion with the plasma membrane. This different mode of entry has a variety of physiological consequences: it influences the kinetics with which the infection proceeds and it markedly influences the cellular response to infection. For instance virus grown in epithelial cells produces a dramatically muted cellular response as compared to cells infected with virus grown in fibroblasts. Many cellular anti-viral genes expressed alter infection with fibroblast-grown virus are not expressed after infection with epithelial cell-grown virus. As a consequence, CMV grown in epithelial cells is predicted to perform differently than does a vaccine than CMV grown in fibroblasts, thus offering a new and unexpected source of diversity for the generation of CMV vaccines. Likewise, propagation of CMV in other cell types, such as endothelial cells or specialized cell types that CMV is able to infect (e.g. neurons, other cells of the central or peripheral nervous systems, smooth muscle cells, hepatocytes, stromal cells, macrophages or dendritic cells) should produce additional novel sources of diversity for the generation of CMV vaccines.

Thus, one aspect of the invention features methods of making CMV vaccines that exploit the variability associated with choosing a cell type in which to propagate the virus. Another aspect features a kit for practicing the methods described above. Another aspect of the invention features vaccine compositions for the prevention or treatment of CMV infection, and methods of immunizing an individual using such compositions. Various embodiments of these aspects of the invention are set forth below.

Methods of Producing CMV Vaccines:

The methods in accordance with an aspect of the invention comprise (1) providing a CMV strain or isolate; (2) propagating the strain or isolate in a cell culture of a selected cell type, and (3) harvesting CMV virions produced by growth in that cell type (referred to herein as "cell type-conditioned CMV") for use in producing a CMV vaccine.

The cell type selected for propagating the CMV prior to its use for vaccine development can be any cell line permissive for CMV infection that produces a yield of virus particles. The virus particles might be highly infectious in some assays or the particles might exhibit limited or no infectivity in many assays. Suitable cell types include, but are not limited to, (1) epithelial cell lines such as ARPE-19, which is exemplified herein and other retinal pigmented epithelial cell lines. e.g., epithelial cell line K-1034 (Ando, Y. et al. 1997, Arch. Virol. 142(8): 1645-1658): HCMC, derived from normal human colonic mucosa (Smith, J D, 1986, J. Virol. 60(2): 583-588): Caco-2 intestinal epithelial cells (Esclatine. A. et al. 2000, J. of Virol. 74 (1): 513-51); SW480, HCT116, HeLa, H1299, and MCF-7 (regarding the latter five. see Wang. D. & T. Shenk, 2005. J. Virol. 79: 10330) (2) endothelial cell lines such as HMEC-1, a human microvascular endothelial line, immortalized with SV-40 virus large T antigen (Guetta. E. et al., 2001, Cardiovascular Research 50: 538-546); HUVEC and LMVEC (regarding the latter two, see Wang. D. & T. Shenk, 2005, J. Virol. 79: 10330); (3) neuronal cells such as SK-N-SH, SK-N-AS and IMR-32 (see Wang, D. & T. Shenk, 2005. J. Virol. 79: 10330) as well as primary epithelial, endothelial, smooth muscle, macrophage and dendritic cells derived from a variety of tissue/organ sources.

Any CMV or combination of CMVs amenable to development as a vaccine is suitable for use as a source of the CMV for the method, as long as they can be grown in at least one selected cell type. In one embodiment, the CMV is human CMV (HCMV), either an isolate that has been previously isolated and characterized or a new isolate of HCMV or an HCMV-like virus. In another embodiment, the CMV originates from another primate, including but not limited to chimpanzee (Davison, A J et al. 2003, J. Gen. Virol. 84: 17-28) and rhesus monkey (Hansen, S G et al. 2003. J. Virol. 77:6620-36: Rivailler, P et al. 2006. J. Virol. 80:4179-82). The CMV can be an unmodified virus from a selected source, or it can be a chimeric virus produced by genetic modification or combination of elements from two or more different CMV strains or isolates.

Methods of making chimeric viruses are known in the art. To this end, at least six strains of human CMV have been cloned as infectious bacterial artificial chromosomes (BAC) and sequenced (Murphy. E et al. 2003. Proc. Natl. Acad. Sci. USA 100: 14976-14981. The BAC sequences are available at GenBank Accession Nos. AC146999 (laboratory strain AD169, from which the BADrUL131 variant described herein was made): AC146851 (laboratory strain Towne): AC146904 (clinical isolate PH): AC146905 (clinical-like isolate Toledo): AC146906 (clinical isolate TR); and AC146907 (clinical isolate FIX). At least two strains of human CMV have been sequenced without prior BAC cloning, and are available at GenBank Accession Nos. BK000394 (laboratory strain AD169) and AY446894 (clinical isolate Merlin). The entire genome of a chimpanzee CMV strain is available at GenBank Accession No. AF480884. The genome sequence of two rhesus CMV strains is also available (Accession Nos. AY186194 and DQ205516). Utilizing the teachings of the present application, the skilled artisan would be able to use any of the aforementioned sequences, or any other publicly available CMV sequence to prepare chimeric CMVs or to otherwise genetically modify a CMV.

It has been demonstrated in accordance with the present invention that laboratory strains of CMV that have been passaged repeatedly in fibroblasts can be successfully conditioned by propagation on the selected cell line. For instance, as described in the Example herein. BADrUL131, a BAC clone of the repeatedly passaged AD169 HCMV strain in which the UL131 ORF has been repaired, was introduced by electroporation into cultured human foreskin fibroblasts, and the resulting virus preparation was amplified once in the epithelial cell line ARPE-19. Thus, various embodiments of the invention comprise the use of CMV (or the genomes of CMV) that has been passaged in a cell type that is different from the cell type selected for the conditioning step. For example, a CMV strain can be passaged multiple times in fibroblasts, then amplified in epithelial cells and thereafter used to produce a vaccine. It will be appreciated that the CMV can be amplified/propagated for one or more rounds in the selected cell type.

In preferred embodiments, the methods of the invention are used to produce live attenuated CMV for use as a vaccine. Methods to attenuate viruses are known in the art. Preferably, attenuated CMV exhibit a diminished capacity for infectivity, and/or pathogenicity, including latency and activation, yet remain capable of inducing an immune response that treats or protects the host against CMV infection. Examples of attenuated CMV strains include, but are not limited to, laboratory strains, such as AD169 and Towne, which replicate almost exclusively in fibroblasts. Such attenuated strains, engineered if necessary to produce the requisite surface protein or protein complexes for appropriate tropism, can be grown epithelial cells or in fibroblasts and thereafter epithelial cells as discussed above, for use in the vaccine composition of the invention.

Serial passage in cultured cells, particularly fibroblasts, can be used to attenuate CMV. Repeated passaging of virally-infected host cells is carried out in vitro until sufficient attenuation of the virus is achieved. Passaging may be conducted under specific environmental conditions, such as modulated temperature, pH, humidity, in order to select for viruses with reduced infectivity or pathogenicity. If this method of attenuation is used, the serially passaged virus is then amplified in the selected cell type for one or more passages to produce the CMV to be used in the vaccine compositions of the invention.

Mutagenesis can also be employed to attenuate a virus. For example, CMV virions can be exposed to ultraviolet or ionizing radiation or chemical mutagens, according to techniques known in the art. In addition to their use to produce chimeric viruses, recombinant techniques can also be used to produce attenuated CMV virions. For instance, site-directed mutagenesis, gene replacement, or gene knockout techniques can be used to derive virus strains with attenuated infectivity, pathogenicity or latency. An example of modifying a CMV by knockout mutagenesis is set forth in WO/2007/038316, which describes CMVs with genomes deleted in one or more latency-promoting genes, displaying an altered ability to enter or maintain a latent state.

In other embodiments. CMV isolated from the selected cell cultures are inactivated or killed and used in vaccine compositions. Methods of inactivating or killing viruses, e.g., with a chemical such as formalin, are well known in the art. It will be understood by the skilled artisan that the killed or inactivated CMV will comprise all or a substantial portion of the components of the viral particle, such that the diversity generated by the amplification in the selected cell type is maintained in the vaccine composition.

The methods of the invention can be used to create combinations of CMVs propagated in different selected cell types, thereby conferring an additional level of diversity to the vaccines that are produced. In one embodiment, a single CMV isolate or strain is used to infect two or more different cultured cell lines of different types. e.g., retinal epithelial cells and endothelial cells. The CMV produced by amplification in the respective cell types is then combined for use in a single vaccine. In another embodiment, two or more different clinical isolates or strains of CMV are used to infect a single selected cell line, and the multi-strain or multi-isolate CMV population produced by amplification in that cell type is used to produce a vaccine. In yet another embodiment, multiple isolates or strains are used to infect two or more different cultured cell lines of different types, and the CMV populations produced by amplification in the respective cell types are combined for use in the vaccine.

Another aspect of the invention features kits for producing CMV vaccine materials in accordance with the methods described above. The kits comprise in separate containers in a single package or in separate containers in a virtual package, as appropriate for the use and kit component, aliquots of cell lines of one or more selected cell types, as well as one or more CMV isolates or strains, or vectors carrying the genomes of such CMV strains, to be introduced into and amplified in the selected cultured cell lines. Such kits also typically contain instructions, or links to instructions, for how to carry out the various steps of the method. Optionally, kits can also comprise culture medium and other reagents suitable for carrying out the cell culture and virus manipulations.

Vaccine Compositions and Methods of Use:

Another aspect of the invention features an immunogenic composition (referred to interchangeably herein as a vaccine composition) comprising a cytomegalovirus (CMV) population or virion components thereof, admixed with a suitable pharmaceutical carrier or adjuvant, wherein the CMV is obtained via propagation in a selected cell type, for instance, an epithelial cell culture. As mentioned above, CMV vaccines have heretofore typically been prepared using CMV propagated in fibroblasts. However, it has been demonstrated in accordance with the present invention that propagation in epithelial cells yields virus that differs from fibroblast-propagated virus in many different ways. Virus produced in epithelial cells preferentially fuses with the plasma membrane, whereas fibroblast-derived virus mostly enters by receptor-mediated endocytosis. In addition, epithelial cell-generated virions had higher intrinsic "fusion from without" activity than fibroblast-generated particles, which influences the kinetics of infection. Furthermore, the two virus preparations trigger different cellular signaling responses, as evidenced by markedly different alterations in the transcriptional profile of infected epithelial cells.

In particular, CMV produced by propagation in epithelial cells have one or more of the following features, as compared with an equivalent strain or isolate of the virus produced by propagation in fibroblasts. First, as mentioned above, they can be distinguished by their entry into the host cells by fusion with host cell plasma membranes. CMV produced on epithelial cells also display greater virion-mediated cell-cell fusion of the host cells as compared with an equivalent CMV population isolated from cultured fibroblasts, as well as accelerated virus growth in the host cells as compared with an equivalent CMV population isolated from culture fibroblasts. In addition, they elicit a subdued cellular response as compared with equivalent CMV propagated in fibroblasts. At 10 hours post-infection about two-thirds fewer genes (~50 versus ~150 genes) exhibit a 2.5 fold or more change in expression level. In addition, epithelial-grown CMV can be characterized by the particular profile of host genes whose expression is changed (increased or decreased) following infection. These gene expression profiles are detailed in the Example, and can involve a change in expression of one or more genes represented by GenBank Accession Nos: AK094860. NM_145023, NM_133492. NM_001039580. NM_001004301, NM_001034, A1369525, AK123066, NM_005345, NM_020731, BC071797. NM_003414, NM_000800, NM_138467, AK090803, AL133118. NM_001165, BG001037. NM_024861, NM_001043, NM 016239, NM 001018084, NM_001037442, NM_017600, NM_022097, NM_175868, NM_032266, NM_003841, NM_005039, NM_145051, NM_004294, AW856073, NM_024050, AF085968, NM_080927, NM_022115, AK056703, NM_000808, NM_012377, NM_006793, NM_031466, NM_005185, NM_139173, BX360933, NM_016125, NM_002104, NM_032188, NM_004185, NM_004843 or NM_173550.

In this aspect of the invention, as in the foregoing aspects of the invention. CMV or a combination of CMVs amenable to development as a vaccine is suitable for use as a source of the aforementioned CMV population, as long as they can be grown in at least one epithelial cell line or another selected cell type. In one embodiment, the CMV is HCMV or an HCMV-like virus. In another embodiment, the CMV originates from another primate, including but not limited to chimpanzee and rhesus monkey, as described above. The CMV can be an unmodified virus from a selected source, or it can be a chimeric virus produced by genetic modification or combination of elements from two or more different CMV strains or isolates, as described above.

In preferred embodiments, the vaccine compositions comprise live attenuated CMV, which can be produced by the methods outlined above, all familiar to the skilled artisan. In other embodiments. CMV isolated from the selected cell cultures are inactivated or killed and used in vaccine compositions.

The vaccine compositions can comprise combinations of different strains or isolates of CMV, which can be propagated on a single epithelial cell cultures or on a number of different epithelial cell cultures, or on cells of another cell type, to generate additional diversity. Furthermore, live attenuated CMV can be combined with killed or inactivated CMV, or with immunogenic components of CMV to produce a combination vaccine, e.g., live attenuated CMV combined with heat killed CMV, or combined with material for a subunit vaccine, or a combination of all three types of materials. Examples of immunogenic CMV polypeptides and complexes suitable for subunit vaccines are described in WO 2007/146024 entitled "Cytomegalovirus Surface Protein Complex for Use in Vaccines and as a Drug Target."

The vaccine composition can further comprise one or more adjuvants. Adjuvants can be any substance that enhances the immune response to the antigens in the vaccine. Non-limiting examples of adjuvants suitable for use in the present invention include Freund's adjuvant, incomplete Freund's adjuvant, saponin, surfactants such as hexadecylamine, octadecylamine, lysolecithin, demethyldioctadecyl ammonium bromide. N,N-dioctadecyl-N'—N-bis (2-hydroxyethylpropane diamine), methoxyhexa-decylglycerol, pluronic polyols, polyanions such as pyran, diethylaminoethyl (DEAE) dextran, dextran sulfate, polybrene, poly IC, polyacrylic acid, carbopol, ethylene maleic acid, aluminum hydroxide, and aluminum phosphate peptides, oil or hydrocarbon emulsions, and the like.

Vaccines can be formulated in aqueous solutions such as water or alcohol, or in physiologically compatible buffers such as Hanks' solution. Ringer's solution, or physiological saline buffer, including PBS. Vaccine formulations can also be prepared as solid form preparations which are intended to be converted, shortly before use, to liquid form preparations suitable for administration to a subject, for example, by constitution with a suitable vehicle, such as sterile water, saline solution, or alcohol, before use.

The vaccine compositions can also be formulated using sustained release vehicles or depot preparations. Such long acting formulations may be administered by implantation (for example subcutaneously or intramuscularly) or by intramuscular injection. Thus, for example, the vaccines may be formulated with suitable polymeric or hydrophobic materials (for example as an emulsion in an acceptable oil) or ion exchange resins, or as sparingly soluble derivatives, for example, as a sparingly soluble salt. Liposomes and emulsions can be used as delivery vehicles suitable for use with hydrophobic formulations. Sustained-release vehicles may, depending on their chemical nature, release the antigens over a range of several hours to several days to several weeks to several months.

The vaccine compositions may further include one or more antioxidants. Exemplary reducing agents include mercaptopropionyl glycine, N-acetylcysteine, β-mercaptoethylamine, glutathione, ascorbic acid and its salts, sulfite, or sodium metabisulfite, or similar species. In addition, antioxidants can also include natural antioxidants such as vitamin E, C, leutein, xanthine, beta carotene and minerals such as zinc and selenium.

Vaccine compositions may further incorporate additional substances to function as stabilizing agents, preservatives, buffers, wetting agents, emulsifying agents, dispersing agents, and monosaccharides, polysaccharides, and salts for varying the osmotic balance. The vaccines can further comprise immunostimulatory molecules to enhance vaccine efficacy. Such molecules can potentiate the immune response, can induce inflammation, and can be any lymphokine or cytokine. Nonlimiting examples of cytokines include interleukin (IL)-1, IL-2, IL-3, IL-4, IL-12, IL-13, granulocyte-macrophage colony stimulating factor (GMCSF), macrophage inflammatory factor, and the like.

Vaccines can be formulated for and administered by infusion or injection (intravenously, intraarterially, intramuscularly, intracutaneously, subcutaneously, intrathecally, intraduodenally, intraperitoneally, and the like). The vaccines can also be administered intranasally, vaginally, rectally, orally, topically, buccally, transmucosally, or transdermally.

An effective antigen dosage to treat against CMV infection can be determined empirically, by means that are well established in the art. The effective dose of the vaccine may depend on any number of variables, including without limitation, the size, height, weight, age, sex, overall health of the subject, the type of formulation, the mode or manner or administration, whether the virus is active or latent, whether the patient is suffering from secondary infections, or other related conditions.

Vaccine regimens can also be based on the above-described factors. Vaccination can occur at any time during the lifetime of the subject, including development of the fetus through adulthood. Supplemental administrations, or boosters, may be required for full protection. To determine whether adequate immune protection has been achieved, seroconversion and antibody titers can be monitored in the patient following vaccination.

The following example is provided to describe the invention in more detail. It is intended to illustrate, not to limit, the invention.

EXAMPLE

Human Cytomegalovirus Uses Two Distinct Pathways to Enter Retinal Pigmented Epithelial Cells The experimental results described in this example demonstrate that HCMV produced in two different cell types enters epithelial cells via different pathways. Virions generated in epithelial cells preferentially enter via fusion at the plasma membrane, whereas virions from fibroblasts enter by pH-dependent endocytosis. The two virus preparations induced markedly different cellular responses.

Materials and Methods

Biological Reagents.
Human foreskin fibroblasts (HFFs) at passage 10 to 15 were maintained in medium with 10% newborn calf serum. Human MRC-5 embryonic lung fibroblasts and ARPE-19 retinal pigmented epithelial cells (American Type Culture Collection) at passage 24 to 34 were maintained in medium with 10% fetal bovine serum. Human renal proximal tubular epithelial cells (hRPTECs) (Cambrex) were grown in medium with 10% fetal bovine serum and used at passage 4 to 5.

BADwt is derived from a BAC clone of the AD169 HCMV strain: BADrUL131 (19, 21) is a derivative of BADwt in which the UL1310RF has been repaired; BFXwt is derived from a BAC clone of the VR1814 clinical HCMV isolate. Viruses were prepared by electroporation of BAC DNAs into HFFs, and the resulting virus preparation was amplified once in ARPE-19 cells or HFFs, unless otherwise specified. Cell-free virions were partially purified by centrifugation through a sorbitol cushion and resuspended in serum-free medium. Virus titers were determined by plaque assay on MRC-5 cells. Neutralization of BADrUL131 was assayed by plaque reduction assay (19), by using purified anti-pUL130 monoclonal antibody (3E3) (19).

Anti-IE1 monoclonal antibody 1B12 was described previously (21). Rabbit anti-Sp100 polyclonal antibody (Chemicon) was used to visualize the ND10s.

Electron Microscropy.

ARPE-19 cells were exposed to virus at 4° C. for 1 h, unbound virus was removed by two washes with cold PBS, growth medium (37° C.) was added for 15 min. cells were rinsed with phosphate-buffered saline (PBS), fixed and processed for electron microscopy, and examined with an FEI Tecnai-T12 microscope at 80 kv.

Assay for the Dependence of Infection on Endosome Acidification.

ARPE-19 cells were pretreated with $NH_4Cl$ or Bafilomycin A1 (BFA) (Sigma) for 1 h at 37° C., followed by infection in the continued presence of the inhibitor. 16 h later, cultures were fixed in 2% paraformaldehyde and permeabilized with 0.1° A Triton X-100. IE1 was identified by immunofluorescence using monoclonal antibody 1B12 (21) plus Alexa 546-conjugated secondary antibody and nuclei were stained with DAPI. Inhibition was calculated as the percentage of IE1-expressing drug-treated relative to untreated cells.

Analysis of the Fusion Activity of Virion Proteins.

To assay "fusion from without", ARPE-19 cells were grown to 90% confluence and infected. After 1 h at 37° C., the inoculum was removed and medium containing 200 µg/ml of phosphonoformic acid (PFA) was added to inhibit viral DNA synthesis. Fusion was monitored by visual inspection for syncytium formation.

A luciferase reporter assay was adapted to quantitatively analyze virion fusion activity. Reporter and effector ARPE-19 cells were prepared by electroporation (90-95% efficiency) with a plasmid carrying a luciferase gene under the control by a T7 promoter and a pcDNA3-T7 polymerase plasmid, respectively. At 24 h post transfection, the cells were mixed at a 1:1 ratio, and incubated at 37° C. for an additional 16 h. The mixed populations were then exposed to HCMV virions at 4° C. for 1 h, after which the monolayer was washed twice with cold PBS followed by addition of buffers (PBS with 10 mM 2-(N-morpholino)ethanesulfonic acid and 10 mM HEPES) with a final pH ranging of 4.5 to 8. After 3 min at 37° C. the buffers were removed, and normal growth medium was added. At 6 hpi, the cells were lysed, and luciferase activity was assayed using a luciferase reporter assay system (Promega).

Assay of Cellular Transcriptional Responses.

Confluent ARPE-19 cells were serum starved for 24 h, followed by mock infection or infection. Total RNA was extracted at 6 or 10 hpi by using Trizol (Invitrogen), and purified with an RNeasy column (Qiagen). The RNA samples were amplified and labeled (cyanine-3) with the Agilent low RNA input fluorescent linear amplification kit. To control for chip to chip variation, a reference RNA (Clontech) was labeled (cyanine-5) and co-hybridized with the probes prepared from mock or HCMV-infected cells. The hybridization was performed in duplicate with Aligent Human 44K oligonucleotide arrays. Arrays were scanned using an Agilent scanner at 5 micron resolution, and images were analyzed with Agilent Feature Extraction software to determine the intensities of fluorescent signals for hybridized spots and for background subtraction. Agilent GeneSpring GX software was used for normalization and quantification of relative RNA changes.

Results

Fibroblast-Derived Virions Activate Immediate-Early Gene Expression in ARPE-19 Cells with Slower Kinetics than Epithelial Cell-Derived Virions.

The AD169 HCMV strain (BADwt) replicates poorly in ARPE-19 epithelial cells due to a mutation in its UL131 gene (10. 21). Repair of the mutation in AD169, producing BADrUL131, restores epithelial cell tropism (21) by allowing production of a gH/gL/pUL128/pUL130/pUL131 virion glycoprotein complex that is required for successful entry into these cells (19, 20).

BADrUL131 grown in ARPE-19 epithelial cells (epiBADrUL131) initiates its program of gene expression in epithelial cells more rapidly than BADrUL131 grown in HFF fibroblasts (fibroBADrUL131) (FIG. 1A). When ARPE-19 cells were infected with epiBADrUL131, ~17% of the cells expressed detectable IE1 protein at 6 h post infection (hpi). IE1 expression was accompanied by disruption of ND10s in the nucleus. In contrast, infection with fibroBADrUL131 led to IE1 expression in only 2.8% of ARPE-19 cells at 6 hpi. The number of IE1-expressing cells, however, increased with time. There was no significant difference in the percentage of IE1-expressing ARPE-19 cells at 24 hpi with virus produced in the two cell types (FIG. 1B).

Virions Produced in HFFs Versus ARPE-19 Cells Enter ARPE-19 Cells Via Distinct Pathways.

An electron microscopic examination of virus entry was performed to determine if the different kinetics of IE1 accumulation for ARPE-19 cell-derived virus versus HFF-derived virus resulted from an event prior to the onset of viral gene expression. ARPE-19 cells incubated with epiBADrUL131 or fibroBADrUL131 were permitted to attach at the cell surface at 4° C. and cultures were shifted to 37° C. for 15 min to allow internalization before processing for microscopy. For each sample, 40-50 cells were examined, with at least 90% of the cells showing either intact virions or capsids. The number of virus particles in each cell varied from 2-8, with most cells showing 2-3 particles.

Figure 2:
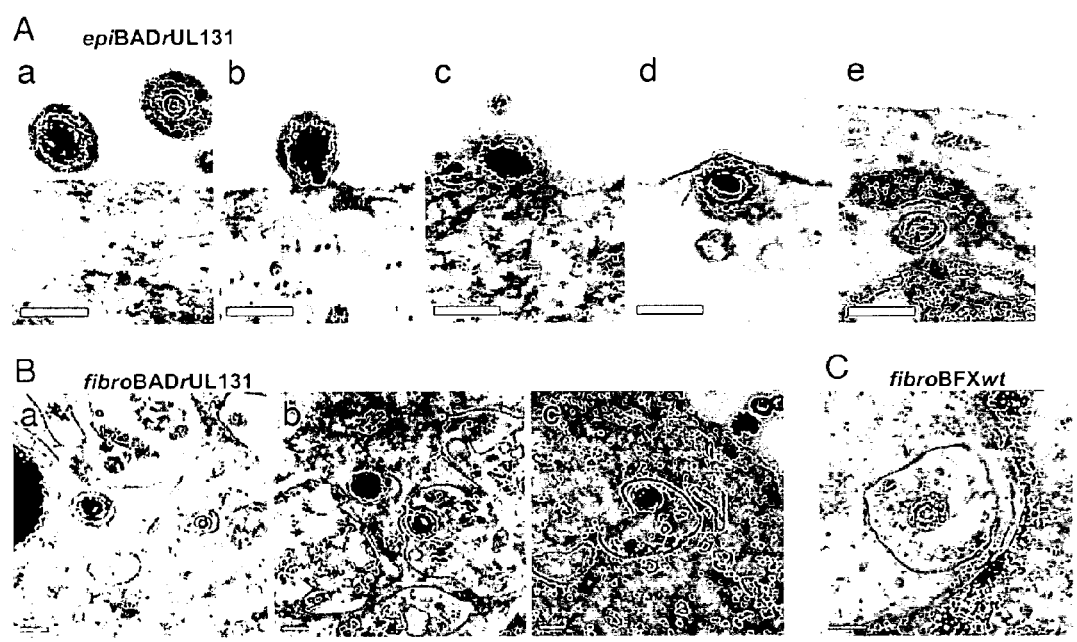
FIG. 2. Electron microscopic analysis of HCMV entry into ARPE-19 cells, epiBADrUL131 or fibroBADrUL131 particles (50 pfu/cell) were bound to cells at 4° C. and then allowed to internalize at 37° C. for 15 min. Representative images are displayed.

In epiBADrUL131-infected ARPE-19 cells, virions were found almost exclusively at the cell surface, with about 97% of the virions at the apical membrane. Some particles were close to the cells but the section did not reveal evidence of contact (FIG. 2A, panel a), and others were captured in the process of fusion at the plasma membrane (FIG. 2A, panels b and c). Capsids beneath the inner surface of the membrane were observed rarely: in fact, only two examples were identified (FIG. 2A, panels d and e). No enveloped virions were found inside the cells. This result indicates that epiBADrUL131 enters the ARPE-19 cells by fusion with the plasma membrane. In contrast, fibroBADrUL131-infected cells contained virions at the cell membrane ~65% of total) and inside the cell within vesicles ~35% of total) (FIG. 2B). The particles within vesicles were enveloped, indicating they entered by endocytosis.

Entry of the BFXwt clinical isolate propagated in fibroblasts was also examined. This clinical isolate accumulated in vesicles within ARPE-19 cells (FIG. 2C), supporting the validity of BADrUL131 as a model for cell entry by a clinical isolate of HCMV.

Infection of ARPE-19 Cells by Fibroblast—but not Epithelial Cell-Derived Virus is pH Dependent.

Figure 3:
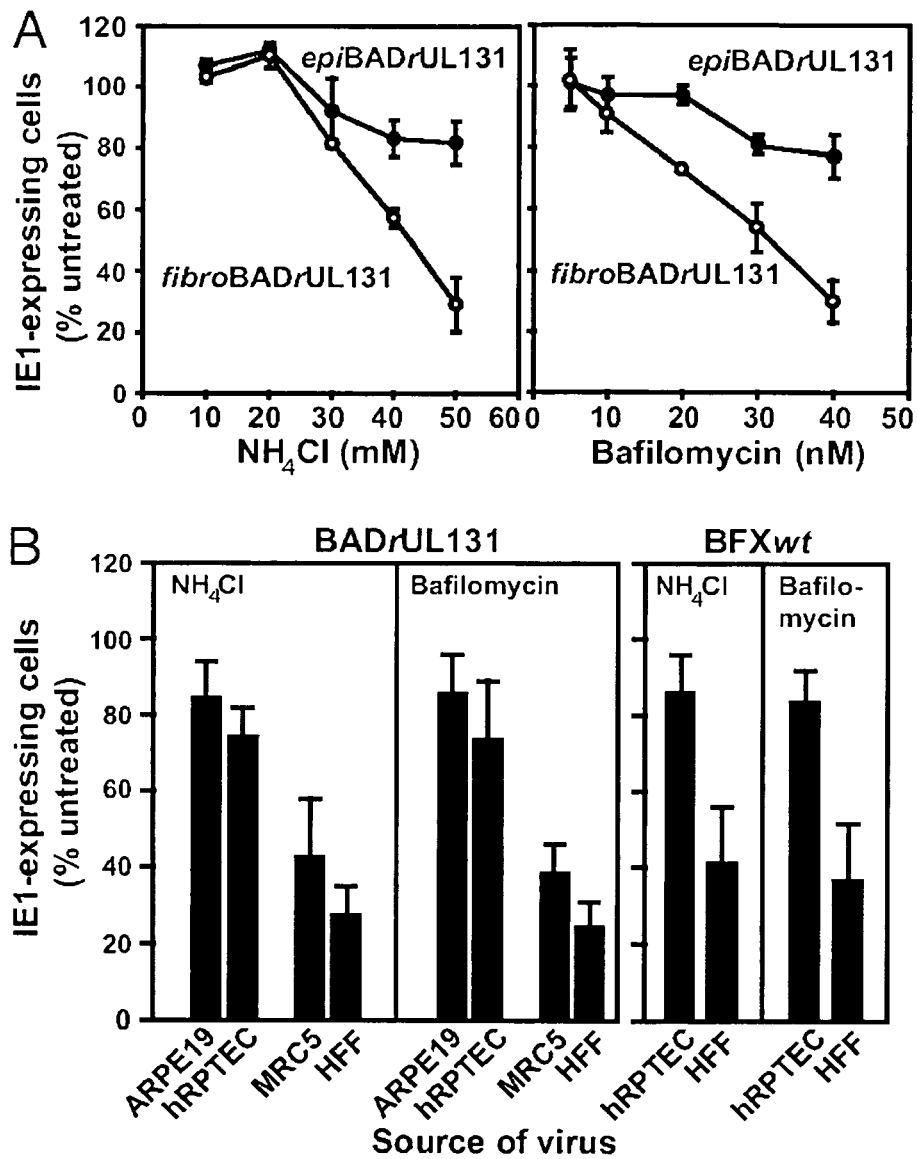
FIG. 3. Effects of inhibitors of endosome acidification and virion source on HCMV entry into ARPE-19 cells. Experiments were performed in triplicate, and the number of positive cells in drug-treated relative to untreated cultures is reported. (A) Cells were pretreated with $NH_4Cl$ or BFA for 1 h, inoculated with epiBADrUL131 or fibroBADrUL131 (1 pfu/cell) and stained for IE1 16 h later. (B) Cells were pretreated with 50 mM $NH_4Cl$ or 40 BFA for 1 h. and then inoculated with BADrUL131 (0.1 pfu/cell) or FIXwt (0.01 pfu/cell) produced in the indicated cell types and stained for IE1 16 h later.

Many viruses that enter cells by endocytosis (1, 4, 10) require acidification of endosomes for the virion envelope to fuse with the endosomal membrane and release the capsid into the cytoplasm. NH$_4$Cl, which buffers endosomal pH, and bafilomycin A1 (BFA), which blocks the endosomal ATPase proton pump, were tested for their effect on infection of ARPE-19 cells. After pretreatment with either agent, cells were infected and cultured in drug-containing medium for a further 16 hr. Successful infections were scored by assaying for IE1-positive cells. Consistent with the ultrastructural analysis described above, pretreatment with either agent had only a modest effect on epiBADrUL131 infection (FIG. 3A). In contrast, both agents inhibited IE1 expression after fibroBADrUL131 infection in a dose dependent manner, indicating that the entry of fibroblast-generated virus was dependent on endosomal acidification. The fact that the agents had little effect on entry by epiBADrUL131 shows that the inhibition of fibroBADrUL131 did not result from toxicity.

It was next determined whether virus grown in other types of epithelial cells and fibroblasts display the same properties as ARPE19- and HFF-derived virions. Virus stocks from hRPTEC epithelial cells and MRC-5 fibroblasts were used to infect ARPE-19 cells after treatment with NH$_4$Cl or BFA, and they responded to the inhibitors exactly as did virus grown in ARPE-19 cells or HFFs (FIG. 3B, left panel). Thus, BADrUL131 produced in two different fibroblasts was substantially more sensitive to the inhibitors than virus produced in two different epithelial cell lines.

The effect of endosomal pH on entry of the BFXwt clinical isolate into ARPE-19 cells was also assayed (FIG. 3B, right panel). NH$_4$Cl or BFA significantly reduced the number of IE1-positive ARPE-19 cells produced by infection with fibroblast-generated BFXwt, but only a slight inhibition was observed after infection with epithelial cell-derived BFXwt.

Virions Produced in Epithelial Cells have Higher Intrinsic Fusion Activity than Virions from Fibroblasts.

As is the case for other herpes viruses. HCMV clinical isolates promote cell-cell fusion that can be detected as early as 3-5 hpi. The rapid production of syncytia without de novo synthesis of virus envelope proteins indicates that it is promoted by "fusion from without", a process by which enveloped virions directly fuse target cells. Since BADrUL131 produced in epithelial cells versus fibroblasts enters epithelial cells differently, the possibility that they would exhibit different "fusion from without" activities was tested.

Figure 4:
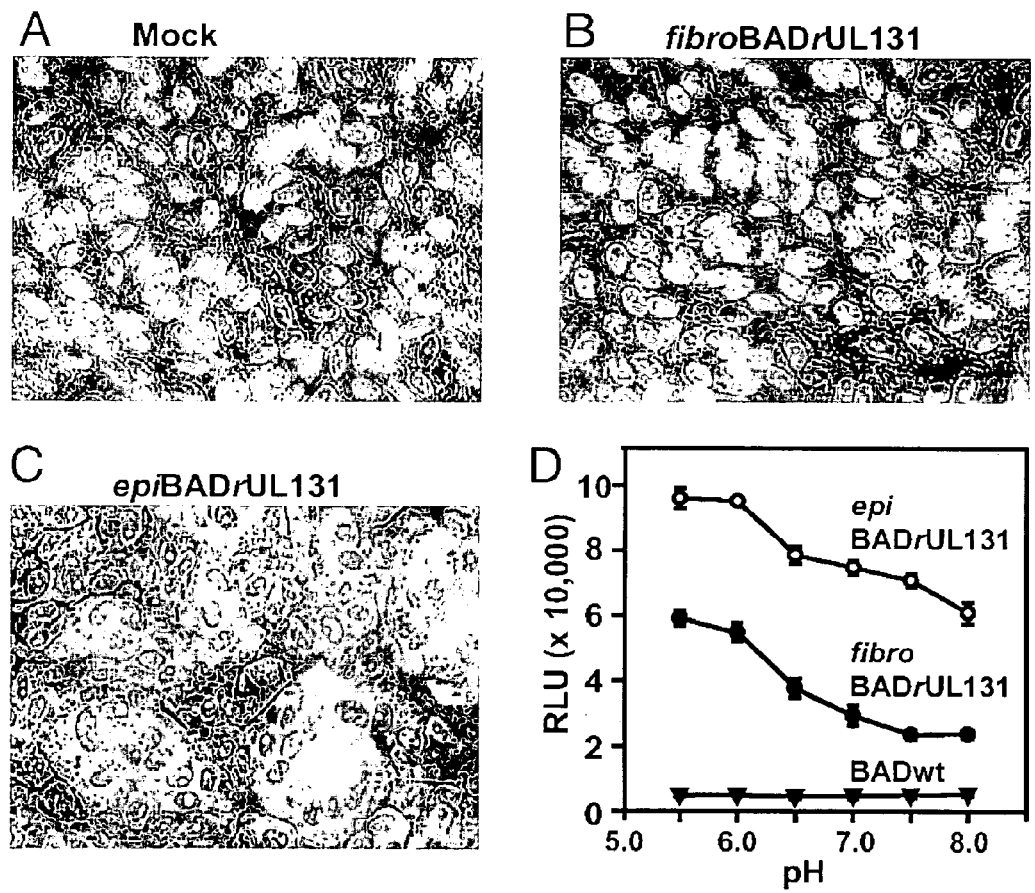
FIG. 4. Fusion from without of ARPE-19 cells induced by epithelial cell-derived virus. (A) Cells were inoculated with epiBADrUL131 or fibroBADrUL131 (20 pfu/cell) and then maintained in medium containing 200 μg/ml of PFA. Phase contrast images were taken at 16 h post infection. (B) A mixture of reporter and effector cells were infected by epiBADrUL131 or fibroBADrUL131 (20 pfu/cell) for at 4° C. for 1 h. The culture was then shifted to 37° C. for 6 h. after which relative luciferase activity was measured.

Mock-infected ARPE-19 cells exhibited no syncytia (FIG. 4A), and syncytia were rarely found after infection with fibroBADrUL131 (FIG. 4B). In contrast, after exposure to epiBADrUL131, cell-cell fusion was detected as early as 6 hpi, and 20-30% of the nuclei were aggregated in syncytia by 24 hpi (FIG. 4C). Cells were treated with PFA, which blocks progression to the late phase of infection, so the fusion must have been induced by epiBADrUL131 particles and not by newly expressed virion proteins.

A luciferase reporter assay was used to quantify the fusion activity of viral particles as well as the effects of pH on fusion from without. Reporter and effector cells received a plasmid containing a luciferase gene driven by a T7 promoter or a T7 RNA polymerase expression plasmid, respectively. The two ARPE-19 derivatives were mixed, and infection-dependent fusion was quantified by assaying luciferase expression, epiBADrUL131 consistently induced higher fusion activity than fibroBADrUL131 (FIG. 4D). At pH 7-8, the activity of fibroBADrUL131 was ~3-fold lower than that of epiBADrUL131. When the cells were treated with low pH buffers after virus adsorption, both virus preparations mediated modestly enhanced fusion. BADwt did not induce fusion in this assay.

The Mode of Entry does not Alter HCMV Cell Tropism.

As discussed above, there is precedent for a herpesvirus to favor entering a specific cell type depending on the cell in which the infecting virus was produced. This phenomenon is different than the one that was observed as described above, i.e. HCMV preparations from different cell types enter epithelial cells by different mechanisms. Nevertheless, it remained possible that the different entry mechanisms would impact on the efficiency of replication and yield, resulting in a tropic effect. Therefore, experiments were conducted to determine whether the mode of entry influenced HCMV plaque production on epithelial cells as compared to fibroblasts (Table 1). Stocks of BADrUL131 were produced in ARPE-19, hRPTEC, HFF or MRC-5 cells and assayed for plaque formation on ARPE-19 or MRC-5 cells (Table 1). Although slightly more plaques were produced on ARPE-19 than MRC-5 cells, neither epithelial cell- nor fibroblast-derived virus preferentially generated plaques on one cell type compared to the other.

TABLE 1

Titration of epithelial cell derived or fibroblast derived BADrUL131 in ARPE19 and MRC5 cells (×10$^5$)

| Source of replication$^a$ | Target cells | | Ratio$^b$ |
|---|---|---|---|
| | ARPE-19 | MRC5 | |
| ARPE-19 | 8.8 | 3.4 | 2.6 |
| hRPTEC | 2.9 | 1.9 | 1.5 |
| MRC5 | 4.3 | 2.7 | 1.6 |
| HFF | 6.8 | 2.7 | 2.5 |

$^a$2 × 10$^5$ pfu of BADrUL131 originally titrated in HFFs were used to infect ARPE-19 or MRC5 cells.
$^b$Ratio of ARPE-19 titer in relation to MRC5 titer.

pUL130-Specific Antibody Blocks ARPE-19 Infection by Both Epithelial- and Fibroblast-Derived Virus.

Figure 5:
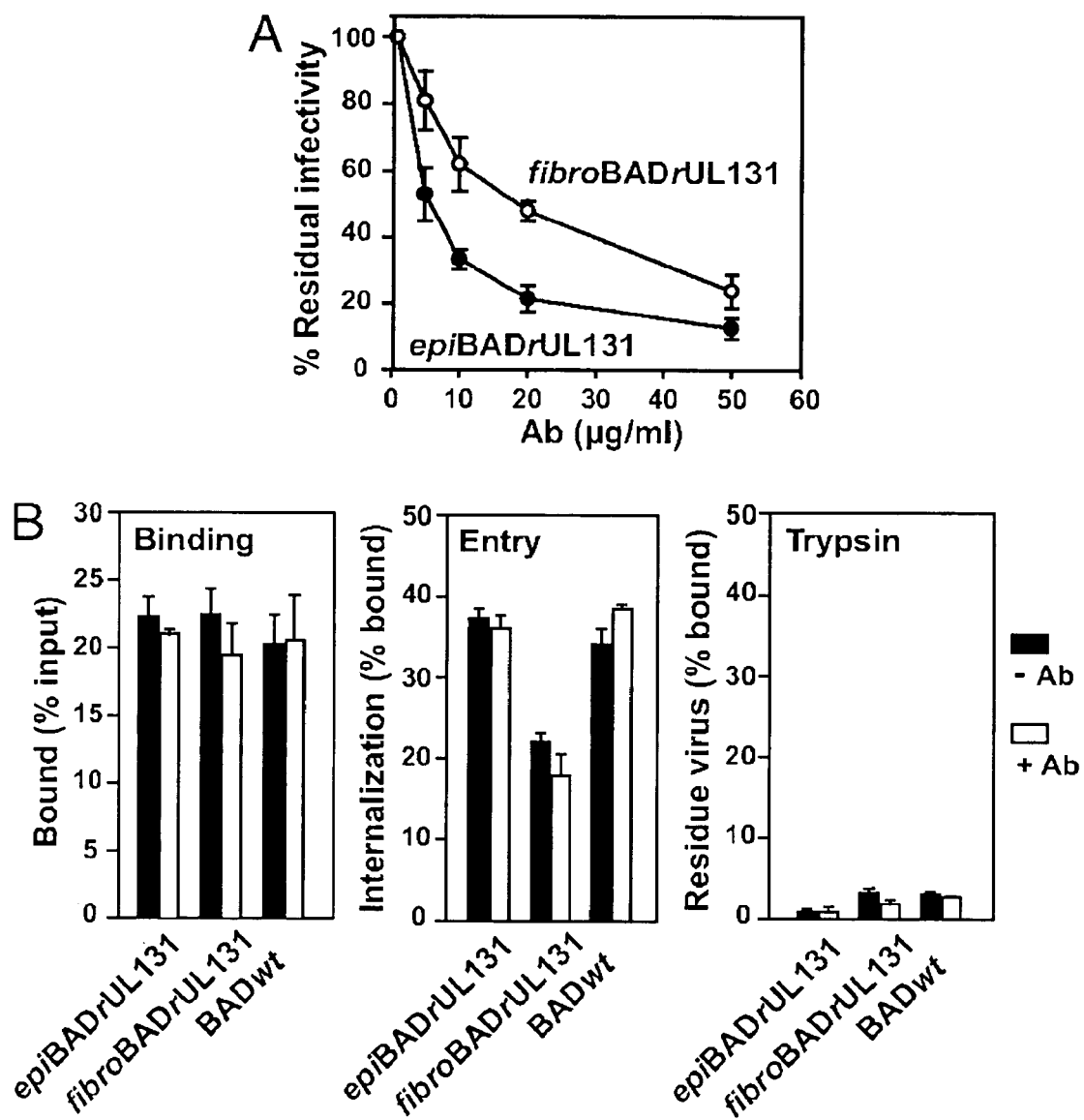
FIG. 5. Effect of pUL130-specific neutralizing antibody on HCMV infection and entry. (A) Epithelial cell- or fibroblast-derived viruses were incubated with various concentrations of anti-pUL130, and residual infectivity was determined. (B) Epithelial cell- or fibroblast-derived virus particles were pretreated with anti-pUL130 at a final concentration of 20 μg/ml or with PBS, and then adsorbed to ARPE-19 cells at 4° C. for 1 h. The cells were washed twice with cold PBS, and viral DNA associated with the cells was extracted to determine the relative numbers of particles attached to the cells. Alternatively, the cells were shifted to 37° C. for 2 h to allow the virus entry. Virions that did not penetrate the cells were removed by EDTA-trypsin treatment. Internalized viral DNA was subsequently quantified by real-time PCR.

A pUL130-specific antibody, which neutralizes HCMV infection of epithelial cells (19), was able to block ARPE-19 infection by either mode of entry (FIG. 5A). It inhibited infection by both viruses in a dose dependent manner, although epiBADrUL131 was somewhat more sensitive to neutralization than fibroBADrUL131. The ability of the antibody to inhibit both modes of entry reinforces the conclusion that the pUL130-containing complex functions whether fusion occurs at the plasma membrane or the endosomal membrane.

It has been reported previously that the gH/gL/pUL128/pUL130/pUL131 complex is dispensable for HCMV to be internalized by endothelial or epithelial cells, because laboratory strains lacking this complex are efficiently endocytosed (10). However, subsequent fusion with endosomal membrane and escape into the cytoplasm requires the complex. Consistent with these earlier results, the antibody to pUL130 did not block binding or internalization of epiBADrUL131, fibroBADrUL131 or BADwt when assayed on ARPE-19 cells (FIG. 5B). However, the total amount of internalized fibroblast-derived virus was lower than that of the epithelial cell-derived virus. This might reflect a reduced rate of internalization, which would be consistent with the delay in onset of IE1 expression by the fibroblast-derived virus (FIG. 1).

epiBADrUL131 and fibroBADrUL131 Induce Different Transcriptional Responses in ARPE-19 Cells.

Like many other viruses, HCMV modulates cellular signaling pathways during entry. One consequence of the altered intracellular signaling is a dramatic change in the cellular transcriptome, which results substantially from contact of virion glycoproteins with the host cell.

Accordingly, the impact of the two entry pathways on the transcriptional response of ARPE-19 cells was investigated. Cells were mock infected or infected with epiBADrUL131 or fibroBADrUL131, and total RNA was purified 6 or 10 h later. Relative RNA levels were analyzed by using microarrays, and infected-cell RNAs whose levels changed by a factor of ≥2.5 relative to mock-infected controls were identified (Tables 2-5). The distributions of RNAs with increased or decreased expression are depicted by Venn diagrams in FIG. 6A.

TABLE 2

Differentially transcribed genes from epiBADrUL131-infected ARP19 cells at 6 h after infection

| Genbank | Fold Change | Gene Name |
|---|---|---|
| NM_020904 | 7.218 | PEPP1 |
| AK124132 | 5.97 | LOC340286 |
| AK074031 | 4.89 | SLIM; FLJ34715 |
| NM_058188 | 4.658 | PRED54; MGC149386; MGC149387 |
| NM_022047 | 4.578 | IBP |
| NM_020436 | 3.172 | DRRS; HSAL4; ZNF797; MGC133050; dJ1112F19.1 |
| NM_001165 | 3.049 | AIP1; API2; MIHC; CIAP2; HAIP1; HIAP1; MALT2; RNF49 |
| NM_001039580 | 3.011 | ASAP; FLJ21159 |
| NM_000364 | 2.91 | CMH2; TnTC; cTnT; CMPD2; MGC3889 |
| NM_005031 | 2.866 | PLM; MGC44983 |
| L08436 | 2.825 | CLP; FLJ43657; MGC19733 |
| NM_145867 | 2.768 | MGC33147 |
| AL133118 | 2.731 | AL133118 |
| NM_001034 | 2.706 | R2; RR2M |
| NM_020943 | 2.674 | KIAA1604 |
| BC039151 | 2.67 | PABPC1L; FLJ42053; dJ1069P2.3 |
| NM_031217 | 2.659 | DKFZP434G2226 |
| NM_003425 | 2.61 | KOX5; ZNF13 |
| NM_000499 | 2.58 | AHH; AHRR; CP11; CYP1; P1-450; P450-C; P450DX |
| NM_182751 | 2.578 | CNA43; PRO2249; MGC126776 |
| NM_144620 | 2.572 | MGC14816; DKFZp313O1122 |
| NM_020359 | 0.4 | PLSCR2 |
| AF085968 | 0.396 | AF085968 |
| NM_053064 | 0.388 | GNG2 |
| NM_005039 | 0.38 | PM; PMF; PMS; Ps 1; Ps 2; PRB1L; PRB1M |
| NM_152525 | 0.373 | FLJ25351; FLJ40332 |
| AK125975 | 0.365 | FLJ43987 |
| NM_175868 | 0.365 | MAGE6; MAGE3B; MAGE-3b; MGC52297 |
| NM_017600 | 0.358 | DKFZp434M0331 |
| NM_006650 | 0.355 | CPX2; 921-L; CPX-2; MGC138492 |
| NM_004294 | 0.343 | RF1; MTTRF1; MGC47721 |
| NM_006434 | 0.343 | CAP; FLAF2; R85FL; SH3D5; SORB1 |
| NM_031466 | 0.339 | NIBP; T1; IBP; MGC4737; MGC4769; KIAA1882 |
| NM_000808 | 0.324 | MGC33793 |
| NM_012377 | 0.324 | OR7C3; OR19-18; CIT-HSP-87M17 |
| NM_001018084 | 0.31 | NM_001018084 |
| NM_024050 | 0.304 | DDA1; PCIA1; MGC2594 |
| NM_005185 | 0.299 | CLP |
| NM_022115 | 0.272 | PFM15; ZNF298; C21orf83 |
| NM_016125 | 0.259 | LOC51136; MGC111090 |
| NM_004843 | 0.256 | CRL1; TCCR; WSX1; IL27R; zcytor1 |
| NM_004334 | 0.242 | CD157 |
| NM_004185 | 0.233 | WNT13; XWNT2 |
| BX360933 | 0.229 | SLC25A5 |
| NM_032188 | 0.222 | MOF; hMOF; FLJ14040 |
| NM_173550 | 0.221 | FLJ39267; FLJ46740; MGC50805 |
| NM_002104 | 0.162 | TRYP2 |

Microarray targets that hybridized with labeled RNA from epiBADrUL131-infected ARPE-19 cells were compared to mock-infected cells, and probe sets whose levels varied by ≥2.5 fold are listed. The Genebank designation, fold change and gene name are listed.

TABLE 3

Differentially transcribed genes from fibroBADrUL131-infected ARP19 cells at 6 h after infection

| Genbank | Fold Change | Gene name |
|---|---|---|
| NM_183040 | 15.03 | SDY; DBND; HPS7; My031; FLJ30031; MGC20210; DKFZP564K192 |
| NM_001165 | 12.48 | AIP1; API2; MIHC; CIAP2; HAIP1; HIAP1; MALT2; RNF49 |
| NM_002852 | 11.21 | TSG-14; TNFAIP5 |
| NM_006509 | 7.008 | I-REL |
| NM_139314 | 6.679 | NL2; ARP4; FIAF; PGAR; HFARP; pp1158; ANGPTL2 |

TABLE 3-continued

Differentially transcribed genes from fibroBADrUL131-infected ARP19 cells at 6 h after infection

| Genbank | Fold Change | Gene name |
| --- | --- | --- |
| NM_002982 | 5.977 | HC11; MCAF; MCP1; MCP-1; SCYA2; GDCF-2 |
| NM_025169 | 5.938 | ZFP; ZNF64; ZKSCAN7; FLJ12738 |
| NM_033066 | 5.144 | DLG6; ALS2CR5 |
| NM_001946 | 4.971 | MKP3; PYST1 |
| NM_000212 | 4.92 | CD61; GP3A; GPIIIa |
| NM_001673 | 4.214 | TS11 |
| NM_004464 | 4.183 | HBGF-5; Smag-82 |
| NM_021101 | 4.072 | CLD1; SEMP1; ILVASC |
| NM_006851 | 4.07 | GLIPR; RTVP1; CRISP7 |
| AK094860 | 3.913 | AK094860 |
| NM_052875 | 3.667 | Pep8b; MGC10485 |
| NM_005347 | 3.648 | BIP; MIF2; GRP78; FLJ26106 |
| NM_022842 | 3.592 | CD318; TRASK; SIMA135 |
| U16307 | 3.36 | GLIPR; RTVP1; CRISP7 |
| NM_000800 | 3.335 | AFGF; ECGF; FGFA; ECGFA; ECGFB |
| NM_000800 | 3.306 | HBGF1; GLIO703; ECGF-beta; FGF-alpha |
| NM_198833 | 3.257 | PI8; CAP2 |
| NM_002053 | 3.21 | GBP1 |
| NM_058179 | 3.161 | PSA; EPIP; PSAT; MGC1460 |
| NM_001004301 | 3.131 | FLJ16542; FLJ34141 |
| NM_180989 | 3.117 | ITR |
| NM_000640 | 3.116 | IL-13R; IL13BP; CD213A2 |
| NM_002658 | 3.09 | ATF; UPA; URK; u-PA |
| NM_018284 | 3.076 | FLJ10961; DKFZp686E0974; DKFZp686L15228 |
| NM_000201 | 3.022 | BB2; CD54; P3.58 |
| NM_005923 | 3.007 | ASK1; MEKK5; MAPKKK5 |
| NM_018836 | 3.001 | MOT8; SHREW1; SHREW-1; RP3-426F10.1 |
| NM_004556 | 2.971 | IKBE |
| NM_022044 | 2.955 | SDF2L1 |
| NM_006611 | 2.954 | Ly49; KLRA#; LY49L; Ly-49L; MGC126520; MGC126522 |
| NM_014314 | 2.935 | RIG-I; FLJ13599; DKFZp434J1111; DKFZp686N19181 |
| NM_003897 | 2.906 | DIF2; IEX1; PRG1; DIF-2; GLY96; IEX-1; IEX-1L |
| NM_006417 | 2.899 | p44; MTAP44 |
| NM_006187 | 2.877 | p100; MGC133260 |
| NR_002186 | 2.876 | DKFZp58611420 |
| NM_033036 | 2.872 | GAL3ST2; GAL3ST-3; MGC142112; MGC142114 |
| NM_014331 | 2.86 | xCT; CCBR1 |
| NM_003786 | 2.831 | MLP2; MRP3; ABC31; MOAT-D; cMOAT2; EST90757 |
| NM_001511 | 2.829 | GRO1; GROa; MGSA; NAP-3; SCYB1; MGSA-a; MGSA alpha |
| NM_000189 | 2.827 | HKI1; HXK2; DKFZp686M1669 |
| NM_001901 | 2.821 | CCN2; NOV2; HCS24; IGFBP8; MGC102839 |
| NM_031217 | 2.811 | DKFZP434G2226 |
| NM_002849 | 2.766 | PTPRQ; EC-PTP; PCPTP1; PTP-SL; PTPBR7 |
| NM_019891 | 2.764 | ERO1LB |
| NM_002234 | 2.745 | HK2; HCK1; PCN1; HPCN1; KV1.5; MGC117058; MGC117059 |
| NM_198569 | 2.739 | DREG; VIGR; PS1TP2 |
| NM_020799 | 2.726 | AMSH-FP; AMSH-LP; ALMalpha; FLJ31524; KIAA1373; etc |
| NM_014632 | 2.726 | KIAA0750; MICAL2PV1; MICAL2PV2 |
| NM_182920 | 2.721 | FLJ42955; KIAA1312 |
| NM_003483 | 2.715 | BABL; LIPO; HMGIC; HMGI-C |
| NM_133492 | 2.706 | ACER1; MGC138327; MGC138329 |
| CR598364 | 2.633 | ENST00000370238 |
| NM_000970 | 2.62 | TXREB1; SHUJUN-2; TAXREB107 |
| NM_005444 | 2.617 | RCD1; CNOT9; RCD1+ |
| NM_194303 | 2.614 | NM_194303 |
| NM_015359 | 2.612 | ZIP14; cig19; LZT-Hs4; KIAA0062 |
| NM_016354 | 2.608 | POAT; OATP1; OATP-E; OATP4A1; OATPRP1; SLC21A12 |
| NM_015009 | 2.607 | LNX3; SEMACAP3 |
| AK124941 | 2.602 | AK124941 |
| NM_001548 | 2.602 | G10P1; IFI56; ISG56; IFI-56; IFNAI1; RNM561; GARG-16 |
| NM_145023 | 2.597 | FLJ32762; DKFZp686N0559; RP11-479G22.1 |
| NM_023070 | 2.592 | FLJ34293; RP11-656D10.1 |
| NM_001902 | 2.584 | MGC9471 |
| NM_004233 | 2.563 | BL11; HB15 |
| NM_020683 | 2.562 | A3AR; AD026; bA552M11.5; RP11-552M11.7 |
| NM_031938 | 2.56 | FLJ34464; B-DIOX-II |
| NM_152649 | 2.55 | FLJ34389 |
| BC048263 | 2.543 | LOC146909 |
| XM_210365 | 2.527 | LOC284288 |
| NM_007107 | 2.515 | TRAPG; SSR gamma |
| NM_002837 | 2.513 | PTPB; HPTPB; FLJ44133; MGC59935; HPTP-BETA; |
| NM_172345 | 2.505 | NM_172345 |
| NM_002609 | 0.4 | JTK12; PDGFR; CD140B; PDGFR1; PDGF-R-beta |
| NM_198353 | 0.4 | KCTD8 |
| NM_003558 | 0.394 | MSS4; STM7 |

TABLE 3-continued

Differentially transcribed genes from fibroBADrUL131-infected ARP19 cells at 6 h after infection

| Genbank | Fold Change | Gene name |
|---|---|---|
| NM_001010911 | 0.392 | bA418C1.3 |
| NM_017644 | 0.391 | DRE1; FLJ25796 |
| NM_052892 | 0.388 | FLJ45333; DKFZp686J19100 |
| NM_175868 | 0.387 | MAGE6; MAGE3B; MAGE-3b; MGC52297 |
| NM_007282 | 0.38 | RZF; MGC13689 |
| NM_005185 | 0.38 | CLP |
| NM_021990 | 0.378 | GABRE |
| AK055156 | 0.375 | FLJ30594; MGC120893; DKFzp761K2322 |
| AF085968 | 0.375 | AF085968 |
| NM_019555 | 0.371 | GEF3; STA3; XPLN; MGC118905; DKFZP434F2429 |
| NM_004294 | 0.368 | RF1; MTTRF1; MGC47721 |
| NM_173039 | 0.365 | AQPX1 |
| BU943730 | 0.364 | BU943730 |
| NM_017600 | 0.364 | DKFZp434M0331 |
| NM_007282 | 0.36 | RZF; MGC13689 |
| AL713743 | 0.357 | FLJ42875; MGC35434; DKFzp761G0122 |
| NM_007314 | 0.347 | ARG; ABLL |
| AK056190 | 0.345 | WHRN; CIP98; USH2D; KIAA1526; RP11-9M16.1; DKFZP434N014 |
| NM_000372 | 0.345 | OCA1A; OCAIA |
| BC015929 | 0.338 | RVR; BD73; HZF2; EAR-1r; Hs.37288 |
| NM_012377 | 0.328 | OR7C3; OR19-18; CIT-HSP-87M17 |
| NM_138440 | 0.324 | SLITL2 |
| NM_001018084 | 0.317 | NM_001018084 |
| NM_000808 | 0.311 | MGC33793 |
| NM_033260 | 0.31 | HFH1 |
| NM_022160 | 0.309 | DMO; MGC163307; MGC163309 |
| BC018597 | 0.308 | BC018597 |
| NM_198404 | 0.305 | bA321C24.3 |
| NM_024050 | 0.303 | DDA1; PCIA1; MGC2594 |
| NM_031466 | 0.299 | NIBP; T1; IBP; MGC4737; MGC4769; KIAA1882 |
| NM_016831 | 0.287 | GIG13 |
| NM_022115 | 0.251 | PFM15; ZNF298; C21orf83 |
| NM_016125 | 0.249 | LOC51136; MGC111090 |
| NM_002104 | 0.242 | TRYP2 |
| NM_013261 | 0.236 | LEM6; PGC1; PGC1A; PGC-1v; PPARGC1; PGC-1(alpha) |
| NM_002167 | 0.211 | HEIR-1 |
| NM_032188 | 0.204 | MOF; hMOF; FLJ14040 |
| BX360933 | 0.197 | SLC25A5 |
| NM_003862 | 0.194 | ZFGF5; FGF-18 |
| NM_173550 | 0.148 | FLJ39267; FLJ46740; MGC50805 |
| NM_004185 | 0.135 | WNT13; XWNT2 |

Microarray targets that hybridized with labeled RNA from fibroBADrUL131-infected ARPE-19 cells were compared to mock-infected cells, and probe sets whose levels varied by ≥2.5 fold are listed. The Genebank designation, fold change, and gene name are listed.

TABLE 4

Differentially transcribed genes from epiBADrUL131-infected ARP19 cells at 10 h after infection

| Genbank | Fold Change | Gene Name |
|---|---|---|
| AK094860 | 5.688 | AK094860 |
| NM_145023 | 4.19 | FLJ32762; DKFZp686N0559; RP11-479G22.1 |
| NM_133492 | 3.456 | ACER1; MGC138327; MGC138329 |
| NM_001039580 | 3.352 | ASAP; FLJ21159 |
| NM_001004301 | 2.982 | FLJ16542; FLJ34141 |
| NM_001034 | 2.911 | R2; RR2M |
| AI369525 | 2.764 | AI369525 |
| AK123066 | 2.753 | AK123066 |
| NM_005345 | 2.729 | HSP72; HSPA1; HSPA1B; HSP70-1 |
| NM_020731 | 2.712 | AHH; AHHR; KIAA1234 |
| BC071797 | 2.631 | BC071797 |
| NM_003414 | 2.609 | HZF2 |
| NM_000800 | 2.576 | AFGF; ECGF; FGFA; ECGFA; ECGFB; HBGF1; GLIO703; etc |
| NM_138467 | 2.571 | C1orf171; FLJ40918 |
| AK090803 | 2.557 | SRrp35; FLJ14459; FLJ33484; FLJ41221; RP11-63L7.3 |
| AL133118 | 2.529 | AL133118 |
| NM_001165 | 2.508 | AIP1; API2; MIHC; CIAP2; HAIP1; HIAP1; MALT2; RNF49 |
| BG001037 | 0.392 | TXNRD1 |
| NM_024861 | 0.388 | FLJ22671; MGC150431; MGC150432 |
| NM_001043 | 0.385 | NET; NAT1; NET1; SLC6A5 |

TABLE 4-continued

Differentially transcribed genes from epiBADrUL131-infected ARP19 cells at 10 h after infection

| Genbank | Fold Change | Gene Name |
| --- | --- | --- |
| NM_016239 | 0.384 | DFNB3; MYO15; DKFZp686N18198 |
| NM_001018084 | 0.383 | NM_001018084 |
| NM_001037442 | 0.381 | RIPX; KIAA0871 |
| NM_017600 | 0.377 | DKFZp434M0331 |
| NM_022097 | 0.369 | LOC63928 |
| NM_175868 | 0.356 | MAGE6; MAGE3B; MAGE-3b; MGC52297 |
| NM_032266 | 0.342 | DKFZp434G118; DKFZp781D2023 |
| NM_003841 | 0.342 | LIT; DCR1; TRID; CD263; TRAILR3; MGC149501; MGC149502 |
| NM_005039 | 0.339 | PM; PMF; PMS; Ps 1; Ps 2; PRB1L; PRB1M |
| NM_145051 | 0.339 | MGC4734; FLJ31197 |
| NM_004294 | 0.336 | RF1; MTTRF1; MGC47721 |
| AW856073 | 0.335 | AW856073 |
| NM_024050 | 0.327 | DDA1; PCIA1; MGC2594 |
| AF085968 | 0.327 | AF085968 |
| NM_080927 | 0.318 | ESDN; CLCP1 |
| NM_022115 | 0.317 | PFM15; ZNF298; C21orf83 |
| AK056703 | 0.309 | LOC219731 |
| NM_000808 | 0.301 | MGC33793 |
| NM_012377 | 0.299 | OR7C3; OR19-18; CIT-HSP-87M17 |
| NM_006793 | 0.298 | AOP1; MER5; AOP-1; SP-22; PRO1748; MGC24293; MGC104387 |
| NM_031466 | 0.289 | NIBP; T1; IBP; MGC4737; MGC4769; KIAA1882 |
| NM_005185 | 0.286 | CLP |
| NM_139173 | 0.286 | MGC131641 |
| BX360933 | 0.28 | SLC25A5 |
| NM_016125 | 0.269 | LOC51136; MGC111090 |
| NM_002104 | 0.251 | TRYP2 |
| NM_032188 | 0.248 | MOF; hMOF; FLJ14040 |
| NM_004185 | 0.245 | WNT13; XWNT2 |
| NM_004843 | 0.237 | CRL1; TCCR; WSX1; IL27R; zcytor1 |
| NM_173550 | 0.208 | FLJ39267; FLJ46740; MGC50805 |

Microarray targets that hybridized with labeled RNA from epiBADrUL131-infected ARPE-19 cells were compared to mock-infected cells, and probe sets whose levels varied by ≥2.5 fold are listed. The Genebank designation, fold change and gene name are listed.

TABLE 5

Differentially transcribed genes from fibroBADrUL131-infected ARP19 cells at 10 h after infection

| Genbank | Fold Change | Gene Name |
| --- | --- | --- |
| AK094860 | 11.26 | AK094860 |
| NM_033066 | 8.751 | DLG6; ALS2CR5 |
| NM_145023 | 6.529 | FLJ32762; DKFZp686N0559; RP11-479G22.1 |
| NM_152377 | 4.463 | FLJ44073; MGC34837 |
| NM_002310 | 4.386 | SWS; SJS2; STWS; CD118 |
| NR_001279 | 4.051 | LOC164380; MGC26611; MGC26924 |
| NM_005345 | 4.008 | HSP72; HSPA1; HSPA1B; HSP70-1 |
| NM_006417 | 3.879 | p44; MTAP44 |
| NM_017638 | 3.783 | p28b; FLJ20045 |
| NM_001165 | 3.695 | AIP1; AP12; MIHC; CIAP2; HAIP1; HIAP1; MALT2; RNF49 |
| NM_000640 | 3.659 | IL-13R; IL13BP; CD213A2 |
| NM_001673 | 3.313 | TS11 |
| NM_002526 | 3.274 | NT; eN; NT5; NTE; eNT; CD73; E5NT |
| NM_003786 | 3.244 | MLP2; MRP3; ABC31; MOAT-D; cMOAT2; EST90757 |
| NM_005527 | 3.229 | hum70t; HSP70-HOM |
| NM_018372 | 3.224 | RIF1; FLJ11269; RP11-96K19.1 |
| NM_133492 | 3.16 | ACER1; MGC138327; MGC138329 |
| NM_033160 | 3.101 | FLJ32813; MGC35232; DKFZp572C163 |
| DB318210 | 3.094 | DB318210 |
| NM_182751 | 3.093 | CNA43; PRO2249; MGC126776 |
| NM_180989 | 3.089 | ITR |
| NM_005345 | 3.048 | HSP72; HSPA1; HSPA1B; HSP70-1 |
| NM_005345 | 3.029 | HSP72; HSPA1; HSPA1B; HSP70-1 |
| NM_000212 | 2.993 | CD61; GP3A; GPIIIa |
| NM_145867 | 2.991 | MGC33147 |
| NM_021813 | 2.976 | BACH2 |
| NM_006187 | 2.943 | p100; MGC133260 |
| CR594200 | 2.942 | LOC643837 |
| NM_012419 | 2.941 | RGSZ2; RGS-17; hRGS17 |
| AF038194 | 2.923 | AF038194 |
| NM_018664 | 2.921 | SNFT; BATF3; JUNDM1 |

TABLE 5-continued

Differentially transcribed genes from fibroBADrUL131-infected ARP19 cells at 10 h after infection

| Genbank | Fold Change | Gene Name |
| --- | --- | --- |
| NM_017577 | 2.907 | FLJ35862; FLJ40464 |
| NM_144633 | 2.887 | ELK; ELK1; elk3; Kv12.1 |
| NM_144620 | 2.86 | MGC14816; DKFZp313O1122 |
| NM_001004301 | 2.859 | FLJ16542; FLJ34141 |
| NM_002852 | 2.847 | TSG-14; TNFAIP5 |
| NM_007107 | 2.839 | TRAPG; SSR gamma |
| NM_032778 | 2.836 | MDIG; NO52; MINA53; FLJ14393; DKFZp762O1912 |
| NM_032523 | 2.828 | ORP6; FLJ36583; MGC59642 |
| NM_005515 | 2.808 | HB9; SCRA1; HOXHB9 |
| NM_002201 | 2.804 | CD25; HEM45 |
| NM_152649 | 2.799 | FLJ34389 |
| NM_033036 | 2.794 | GAL3ST2; GAL3ST-3; MGC142112; MGC142114 |
| NM_006509 | 2.791 | I-REL |
| NM_004233 | 2.789 | BL11; HB15 |
| NM_180989 | 2.772 | ITR |
| NM_020988 | 2.735 | GNAO; G-ALPHA-o; DKFZp686O0962 |
| U16307 | 2.687 | GLIPR; RTVP1; CRISP7 |
| NM_003706 | 2.672 | CPLA2-gamma; DKFZp586C0423 |
| NM_153689 | 2.662 | FLJ38973 |
| NM_000800 | 2.653 | AFGF; ECGF; FGFA; ECGFA; ECGFB; HBGF1; GLIO703; etc |
| BC043212 | 2.643 | LOC402125 |
| NM_002670 | 2.619 | I-PLASTIN |
| NM_152408 | 2.614 | FLJ35779; MGC120442; MGC120443; MGC120444 |
| NM_198951 | 2.613 | TG2; TGC |
| NM_012329 | 2.595 | MMA; PAQR11 |
| NM_001009954 | 2.589 | FLJ20105; MGC131695 |
| NM_032228 | 2.585 | FAR1; FLJ22728; FLJ33561 |
| AI369525 | 2.584 | AI369525 |
| NM_004170 | 2.583 | EAAC1; EAAT3 |
| NM_002930 | 2.571 | RIN; RIBA; ROC2 |
| AK023856 | 2.569 | LOC339803 |
| NM_024525 | 2.558 | FLJ22584 |
| NM_152649 | 2.553 | FLJ34389 |
| NM_181795 | 2.552 | PRKACN2; FLJ23817 |
| BC039151 | 2.549 | PABPC1L; FLJ42053; dJ1069P2.3 |
| NM_006547 | 2.525 | IMP3; KOC1; IMP-3; VICKZ3; DKFZp686F1078 |
| NM_000641 | 2.521 | AGIF; IL-11 |
| NM_145306 | 2.506 | C10orf35 |
| AK021804 | 0.398 | AK021804 |
| NM_007211 | 0.397 | HoJ-1; C12orf2 |
| NM_203434 | 0.397 | MGC70833; bA247A12.2 |
| NM_000362 | 0.397 | SFD; K222; K222TA2; HSMRK222 |
| AK056703 | 0.395 | LOC219731 |
| NM_003558 | 0.395 | MSS4; STM7 |
| NM_016831 | 0.394 | GIG13 |
| NM_024861 | 0.394 | FLJ22671; MGC150431; MGC150432 |
| BF514513 | 0.393 | BF514513 |
| NR_002819 | 0.392 | MALAT-1 |
| NM_002609 | 0.391 | JTK12; PDGFR; CD140B; PDGFR1; PDGF-R-beta |
| NM_018027 | 0.391 | FRMD4; FLJ10210; KIAA1294; bA295P9.4 |
| NM_001010911 | 0.39 | bA418C1.3 |
| AW444553 | 0.389 | FAM84B |
| AK056190 | 0.388 | WHRN; CIP98; USH2D; KIAA1526; RP11-9M16.1 |
| NM_175868 | 0.385 | MAGE6; MAGE3B; MAGE-3b; MGC52297 |
| AB051431 | 0.385 | KIAA1644; MGC125851; MGC125852 |
| NM_001003683 | 0.384 | HCAM1; HSPDE1A; MGC26303 |
| NM_004294 | 0.384 | RF1; MTTRF1; MGC47721 |
| NM_006516 | 0.383 | GLUT; GLUT1; MGC141895; MGC141896 |
| BX104999 | 0.382 | BX104999 |
| AL713743 | 0.381 | FLJ42875; MGC35434; DKFZp761G0122 |
| NM_000322 | 0.381 | RDS; RP7; rd2; AVMD; PRPH; AOFMD; TSPAN22 |
| NM_007314 | 0.381 | ARG; ABLL |
| NM_018371 | 0.376 | ChGn; FLJ11264; beta4GalNAcT |
| NR_002802 | 0.376 | TncRNA |
| DB527271 | 0.376 | DB527271 |
| NM_006393 | 0.374 | LNEBL; bA56H7.1; MGC119746; MGC119747 |
| NM_013989 | 0.372 | D2; 5DI1; SelY, TXDI2 |
| NM_017600 | 0.37 | DKFZp434M0331 |
| BC011595 | 0.369 | NMB; HGFIN |
| AF085968 | 0.366 | AF085968 |
| BC018597 | 0.365 | BC018597 |
| NM_014729 | 0.362 | TOX1; KIAA0808 |
| NM_001003940 | 0.362 | FLJ00065 |
| NM_000372 | 0.358 | OCA1A; OCA1A |
| NM_019555 | 0.358 | GEF3; STA3; XPLN; MGC118905; DKFZP434F2429 |

TABLE 5-continued

Differentially transcribed genes from fibroBADrUL131-infected ARP19 cells at 10 h after infection

| Genbank | Fold Change | Gene Name |
| --- | --- | --- |
| NM_022115 | 0.357 | PFM15; ZNF298; C21orf83 |
| NM_198353 | 0.355 | KCTD8 |
| NM_032434 | 0.355 | KIAA1805; MGC111046 |
| AK055386 | 0.355 | AK055386 |
| NM_006933 | 0.352 | SMIT; SMIT2 |
| CR622110 | 0.35 | CR622110 |
| AW856073 | 0.347 | AW856073 |
| NM_015074 | 0.345 | KLP; CMT2; CMT2A; CMT2A1; HMSNI1 |
| NM_032866 | 0.342 | JACOP; FLJ14957; KIAA1749; MGC138254 |
| NM_012377 | 0.342 | OR7C3; OR19-18; CIT-HSP-87M17 |
| NM_005261 | 0.341 | KIR; MGC26294 |
| AK023391 | 0.339 | AK023391 |
| NM_002214 | 0.339 | ITGB8 |
| NM_182728 | 0.339 | LAT2; LPI-PC1 |
| NM_024050 | 0.338 | DDA1; PCIA1; MGC2594 |
| NM_005185 | 0.338 | CLP |
| NM_016613 | 0.337 | AD021; AD036; FLJ38155; DKFZp434L142 |
| NM_000782 | 0.336 | CP24; CYP24; MGC126273; MGC126274; P450-CC24 |
| NM_001624 | 0.335 | ST4 |
| NM_007282 | 0.333 | RZF; MGC13689 |
| NM_001037442 | 0.327 | RIPX; KIAA0871 |
| NM_004318 | 0.32 | BAH; HAAH; JCTN; junctin; CASQ2BP1 |
| BU943730 | 0.32 | BU943730 |
| NM_205849 | 0.319 | FLJ40182 |
| NM_000808 | 0.315 | MGC33793 |
| NM_033260 | 0.313 | HFH1 |
| NM_000916 | 0.309 | OT-R |
| NM_032188 | 0.309 | MOF; hMOF; FLJ14040 |
| BX360933 | 0.306 | SLC25A5 |
| NM_014351 | 0.304 | NST; BRSTL1; SULTX3; BR-STL-1; MGC40032; DJ388M5.3; etc |
| NM_002167 | 0.3 | HEIR-1 |
| NM_001033086 | 0.298 | dJ631M13.5; RP11-189J1.1 |
| NM_000372 | 0.292 | OCA1A; OCA1A |
| NM_001002926 | 0.289 | TWISTNB |
| AK094143 | 0.288 | C14orf78; KIAA2019 |
| NM_004466 | 0.287 | GPC5 |
| NM_031466 | 0.276 | NIBP; T1; IBP; MGC4737; MGC4769; KIAA1882 |
| NM_013261 | 0.271 | LEM6; PGC1; PGC1A; PGC-1v; PPARGC1; PGC-1(alpha) |
| NM_000693 | 0.267 | ALDH6; RALDH3; ALDH1A6 |
| NM_016125 | 0.26 | LOC51136; MGC111090 |
| AK124390 | 0.23 | AK124390 |
| NM_002104 | 0.228 | TRYP2 |
| NM_005341 | 0.209 | HKR3; pp9964 |
| NM_173082 | 0.202 | FLJ27258; FLJ37625; FLJ45012 |
| NM_173550 | 0.191 | FLJ39267; FLJ46740; MGC50805 |
| NM_004185 | 0.133 | WNT13; XWNT2 |
| NM_021727 | 0.0415 | CYB5RP; LLCDL3 |

Microarray targets that hybridized with labeled RNA from fibroBADrUL131-infected ARPE-19 cells were compared to mock-infected cells, and probe sets whose levels varied by ≥2.5 fold are listed. The Genebank designation, fold change and gene name are listed.

Figure 6:
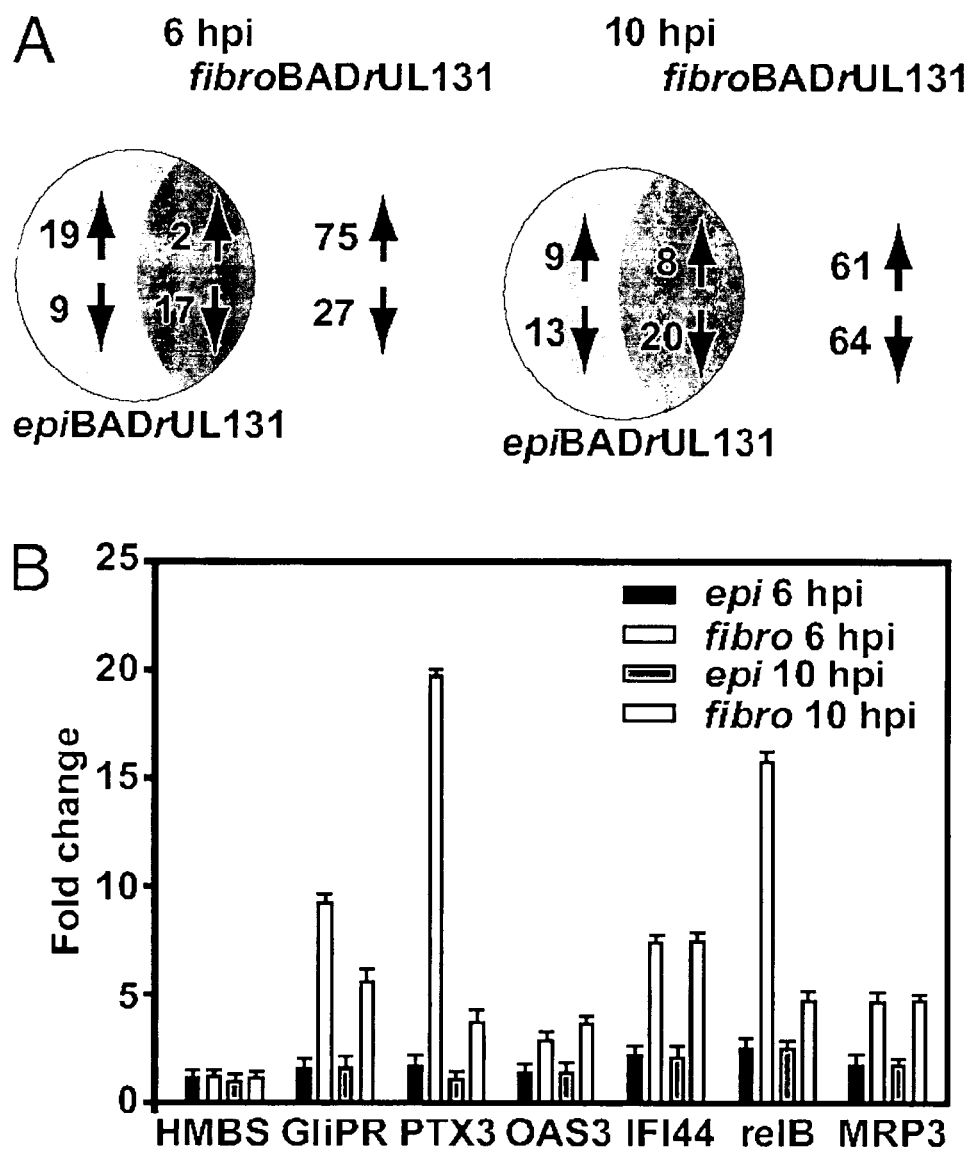
FIG. 6. Modulation of the ARPE-19 transcriptome by HCMV produced in epithelial cells versus fibroblasts. (A) Venn diagrams depict the distribution of differentially regulated genes at 6 h or 10 hpi with epiBADrUL131 or fibroBADrUL131 (3 pfu/cell) relative to mock infection. (B) Changes in relative RNA levels assayed by real-time RT PCR. The genes tested are hydroxymethylbilane synthase (HMBS, NM_000190). GLI pathogenesis-related 1 (glioma) (GliPR, NM_006851), pentraxin-related gene, rapidly induced by IL-1 beta (PTX3, NM_002852), 2'-5'-oligoadenylate synthetase 3 (OAS3, NM_006187), interferon-induced protein 44 (IFI44, NM_006417), v-rel reticuloendotheliosis viral oncogene homolog B, nuclear factor of kappa light polypeptide gene enhancer in B-cells 3 (relB, NM_006509), and ATP-binding cassette, sub-family C (CFTR/MRP), member 3 (MRP3, NM_003786).

At 6 h after epiBADrUL131 infection, the levels of 47 RNAs were changed as compared to mock-infected cells, and 121 RNAs were altered in fibroBADrUL131-infected versus mock-infected cells. The set of modulated RNAs was substantially different for the two viruses: only 19 RNAs were altered after infection with either epiBADrUL131 or fibroBADrUL131. Although there might be several instances in which a gene was altered by one virus by a factor of ≥2.5-fold, while the other virus induced a more modest alteration that fell below the cut-off, inspection of the data revealed that this was not common. At 10 hpi, the number of host cell RNAs modulated by epiBADrUL131 increased only slightly (50 RNAs), whereas a more substantial increase was observed for fibroBADrUL131 (153 RNAs). At the later time, the number of RNAs modulated by both viruses increased to a limited extent (28 RNAs). The microarray results were confirmed by real time RT-PCR for one RNA that was not altered and six RNAs that were altered by infection (FIG. 6B).

To further compare the modulation of RNA levels by fibroBADrUL131 versus epiBADrUL131, the array results were filtered using a gene list comprised of four Gene Ontology groups: host-pathogen interaction (GO:0030383), cell communication (GO:0007154), viral life cycle (GO: 0016032) and cell-cell signaling (GO:0007267). Nearly one third of the mRNAs (70 of 222) that were regulated greater than 2.5 fold in fibroBADrUL131-infected ARPE-19 cells were present in the combined grouping (Table 6). In marked contrast, only one of 86 RNAs induced by epiBADrUL131 was found in these four Gene Ontology groups. The two virus preparations generated substantially different transcriptional responses upon infection of epithelial cells.

TABLE 6 fibroBADrUL131-modified cellular RNA levels

| Genbank | Fold Change 6 hpi | Fold Change 10 hpi | Gene Name |
|---|---|---|---|
| NM_006509 | 7.008 | 2.791 | I-REL |
| NM_139314 | 6.679 | 2.067 | NL2; ARP4; FIAF; PGAR; HFARP; pp1158; ANGPTL2 |
| NM_002982 | 5.977 | nc | HC11; MCAF; MCP1; MCP-1; SCYA2; GDCF-2; etc |
| NM_000212 | 4.92 | 2.993 | CD61; GP3A; GPIIIa |
| NM_002310 | nc | 4.386 | SWS; SJS2; STWS; CD118 |
| NM_004464 | 4.183 | 2.264 | HBGF-5; Smag-82 |
| NM_021101 | 4.072 | nc | CLD1; SEMP1; ILVASC |
| NM_006851 | 4.07 | 2.364 | GLIPR; RTVP1; CRISP7 |
| NM_005347 | 3.648 | nc | BIP; MIF2; GRP78; FLJ26106 |
| U16307 | 3.36 | 2.687 | GLIPR; RTVP1; CRISP7 |
| NM_000800 | 3.335 | 2.115 | AFGF; ECGF; FGFA; ECGFA; ECGFB; HBGF1; etc |
| NM_002526 | nc | 3.274 | NT; eN; NT5; NTE; eNT; CD73; E5NT |
| NM_005527 | nc | 3.229 | hum70t; HSP70-HOM |
| NM_002053 | 3.21 | nc | GBP1 |
| NM_180989 | 3.117 | nc | ITR |
| NM_000640 | 3.116 | 3.659 | IL-13R; IL13BP; CD213A2 |
| NM_002658 | 3.09 | nc | ATF; UPA; URK; u-PA |
| NM_180989 | nc | 3.089 | ITR |
| NM_018284 | 3.076 | 2.185 | FLJ10961; DKFZp686E0974; DKFZp686L15228 |
| NM_005345 | nc | 3.048 | HSP72; HSPA1; HSPA1B; HSP70-1 |
| NM_000201 | 3.022 | nc | BB2; CD54; P3.58 |
| NM_004556 | 2.971 | nc | IKBE |
| NM_006611 | 2.954 | 2.263 | Ly49; KLRA#; LY49L; Ly-49L; MGC126520; etc |
| NM_014314 | 2.935 | 2.071 | RIG-1; FLJ13599; DKFZp434J1111; DKFZp686N19181 |
| NM_003897 | 2.906 | nc | DIF2; IEX1; PRG1; DIF-2; GLY96; IEX-1; IEX-1L |
| NM_006417 | 2.899 | 3.879 | p44; MTAP44 |
| NM_144633 | nc | 2.887 | ELK; ELK1; elk3; Kv12.1 |
| NM_006187 | 2.877 | 2.943 | p100; MGC133260 |
| NM_032778 | nc | 2.836 | MDIG; NO52; MINA53; FLJ14393; DKFZp762O1912 |
| NM_003786 | 2.831 | 3.244 | MLP2; MRP3; ABC31; MOAT-D; cMOAT2; EST90757 |
| NM_001511 | 2.829 | nc | GRO1; GROa; MGSA; NAP-3; SCYB1; MGSA-a; etc |
| NM_001901 | 2.821 | nc | CCN2; NOV2; HCS24; IGFBP8; MGC102839 |
| NM_002849 | 2.766 | nc | PTPRQ; EC-PTP; PCPTP1; PTP-SL; PTPBR7 |
| NM_002234 | 2.745 | nc | HK2; HCK1; PCN1; HPCN1; KV1.5; MGC117058; etc |
| NM_198569 | 2.739 | 2.182 | DREG; VIGR; PS1TP2 |
| NM_000970 | 2.62 | nc | TXREB1; SHUJUN-2; TAXREB107 |
| NM_198951 | nc | 2.613 | TG2; TGC |
| NM_015359 | 2.612 | nc | ZIP14; cig19; LZT-Hs4; KIAA0062 |
| NM_001548 | 2.602 | nc | G10P1; IF156; ISG56; IF1-56; IFNAI1; RNM561; etc |
| NM_012329 | nc | 2.595 | MMA; PAQR11 |
| NM_002930 | nc | 2.571 | RIN; RIBA; ROC2 |
| NM_004233 | 2.563 | 2.789 | BL11; HB15 |
| NM_020683 | 2.562 | nc | A3AR; AD026; bA552M11.5; RP11-552M11.7 |
| NM_181795 | nc | 2.552 | PRKACN2; FLJ23817 |
| NM_006547 | nc | 2.525 | IMP3; KOC1; IMP-3; VICKZ3; DKFZp686F1078 |
| NM_000641 | nc | 2.521 | AGIF; IL-11 |
| NM_172345 | 2.505 | nc | NM_172345 |
| NM_012419 | 2.359 | 2.941 | RGSZ2; RGS-17; hRGS17 |
| NM_020988 | 2.188 | 2.735 | GNAO; G-ALPHA-o; DKFZp686O0962 |
| NM_002201 | 2.028 | 2.804 | CD25; HEM45 |
| NM_004318 | 0.495 | 0.32 | BAH; HAAH; JCTN; junctin; CASQ2BP1 |
| NM_013989 | 0.492 | 0.372 | D2; 5DII; SelY; TXDI2 |
| NM_005261 | 0.468 | 0.341 | KIR; MGC26294 |
| NM_000916 | 0.434 | 0.309 | OT-R |
| NM_014351 | 0.408 | 0.304 | NST; BRSTL1; SULTX3; BR-STL-1; MGC40032; etc |
| NM_002609 | 0.4 | 0.391 | JTK12; PDGFR; CD140B; PDGFR1; PDGF-R-beta |
| NM_007211 | nc | 0.397 | HoJ-1; C12orf2 |
| NM_001003683 | nc | 0.384 | HCAM1; HSPDE1A; MGC26303 |
| NM_006516 | nc | 0.383 | GLUT; GLUT1; MGC141895; MGC141896 |
| NM_000322 | nc | 0.381 | RDS; RP7; rd2; AVMD; PRPH; AOFMD; TSPAN22 |
| NM_021990 | 0.378 | 0.49 | GABRE |
| NM_018371 | nc | 0.376 | ChGn; FLJ11264; beta4GalNAcT |
| NM_019555 | 0.371 | 0.358 | GEF3; STA3; XPLN; MGC118905; DKFZP434F2429 |
| NM_007314 | 0.347 | 0.381 | ARG; ABLL |
| NM_002214 | nc | 0.339 | ITGB8 |
| NM_182728 | nc | 0.339 | LAT2; LPI-PC1 |
| BC015929 | 0.338 | 0.453 | RVR; BD73; HZF2; EAR-1r; Hs.37288 |

TABLE 6-continued fibroBADrUL131-modified cellular RNA levels

| Genbank | Fold Change 6 hpi | Fold Change 10 hpi | Gene Name |
|---|---|---|---|
| NM_016831 | 0.287 | 0.394 | GIG13 |
| NM_013261 | 0.236 | 0.271 | LEM6; PGC1; PGC1A; PGC-1v; PPARGC1; etc |
| NM_003862 | 0.194 | nc | ZFGF5; FGF-18 |

Four GO groups were combined: host-pathogen interaction (GO: 0030383), cell communication (GO: 0007154), viral life cycle (GO: 0016032) and cell-cell signaling (GO: 0007267). The set of 9276 genes was used to filter array results from fibroBADrUL131-infected ARPE-19 cells. Genbank identifiers and gene names are shown along with the fold induction or repression at 6 and 10 hpi.
Probe sets that did not change by ≥2.5 compared to mock-infected cells are designated by "nc" for no change.

DISCUSSION

ARPE-19 epithelial cells can be infected by HCMV through two different routes: fusion at the plasma membrane or endocytosis followed by fusion at the endosomal membrane. Both modes of entry initiate a productive infection. The route of entry depends on the cell type in which the virus was propagated. HCMV from epithelial cells enters by the former route, and virus grown in fibroblasts follows the latter path. This conclusion follows from ultrastructural analysis and differential sensitivity of infection to agents that block acidification of endosomes. The observation that virus grown in epithelial cells has greater "fusion from without" activity than does virus produced in fibroblasts reinforces the view that the two virus preparations interact with ARPE-19 cells in a fundamentally different manner. Importantly, both modes of entry require pUL130 function because pUL130 antibody neutralized infection by virus produced from either source. The gH/gL/pUL128/pUL130/pUL131 complex functions at the ARPE-19 plasma membrane if the infecting virus has been produced in epithelial cells and at the endosomal membrane if the virus was grown in fibroblasts. Neutralized virus in the endosome fails to escape and presumably suffers the same fate as AD169, which lacks the pUL130-containing complex and accumulates in epithelial cell endosomes without initiating a productive infection (10).

Virus grown in fibroblasts induces IE1 protein accumulation in ARPE-19 cells after a delay relative to virus from epithelial cells, suggesting that some aspect of entry by endocytosis proceeds more slowly than entry by fusion at the plasma membrane. Many virions are evident in endosomes, but no capsids were seen in the cytoplasm after entry of fibroblast-generated virus; and capsids were found rarely in the cytoplasm of cells infected with epithelial cell-produced virus. Apparently, virions linger for a time in endosomes, but once a capsid is freed of its envelope and reaches the cytoplasm, it is rapidly disassembled.

How are HCMV virions produced in the two cell types different? It appears different "fusion from without" activities provide an indication. Not only did epiBADrUL131 induce fusion more efficiently than fibroBADrUL131, but lowered pH enhanced the activities of both virus preparations. Without intending to be bound or limited by any explanation of mechanism, it is possible that fusion of membranes requires a threshold of fusion activity. The ability of pUL130 antibody to neutralize both virus preparations indicates that both depend on the gH/gL/pUL128/pUL130/pUL131 complex for fusion, so experiments were devised to test the hypothesis that the viruses contain different amounts of the complex. Several of its constituents were assayed, and it was found that a slightly higher ratio (~2-fold) of gH/gL/pUL128/pUL130/pUL131 to gH/gL/gO were present in epiBADrUL131 particles than in fibroBADrUL131 particles. The levels of gB, pp28 and pp65 were similar in the two virion preparations.

There is precedent in EBV for production of viruses with different relative amounts of a 01 complex: particles produced by B cells are deficient for gH/gL/gp42 (18). However, other factors may be involved. Perhaps a constituent of the complex that was not assayed is altered. Alternatively, the ratio of the gH complex to one or more additional virion glycoprotein complexes might modify fusion activity. Finally, it may be that an unidentified cell protein, supplied to the virions when they are produced within epithelial cells or fibroblasts, might alter the complex.

Are there physiological consequences to the two modes of entry? epiBADrUL131 and fibroBADrUL131 induced markedly different cellular transcriptional responses after infection of ARPE-19 cells. Assuming that the difference is indeed due to virions or virions plus specifically associated cellular factors, the microarray experiment demonstrates a strikingly different transcriptional response to infection. Endocytosis is intimately involved in the regulation of signaling by cell surface molecules. As a consequence, a virus might modulate cell signaling, and the cellular transcriptome, differently if it enters by fusion at the plasma membrane versus endocytosis. The differences in cell signaling likely have physiological consequences that are not detected in cultured cells, such as effects on virus spread, immune evasion, or virulence.

REFERENCES

1. Miller, N. & Hutt-Fletcher, L. M. (1992) *J Virol* 66, 3409-14.
2. Nemerow, G. R. & Cooper. N. R. (1984) *Virology* 132, 186-98.
3. Nicola, A. V., Hou. J. Major, E. O. & Straus, S. E. (2005) *J Virol* 79, 7609-16.
4. Nicola, A. V., McEvoy, A. M. & Straus, S. E. (2003) *J Virol* 77, 5324-32.
5. Milne, R. S., Nicola, A. V., Whitbeck, J. C., Eisenberg. R. J. & Cohen. G. H. (2005) *J Virol* 79, 6655-63.
6. Wittels, M. & Spear. P. G. (1991) *Virus Res* 18, 271-90.
7. Plachter, B., Sinzger, C. & Jahn, G. (1996) *Adv Virus Res* 46, 195-261.
8. Compton, T., Nepomuceno, R. R. & Nowlin, D. M. (1992) *Virology* 191, 387-95.
9. Bodaghi, B., Goureau. O., Zipeto, D., Laurent. L., Virelizier. J. L. & Michelson. S. (1999) *J Immunol* 162.957-64.
10. Ryckman, B. J. Jarvis. M. A. Drummond, D. D., Nelson. J. A. & Johnson. D. C. (2006)*J Virol* 80, 710-22.

11. Wang, X. Kenyon. W. J. Li, Q., Mullberg, J. & Hutt-Fletcher, L. M. (1998) *J Virol* 72, 5552-8.
12. Li, Q., Turk. S. M. & Hutt-Fletcher, L. M. (1995) *J Virol* 69, 3987-94.
13. Hutt-Fletcher, L. M. & Lake, C. M. (2001) *Curr Top Microbiol Immunol* 258, 51-64.
14. Haan, K. M., Kwok. W. W., Longnecker. R. & Speck, P. (2000) *J Virol* 74, 2451-4.
15. Haan, K. M. & Longnecker. R. (2000) *Proc Natl Acad Sci USA* 97, 9252-7.
16. Li, Q., Spriggs. M. K., Kovats. S., Turk, S. M., Comeau. M. R. Nepom, B. & Hun-Fletcher, L. M. (1997) *J Virol* 71, 4657-62.
17. Wang, X. & Hutt-Fletcher, L. M. (1998) *J Virol* 72, 158-63.
18. Borza, C. M. & Hun-Fletcher, L. M. (2002) *Nat Med* 8, 594-9.
19. Wang, D. & Shenk, T. (2005) *Proc Natl Acad Sci USA* 102, 18153-8.
20. Adler, B. Scrivano. L., Ruzcics, Z., Rupp. B. Sinzger. C. & Koszinowski. U. (2006) *J Gen Virol* 87, 2451-2460.
21. Wang, D. & Shenk, T. (2005) *J Virol* 79, 10330-8.
22. Hahn, G., Revello, M. G. Patrone, M., Percivalle. E. Campanini. G. Sarasini, A., Wagner, M., Gallina, A., Milanesi, G., Koszinowski, U. Baldanti, F. & Gema. G. (2004) *J Virol* 78, 10023-33.

The present invention is not limited to the embodiments described and exemplified above, but is capable of variation and modification within the scope of the appended claims.

What is claimed is:

1. A method of making an immunogenic composition comprising a population of live attenuated, inactivated or killed cytomegaloviruses (CMVs), or virion components thereof, comprising:
   a) passaging two or more strains or isolates of CMV having a gene encoding a functional pUL131 protein in a fibroblast,
   b) amplifying the two or more strains or isolates of CMV in an epithelial cell, thereby producing cell type-conditioned CMVs; and c) producing a population of live attenuated, inactivated, or killed CMVs from the cell type-conditioned CMVs, thereby producing the immunogenic composition.

2. The method of claim 1, wherein the two or more strains or isolates of CMV are human CMV strains or isolates.

3. The method of claim 1, comprising amplifying the two or more strains or isolates of CMV in two or more different epithelial cells and combining the cell type-conditioned CMVs from the two or more different epithelial cells.

* * * * *

UNITED STATES PATENT AND TRADEMARK OFFICE
CERTIFICATE OF CORRECTION

| | | |
|---|---|---|
| PATENT NO. | : 9,439,960 B2 | Page 1 of 1 |
| APPLICATION NO. | : 12/681504 | |
| DATED | : September 13, 2016 | |
| INVENTOR(S) | : Thomas Shenk et al. | |

It is certified that error appears in the above-identified patent and that said Letters Patent is hereby corrected as shown below:

TITLE PAGE

Item 22: delete "Oct. 1, 2008" and replace it with --Oct. 10, 2008--.

IN THE SPECIFICATION

Please delete the following paragraph, located in column 1, lines 4-8:

"Pursuant to 35 U.S.C. §202(c), it is acknowledged that the United States governent may have certain rights in the invention described herein, which was made in part with funds from the National Institutes of Health under Grant Nos.: CA85786, CA82396, AI54430 and GM71508."

Please insert the following paragraph in column 1, at line 24, before the "FIELD OF THE INVENTION":

--GOVERNMENT SUPPORT
This invention was made with government support under Grants Nos. GM071508, CA082396, CA085786 and AI055430 awarded by the National Institutes of Health. The government has certain rights in the invention.--.

Signed and Sealed this
Twenty-ninth Day of November, 2016

Michelle K. Lee
*Director of the United States Patent and Trademark Office*